US012162882B2

(12) United States Patent
Verner et al.

(10) Patent No.: US 12,162,882 B2
(45) Date of Patent: Dec. 10, 2024

(54) QUINOLONE DERIVATIVES AS FIBROBLAST GROWTH FACTOR RECEPTOR INHIBITORS

(71) Applicant: Principia Biopharma Inc., Bridgewater, NJ (US)

(72) Inventors: Erik Verner, Belmont, CA (US); Kenneth Albert Brameld, Menlo Park, CA (US)

(73) Assignee: PRINCIPIA BIOPHARMAC, INC., Bridgewater, NJ (US)

( * ) Notice: Subject to any disclaimer, the term of this patent is extended or adjusted under 35 U.S.C. 154(b) by 0 days.

(21) Appl. No.: 18/217,002

(22) Filed: Jun. 30, 2023

(65) Prior Publication Data
US 2024/0092777 A1    Mar. 21, 2024

Related U.S. Application Data

(63) Continuation of application No. 17/306,528, filed on May 3, 2021, now abandoned, which is a continuation of application No. 16/383,237, filed on Apr. 12, 2019, now Pat. No. 11,078,199, which is a continuation of application No. 15/806,525, filed on Nov. 8, 2017, now Pat. No. 10,294,223, which is a continuation of application No. 15/022,869, filed as application No. PCT/US2015/014460 on Feb. 4, 2015, now Pat. No. 9,815,834.

(60) Provisional application No. 62/069,932, filed on Oct. 29, 2014, provisional application No. 62/007,562, filed on Jun. 4, 2014, provisional application No. 61/937,211, filed on Feb. 7, 2014.

(51) Int. Cl.
| | |
|---|---|
| *C07D 471/04* | (2006.01) |
| *A61K 31/519* | (2006.01) |
| *A61K 31/5377* | (2006.01) |
| *A61K 45/06* | (2006.01) |
| *C07D 487/04* | (2006.01) |
| *C07D 519/00* | (2006.01) |

(52) U.S. Cl.
CPC .......... *C07D 471/04* (2013.01); *A61K 31/519* (2013.01); *A61K 31/5377* (2013.01); *A61K 45/06* (2013.01); *C07D 487/04* (2013.01); *C07D 519/00* (2013.01)

(58) Field of Classification Search
CPC . A61K 31/5377; A61K 31/519; C07D 471/04
See application file for complete search history.

(56) References Cited

U.S. PATENT DOCUMENTS

| | | | |
|---|---|---|---|
| 5,620,981 A | 4/1997 | Blankley et al. | |
| 9,567,334 B2 | 2/2017 | Verner et al. | |
| 9,630,963 B2 | 4/2017 | Brameld et al. | |
| 9,815,834 B2 | 11/2017 | Verner et al. | |
| 10,294,223 B2 | 5/2019 | Verner et al. | |
| 10,538,517 B2 | 1/2020 | Brameld et al. | |
| 10,538,518 B2 | 1/2020 | Zhu et al. | |
| 10,899,760 B2 | 1/2021 | Zhu et al. | |
| 11,078,199 B2 | 8/2021 | Verner et al. | |
| 2005/0009849 A1 | 1/2005 | Veach et al. | |
| 2005/0107408 A1 | 5/2005 | Goldstein et al. | |
| 2009/0036472 A1 | 2/2009 | Palle et al. | |
| 2021/0147417 A1 | 5/2021 | Zhu et al. | |
| 2021/0292323 A1 | 9/2021 | Verner et al. | |

FOREIGN PATENT DOCUMENTS

| | | | |
|---|---|---|---|
| EP | 2230243 A1 | 9/2010 | |
| RU | 2348632 C2 | 3/2009 | |
| RU | 2006120486 A | 3/2009 | |
| WO | 2005047284 A1 | 5/2005 | |
| WO | 2005105097 A2 | 11/2005 | |
| WO | 2008150260 A1 | 12/2008 | |
| WO | 2012158843 A2 | 11/2012 | |
| WO | WO 2012/159550 | * 11/2012 | |
| WO | 2014011900 A2 | 1/2014 | |
| WO | 2014182829 A1 | 11/2014 | |
| WO | 2015120049 A1 | 8/2015 | |

OTHER PUBLICATIONS

Aitken, R., et al., "Flash vacuum pyrolysis over magnesium. Part 1. Pyrolysis of benzylic,other ary/alkyl and aliphatic halides," Journal of Chemical Society, Perkins Transactions, vol. 1, pp. 402-415, 2002.
Biancalani, C., et al., "Further studies on Arylpiperazinyl Alkyl Pyridazinones: Discovery of an exceptionally potent, orally active, antinociceptive agent in thermally induced pain," Journal of Medicinal Chemistry, vol. 52, pp. 7397-7409, 2009.
Billerey, C., et al., "Frequent FGFR3 mutations in papillary non-invasive bladder (pTa) tumors," American Journal of Pathology, vol. 158, pp. 1955-1959, 2001.
Bradshaw et al. Prolonged and tunable residence time using reversible covalent kinase inhibitors, Nature Chemical Biology, 2015, 11(7): 525-531 May 25, 2015.
Federal Register, vol. 76, No. 27, Wednesday Feb. 9, 2011, p. 7166.
Hamby, J., et al., "Structure-activity relationships for a novel series of pyrido[2,3-d]pyrimidine tyrosine kinase inhibitors," Journal of Medicinal Chemistry, vol. 40, pp. 2296-2303, 1997.
Hammerman, P., et al., "Genomic characterization and targeted therapeutics in squamous cell lung cancer [abstract]," Proceedings of the 14th World Conference on Lung Cancer, Jul. 3-7, 2011, Aurora, CO.

(Continued)

*Primary Examiner* — Marcos L Sznaidman
(74) *Attorney, Agent, or Firm* — McNeill PLLC

(57) ABSTRACT

Compounds that are Fibroblast Growth Factor Inhibitors (FGFR) and are therefore useful for the treatment of diseases treatable by inhibition of FGFR are disclosed. Also disclosed are pharmaceutical compositions containing such compounds and processes for preparing such compounds.

11 Claims, 3 Drawing Sheets

(56) References Cited

OTHER PUBLICATIONS

International Search Report for PCT/US2015/014460, issued Apr. 22, 2015, 3 pages.

International Search Report for PCT/US2016/046304, issued Oct. 7, 2016, 7 pages.

Jang, J.H., et al., "Mutations in fibroblast growth factor receptor 2 and fibroblast growth factor receptor 3 genes associated with human gastric and colorectal cancers," Cancer Research, vol. 61, pp. 3541-3543, 2001.

Keats, J.J., et al., "Ten years and counting: so what do we know about t(4;14)(p16;q32)(see Keats, J.J., et al., 2006. Ten years and counting: so what do we know about t(4;14)(p16;q32) multiple myeloma," Leukemia Lymphoma, vol. 47, pp. 2289-2300, 2006.

Patent Cooperation Treaty, International Search Report for PCT/US2016/033065, dated Jul. 27, 2016, 5 pages Jul. 26, 2016.

Pollock, P.M., et al., "Frequent activating FGFR2 mutations in endometrial carcinomas parallel germline mutations associated with craniosynostosis and skeletal dysplasia syndromes," Oncogene, vol. 26, pp. 7158-7162, 2007.

Ray, M. E., et al., "Genomic and expression analysis of the 8p11-12 amplicon in human breast cancer cell lines," Cancer Research, vol. 64, pp. 40-47, 2004.

Sahadevan, K., D., et al., "Selective over-expression of fibroblast growth factor receptors 1 and 4 in clinical prostate cancer," Journal of Pathology, vol. 213, pp. 82-90, 2007.

Search Report for Russian Application No. 2016130932, issued Jun. 19, 2018, 2 pages.

Tan et al., Development of covalent inhibitors that can overcome resistance to first-generation FGFR kinase inhibitors. Proc Natl Acad Sci U S A 111, E4869-E4877 (2014).

Thompson et al., 3-{3,5-Dimethoxyphenyl)-1,6-naphthyridine-2,7-diamines and related 2-urea derivatives are potent ; 1nd selective inhibitors of the FGF receptor-1 tyrosine kinase. J Med Chem 43, 4200-11 (2000).

Thompson et al., Synthesis and structure-activity relationships of soluble ?-substituted 3-(3,5-dimethoxyphenyl)-1,6-riaphthyridin-2-amines and related ureas as dual inhibitors of the fibroblast growth J Med Chem 48, 4628-53 (2005).

Yang, D., et al., "Application of a C-C Bond-Forming Conjugate Addition Reaction in Asymmetric Dearomatization of Beta-Naphthols," Angewandte Chemie International Edition, vol. 54, pp. 9523-9527, 2015.

Zhou et al., A structure-guided approach to creating covalent FGFR inhibitors. Chem Biol 17, 285-95 (2010).

Zhu et al., Pending U.S. Appl. No. 17/155,726, filed Jan. 22, 2021 (not enclosed).

Verner et al., U.S. Appl. No. 17/306,528, filed May 3, 2021.

* cited by examiner

QUINOLONE DERIVATIVES AS FIBROBLAST GROWTH FACTOR RECEPTOR INHIBITORS

CROSS-REFERENCE TO RELATED APPLICATIONS

The present application is a continuation of U.S. application Ser. No. 17/306,528, filed May 3, 2021, which is a continuation of U.S. application Ser. No. 16/383,237, filed Apr. 12, 2019, now issued as U.S. Pat. No. 11,078,199, which is a continuation of U.S. application Ser. No. 15/806,525, filed on Nov. 8, 2017, now issued as U.S. Pat. No. 10,294,223, which is a continuation of U.S. application Ser. No. 15/022,869, filed on Mar. 17, 2016, now issued as U.S. Pat. No. 9,815,834, which is the National Stage of International Application No. PCT/US2015/014460, filed on Feb. 4, 2015, which claims priority to each of U.S. Provisional Application No. 61/937,211, filed on Feb. 7, 2014, U.S. Provisional Application No. 62/007,562, filed Jun. 4, 2014, and U.S. Provisional Application No. 62/069,932, filed Oct. 29, 2014. The contents of each of the above-identified applications are incorporated by reference in their entirety as if recited in full herein.

FIELD OF THE DISCLOSURE

The present disclosure provides certain compounds that are Fibroblast Growth Factor Receptor Inhibitors (FGFR) and are therefore useful for the treatment of diseases treatable by inhibition of FGFR. Also provided are pharmaceutical compositions containing such compounds and processes for preparing such compounds.

BACKGROUND

Fibroblast growth factors (FGFs) and their receptors (FGFRs) play important roles in physiological processes relating to tissue repair, hematopoiesis, bone growth, angiogenesis and other aspects of embryonic development. Alterations in the FGF signaling pathway have also emerged as important drivers in human disease. FGF signaling can be deregulated through multiple mechanisms, including gene amplification, activating mutations and translocations, over-expression, altered FGFR gene splicing, and autocrine or paracrine overproduction of the ligands of FGFR. Deregulated FGF signaling has been documented in human tumors, including breast (see Ray, M. E., et. al., 2004. Genomic and expression analysis of the 8p11-12 amplicon in human breast cancer cell lines. *Cancer Res* 64:40-47), multiple myeloma (see Keats, J. J., et. al., 2006. Ten years and counting: so what do we know about t(4;14)(p16;q32) multiple myeloma. *Leuk Lymphoma* 47:2289-2300), non-invasive bladder (see Billerey, C., et al. 2001. Frequent FGFR3 mutations in papillary non-invasive bladder (pTa) tumors. *Am J Pathol* 158:1955-1959), endometrial (see Pollock, P. M., et al. 2007. Frequent activating FGFR2 mutations in endometrial carcinomas parallel germline mutations associated with craniosynostosis and skeletal dysplasia syndromes. *Oncogene* 26:7158-7162), gastric (see Jang, J. H., et. al., 2001. Mutations in fibroblast growth factor receptor 2 and fibroblast growth factor receptor 3 genes associated with human gastric and colorectal cancers. *Cancer Res* 61:3541-3543), prostate cancers (see Sahadevan, K., D et. al., 2007. Selective over-expression of fibroblast growth factor receptors 1 and 4 in clinical prostate cancer. *J Pathol* 213:82-90), lung (see Hammerman P, et al. Genomic characterization and targeted therapeutics in squamous cell lung cancer [abstract]; Proceedings of the 14th World Conference on Lung Cancer; 2011 3-7 Jul.; Aurora (CO); and International Association for the Study of Lung Cancer; 2011), esophageal (see Hanada K, et al., Identification of fibroblast growth factor-5 as an overexpressed anti-gen in multiple human adenocarcinomas. Cancer Res 2001; 61: 5511-6), cholangiocarcinoma (see Arai, Y., et al. 2014. Fibroblast growth factor receptor 2 tyrosine kinase fusions define a unique molecular subtype of cholangiocarcinoma. Hepatology 59, 1427-1434 and Borad, M. J., et al. 2014). Integrated genomic characterization reveals novel, therapeutically relevant drug targets in FGFR and EGFR pathways in sporadic intrahepatic cholangiocarcinoma. PLoS genetics 10, e1004135), glioblastoma (see Rand V., et. al. Sequence survey of receptor tyrosine kinases reveals mutations in glioblastomas. Proc Natl Acad Sci USA 2005; 102: 14344-9 and Parker, et. al. 2014. Emergence of FGFR family gene fusions as therapeutic targets in a wide spectrum of solid tumours. The Journal of pathology 232, 4-15). FGFR1 translocations and FGFR1 fusions are frequently observed in 8p11 myeloproliferative syndromes (Jackson, C. C., Medeiros, L. J., and Miranda, R. N. (2010). 8p11 myeloproliferative syndrome: a review. Human pathology 41, 461-476). Activating mutations in FGFR3 have been shown to cause a number of dwarf syndromes (see Harada, D., et. al., 2009. FGFR3-related dwarfism and cell signaling. *J Bone Miner Metab* 27:9-15) including achondroplasia (see Bellus, G. A., et. al., 1995. Achondroplasia is defined by recurrent G380R mutations of FGFR3. *Am J Hum Genet* 56:368-373; Bellus, G. A., et. al., 1995. A recurrent mutation in the tyrosine kinase domain of fibroblast growth factor receptor 3 causes hypochondroplasia. *Nat Genet* 10:357-359; and Rousseau, F., et. al., 1994. Mutations in the gene encoding fibroblast growth factor receptor-3 in achondroplasia. *Nature* 371:252-254), Crouzon dermoskeletal syndromes (see Robin, N. H., et. al., 1993. FGFR-Related Craniosynostosis Syndromes), hyopochondroplasia (see Prinos, P., et. al., 1995. A common FGFR3 gene mutation in hypochondroplasia. *Hum Mol Genet* 4:2097-2101), Muenke syndrome (see Muenke, M., et al. 1997. A unique point mutation in the fibroblast growth factor receptor 3 gene (FGFR3) defines a new craniosynostosis syndrome. *Am J Hum Genet* 60:555-564), SADDAN (severe achondroplasia with developmental delay and acanthosis nigricans) (see Bellus, G. A., et al. 1999. Severe achondroplasia with developmental delay and acanthosis nigricans (SADDAN): phenotypic analysis of a new skeletal dysplasia caused by a Lys650Met mutation in fibroblast growth factor receptor 3. *Am J Med Genet* 85:53-65; Tavormina, P. L., et al. 1999. A novel skeletal dysplasia with developmental delay and acanthosis nigricans is caused by a Lys650Met mutation in the fibroblast growth factor receptor 3 gene. *Am J Hum Genet* 64:722-731), thanatophoric dysplasia (see d'Avis, P. Y., et. al., 1998. Constitutive activation of fibroblast growth factor receptor 3 by mutations responsible for the lethal skeletal dysplasia thanatophoric dysplasia type I. *Cell Growth Differ* 9:71-78; Kitoh, H., et. al., 1998. Lys650Met substitution in the tyrosine kinase domain of the fibroblast growth factor receptor gene causes thanatophoric dysplasia Type I. Mutations in brief no. 199. Online. *Hum Mutat* 12:362-363; and Tavormina, P. L., et. al., 1995. Thanatophoric dysplasia (types I and II) caused by distinct mutations in fibroblast growth factor receptor 3. *Nat Genet* 9:321-328), platyspondylic lethal skeletal dysplasia (see Brodie, S. G., et. al., 1999. Platyspondylic lethal skeletal dysplasia, San Diego type, is caused by FGFR3 mutations. *Am J Med Genet*

84:476-480), and cervical cancer (see Cappellen, D., et. al., 1999. Frequent activating mutations of FGFR3 in human bladder and cervix carcinomas. *Nat Genet* 23:18-20). Activating mutations in FGFR4 have been identified in rhabdomyosarcoma (see Shukla, N., et. al., Oncogene mutation profiling of pediatric solid tumors reveals significant subsets of embryonal rhabdomyosarcoma and neuroblastoma with mutated genes in growth signaling pathways. *Clin Cancer Res* 18:748-757 and Marshall, A. D., et. al., PAX3-FOXO1 and FGFR4 in alveolar rhabdomyosarcoma. *Mol Carcinog* 51:807-815). For these reasons, FGFRs are attractive therapeutic target for the treatment of diseases.

SUMMARY

Provided is a compound of Formula (III):

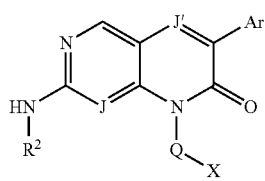
(III)

wherein:
J is N or CH;
J' is N or $CR^1$ where $R^1$ is hydrogen, halo, alkyl, or cycloalkyl;
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
$R^2$ is hydrogen, alkyl, alkynyl, acyl, alkoxycarbonyl, haloalkyl, cycloalkyl optionally substituted with amino, alkylamino, dialkylamino, or hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, alkoxy, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, hydroxy, alkoxy, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and
(i) Q is alkylene or substituted alkylene; and
X is a group of formula (a), (b), (c), or (h):

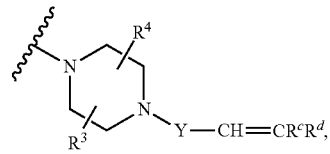
(a)

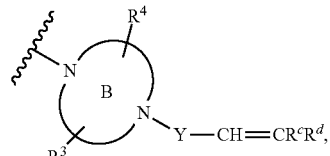
(b)

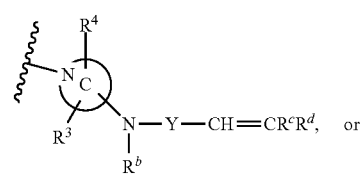
(c)

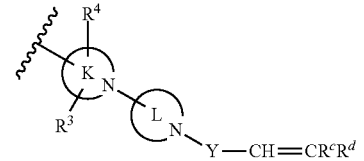
(h)

wherein:
ring B is aza bridged heterocycloamino or aza spiroheterocycloamino;
ring C is azetidinyl, pyrrolidinyl, piperidinyl, bridged heterocycloamino, or spiro heterocycloamino wherein the nitrogen atom in aforementioned (a), (b) and (c) rings is attached to the Q group;
rings K and L are independently azetidinyl, pyrrolidinyl, piperidinyl, or homopiperidinyl;
each $R^3$ is hydrogen, alkyl, haloalkyl, hydroxy, alkoxy, or halo; and
each $R^4$ is hydrogen, alkyl, hydroxy, alkoxy, or halo; or
(ii) Q is heteroalkylene, substituted heteroalkylene, or aminoheteroalkylene, and
X is a group of formula (d) or (e):

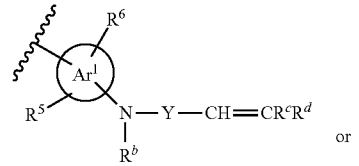
(d)

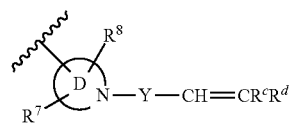
(e)

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;

$R^6$ is hydrogen, alkyl, cycloalkyl, hydroxy, alkoxy, halo, haloalkyl, haloalkoxy, or cyano; and $R^7$ and $R^8$ are independently hydrogen, alkyl, hydroxy, alkoxy, or halo; or (iii) Q is -alkylene-cycloalkylene-alkylene-, and X is a group of formula (f) or (g):

(f)

(g)

wherein:

$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;

ring E is heterocycloamino, bridged heterocycloamino, or spiroheterocycloamino;

$R^9$ is hydrogen, alkyl, hydroxy, alkoxy, halo, haloalkyl, haloalkoxy, or cyano;

$R^{10}$ is hydrogen, alkyl, cycloalkyl, hydroxy, alkoxy, halo, haloalkyl, haloalkoxy, or cyano; and $R^{11}$ and $R^{12}$ are independently hydrogen, alkyl, hydroxy, alkoxy, or halo;

each Y is —CO— or —SO$_2$—;

each $R^b$ is hydrogen or alkyl;

each $R^c$ is hydrogen, alkyl, or substituted alkyl; and each $R^d$ is hydrogen or alkyl; or each $R^d$ and the hydrogen atom on carbon attached to group Y can form a bond to give a triple bond $$\left( -\!\!-\!\!Y\!\!-\!\!C\!\equiv\!CR^c \right);$$

and/or a pharmaceutically acceptable salt thereof;

provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —NR$^b$—Y—CH═CR$^c$R$^d$ are meta or para to each other; (2) when ring D or E is piperidinyl, then Q and —Y—CH═CR$^c$R$^d$ are meta or para to each other; (3) when ring D or E is piperazinyl, then Q and —Y—CH═CR$^c$R$^d$ are para to each other; and (4) when ring C, D, or E is pyrrolidinyl or azetidinyl, then Q and —NR$^b$—Y—CH═CR$^c$R$^d$ or Q and —Y—CH═CR$^c$R$^d$ are (1,3) to each other.

Also, provided is a compound of Formula (I'):

(I')

wherein:

J is N or CH;

Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;

$R^1$ is hydrogen, halo, alkyl, or cycloalkyl;

$R^2$ is hydrogen, alkyl, alkynyl, acyl, alkoxycarbonyl, haloalkyl, cycloalkyl optionally substituted with amino, alkylamino, dialkylamino, or hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, optionally substituted heterocyclyl, —NR$^g$(alkylene)$_n$-Z—CH═CR$^e$R$^f$ and —Z—CH═CR$^e$R$^f$ provided —Z—CH═CR$^e$R$^f$ is attached to a ring nitrogen in the heterocyclyl ring), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, heteroaryl (where phenyl, phenyl ring in aralkyl, heteroaryl ring in heteroaralkyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, optionally substituted heterocyclyl, or —NR$^g$(alkylene)$_n$-Z—CH═CR$^e$R$^f$), or —Z—CH═CR$^e$R$^f$;

where:

n is 0-3;

each Z is —CO— or —SO$_2$—;

each $R^e$ is hydrogen, alkyl, or substituted alkyl;

each $R^f$ is hydrogen or alkyl; or each $R^f$ and the hydrogen atom on carbon attached to group Z can form a bond to give a triple bond $$\left( -\!\!-\!\!Z\!\!-\!\!C\!\equiv\!CR^e \right);$$

and
each $R^g$ is hydrogen or alkyl; and
(i) -Q-X is cycloalkyl, cycloalkylalkyl, haloalkyl, hydroxyalkyl, alkoxyalkyl, alkoxyalkyloxyalkyl, aminoalkyl, phenyl, 5- or 6-membered heteroaryl, phenylalkyl, 5- or 6-membered heteroaralkyl (where phenyl, phenyl ring in phenylalkyl, 5- or 6-membered heteroaryl, and heteroaryl ring in 5- or 6-membered heteroaralkyl are optionally substituted with one, two, or three substituents independently selected from alkyl, cycloalkyl, hydroxy, alkoxy, halo, haloalkyl, haloalkoxy, and cyano), heterocyclyl, heterocyclylalkyl, or heterocyclylheteroalkyl (where the heterocyclyl ring in heterocyclyl, heterocyclylalkyl, and heterocyclylheteroalkyl is optionally substituted with one, two, or three substituents independently selected from alkyl, halo, haloalkyl, acyl, acylamino, hydroxy, hydroxyalkyl, alkoxyalkyl, aminoalkyl, optionally substituted aryl, optionally substituted heteroaryl, and optionally substituted heterocyclyl); or
(ii) Q is alkylene; and
X is a group of formula (a), (b), or (c):

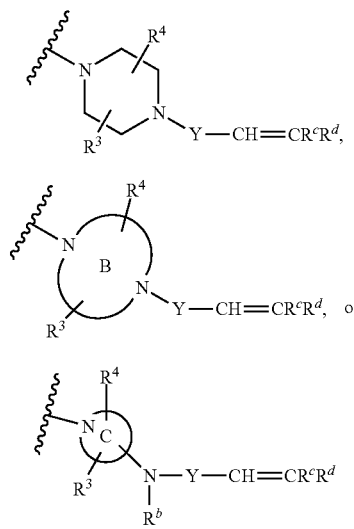

(a)

(b)

(c)

wherein:
ring B is aza bridged heterocycloamino or aza spiroheterocycloamino;
ring C is azetidinyl, pyrrolidinyl, piperidinyl, bridged heterocycloamino, or spiro heterocycloamino;
each $R^3$ is hydrogen, alkyl, haloalkyl, hydroxy, alkoxy, or halo; and
each $R^4$ is hydrogen, alkyl, hydroxy, alkoxy, or halo; or
(iii) Q is heteroalkylene and
X is a group of formula (d) or (e):

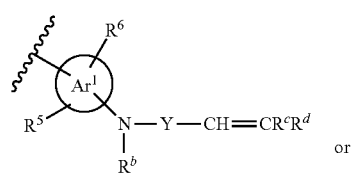

(d)

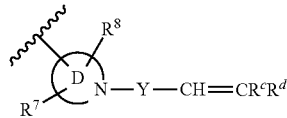

(e)

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or
(iv) Q is -alkylene-cycloalkylene-alkylene-, and
X is a group of formula (f) or (g):

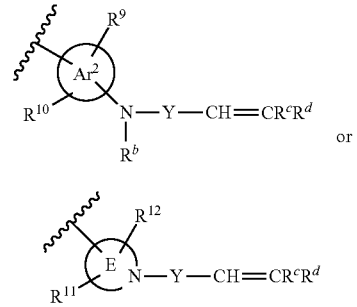

(f)

or (g)

wherein:
$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —$SO_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

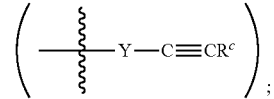

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —NR$^b$—Y—CH=CR$^c$R$^d$ are meta or para to each other; (2) when ring D or E is piperidinyl, then Q and —Y—CH=CR$^c$R$^d$ are meta or para to each other; (3) when ring D or E is piperazinyl, then Q and —Y—CH=CR$^c$R$^d$ are para to each other; (4) when ring C, D, or E is pyrrolidinyl or azetidinyl, then Q and —NR$^b$—Y—CH=CR$^c$R$^d$ or Q and —Y—CH=CR$^c$R$^d$ are (1,3) to each other; and (5) when Q is not a group of formula (a), (b), (c), (d), (e), (f), or (g), then R$^2$ is (i) —Z—CH=CR$^e$R$^f$ or (ii) heterocyclyl substituted with at least —Z—CH=CR$^e$R$^f$ or —NR$^g$(alkylene)$_n$-Z—CH=CR$^e$R$^f$ or (iii) aralkyl, heteroaralkyl, phenyl, or heteroaryl (where phenyl, phenyl ring in aralkyl, heteroaryl, and heteroaryl ring in heteroaralkyl are substituted with at least —NR$^g$(alkylene)$_n$-Z—CH=CR$^e$R$^f$).

In a first aspect, provided is a compound of Formula (I):

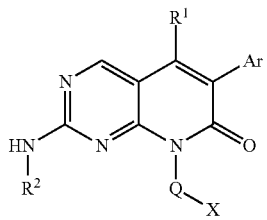

(I)

wherein:

Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;

R$^1$ is hydrogen, halo, alkyl, or cycloalkyl;

R$^2$ is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, optionally substituted heterocyclyl, —NR$^g$(alkylene)$_n$-Z—CH=CR$^e$R$^f$ and —Z—CH=CR$^e$R$^f$ provided —Z—CH=CR$^e$R$^f$ is attached to a ring nitrogen in the heterocyclyl ring), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, heteroaryl (where the phenyl ring in aralkyl, the heteroaryl ring in heteroaralkyl, phenyl, and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, optionally substituted heterocyclyl, or —NR$^g$(alkylene)$_n$-Z—CH=CR$^e$R$^f$), or —Z—CH=CR$^e$R$^f$;

where:

n is 0-3;

each Z is —CO— or —SO$_2$—;

each R$^e$ is hydrogen, alkyl, or substituted alkyl;

each R$^f$ is hydrogen or alkyl; or each R$^f$ and the hydrogen atom on carbon attached to group Z can form a bond to give a triple bond

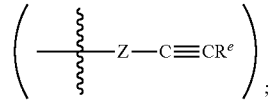

and each R$^g$ is hydrogen or alkyl; and (i) -Q-X is cycloalkyl, cycloalkylalkyl, haloalkyl, hydroxyalkyl, alkoxyalkyl, alkoxyalkyloxyalkyl, aminoalkyl, phenyl, 5- or 6-membered heteroaryl, phenylalkyl, 5- or 6-membered heteroaralkyl (where phenyl, the phenyl ring in phenylalkyl, 5- or 6-membered heteroaryl, and the heteroaryl ring in 5- or 6-membered heteroaralkyl are optionally substituted with one, two, or three substituents independently selected from alkyl, cycloalkyl, hydroxy, alkoxy, halo, haloalkyl, haloalkoxy, and cyano), heterocyclyl, heterocyclylalkyl, or heterocyclylheteroalkyl (where the heterocyclyl ring in heterocyclyl, heterocyclylalkyl, and heterocyclylheteroalkyl is optionally substituted with one, two, or three substituents independently selected from alkyl, halo, haloalkyl, acyl, acylamino, hydroxy, hydroxyalkyl, alkoxyalkyl, aminoalkyl, optionally substituted aryl, optionally substituted heteroaryl, and optionally substituted heterocyclyl); or (ii) Q is alkylene; and X is a group of formula (a), (b), or (c):

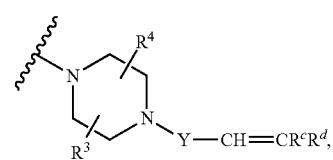

(a)

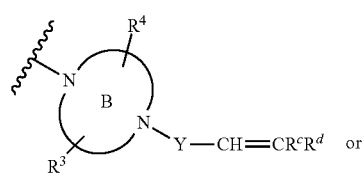

(b)

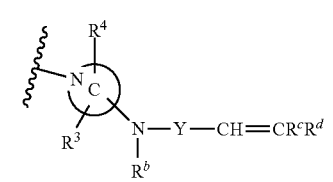

(c)

wherein:

ring B is aza bridged heterocycloamino or aza spiroheterocycloamino;

ring C is azetidinyl, pyrrolidinyl, piperidinyl, bridged heterocycloamino, or spiro heterocycloamino wherein the nitrogen atom in aforementioned (a), (b), and (c) rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or
(iii) Q is heteroalkylene, and
X is a group of formula (d) or (e):

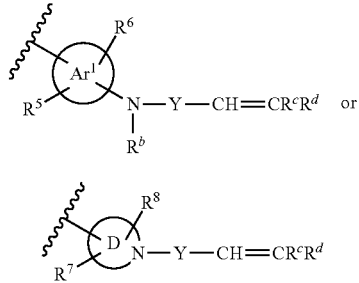

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or
(iv) Q is -alkylene-cycloalkylene-alkylene-, and
X is a group of formula (f) or (g):

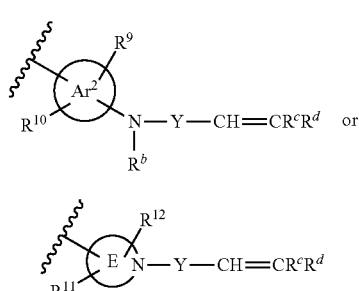

wherein:
$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —SO$_2$—;

each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

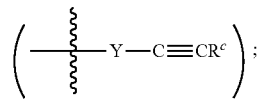

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —NR$^b$—Y—CH=CR$^c$R$^d$ are meta or para to each other; (2) when ring D or E is piperidinyl, then Q and —Y—CH=CR$^c$R$^d$ are meta or para to each other; (3) when ring D or E is piperazinyl, then Q and —Y—CH=CR$^c$R$^d$ are para to each other; (4) when ring C, D, or E is pyrrolidinyl or azetidinyl, then Q and —NR$^b$—Y—CH=CR$^c$R$^d$ or Q and —Y—CH=CR$^c$R$^d$ are (1,3) to each other; and (5) when Q is not a group of formula (a), (b), (c), (d), (e), (f), or (g), then $R^2$ is (i) —Z—CH=CR$^e$R$^f$ or (ii) heterocyclyl substituted with at least —Z—CH=CR$^e$R$^f$ or —NR$^g$(alkylene)$_n$-Z—CH=CR$^e$R$^f$ or (iii) aralkyl, heteroaralkyl, phenyl, or heteroaryl (where phenyl, phenyl ring in aralkyl, heteroaryl, and heteroaryl ring in heteroaralkyl are substituted with at least —NR$^g$(alkylene)$_n$ -Z—CH=CR$^e$R$^f$).
In one embodiment of the first aspect, provided is a compound of Formula (IA):

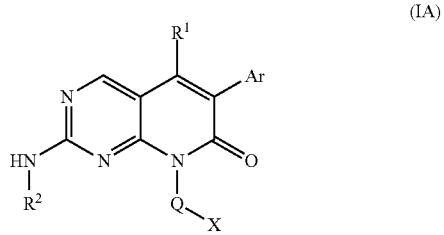

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, or cyano;
$R^1$ is hydrogen, halo, or alkyl;
$R^2$ is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl); and (i) Q is alkylene; and X is a group of formula (a), (b), or (c):

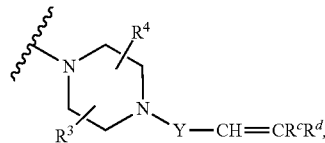

(a)

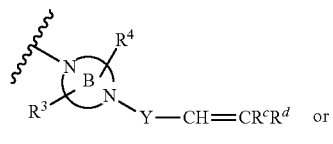

(b)

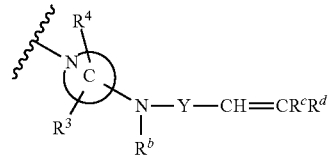

(c)

wherein:
ring B is aza bridged heterocycloamino or aza spiroheterocycloamino;
ring C is azetidinyl, pyrrolidinyl, piperidinyl, bridged heterocycloamino, or spiro heterocycloamino wherein the nitrogen atom in aforementioned (a), (b), and (c) rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or (ii) Q is heteroalkylene and
X is a group of formula (d) or (e):

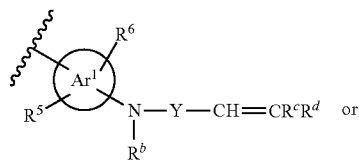

(d)

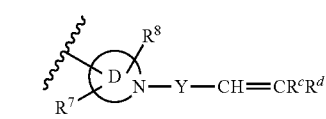

(e)

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or (iii) Q is -alkylene-cycloalkylene-alkylene-, and
X is a group of formula (f) or (g):

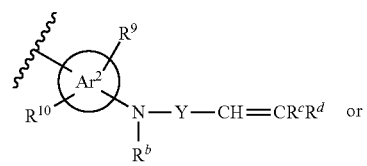

(f)

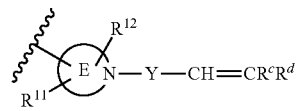

(g)

wherein:
$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —$SO_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

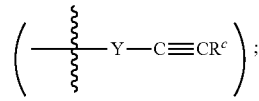

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —$NR^b$—Y—CH=$CR^cR^d$ are meta or para to each other; (2) when ring D or E is piperidinyl, then Q and —Y—CH=$CR^cR^d$ are meta or para to each other; (3) when ring D or E is piperazinyl, then Q and —Y—CH=$CR^cR^d$ are para to each other; and (4) when ring C, D, or E is pyrrolidinyl or azetidinyl, then Q and —$NR^b$—Y—CH=$CR^cR^d$ or Q and —Y—CH=$CR^cR^d$ are (1,3) to each other.

In another embodiment of the first aspect, provided is a compound of Formula (IB):

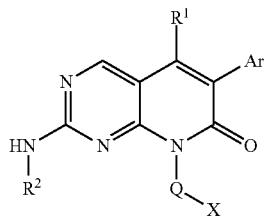

(IB)

wherein:
- Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
- $R^1$ is hydrogen, halo, alkyl, or cycloalkyl;
- $R^2$ is heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, optionally substituted heterocyclyl, —$NR^g$(alkylene)$_n$-Z—CH=$CR^eR^f$ or —Z—CH=$CR^eR^f$ provided —Z—CH=$CR^eR^f$ is attached to a ring nitrogen in the heterocyclyl ring), phenyl, heteroaryl (where phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, optionally substituted heterocyclyl, or —NH(alkylene)$_n$-Z—CH=$CR^eR^f$), or —Z—CH=$CR^eR^f$; provided that when $R^2$ is heterocyclyl then the heterocyclyl ring is substituted with at least —$NR^g$(alkylene)$_n$-Z—CH=$CR^eR^f$ or —Z—CH=$CR^eR^f$ and when $R^2$ is phenyl or heteroaryl then the phenyl or heteroaryl ring is substituted with at least —$NR^g$(alkylene)$_n$-Z—CH=$CR^eR^f$;
- where:
- each Z is —CO— or —$SO_2$—;
- each $R^e$ is hydrogen, alkyl, or substituted alkyl;
- each $R^f$ is hydrogen or alkyl; or
- each $R^f$ and the hydrogen atom on carbon attached to group Z can form a bond to give a triple bond

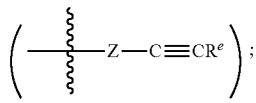

and
- each $R^g$ is hydrogen or alkyl; and
- Q-X is cycloalkyl, cycloalkylalkyl, haloalkyl, hydroxyalkyl, alkoxyalkyl, alkoxyalkyloxyalkyl, aminoalkyl, phenyl, 5- or 6-membered heteroaryl, phenylalkyl, 5- or 6-membered heteroaralkyl (where phenyl, the phenyl ring in phenylalkyl, 5- or 6-membered heteroaryl, and the heteroaryl ring in 5- or 6-membered heteroaralkyl are optionally substituted with one, two, or three substituents independently selected from alkyl, cycloalkyl, hydroxy, alkoxy, halo, haloalkyl, haloalkoxy, and cyano), heterocyclyl, heterocyclylalkyl, and heterocyclylheteroalkyl (where the heterocyclyl ring in heterocyclyl heterocyclylalkyl, and heterocyclylheteroalkyl is optionally substituted with one, two, or three substituents independently selected from alkyl, halo, haloalkyl, acyl, acylamino, hydroxy, hydroxyalkyl, alkoxyalkyl, aminoalkyl, optionally substituted aryl, optionally substituted heteroaryl, and optionally substituted heterocyclyl).

In a third embodiment of the first aspect, provided is a compound of Formula (IC):

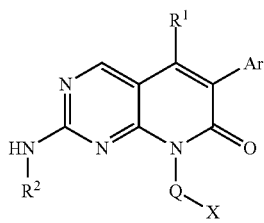

(IC)

wherein:
- Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, or cyano;
- $R^1$ is hydrogen, halo, alkyl, or cycloalkyl;
- $R^2$ is heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, optionally substituted heterocyclyl, —$NR^g$(alkylene)$_n$-Z—CH=$CR^eR^f$ and —Z—CH=$CR^eR^f$ provided —Z—CH=$CR^eR^f$ is attached to a ring nitrogen in the heterocyclyl ring), phenyl, heteroaryl (where phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, optionally substituted heterocyclyl, or —$NR^g$(alkylene)$_n$-Z—CH=$CR^eR^f$), or —Z—CH=$CR^eR^f$; provided that when $R^2$ is heterocyclyl then the heterocyclyl ring is substituted with at least —$NR^g$(alkylene)$_n$-Z—CH=$CR^eR^f$ or —Z—CH=$CR^eR^f$ and when $R^2$ is phenyl, or heteroaryl then the phenyl or heteroaryl ring is substituted with at least —$NR^g$(alkylene)$_n$-Z—CH=$CR^eR^f$;
- where:
- n is 0-3;
- each Z is —CO— or —$SO_2$—;
- each $R^e$ is hydrogen, alkyl, or substituted alkyl;
- each $R^f$ is hydrogen or alkyl; or
- each $R^f$ and the hydrogen atom on carbon attached to group Z can form a bond to give a triple bond

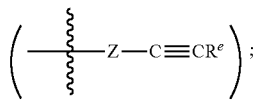

and
each $R^g$ is hydrogen or alkyl; and
(i) Q is alkylene; and
X is a group of formula (a), (b), or (c):

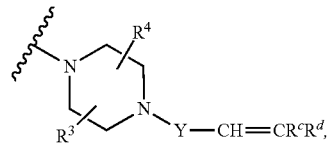

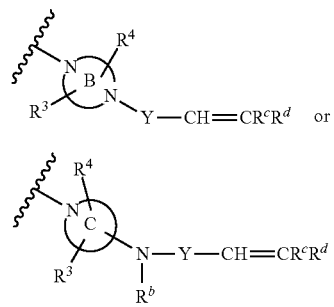

wherein:
ring B is a aza bridged heterocycloamino or aza spiroheterocycloamino;
ring C is azetidinyl, pyrrolidinyl, piperidinyl, bridged heterocycloamino, or spiroheterocycloamino;
each $R^3$ is hydrogen, alkyl, haloalkyl, hydroxy, alkoxy, or halo; and
each $R^4$ is hydrogen, alkyl, hydroxy, alkoxy, or halo; or
(ii) Q is heteroalkylene, and
X is a group of formula (d) or (e):

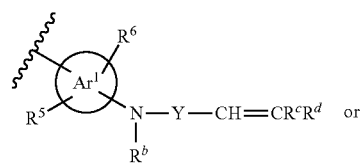

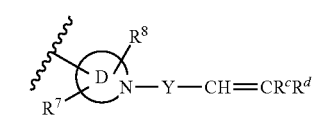

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or
(iii) Q is -alkylene-cycloalkylene-alkylene-, and
X is a group of formula (f) or (g):

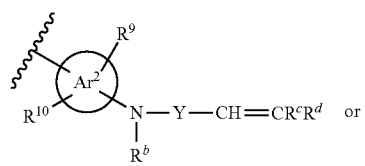

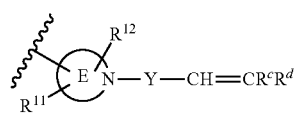

wherein:
$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —$SO_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

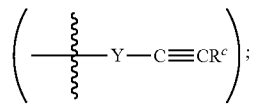

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —$NR^b$—Y—CH=$CR^cR^d$ are meta or para to each other; (2) when ring D or E is piperidinyl, then Q and —Y—CH=$CR^cR^d$ are meta or para to each other; (3) when ring D or E is piperazinyl, then Q and —Y—CH=$CR^cR^d$ are para to each other; (4) when ring C, D, or E is pyrrolidinyl or azetidinyl, then Q and —$NR^b$—Y—CH=$CR^cR^d$ or Q and —Y—CH=$CR^cR^d$ are (1,3) to each other.

The compounds of Formulae (IA) are a subset of compounds of Formula (III).

In one embodiment, the compounds of Formula (III), (I'), (I) and/or a pharmaceutically acceptable salt thereof (and any embodiments thereof disclosed herein), when substituted with —$NR^b$—Y—CH=$CR^cR^d$ or —Y—CH=$CR^cR^d$ group, can form an irreversible covalent bond with Cys488 of FGFR1, Cys491 of FGFR2, Cys482 of FGFR3, and/or Cys477 of FGFR4. In another embodiment, when the compound of Formula (III), (I') (IB) (and any embodiments thereof) is substituted with —NR$^g$(alkylene)$_n$-Z—CH=CR$^e$R$^f$ or —Z—CH=CR$^e$R$^f$ group it can form an irreversible covalent bond with Cys552 of FGFR4.

In another embodiment, the irreversibility of the covalent bond formed by a compound Formulae (III), (I'), (I) and/or a pharmaceutically acceptable salt thereof (and any embodiments thereof disclosed herein) with FGFR 1, 2, 3 and/or 4 is determined by the Mass spec method described in Biological Examples 6 or 7 below. In another embodiment, the irreversibility of the covalent bond formed by a compound Formulae (III), (I'), (I) and/or a pharmaceutically acceptable salt thereof (and any embodiments thereof disclosed herein) with Cys488 of FGFR1, Cys491 of FGFR2, Cys482 of FGFR3, and/or Cys477 or Cys552 of FGFR4 is determined by the Mass spec method described in Biological Example 7, Method B below.

In a second aspect, this disclosure is directed to a pharmaceutical composition comprising a compound of the present disclosure, e.g., Formula (III), (I') or (I) (or any of the embodiments thereof described herein), and/or a pharmaceutically acceptable salt thereof; and a pharmaceutically acceptable excipient.

In a third aspect, this disclosure is directed to a method of treating a disease treatable by inhibition of one or more FGFRs, in particular one or more of FGFR 1, 2, 3, and 4, in a patient in recognized need of such treatment which method comprises administering to the patient in recognized need thereof, a pharmaceutical composition comprising a compound of the present disclosure, e.g., Formula (III), (I') or (I) (or any of the embodiments thereof described herein) and/or a pharmaceutically acceptable salt thereof in a therapeutically effective amount, and a pharmaceutically acceptable excipient. In one embodiment the disease is cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholangiosarcoma, glioma, cholangiocarcinoma, 8,11 myeloproliferative syndrome, myeloproliferative disorders involving FGFR translocations/fusions, alveolar rhabdomyosarcoma, malignant rhabdoid tumors, and prostate cancers. In another embodiment, the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the cancer is glioblastoma, muscle invasive bladder or renal cancer.

In another embodiment, the compound of the present disclosure, e.g., Formula (III), (I') or (I) (and any embodiments thereof described herein) and/or a pharmaceutically acceptable salt thereof is useful for the treatment of excessive FGF23 and hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In a fourth aspect, the disclosure is directed to a compound of the present disclosure, e.g., Formula (III), (I') or (I) (or any embodiments thereof described herein) and/or a pharmaceutically acceptable salt thereof for use as a medicament. In one embodiment, the compound of the present disclosure, e.g., Formula (III), (I') or (I) (and any embodiments thereof described herein) and/or a pharmaceutically acceptable salt thereof is useful for the treatment of cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholioangiosarcoma, glioma, cholioangiocarcinoma, 8,11 myeloproliferative syndrome, myeloproliferative disorders involving FGFR translocations/fusions, alveolar rhabdomyosarcoma, malignant rhabdoid tumors, and prostate cancers. In another embodiment, the compound of the present disclosure, e.g., Formula (III), (I') or (I) (and any embodiments thereof described herein) and/or a pharmaceutically acceptable salt thereof is useful for the treatment of dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the compound of the present disclosure, e.g., Formula (III), (I') or (I) (and any embodiments thereof described herein) and/or a pharmaceutically acceptable salt thereof is useful for the treatment of excessive FGF23 and hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In a fifth aspect provided is the use of a compound of the present disclosure, e.g., Formula (III), (I') or (I) and/or a pharmaceutically acceptable salt thereof (and any embodiments thereof disclosed herein) in the manufacture of a medicament for treating a disease in a patient in which the activity of FGFR contributes to the pathology and/or symptoms of the disease. In one embodiment the disease is cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholioangiosarcoma, glioma, cholioangiocarcinoma, 8,11 myeloproliferative syndrome, myeloproliferative disorders involving FGFR translocations/fusions, alveolar rhabdomyosarcoma, malignant rhabdoid tumors, and prostate cancers. In another embodiment the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the disease is hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In any of the aforementioned aspects involving the treatment of cancer, are further embodiments comprising administering the compound of the present disclosure, e.g., Formula (III), (I') or (I) and/or a pharmaceutically acceptable salt thereof (or any embodiments thereof disclosed herein) in combination with at least one additional anticancer agent such as an EGFR inhibitor gefitinib, erlotinib, afatinib, icotinib, neratinib, rociletinib, cetuximab, panitumumab, zalutumumab, nimotuzumab, or matuzumab. In another embodiment, the compound of the present disclosure, e.g., Formula (III), (I') or (I) (and any embodiments thereof described herein) and/or a pharmaceutically acceptable salt thereof is administered in combination with a HER2/neu inhibitor including lapatinib, trastuzumab, and pertuzumab. In another embodiment, the compound of the present disclosure, e.g., Formula (III), (I') or (I) (and any embodiments thereof described herein) and/or a pharmaceutically acceptable salt thereof is administered in combination with a PI3k/mTOR inhibitor including idelalisib, buparlisib, BYL719, and LY3023414. When combination therapy is used, the agents can be administered simultaneously or sequentially.

In a sixth aspect, provided is an intermediate of Formula (II):

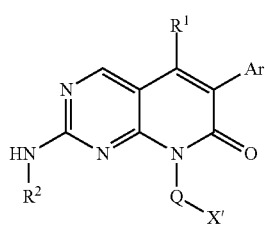

(II)

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, or cyano;
$R^1$ is hydrogen, halo, alkyl, or cycloalkyl;
$R^2$ is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl, and heteroaryl are optionally substituted with one, two, or three substituents where two of the optional substituents are independently selected from alkyl, hydroxy, alkoxy, halo, haloalkyl, haloalkoxy, and cyano and the one of the optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and
(i) Q is alkylene; and
X' is a group of formula (a'), (b'), or (c'):

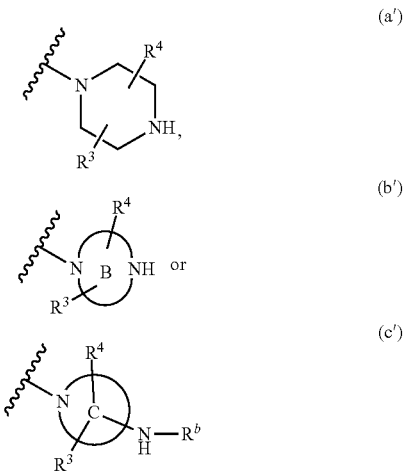

wherein:
ring B is a aza bridged heterocycloamino or aza spiroheterocycloamino;
ring C is azetidinyl, pyrrolidinyl, piperidinyl, bridged heterocycloamino, or spiro heterocycloamino wherein the nitrogen atom in aforementioned (a'), (b'), and (c') rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or
(ii) Q is heteroalkylene, and
X' is a group of formula (d') or (e'):

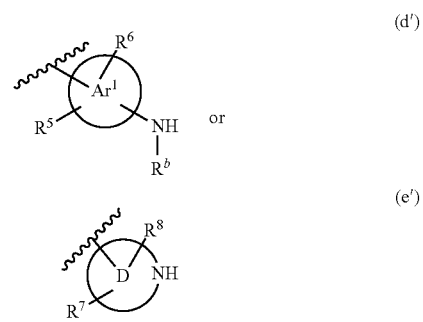

wherein:
$Ar^1$ is 5- or 6-membered cycloalkylene, phenylene, or 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or
(iii) Q is -alkylene-cycloalkylene-alkylene-, and
X' is a group of formula (f') or (g'):

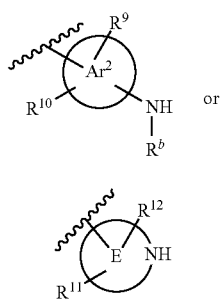

(f')

(g')

wherein:
Ar² is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo; and
$R^b$ is hydrogen or alkyl; and/or a salt thereof,
provided that: (1) when (i) Ar¹ is phenylene or 6-membered heteroarylene or (ii) Ar² is phenylene, 6-membered heteroarylene or piperidin-1-yl or (iii) ring C is piperidinyl, then Q and —NHR$^b$ in piperidinyl ring are meta or para to each other; (2) when ring D or E is piperidinyl, then Q and the NH group in the piperidinyl ring are meta or para to each other; (3) when ring D or E is piperazinyl, then Q and the NH group in the piperazinyl ring are para to each other; and (4) when ring C, D, or E is pyrrolidinyl or azetidinyl, then Q and the NH group in the pyrrolidinyl and azetidinyl rings are (1,3) to each other.

In one embodiment of the sixth aspect, $R^1$, $R^2$, Ar, Q, and X' are as defined in embodiments A, B, C, D, E, F, G, and H below and groups contained therein except the Y—CH=CR$^c$R$^d$ in X is replaced by hydrogen. In another embodiment of the sixth aspect, -Q-X' is 3-piperazin-1-ylpropyl. In yet another embodiment of the sixth aspect, $R^1$ is hydrogen, $R^2$ is hydrogen, alkyl, acyl, alkoxyalkyloxyalkyl, or alkoxyalkyl, (preferably $R^2$ is hydrogen, methyl, methylcarbonyl, methoxyethyloxyethyl, or —*CH(CH$_3$)CH$_2$—OCH$_3$ where the stereochemistry at *C is (R) or (S)), Ar is 2-chloro-3,5-dimethoxyphenyl or 2,6-dichloro-3,5-dimethoxyphenyl, and -Q-X' is

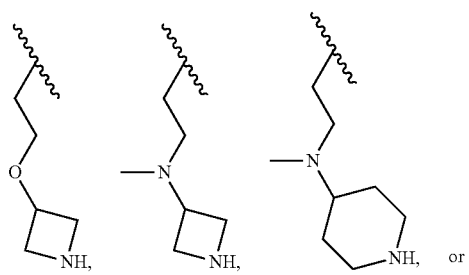

-continued

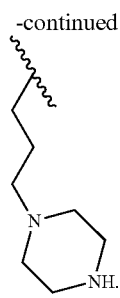

Preferably, Q-X' is

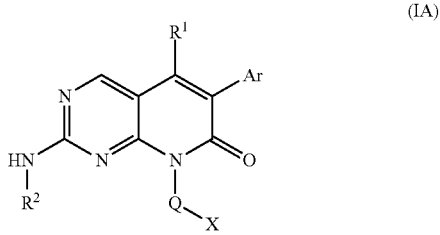

In a seventh aspect, provided is a process of making a compound of Formula (IA):

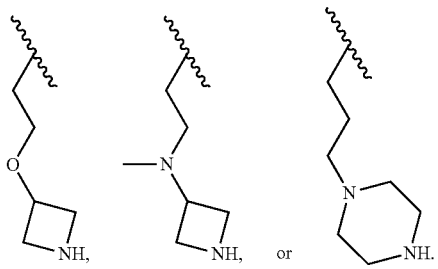

(IA)

where Ar, $R^1$, $R^2$, Q, and X are as defined in the compound of Formula (IA) above, comprising:
reacting a compound of formula (II):

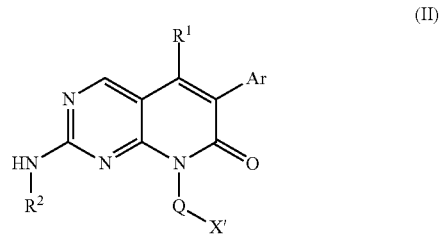

(II)

where $R^1$ is hydrogen, alkyl, or halo, Ar, $R^2$, Q, and X' are as defined in the compound of Formula (II) above;
(i) with a compound of formula R$^c$R$^d$C=CHYLG or R$^c$C=CYLG where Y is —CO— or —SO$_2$—, R$^c$ and R$^d$ are as defined in Formula (IA) above, and LG is a leaving group under acylating reaction conditions; or
(ii) with a compound of formula R$^c$R$^d$C=CHCOOH under amino acid reaction conditions;
(iii) optionally converting the compound of Formula (IA) obtained from step (i) or (ii) to an acid addition salt; or (iv) optionally converting the compound of Formula (IA) obtained from step (i) or (ii) to the free base.

In one embodiment of the seventh aspect, the process is directed to making a compound of Formula (IA) where $R^2$ is hydrogen, alkyl, acyl, alkoxyalkyloxyalkyl, or alkoxyalkyl, (preferably $R^2$ is hydrogen, methyl, methylcarbonyl, methoxyethyloxyethyl, or —*CH(CH$_3$)CH$_2$—OCH$_3$ where the stereochemistry at *C is (R) or (S)), Ar is 2-chloro-3,5-dimethoxyphenyl or 2,6-dichloro-3,5-dimethoxyphenyl, Q-X' is , , , or

.

Preferably, -Q-X' is

, , or

,

Y is O and $R^c$ and $R^d$ are hydrogen; comprising:

reacting a compound of Formula (II) where $R^2$ is hydrogen, alkyl, acyl, alkoxycarbonyl, alkoxyalkyloxyalkyl, or alkoxyalkyl, (preferably $R^2$ is hydrogen, methyl, acetyl, methoxycarbonyl, methoxyethyloxyethyl, or —*CH(CH$_3$)CH$_2$—OCH$_3$ where the stereochemistry at *C is (R) or (S)), Ar is 2-chloro-3,5-dimethoxyphenyl or 2,6-dichloro-3,5-dimethoxyphenyl, and -Q-X' is , , , or

;

preferably

, , or

;

(i) with a compound of formula CH$_2$=CHCOLG where LG is a leaving group under acylating reaction conditions; or
(ii) with a compound of formula CH$_2$=CHCOOH under amino acid reaction conditions;
(iii) optionally converting the compound obtained from step (i) or (ii) to an acid addition salt; or
(iv) optionally converting the compound obtained from step (i) or (ii) to the free base.

In yet another embodiment of the seventh aspect and embodiments therein, LG is halo, preferably chloro.

In an eighth aspect, provided is an intermediate of Formula (IIA):

(IIA)

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, or cyano;
$R^1$ is hydrogen, halo, alkyl, or cycloalkyl;
$R^2$ is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl, and heteroaryl are optionally substituted with one, two, or three substituents where two of the optional substituents are independently selected from alkyl, hydroxy, alkoxy, halo, haloalkyl, haloalkoxy, and cyano and the one of the optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and
(i) Q is alkylene; and
X' is a group of formula (h'):

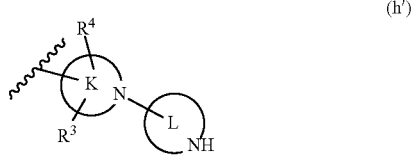

(h')

wherein:
rings K and L are independently azetidinyl, pyrrolidinyl, piperidinyl, or homopiperidinyl; each $R^3$ is hydrogen, alkyl, haloalkyl, hydroxy, alkoxy, or halo; and
each $R^4$ is hydrogen, alkyl, hydroxy, alkoxy, or halo; or
(ii) Q is aminoheteroalkylene and
X' is a group of formula (d') or (e'):

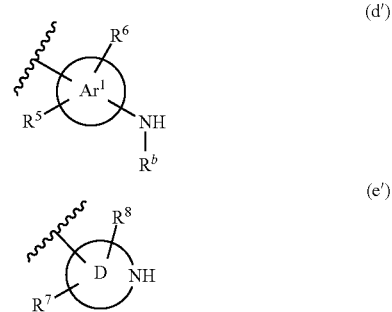

wherein:
$Ar^1$ is phenylene or 5- or 6-membered heteroarylene;
ring D is heterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or and/or a salt thereof, and
$R^b$ is hydrogen or alkyl;
provided that: (1) when (i) $Ar^1$ is phenylene or 6-membered heteroarylene, then Q and $NHR^b$ are meta or para to each other; (2) when ring D is piperidinyl, then Q and the NH group in the piperidinyl ring are meta or para to each other; (3) when ring D is piperazinyl, then Q and the NH group in the piperazinyl ring are para to each other; and (4) when ring D is pyrrolidinyl or azetidinyl, then Q and the NH group in the pyrrolidinyl and azetidinyl rings are (1,3) to each other.

In one embodiment of the seventh aspect, $R^1$, $R^2$, Ar, Q, and X' are as defined in embodiments (Mb-(Mi) below.

BRIEF DESCRIPTION OF THE FIGURES

Tumor growth inhibition in a SNU-16 human gastric carcinoma xenograft model conducted as described in Biological Example 4 below for compounds of synthetic Example Nos. 61 and 80 are shown in FIGS. 1 and 2 respectively.

pFGFR inhibition in a SNU-16 xenograft model conducted as described in Biological Example 4 below for compounds of synthetic Example Nos. 14 and 38 is shown in FIG. 3.

DEFINITIONS

Figure 1:
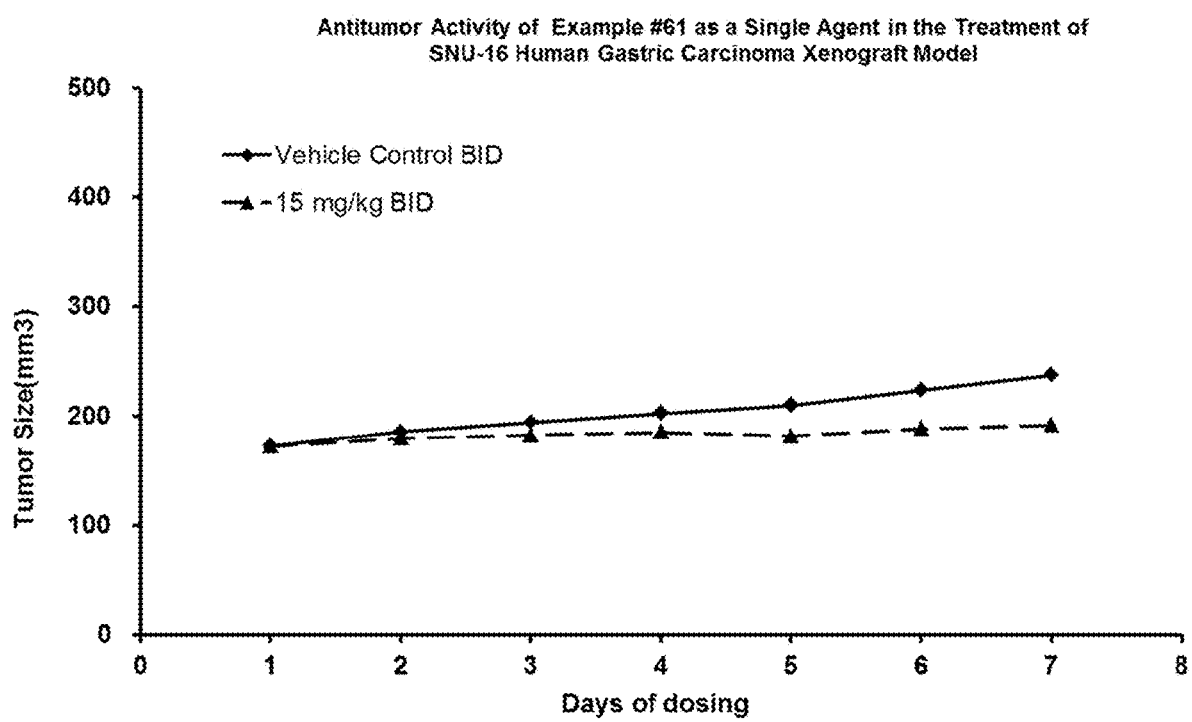

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen or alkyl as defined above, e.g., aminomethyl, aminoethyl, methylaminomethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxyalkyloxyalkyl" means a -alkylene-(O)R radical where R is alkoxyalkyl as defined above, e.g., methoxyethoxymethyl, ethoxyethoxyethyl, and the like.

"Alkoxyalkyloxy" means a —(O)R radical where R is alkoxyalkyl as defined above, e.g., methoxyethoxy, ethoxyethoxy, and the like.

"Alkoxycarbonyl" means a —C(O)OR radical where R is alkyl as defined above, e.g., methoxycarbonyl, ethoxycarbonyl, and the like.

"Acyl" means a —C(O)R radical where R is alkyl as defined above, e.g., methylcarbonyl, ethylcarbonyl, and the like.

"Acylamino" means a —NHC(O)R radical where R is alkyl as defined above, e.g., methylcarbonyl, ethylcarbonyl, and the like.

"Aralkyl" means a -(alkylene)-R radical where R is aryl as defined above, e.g., benzyl, phenethyl, and the like.

"Aryl" means a monovalent monocyclic or bicyclic aromatic hydrocarbon radical of 6 to 10 ring atoms e.g., phenyl or naphthyl.

"Aza bridged heterocycloamino" means a saturated bicyclic ring having 7 to 10 ring atoms with two or more atoms in common and in which one, two, or three ring atoms are heteroatom selected from N, O, or $S(O)_n$, where n is an integer from 0 to 2, the remaining ring atoms being C provided at least two ring atom are N e.g., octahydropyrrolo[3,4-c]pyrrolyl, octahydro-1H-pyrrolo[3,4-c]pyridine, or decahydro-2,6-naphthyridine, and the like.

"Aminoheteroalkylene" means alkylene as defined above wherein one carbon atom in the alkylene chain is replaced by —NR$^y$— where R$^y$ is hydroxyalkyl, alkoxyalkyl, alkoxyalkyloxyalkyl, or -(alkylene)-NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo as defined herein.

"Bridged heterocycloamino" means a saturated bicyclic ring having 7 to 10 ring atoms with two or more atoms in common and in which one, two, or three ring atoms are heteroatom selected from N, O, or $S(O)_n$, where n is an integer from 0 to 2, the remaining ring atoms being C provided at least one ring atom are N e.g., octahydropyrrolo[3,4-c]pyrrolyl, 2-azabicyclo[2.2.1]heptanyl, 7-azabicyclo[4.2.0]octane, octahydro-1H-pyrrolo[3,4-c]pyridine, or decahydro-2,6-naphthyridine, and the like.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Cycloalkylene" means a divalent cycloalkyl as defined above, unless stated otherwise.

"Carboxy" means —COOH.

"Dialkylamino" means a —NRR' radical where R and R' are alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocyclylheteroalkyl" means a -(heteroalkylene)-R radical where R is heterocyclyl ring and heterocyclyl and heteroalkylene are as defined herein e.g., piperidin-4-yloxyethyl, azetidin-3-yloxyethyl, and the like.

"Heterocycloamino" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocycloamino ring can optionally be substituted with one, two, or three substituents independently selected from alkyl, hydroxyl, alkoxy, amino, alkylamino, and dialkylamino.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

"Heteroalkylene" means alkylene as defined above wherein one, two, or three carbon atoms in the alkylene chain are independently replaced by a heteroatom selected from —NR—, O, S, and $SO_2$ where R is hydrogen or alkyl as defined above, e.g., —$CH_2$—$CH_2$—O—, —$CH_2$—$CH_2$—NH—, —$CH_2$—$CH_2$—N($CH_3$)—, and the like.

The present disclosure also includes protected derivatives of compounds of the present disclosure (I). For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, P A, 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Oxo" or "carbonyl" means =(O) group.

"Optionally substituted aryl" means aryl as defined above that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Phenylene" means a divalent phenyl group.

"Substituted alkyl" means alkyl group as defined herein which is substituted with one, two, or three substituents independently selected from hydroxy, alkoxy, or —NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Substituted alkylene" means alkylene group as defined herein which is substituted with hydroxy, alkoxy, alkoxyalkyloxy, or —NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Substituted heteroalkylene" means heteroalkylene or group as defined herein which is substituted with hydroxy, alkoxy, alkoxyalkyloxy, or —NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Spiroheterocycloamino" means a saturated bicyclic ring having 6 to 10 ring atoms in which one, two, or three ring atoms are heteroatom selected from N, O, or $S(O)_n$, where n is an integer from 0 to 2, the remaining ring atoms being C provided at least one ring atom is N and the rings are connected through only one atom, the connecting atom is also called the spiroatom, most often a quaternary carbon ("spiro carbon"). Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

"Aza spiroheterocycloamino" means a saturated bicyclic ring having 6 to 10 ring atoms in which one, two, or three ring atoms are heteroatom selected from N, O, or $S(O)_n$, where n is an integer from 0 to 2, the remaining ring atoms being C provided at least two ring atoms are N and the rings are connected through only one atom, the connecting atom is also called the spiroatom, most often a quaternary carbon ("spiro carbon").

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of the present disclosure and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

EMBODIMENTS

Embodiment AA

In embodiment AA, the compounds of Formula (I') and/or a pharmaceutically acceptable salt thereof as defined in the Summary above are those where J is CH.

Embodiment A

In embodiment A, in one group of compounds, the compounds of Formula (I') and/or a pharmaceutically acceptable salt thereof as defined in Embodiment AA and the compounds of Formula (I) and/or a pharmaceutically acceptable salt thereof as defined in the first aspect (i.e., in the Summary above) are those where $R^1$ is hydrogen. In embodiment A, in another group of compounds, the compounds of Formula (I') and/or a pharmaceutically acceptable salt thereof as defined in Embodiment AA and the compounds of Formula (I) and/or a pharmaceutically acceptable salt thereof as defined in the first aspect above are those where $R^1$ is cyclopropyl. In embodiment A, in yet another group of compounds, the compounds of Formula (I') and/or a pharmaceutically acceptable salt thereof as defined in Embodiment AA and the compounds of Formula (I) and/or a pharmaceutically acceptable salt thereof as defined in the first aspect above are those where $R^1$ is methyl. In embodiment A, in yet another group of compounds, the compounds of Formula (I') and/or a pharmaceutically acceptable salt thereof as defined in Embodiment AA and the compounds of Formula (I) and/or a pharmaceutically acceptable salt thereof as defined in the first aspect above are those where $R^1$ is chloro or fluoro.

Embodiment B

In Embodiment B, the compounds of Formula (I') and/or a pharmaceutically acceptable salt thereof as defined in Embodiment AA, the compounds of Formula (I) and/or a pharmaceutically acceptable salt thereof as defined in the first aspect in the Summary and/or the groups of compounds and/or a pharmaceutically acceptable salt thereof as defined in Embodiment A above, are those where Ar is phenyl optionally substituted with one, two, three, or four substituents independently selected from alkyl, hydroxy, alkoxy, halo, haloalkyl, haloalkoxy, and cyano. For sake of clarity, Embodiment B, contains 10 groups of compounds (each group of compounds includes pharmaceutically acceptable salts of the compounds contained within that group); a first group consists of compounds of Formula (I') disclosed in Embodiment AA and/or a pharmaceutically acceptable salt thereof, the second group consists of compounds of Formula (I) disclosed in the first aspect in the Summary and/or a pharmaceutically acceptable salt thereof and the rest of the eight groups of compounds are those disclosed in Embodiment A and/or a pharmaceutically acceptable salt thereof (in Embodiment A each group of compounds with a different $R^1$ group, i.e., only hydrogen or only methyl or only chloro or fluoro, or only cycloalkyl, is separate group). The same analysis applies when determining the number of groups of compounds in each of the embodiments below.

(Bi) Within the groups of compounds in embodiment B and/or a pharmaceutically acceptable salt thereof, in one group of compounds and/or salts thereof, Ar is a phenyl ring optionally substituted with one, two, three, or four substituents independently selected from methyl, alkoxy, hydroxy, chloro, fluoro, trifluoromethyl, difluoromethyl, trifluoromethoxy, difluoromethoxy, and cyano.

(Bii) Within the groups of compounds in embodiment B and/or a pharmaceutically acceptable salt thereof, in another group of compounds and/or salts thereof, Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl. Within these groups of compounds, in one group of compounds and/or salts thereof, Ar is 2-halo-3,5-dimethoxyphenyl, 2,6-dihalo-3,5-dimethoxyphenyl, 3,5-dimethoxyphenyl, or 2-halophenyl.

(Biii) Within the groups of compounds in embodiment B and/or a pharmaceutically acceptable salt thereof, in yet another group of compounds and/or salts thereof, Ar is 2-halo-3,5-dimethoxyphenyl or 2,6-dihalo-3,5-dimethoxyphenyl. Within the groups in embodiment B, in yet another group of compounds and/or a pharmaceutically acceptable salt thereof, Ar is 2-halo-3,5-dimethoxyphenyl.

(Biv) Within the groups of compounds in embodiment B and/or a pharmaceutically acceptable salt thereof, in yet another group of compounds and/or a pharmaceutically acceptable salt thereof, Ar is 2,6-dihalo-3,5-dimethoxyphenyl.

Within the groups of compounds contained in embodiment B and/or a pharmaceutically acceptable salt thereof and groups contained therein i.e., (Bi)-(Biv) above, where Ar is a phenyl substituted with a halo group (e.g., 2-halo-3,5-dimethoxyphenyl or 2,6-dihalo-3,5-dimethoxy-phenyl), in one group of compounds, halo is fluoro.

Within the groups of compounds contained in embodiment B and/or a pharmaceutically acceptable salt thereof and groups contained therein i.e., (Bi)-(Biv) above, where Ar is a phenyl substituted with a halo group (e.g., 2-halo-3,5-dimethoxyphenyl or 2,6-dihalo-3,5-dimethoxy-phenyl), in another group of compounds and/or a pharmaceutically acceptable salt thereof, halo is chloro.

Embodiment C

In Embodiment C, the compounds of Formula (I') and/or a pharmaceutically acceptable salt thereof as defined in Embodiment AA, the compounds of Formula (I) and/or a pharmaceutically acceptable salt thereof as defined in the first aspect and/or the groups of compounds in Embodiment A and/or a pharmaceutically acceptable salt thereof, are those wherein Ar is heteroaryl (such as pyridinyl or thienyl) ring optionally substituted with one, two, or three substituents independently selected from alkyl, hydroxy, alkoxy, halo, haloalkyl, haloalkoxy, and cyano.

(Ci) Within the groups of compounds in embodiment C and/or a pharmaceutically acceptable salt thereof, in one group of compounds and/or salts thereof, Ar is heteroaryl (such as pyridinyl or thienyl) ring optionally substituted with one, two, or three substituents independently selected from methyl, alkoxy, hydroxy, chloro, fluoro, trifluoromethyl, difluoromethyl, trifluoromethoxy, difluoromethoxy, and cyano.

Embodiment D

In Embodiment D, the compounds of Formula (I') and/or a pharmaceutically acceptable salt thereof as defined in Embodiment AA, the compounds of Formula (I) and/or a pharmaceutically acceptable salt thereof as defined in first aspect above, the groups of compounds in embodiments A, B, and/or C and/or a pharmaceutically acceptable salt thereof, and groups of compounds contained within each of the groups in embodiments A, B, and C and/or a pharmaceutically acceptable salt thereof, are those wherein:
(i) Q is alkylene; and
X is a group of formula (a), (b), or (c):

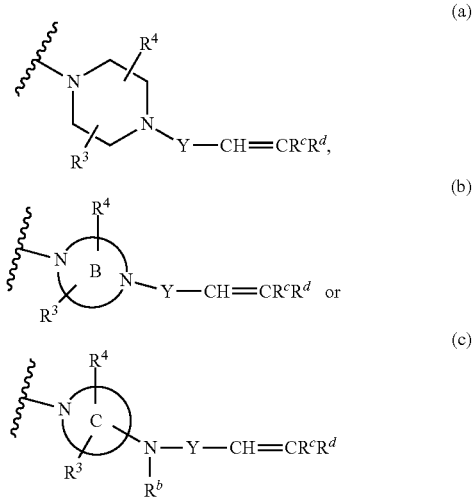

wherein:
ring B is a aza bridged heterocycloamino or aza spiroheterocycloamino;
ring C is azetidinyl, pyrrolidinyl, piperidinyl, bridged heterocycloamino, or spiro heterocycloamino;
each $R^3$ is hydrogen, alkyl, haloalkyl, hydroxy, alkoxy, or halo; and
each $R^4$ is hydrogen, alkyl, hydroxy, alkoxy, or halo; or
(ii) Q is heteroalkylene, and
X is a group of formula (d) or (e):

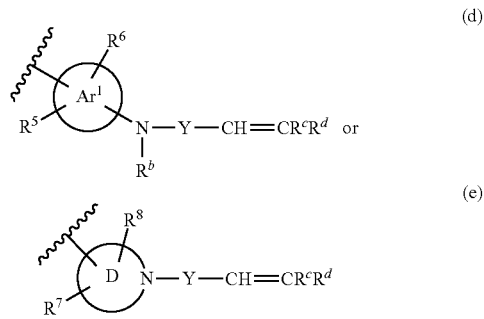

wherein:
$Ar^1$ is 5- or 6-membered cycloalkylene, phenylene, or 5- or 6-membered heteroarylene;

ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or (iii) Q is -alkylene-cycloalkylene-alkylene- and X is a group of formula (f) or (g):

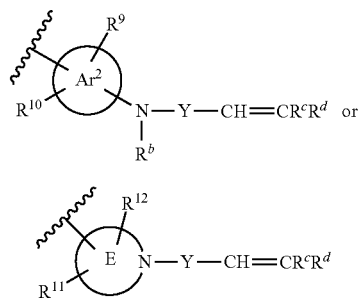

wherein:
$Ar^2$ is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —SO$_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

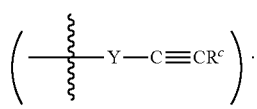

Embodiment E

In Embodiment E, the compounds of Formula (I') and/or a pharmaceutically acceptable salt thereof as defined in Embodiment AA, the compounds of Formula (I) and/or a pharmaceutically acceptable salt thereof as defined in the first aspect, the groups of compounds in embodiments A, B, C, and/or D and/or a pharmaceutically acceptable salt thereof, and groups of compounds contained within each of the groups in embodiments A, B, C, and/or D and/or a pharmaceutically acceptable salt thereof, are those wherein Q is alkylene. Within these groups, in one group of compounds and/or a pharmaceutically acceptable salt thereof, Q is ethylene or propylene. Within these groups, in another group of compounds and/or a pharmaceutically acceptable salt thereof, Q is ethylene. Within these groups, in yet another group of compounds and/or a pharmaceutically acceptable salt thereof, Q is n-propylene.

(Ei) Within the groups of compounds in (E) and/or a pharmaceutically acceptable salt thereof and groups of compounds and/or a pharmaceutically acceptable salt thereof contained therein, in one group of compounds and/or a pharmaceutically acceptable salt thereof, X is a group of formula (a). Within the groups in (Ei), in one group of compounds and/or a pharmaceutically acceptable salt thereof,

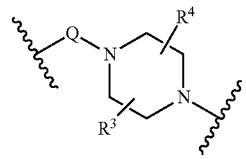

in -Q-X of formula

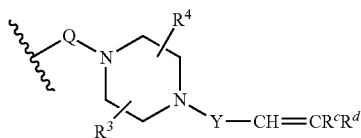

is:

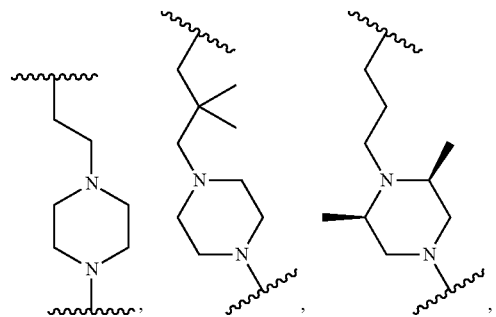

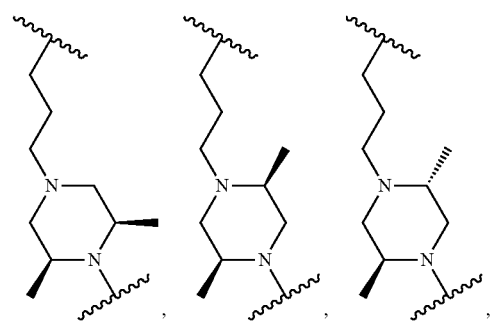

-continued

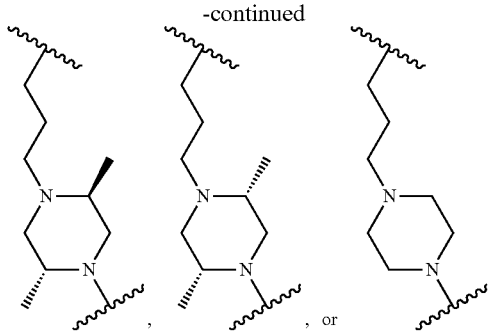

, or

Within the groups of compounds in (Ei) and/or a pharmaceutically acceptable salt thereof, in yet another group of compounds and/or a pharmaceutically acceptable salt thereof,

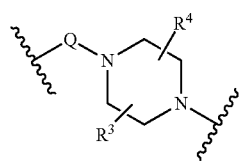

in -Q-X of formula

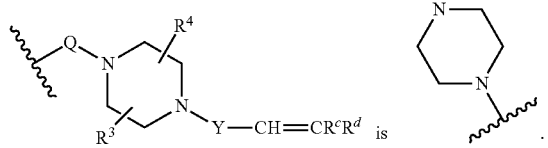

(Eii) Within the groups of compounds in (E) and/or a pharmaceutically acceptable salt thereof and groups of compounds and/or a salt thereof contained therein, in another group of compounds, X is a group of formula (b). Within groups of compounds in (Eii) and/or a pharmaceutically acceptable salt thereof, in one group of compounds and/or a pharmaceutically acceptable salt thereof, ring B is bridged heterocycloamino. Within groups of compounds in (Eii) and/or a pharmaceutically acceptable salt thereof, in another group of compounds and/or a pharmaceutically acceptable salt thereof, ring B is spiro heterocycloamino. Within groups of compounds in (Eii) and/or a pharmaceutically acceptable salt thereof, in yet another group of compounds and/or a pharmaceutically acceptable salt thereof

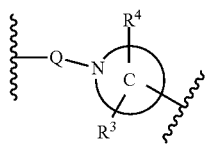

in-Q-X of formula

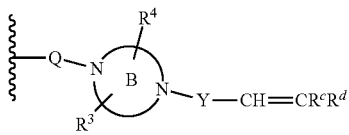

is:

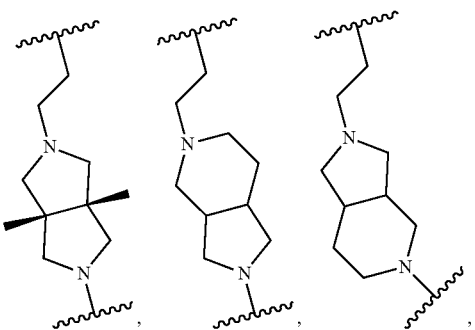

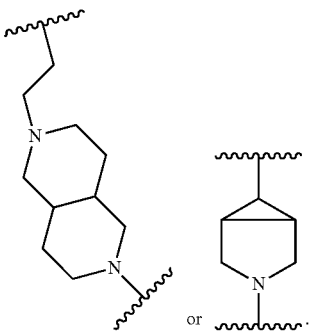

(Eiii) Within the groups of compounds in (E) and/or a pharmaceutically acceptable salt thereof and groups of compounds and/or a pharmaceutically acceptable salt thereof contained therein, in one group of compounds and/or a pharmaceutically acceptable salt thereof, X is a group of formula (c). Within the groups of compounds in (Eiii) and/or a pharmaceutically acceptable salt thereof, in one group of compounds and/or a pharmaceutically acceptable salt thereof, ring C is piperidin-1-yl in which —NR$^b$—Y—CH=CR$^c$R$^d$ is attached to carbon that is meta or para to the piperidinyl ring nitrogen. Within the groups of compounds in (Eiii) and/or a pharmaceutically acceptable salt thereof, in another group of compounds and/or salts thereof, in -Q-X of formula
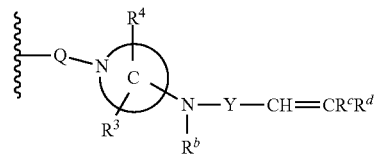
is:
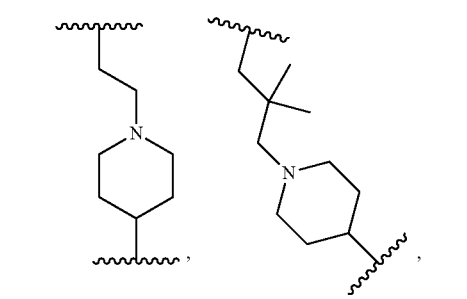
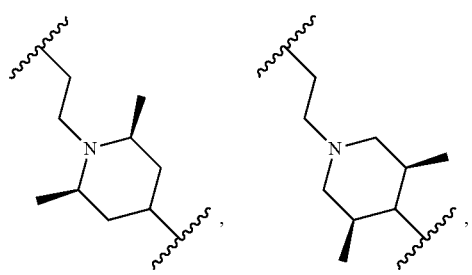
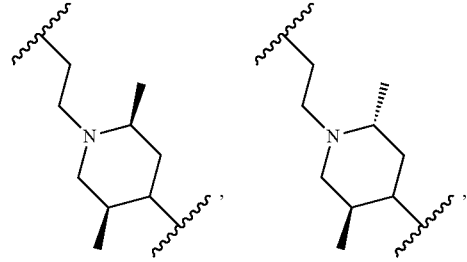
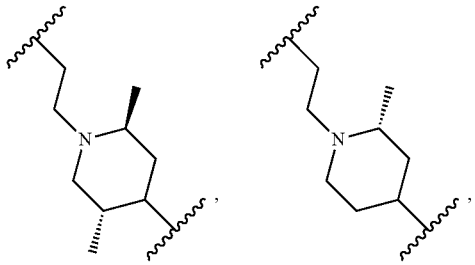
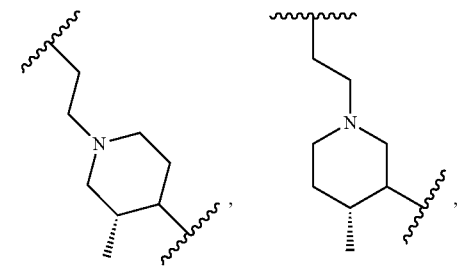
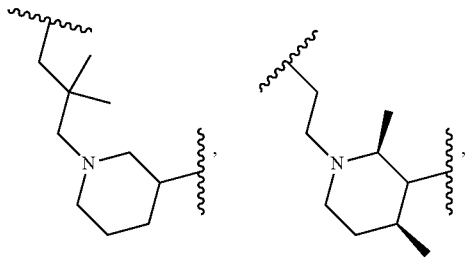
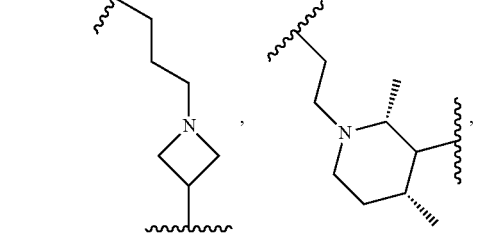
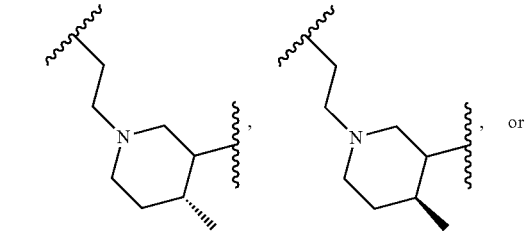
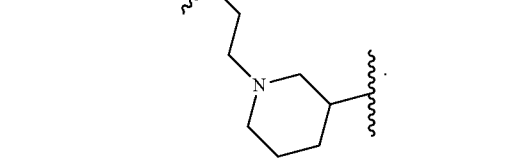
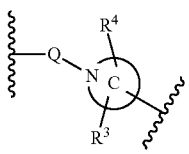
Preferably,
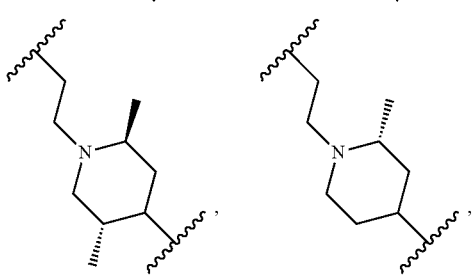
in -QX is:
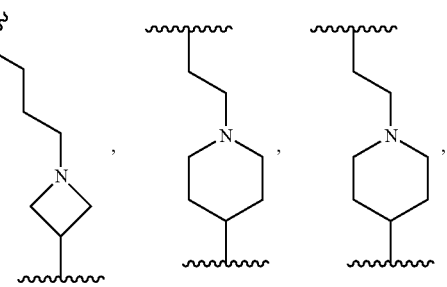

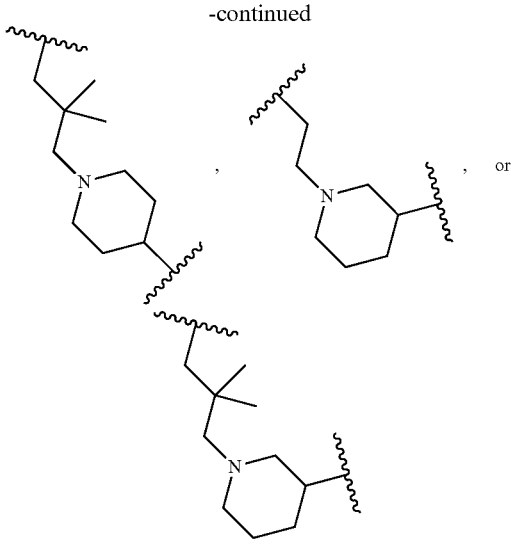

Within the groups of compounds in (Eiii) and/or a pharmaceutically acceptable salt thereof, in one group of compounds and/or a pharmaceutically acceptable salt thereof $R^b$ is hydrogen.

(Eiv) Within the groups of compounds in (E) and/or a pharmaceutically acceptable salt thereof and groups of compounds and/or a pharmaceutically acceptable salt thereof contained therein, in yet another one group of compounds and/or a pharmaceutically acceptable salt thereof, X is a ring of formula (c) where ring C is bridged heterocycloamino.

(Ev) Within the groups of compounds in (E) and/or a pharmaceutically acceptable salt thereof and groups of compounds and/or a pharmaceutically acceptable salt thereof contained therein, in one group of compounds and/or a pharmaceutically acceptable salt thereof X is a ring of formula (c) where ring C is spiro heterocycloamino.

Embodiment F

In embodiment F, the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C and/or (D) above and/or a pharmaceutically acceptable salt thereof, and groups of compounds contained within each of the groups in embodiments A, B, C and/or (D) and/or a pharmaceutically acceptable salt thereof, are those wherein Q is heteroalkylene. Within these groups of compounds and/or a pharmaceutically acceptable salt thereof, in one group of compounds and/or a pharmaceutically acceptable salt thereof, Q is —(CH$_2$)$_2$—O—, —(CH$_2$)$_2$—S—, or —(CH$_2$)$_2$—NH—. Within these groups of compounds and/or a pharmaceutically acceptable salt thereof, in another group of compounds and/or a pharmaceutically acceptable salt thereof, Q is —(CH$_2$)$_2$—NH—. Within these groups of compounds and/or a pharmaceutically acceptable salt thereof, in yet another group of compounds and/or a pharmaceutically acceptable salt thereof Q is —(CH$_2$)$_2$—O—. Within these groups of compounds and/or a pharmaceutically acceptable salt thereof, in yet another group of compounds and/or a pharmaceutically acceptable salt thereof Q is —(CH$_2$)$_2$—N(alkyl)-.

(Fi) Within the groups of compounds in (F) and/or a pharmaceutically acceptable salt thereof and groups of compounds and/or a pharmaceutically acceptable salt thereof contained therein, in one group of compounds and/or a pharmaceutically acceptable salt thereof, X is a group of formula (d). Within the groups of compounds in (Fi) and/or a pharmaceutically acceptable salt thereof in one group of compounds and/or a pharmaceutically acceptable salt thereof, Ar$^1$ is phenylene or 5- or 6-membered heteroarylene ring. Within the groups of compounds in (Fi) and/or a pharmaceutically acceptable salt thereof, in another group of compounds and/or a pharmaceutically acceptable salt thereof, Ar$^1$ is phenylene. Within groups of compounds in (Fi) and/or a pharmaceutically acceptable salt thereof, in yet another group of compounds and/or a pharmaceutically acceptable salt thereof, Ar$^1$ is 5- or 6-membered heteroarylene ring. Within groups of compounds in (Fi) and/or a pharmaceutically acceptable salt thereof, in yet another group of compounds and/or a pharmaceutically acceptable salt thereof, Ar$^1$ is pyridinyl, pyrimidinyl, pyridazinyl, thiazolyl, thienyl, oxazolyl, or imidazolyl. Within groups of compounds in (Fi) and/or a pharmaceutically acceptable salt thereof, in yet another group of compounds and/or a pharmaceutically acceptable salt thereof,

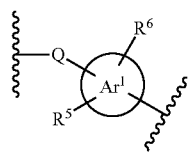

in -Q-X of formula

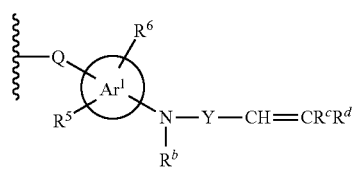

is:

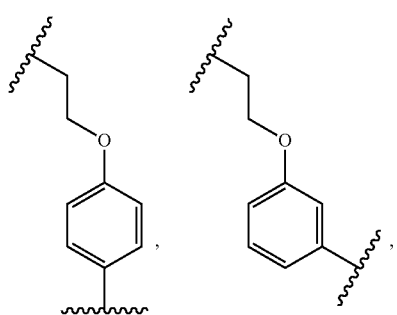

-continued

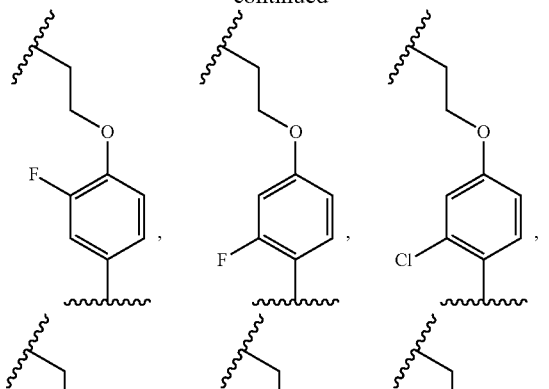

Preferably,

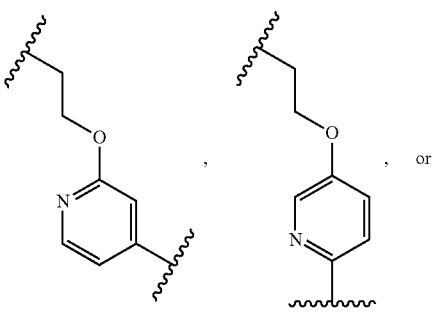

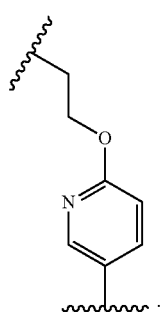

Within the groups of compounds in (Fi) and/or a pharmaceutically acceptable salt thereof and groups of compounds or a pharmaceutically acceptable salt thereof contained therein, in one group of compounds and/or a pharmaceutically acceptable salt thereof, $R^b$ is hydrogen.

(Fii) Within the groups of compounds in (F) and groups of compounds and/or a pharmaceutically acceptable salt thereof contained therein, in another group of compounds and/or a pharmaceutically acceptable salt thereof, X is a group of formula (e), preferably (e) is where ring D is azetidinyl, pyrrolidinyl, or piperidinyl. Within groups of compounds in (Fii) and/or a pharmaceutically acceptable salt thereof and groups contained therein, in one group of compounds and/or a pharmaceutically acceptable salt thereof,

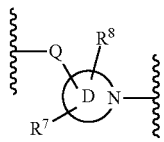

in -Q-X of formula

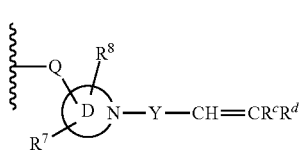

is:
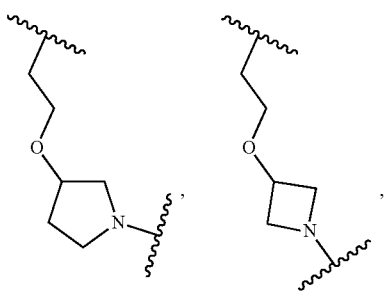
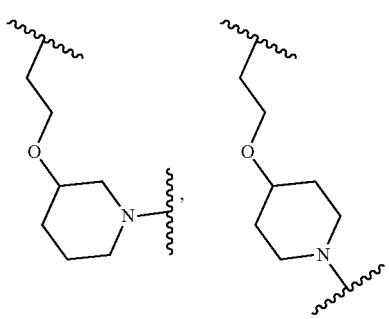
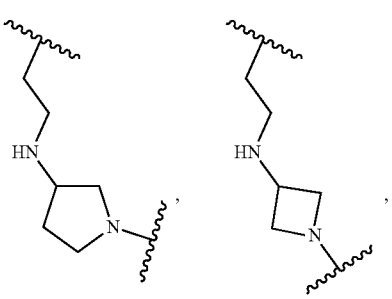
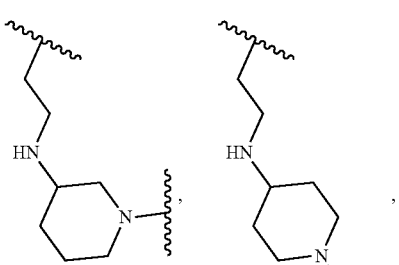
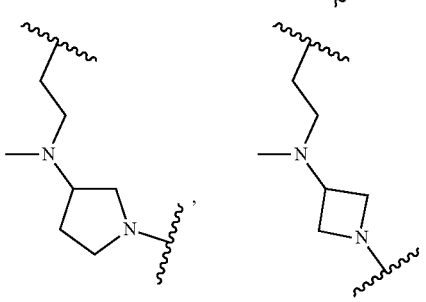
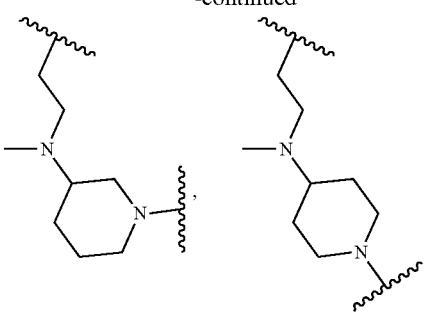 or
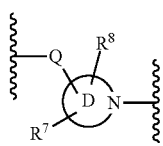
Within groups of compounds in (Fii) and/or a pharmaceutically acceptable salt thereof and groups contained therein, in one group of compounds and/or a pharmaceutically acceptable salt thereof,
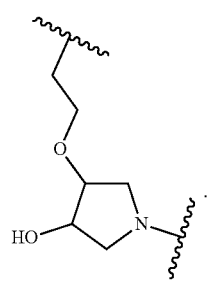
in -Q-X of formula
$$\text{\textasciitilde}\!-\!Q\!-\!\overset{R^8}{\underset{R^7}{D}}\!N\!-\!Y\!-\!CH\!=\!CR^cR^d$$
is:
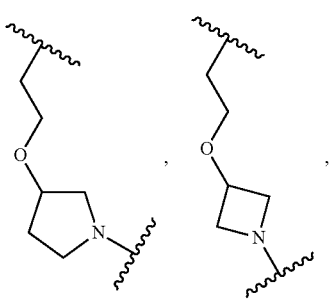

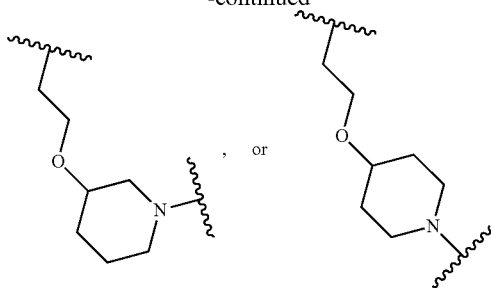, or 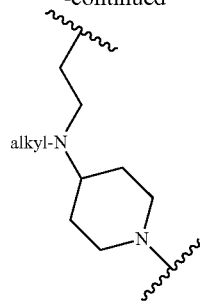

Within groups of compounds in (Fii) and/or a pharmaceutically acceptable salt thereof and groups contained therein, in another group of compounds and/or a pharmaceutically acceptable salt thereof,

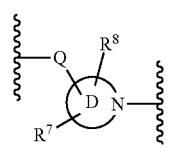

in -Q-X of formula

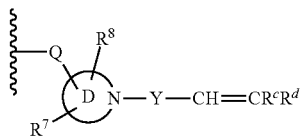 is 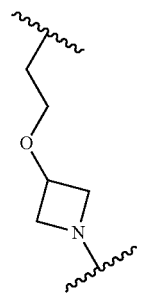

Within groups of compounds in (Fii) and/or a pharmaceutically acceptable salt thereof and groups contained therein, in another group of compounds and/or a pharmaceutically acceptable salt thereof,

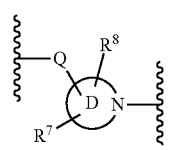

in -Q-X of formula R

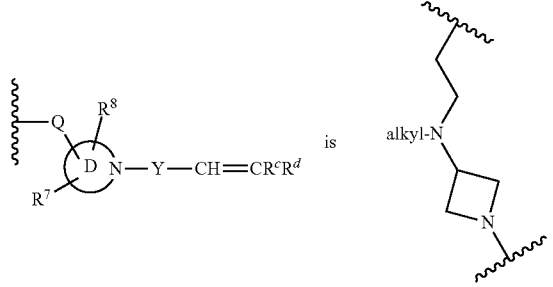 is 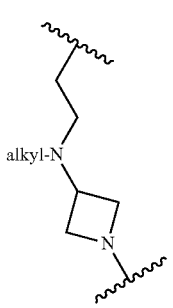

preferably

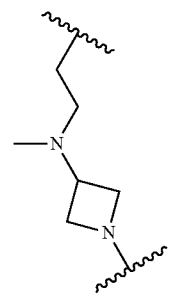

Preferably,

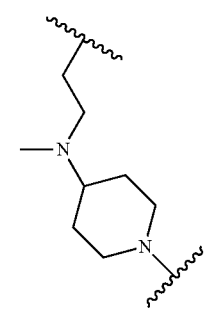 [SMILES: *CCN(C)C1CCN(*)CC1]

(Fiii) Within the groups of compounds in (F) and/or a pharmaceutically acceptable salt thereof and groups of compounds and/or a pharmaceutically acceptable salt thereof contained therein, in another group of compounds and/or a pharmaceutically acceptable salt thereof, X is a group of formula (e) where ring D is bridged- or spiro-heterocycloamino.

Embodiment G

In embodiment G, the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, and/or D above and/or a pharmaceutically acceptable salt thereof, and groups of compounds and/or a pharmaceutically acceptable salt thereof contained within each of the groups in embodiments A, B, C or D are those wherein Q is -alkylene-cycloalkylene-alkylene-. Within these groups of compounds and/or a pharmaceutically acceptable salt thereof, in one group of compounds and/or salts thereof, Q is —(CH$_2$)-cyclopropylene-(CH$_2$)—.

(Gi) Within the groups of compounds in (G) and/or a pharmaceutically acceptable salt thereof and groups of compounds and/or a pharmaceutically acceptable salt thereof contained therein, in one group of compounds and/or a pharmaceutically acceptable salt thereof, X is a group of formula (f). Within groups of compounds and/or a pharmaceutically acceptable salt thereof in (Gi), in one group of compounds and/or a pharmaceutically acceptable salt thereof, $Ar^2$ is phenylene or 5- or 6-membered heteroarylene ring. Within groups of compounds and/or a pharmaceutically acceptable salt thereof in (Gi), in another group of compounds and/or a pharmaceutically acceptable salt thereof, $Ar^2$ is phenylene. Within groups of compounds in (Gi) and/or a pharmaceutically acceptable salt thereof, in yet another group of compounds and/or a pharmaceutically acceptable salt thereof, $Ar^2$ is 5- or 6-membered heteroarylene ring.

Within groups of compounds and/or a pharmaceutically acceptable salt thereof in (Gi), in yet another group of compounds and/or a pharmaceutically acceptable salt thereof, $Ar^2$ is pyridinyl, pyrimidinyl, pyridazinyl, thiazolyl, thienyl, oxazolyl, or imidazolyl.

Within the groups of compounds in (Gi) and/or a pharmaceutically acceptable salt thereof, in yet another group of compounds and/or a pharmaceutically acceptable salt thereof

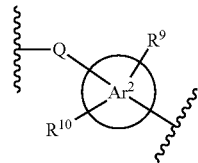

in-Q-X of formula

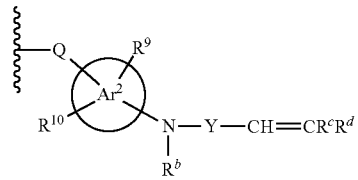

is:

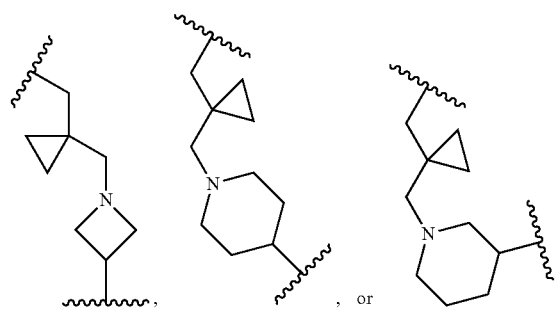

where $R^b$ is hydrogen or alkyl, preferably hydrogen.

(Gii) Within the groups of compounds in (G) and/or a pharmaceutically acceptable salt thereof and groups of compounds and/or a pharmaceutically acceptable salt thereof contained therein, in one group of compounds and/or salts thereof, X is a group of formula (g) where ring E is azetidinyl, pyrrolidinyl, or piperidinyl. With the groups in (Gii), in one group of compounds

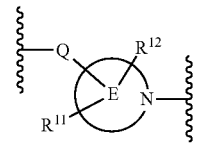

in -Q-X of formula

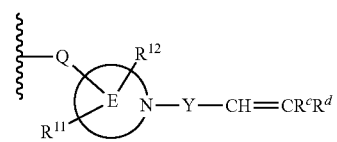

is:

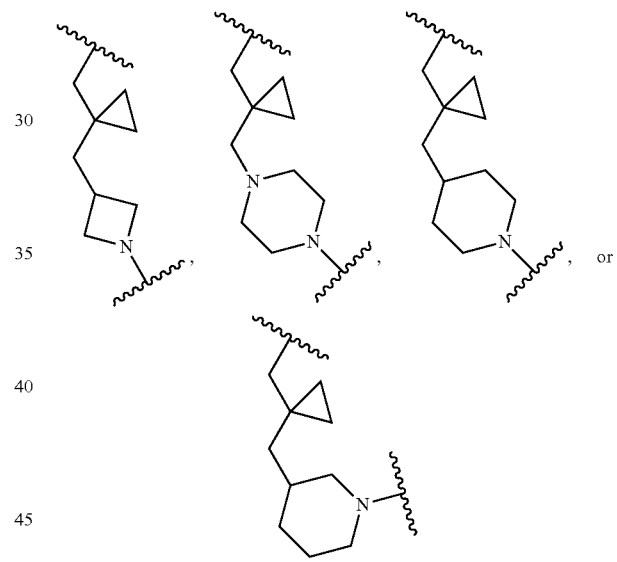

Embodiment H

In embodiment H, the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, D, E, F, and/or G above and/or a pharmaceutically acceptable salt thereof, and groups of compounds and/or a pharmaceutically acceptable salt thereof contained within each of the groups in embodiments A, B, C, D, E, F, and/or G and/or a pharmaceutically acceptable salt thereof are those wherein $R^2$ is hydrogen, alkyl, alkynyl, acyl, alkoxycarbonyl, haloalkyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl). Within the groups in embodiment H, in one group of compounds and/or salt thereof, $R^2$ is alkyl, alkynyl, acyl, alkoxycarbonyl, haloalkyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two substituents are independently selected from alkyl, hydroxy, alkoxy, halo, haloalkyl, haloalkoxy, and cyano and the third substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

(Hi) Within the groups of compounds in H and/or a pharmaceutically acceptable salt thereof and group of compounds and/or salt thereof contained therein, in one group of compounds and/or a pharmaceutically acceptable salt thereof, $R^2$ is alkyl, cycloalkylalkyl, aminoalkyl, hydroxyalkyl, alkoxyalkyloxyalkyl, or heterocyclylalkyl (wherein the heterocyclyl ring in heterocyclylalkyl is optionally substituted one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl).

Within the groups of compounds in (Hi) and/or a salt thereof, in one group of compounds and/or a pharmaceutically acceptable salt thereof, $R^2$ is alkyl, cycloalkylalkyl, hydroxyalkyl, alkoxyalkyloxyalkyl, or heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl).

(Hii) Within the groups of compounds in H and/or a pharmaceutically acceptable salt thereof and group of compounds and/or salt thereof contained therein, in yet another group of compounds and/or a pharmaceutically acceptable salt thereof, $R^2$ is alkyl, preferably methyl, ethyl, or isopropyl.

(Hiii) Within the groups of compounds in H and/or a pharmaceutically acceptable salt thereof and group of compounds and/or salt thereof contained therein, in yet another group of compounds and/or a pharmaceutically acceptable salt thereof, $R^2$ is cycloalkylalkyl, preferably cyclopropylmethyl, cyclopropylethyl, or cyclopentylmethyl.

(Hiv) Within the groups of compounds in H and/or a pharmaceutically acceptable salt thereof and group of compounds and/or salt thereof contained therein, in yet another group of compounds and/or a pharmaceutically acceptable salt thereof, $R^2$ is hydroxyalkyl, preferably $R^2$ is hydroxyethyl, hydroxypropyl or hydroxybutyl, more preferably $R^2$ is 2-hydroxyethyl or 2-hydroxy-2-methylpropyl.

(Hv) Within the groups of compounds in H and/or a pharmaceutically acceptable salt thereof and group of compounds and/or salt thereof contained therein, in yet another group of compounds and/or a pharmaceutically acceptable salt thereof, $R^2$ is heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, aminoalkyl, optionally substituted aryl, optionally substituted heteroaryl, and optionally substituted heterocyclyl), preferably $R^2$ is tetrahydrofuran-3-ylmethyl, tetrahydropyran-4-ylmethyl, piperidin-4-ylmethyl, piperazin-4-ethyl, or morpholin-4-ylethyl wherein the morpholin-4-yl, piperazinyl and piperidinyl rings in the above groups are optionally substituted with one, two, or three substituents independently selected from alkyl, alkyl, acyl, alkoxycarbonyl, hydroxyalkyl, aminoalkyl, optionally substituted aryl, optionally substituted heteroaryl, and optionally substituted heterocyclyl), more preferably $R^2$ is 1-methylpiperidin-4-ylmethyl, 2-morpholin-4-ylethyl, tetrahydrofuran-3-ylmethyl, tetrahydropyran-4-ylmethyl or 2-(1-methylpiperazin-4-yl)ethyl.

(Hvi) Within the groups of compounds in H and/or a pharmaceutically acceptable salt thereof and group of compounds and/or salt thereof contained therein, in yet another group of compounds and/or a pharmaceutically acceptable salt thereof, $R^2$ is heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heteroaralkyl, phenyl, or heteroaryl where phenyl and heteroaryl are optionally substituted with one, two, or three substituents where two of the optional substituents are independently selected from alkyl, hydroxy, alkoxy, halo, haloalkyl, haloalkoxy, and cyano and the third optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl, preferably $R^2$ is tetrahydrofuran-3-yl or tetrahydropyran-4-yl.

(Hvii) Within the groups of compounds in H and/or a pharmaceutically acceptable salt thereof and group of compounds and/or salt thereof contained therein, in yet another group of compounds and/or a pharmaceutically acceptable salt thereof, $R^2$ is:

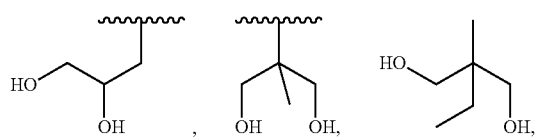

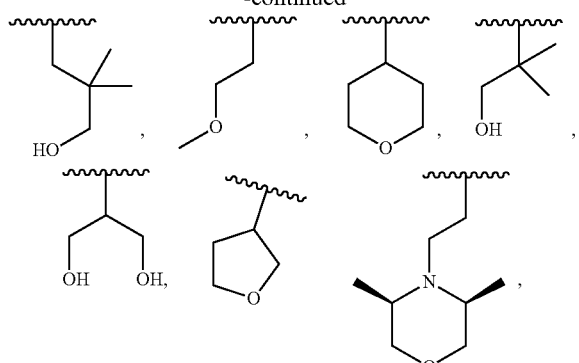
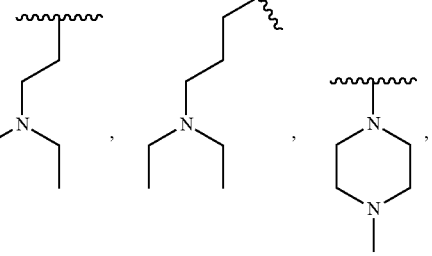
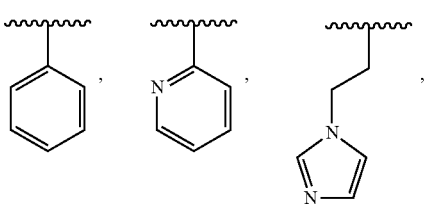
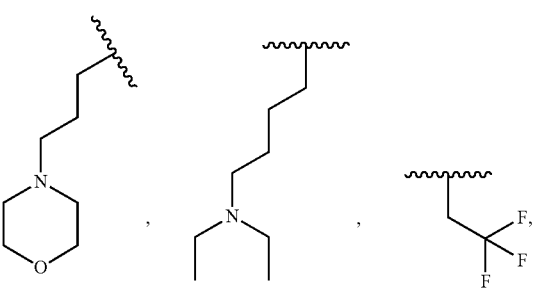
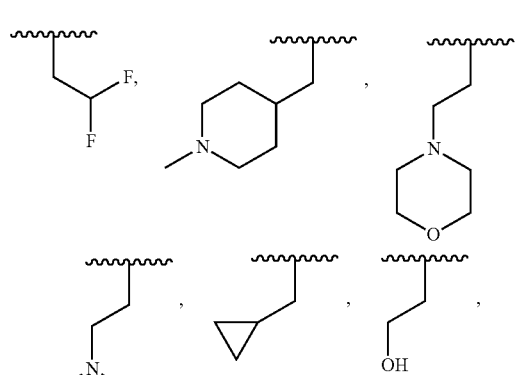
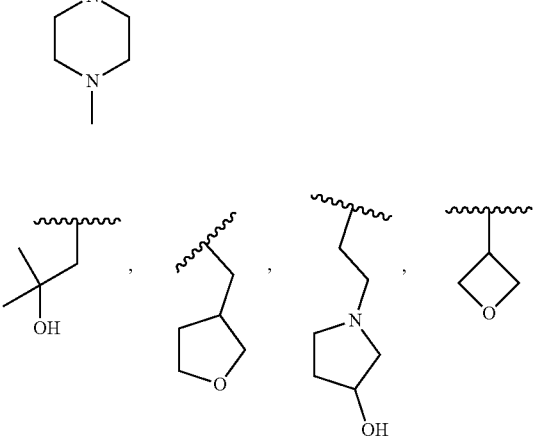

-continued

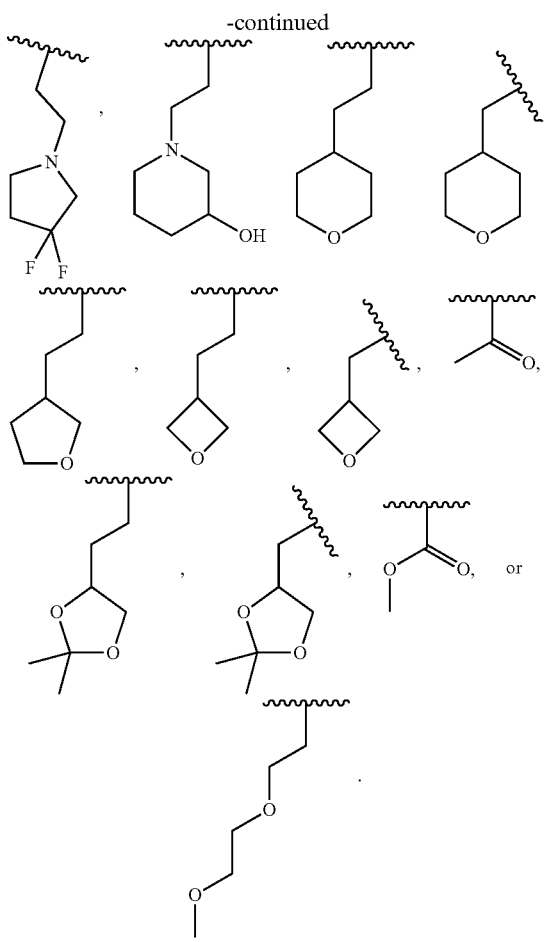

(Hviii) Within the groups of compounds in H and/or a pharmaceutically acceptable salt thereof and group of compounds and/or salt thereof contained therein, in yet another group of compounds and/or a pharmaceutically acceptable salt thereof, $R^2$ is:

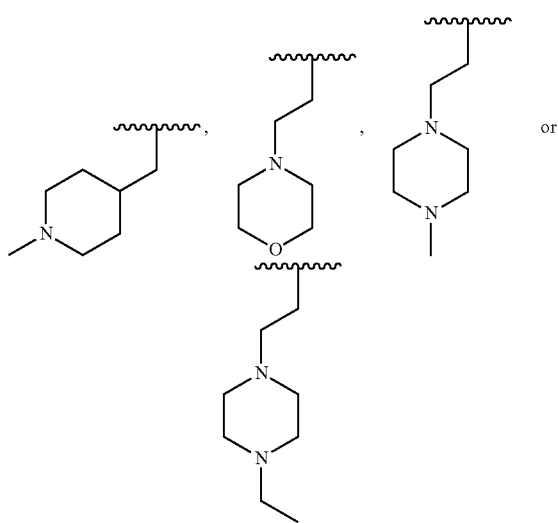

when X is $Ar^1$ or $Ar^2$ where $Ar^1$ and $Ar^2$ are independently phenylene or 5- or 6-membered heteroarylene or X is a ring of formula (e), preferably ring D is heterocycloamino, more preferably azetidinyl, pyrrolidinyl or piperidinyl.

(Hix) Within the groups in H and group of compounds and/or salt thereof contained therein, in yet another group of compounds and/or a pharmaceutically acceptable salt thereof, $R^2$ is:

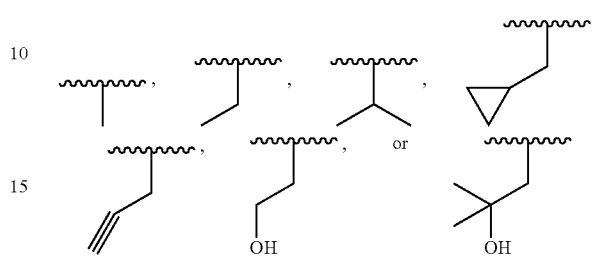

when X is a group of formula (a), (b), (c), or (e), preferably X is azetidinyl, piperazinyl or piperidinyl.

(Hx) Within the groups of compounds in H and/or a pharmaceutically acceptable salt thereof and group of compounds and/or salt thereof contained therein, in yet another group of compounds and/or salts thereof, $R^2$ is hydrogen.

(Hxi) Within the groups of compounds in H and/or a pharmaceutically acceptable salt thereof and group of compounds and/or salt thereof contained therein, in yet another group of compounds and/or salts thereof, $R^2$ is acetyl, methoxycarbonyl, or methoxyethyloxyethyl.

(Hxii) Within the groups of compounds in H and/or a pharmaceutically acceptable salt thereof and group of compounds and/or salt thereof contained therein, in yet another group of compounds and/or salts thereof, $R^2$ is hydrogen, alkyl, acyl, alkoxyalkyloxyalkyl, or alkoxyalkyl, preferably $R^2$ is hydrogen, methyl, methylcarbonyl, methoxyethyloxyethyl, or —*CH(CH$_3$)CH$_2$—OCH$_3$ where the stereochemistry at *C is (R) or (S), preferably (S).

Embodiment I

In embodiment I, the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, and/or C above and/or a pharmaceutically acceptable salt thereof, and groups of compounds and/or a pharmaceutically acceptable salt thereof contained within each of the groups in embodiments A, B, or C, are those wherein -Q-X is haloalkyl, hydroxyalkyl, alkoxyalkyl, alkoxyalkyloxyalkyl, aminoalkyl, phenyl, 5- or 6-membered heteroaryl, phenylalkyl, 5- or 6-membered heteroaralkyl (where the phenyl, phenyl in phenylalkyl, 5- or 6-membered heteroaryl, and heteroaryl ring in 5- or 6-membered heteroaralkyl are optionally substituted with one, two, or three substituents independently selected from alkyl, cycloalkyl, hydroxy, alkoxy, halo, haloalkyl, haloalkoxy, and cyano), heterocyclyl, heterocyclylalkyl, and heterocyclylheteroalkyl (where the heterocyclyl ring in heterocyclyl heterocyclylalkyl, and heterocyclylheteroalkyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl). Within these groups of compounds and/or a pharmaceutically acceptable salt thereof, in one group of compounds -Q-X is:

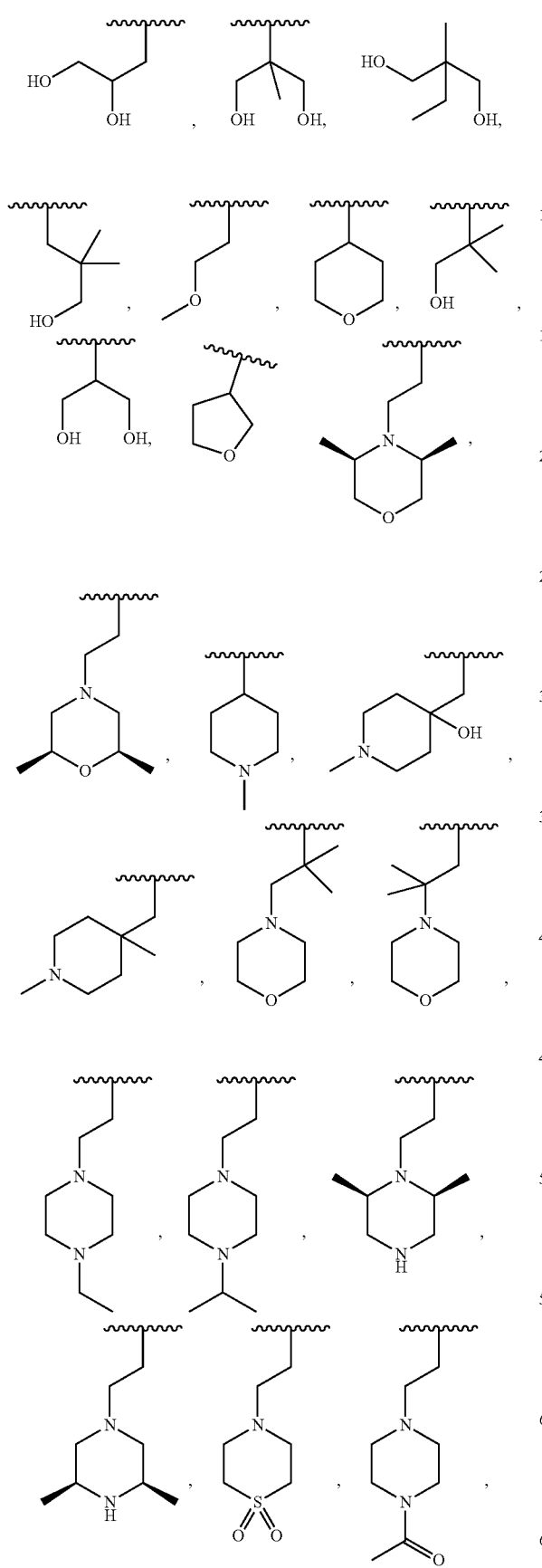
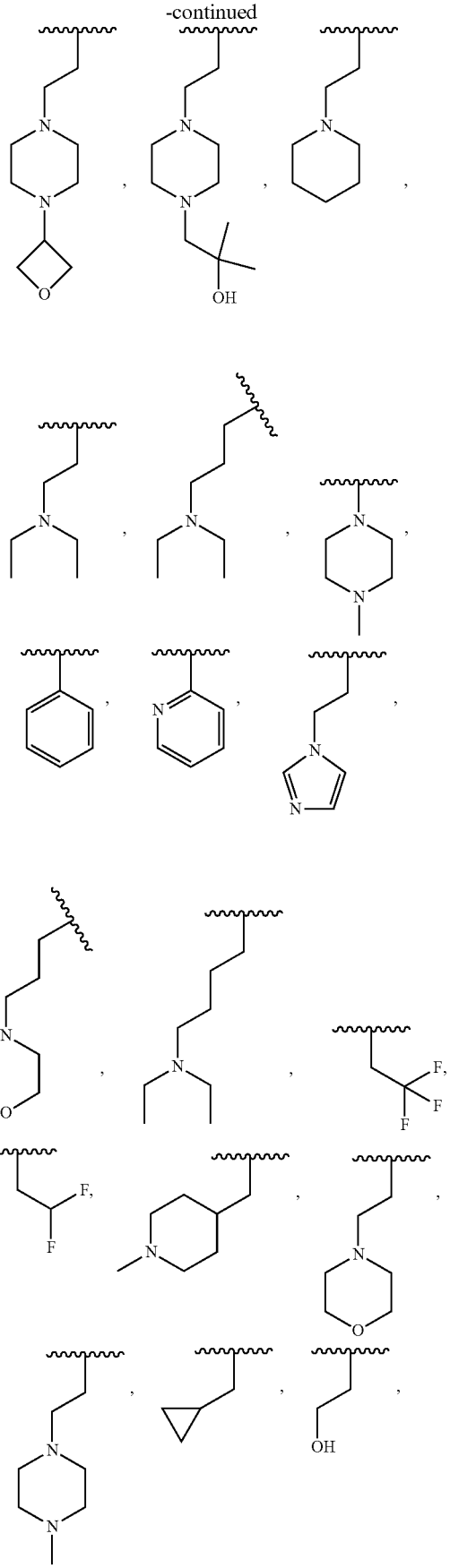

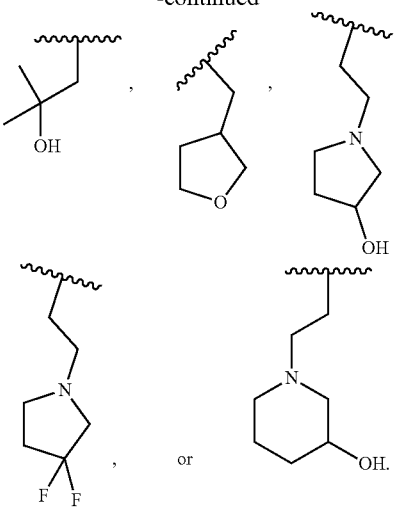

Embodiment J

In embodiment J, the compounds of Formula (I') and/or a pharmaceutically acceptable salt thereof as defined in Embodiment AA, the compound of Formula (I) and/or a pharmaceutically acceptable salt thereof as defined in the first aspect above, the groups of compounds in embodiments A, B, C, and/or I above and/or a pharmaceutically acceptable salt thereof, and groups of compounds and/or a pharmaceutically acceptable salt thereof contained within each of the groups in embodiments A, B, C, or I, are those wherein $R^2$ is a group of formula:

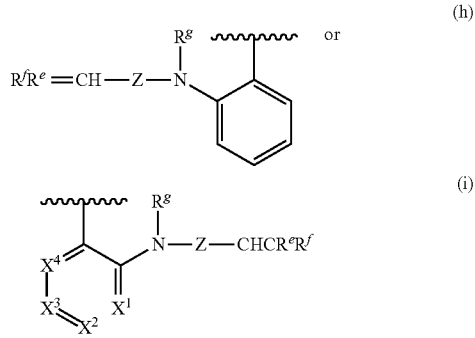

wherein $X^1$-$X^4$ are independently CH or N, provided not more than two $X^1$-$X^4$ are N and the rings are optionally substituted with one or two substituents independently selected from alkyl, hydroxy, alkoxy, halo, haloalkyl, haloalkoxy, or cyano. Preferably, the substituent is methyl, ethyl, methoxy, chloro, fluoro, difluoromethyl, trifluoromethyl, cyano or trifluoromethoxy. More preferably, one of the substituent is located on carbon adjacent to the carbon attaching the $R^2$ group to the amino group. Within these groups of compounds, and/or salt thereof, in one group of compound $R^9$ is hydrogen.

Embodiment K

In embodiment K, the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, D, E, F, G, H, I, and/or J above and/or a pharmaceutically acceptable salt thereof, and groups of compounds and/or a pharmaceutically acceptable salt thereof contained within each of the groups in embodiments A, B, C, D, E, F, G, H, I, and/or J are those wherein Y and Z are —CO—.

Embodiment L (Li) In (Li), the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, D, E, F, G, H, I, J, and/or K and/or a pharmaceutically acceptable salt thereof and groups of compounds and/or a pharmaceutically acceptable salt thereof contained within each of the groups in embodiments A, B, C, D, E, F, G, H, I, J, and/or K are those wherein $R^c$, $R^d$, $R^e$ and R are hydrogen.

(Lii) In (Lii), the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, D, E, F, G, H, I, J, and/or K and/or a pharmaceutically acceptable salt thereof and groups of compounds and/or a pharmaceutically acceptable salt thereof contained within each of the groups in embodiments A, B, C, D, E, F, G, H, I, J, and/or K are those wherein $R^c$ and $R^e$ are alkyl and $R^d$ and $R^f$ are hydrogen. Within these groups of compounds and/or a pharmaceutically acceptable salt thereof in one group of compounds and/or salts thereof $R^c$ and $R^e$ are methyl.

(Liii) In (Liii), the compounds of Formula (I') and/or a pharmaceutically acceptable salt thereof as defined in Embodiment AA, the compounds of Formula (I) and/or a salt thereof as defined in the first aspect above, the groups of compounds in embodiments A, B, C, D, E, F, G, H, I, J, and K and/or a pharmaceutically acceptable salt thereof and groups of compounds and/or a pharmaceutically acceptable salt thereof contained within each of the groups in embodiments A, B, C, D, E, F, G, H, I, J, and/or K are those wherein $R^c$ and $R^e$ are —CH$_2$NRR', where R is hydrogen, alkyl, hydroxyalkyl, alkoxyalkyl, or heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino and $R^d$ and $R^f$ are hydrogen.

(Liv) In (Liv), the compounds of Formula (I') and/or a pharmaceutically acceptable salt thereof as defined in Embodiment AA, the compounds of Formula (I) and/or a pharmaceutically acceptable salt thereof as defined in the first aspect above, the groups of compounds in embodiments A, B, C, D, E, F, G, H, I, J, and K and/or a pharmaceutically acceptable salt thereof and groups of compounds and/or a pharmaceutically acceptable salt thereof contained within each of the groups in embodiments A, B, C, D, E, F, G, H, I, J, and/or K are those wherein $R^d$ and R and the hydrogen atom on carbon attached to group Y and AA respectively form a bond to give a triple bond. Within these groups of compounds and/or a pharmaceutically acceptable salt thereof in one group of compounds and/or salts thereof $R^c$ and $R^e$ are methyl.

Embodiment (M)

In embodiment (M), the compounds of Formula (III) are those wherein:
(i) Q is alkylene or substituted alkylene; and
X is a group of formula (a), (b), (c), or (h):

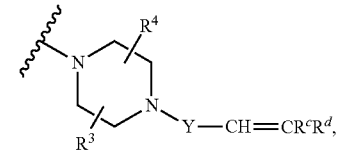
(a)

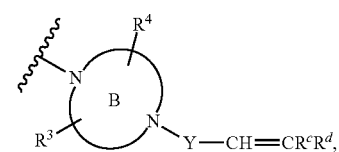
(b)

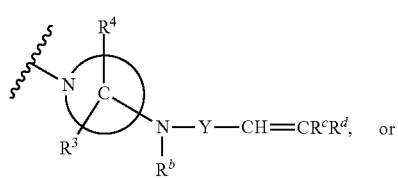
(c)

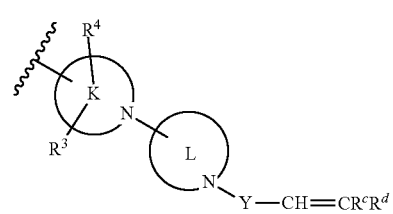
(h)

or
(ii) Q is substituted heteroalkylene, or aminoheteroalkylene; and
X is a group of formula (d) or (e):

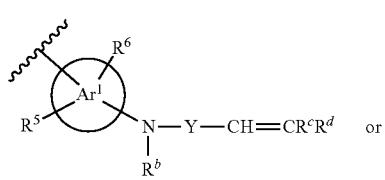
(d)

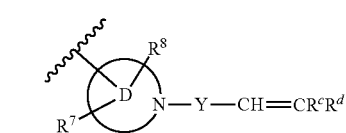
(e)

(Ma) In (Ma), the compounds of embodiment (M), are those where X is a group of formula (a), (c), (h), or (e).
(Mb) In (Ma), the compounds of embodiment (M), are those where Q is a alkylene and X is a group of formula (h). Within compounds in (Mb), in one group compounds, -Q-X— is

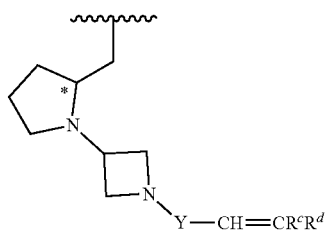

Where *C is (R) or (S) or a mixture thereof.
(Mc) In (Mc), the compounds of embodiment (M), are those where Q is a aminoheteroalkylene and X is a group of formula (e). Within compounds in (Mc), in one group compounds, -Q-X— is

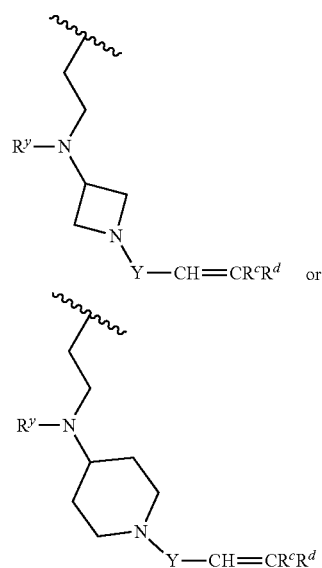

where $R^y$ is hydroxyalkyl, alkoxyalkyl, alkoxyalkyloxyalkyl, or -(alkylene)-NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo. Preferably $R^y$ is hydroxyalkyl, alkoxyalkyl, or aminoalkyl, preferably $R^y$ is 2-hydroxyethyl or 2-alkoxyethyl.

(Md) In (Md), the compounds in embodiments (M), (Ma), (Mb), (Mc), and groups contained therein are those where J is N.

(Me) In (Me), the compounds of embodiments (M), (Ma), (Mb), (Mc), and (Md), and groups contained therein are those where J is CH.

(Mf) In (Mf), the compounds of embodiments (M), (Ma), (Mb), (Mc), (Md), and (Me) and groups contained therein are those where $R^1$ is as defined in embodiment A above and groups contained therein.

(Mg) In (Mg), the compounds of embodiments (M), (Ma), (Mb), (Mc), (Md), (Me), and (Mf) and groups contained therein are those where Ar is as defined in Embodiment B or Embodiment C and groups contained therein.

(Mh) In (Mh), the compounds of embodiments (M), (Ma), (Mb), (Mc), (Md), (Me), (Mf) and (Mg) and groups contained therein are those where R² is as defined in embodiment H and groups contained therein.

(Mi) In (Mi), the compounds of embodiments (M), (Ma), (Mb), (Mc), (Md), (Me), (Mf), (Mg) and (Mh) and groups contained therein are those where Y is —CO—.

(Mj) In (Mj), the compounds of embodiments (M), (Ma), (Mb), (Mc), (Md), (Me), (Mf), (Mg), and (Mi) and groups contained therein are those where $R^c$ and $R^d$ are is as defined in embodiment L and groups contained therein.

Embodiment (N)

In further embodiments 1-40 below, the present disclosure includes:
1. A compound of Formula (I):

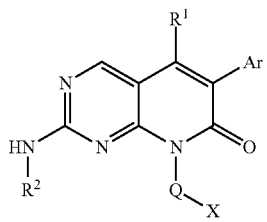

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
R¹ is hydrogen, halo, alkyl, or cycloalkyl;
R² is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, optionally substituted heterocyclyl, —NR$^g$(alkylene)$_n$-Z—CH=CR$^e$R$^f$ and —Z—CH=CR$^e$R$^f$ provided —Z—CH=CR$^e$R$^f$ is attached to a ring nitrogen in the heterocyclyl ring), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, heteroaryl (where phenyl, phenyl in aralkyl, heteroaryl ring in heteroaralkyl, and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, optionally substituted heterocyclyl or —NR$^g$(alkylene)$_n$-Z—CH=CR$^e$R$^f$), or —Z—CH=CR$^e$R$^f$;

where:
n is 0-3;
each Z is —CO— or —SO₂—;
each R$^e$ is hydrogen, alkyl, or substituted alkyl; R$^f$ is hydrogen or alkyl; or
each R$^f$ and the hydrogen atom on carbon attached to group Z can form a bond to give a triple bond

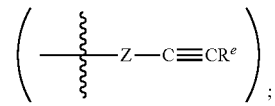

and
each R$^g$ is hydrogen or alkyl; and
(i) -Q-X is cycloalkyl, cycloalkylalkyl, haloalkyl, hydroxyalkyl, alkoxyalkyl, alkoxyalkyloxyalkyl, aminoalkyl, phenyl, 5- or 6-membered heteroaryl, phenylalkyl, 5- or 6-membered heteroaralkyl (where the phenyl ring in phenylalkyl, 5- or 6-membered heteroaryl, and heteroaryl ring in 5- or 6-membered heteroaralkyl are optionally substituted with one, two, or three substituents independently selected from alkyl, cycloalkyl, hydroxy, alkoxy, halo, haloalkyl, haloalkoxy, and cyano), heterocyclyl, heterocyclylalkyl, or heterocyclylheteroalkyl (where the heterocyclyl ring in heterocyclylalkyl, or heterocyclylheteroalkyl is optionally substituted with one, two, or three substituents independently selected from alkyl, halo, acyl, acylamino, hydroxy, hydroxyalkyl, alkoxyalkyl, aminoalkyl, optionally substituted aryl, optionally substituted heteroaryl, and optionally substituted heterocyclyl); or
(ii) Q is alkylene; and
X is a group of formula (a), (b), or (c):

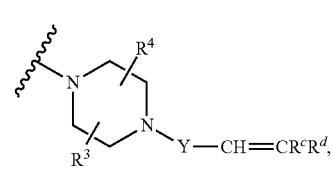

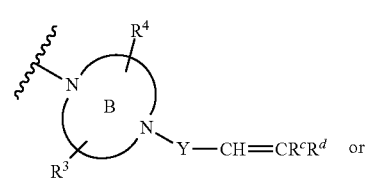

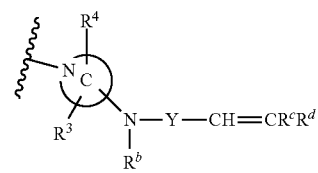

wherein:
ring B is a aza bridged heterocycloamino or aza spiroheterocycloamino;
ring C is azetidinyl, pyrrolidinyl, piperidinyl, bridged heterocycloamino, or spiro heterocycloamino;

each R³ is hydrogen, alkyl, haloalkyl, hydroxy, alkoxy, or halo; and
each R⁴ is hydrogen, alkyl, hydroxy, alkoxy, or halo; or
(iii) Q is heteroalkylene, and
X is a group of formula (d) or (e):

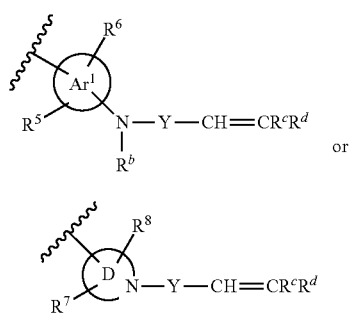

wherein:
Ar¹ is 5- or 6-membered cycloalkylene, phenylene, or 5- or 6-membered heteroarylene;
ring D is heterocycloamino, bridged heterocycloamino, or spiroheterocycloamino;
R⁵ is hydrogen, alkyl, hydroxy, alkoxy, halo, haloalkyl, haloalkoxy, or cyano;
R⁶ is hydrogen, alkyl, cycloalkyl, hydroxy, alkoxy, halo, haloalkyl, haloalkoxy, or cyano; and
R⁷ and R⁸ are independently hydrogen, alkyl, hydroxy, alkoxy, or halo; or
(iv) Q is -alkylene-cycloalkylene-alkylene- and
X is a group of formula (f) or (g):

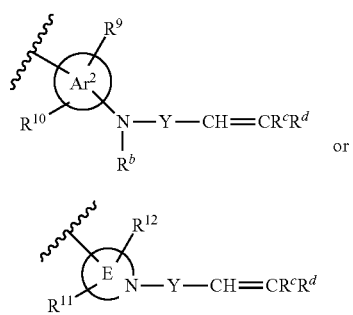

wherein:
Ar² is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
R⁹ is hydrogen, alkyl, hydroxy, alkoxy, halo, haloalkyl, haloalkoxy, or cyano;
R¹⁰ is hydrogen, alkyl, cycloalkyl, hydroxy, alkoxy, halo, haloalkyl, haloalkoxy, or cyano; and
R¹¹ and R¹² are independently hydrogen, alkyl, hydroxy, alkoxy, or halo;
each Y is —CO— or —SO₂—;
each R^b is hydrogen or alkyl;
each R^c is hydrogen, alkyl, or substituted alkyl; and each R^d is hydrogen or alkyl; or
R^d and the hydrogen atom on carbon attached to group Y can form a bond to give a triple bond

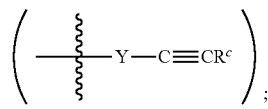

and/or a pharmaceutically acceptable salt thereof;
provided that: (1) when (i) Ar¹ is phenylene or 6-membered heteroarylene or (ii) Ar² is phenylene, 6-membered heteroarylene or piperidin-1-yl or (iii) ring C is piperidinyl, then Q and —NR^b—Y—CH=CR^cR^d are meta or para to each other; (2) when ring D, or E is piperidinyl, then Q and —Y—CH=CR^cR^d are meta or para to each other; (3) when ring D or E is piperazinyl, then Q and —Y—CH=CR^cR^d are para to each other; (4) when ring C, D, or E is pyrrolidinyl or azetidinyl, then Q and —Y—CH=CR^cR^d are (1,3) to each other; and (5) when Q is not a group of formula (a), (b), (c), (d), (e), (f), or (g), then R² is (i) —Z—CH=CR^eR^f or (ii) heterocyclyl substituted with at least —Z—CH=CR^eR^f or —NR^g(alkylene)ₙ-Z—CH=CR^eR^f or (iii) aralkyl, heteroaralkyl, phenyl, or heteroaryl (where phenyl, phenyl ring in aralkyl, heteroaryl, and heteroaryl ring in heteroaralkyl are substituted with at least —NR^g(alkylene)ₙ-Z—CH=CR^eR^f).

2. A compound of Formula (IA):

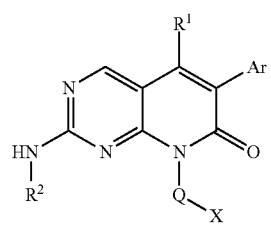

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
R¹ is hydrogen, halo, or alkyl;
R² is hydrogen, alkyl, acyl, alkoxycarbonyl, alkynyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one two, or three substituents independently selected from alkyl, hydroxy, halo, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl); and (i) Q is alkylene; and
X is a group of formula (a), (b), or (c):

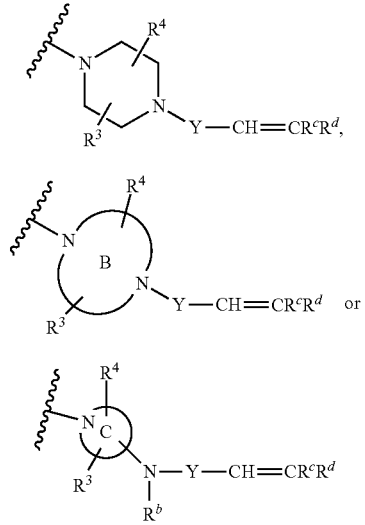

wherein:
ring B is a aza bridged heterocycloamino or aza spiroheterocycloamino;
ring C is azetidinyl, pyrrolidinyl, piperidinyl, bridged heterocycloamino, or spiro heterocycloamino wherein the nitrogen atom in aforementioned (a), (b) and (c) rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or (ii) Q is heteroalkylene, and
X is a group of formula (d) or (e):

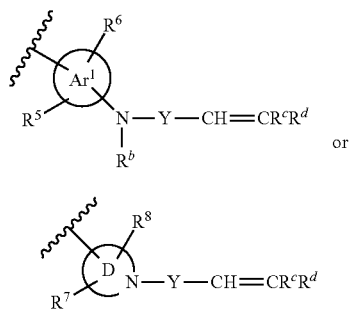

wherein:
$Ar^1$ is 5- or 6-membered cycloalkylene, phenylene, or 5- or 6-membered heteroarylene;

Ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; and (iii) Q is -alkylene-cycloalkylene-alkylene- and
X is a group of formula (f) or (g):

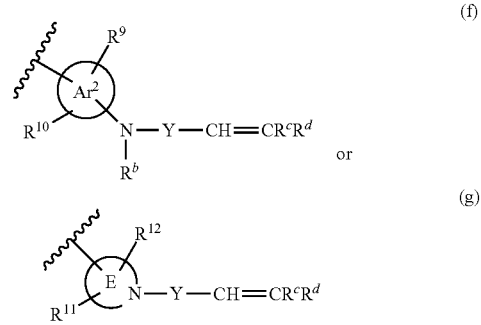

wherein:
$Ar^2$ is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —SO$_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

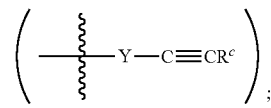

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —NR$^b$—Y—CH=CR$^c$R$^d$ are meta or para to each other; (2) when ring D or E is piperidinyl, then Q and —Y—CH=CR$^c$R$^d$ are meta or para to each other; (3) when ring D or E is piperazinyl, then Q and —Y—CH=CR$^c$R$^d$ are para to each other; and (4) when ring C, D, or E is pyrrolidinyl or azetidinyl, then Q and —NR$^b$—Y—CH=CR$^c$R$^d$ or Q and —Y—CH=CR$^c$R$^d$ are (1,3) to each other.

3. The compound of embodiment 1 or 2 or a pharmaceutically acceptable salt thereof wherein $R^1$ is hydrogen.

4. The compound of embodiment 1, 2, or 3 or a pharmaceutically acceptable salt thereof wherein Ar is phenyl optionally substituted with one, two, three, or four substituents independently selected from alkyl, hydroxy, alkoxy, halo, haloalkyl, haloalkoxy, or cyano.

5. The compound of embodiment 1, 2 or 3 or a pharmaceutically acceptable salt thereof wherein Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl 6. The compound of embodiment 1, 2 or 3 or a pharmaceutically acceptable salt thereof wherein Ar is 2-chloro-3,5-dimethoxy-phenyl, 3,5-dimethoxyphenyl, 2-chlorophenyl, or 2,6-dichloro-3,5-dimethoxyphenyl.

7. The compound of embodiment 1, 2, or 3 or a pharmaceutically acceptable salt thereof wherein Ar is heteroaryl ring optionally substituted with one, two, or three substituents independently selected from alkyl, hydroxy, alkoxy, halo, haloalkyl, haloalkoxy, or cyano.

8. The compound of any one of embodiments 2 to 7 or a pharmaceutically acceptable salt thereof wherein Q is alkylene and X is a group of formula (a).

9. The compound of any one of embodiments 2 to 7 or a pharmaceutically acceptable salt thereof wherein Q is n-propylene and X is a group of formula (a).

10. The compound of embodiment 8 or a pharmaceutically acceptable salt thereof wherein

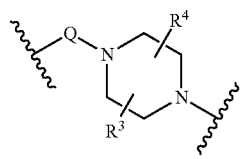

in -Q-X of formula

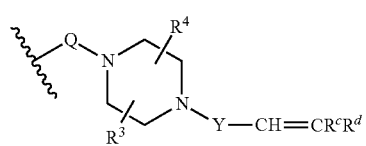

is selected from:

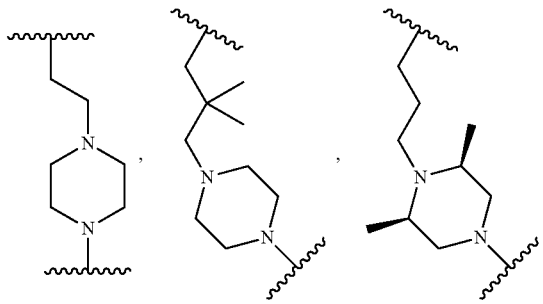

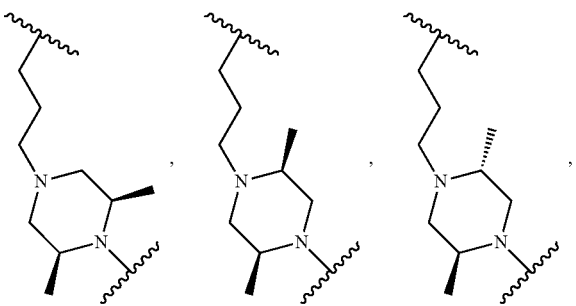

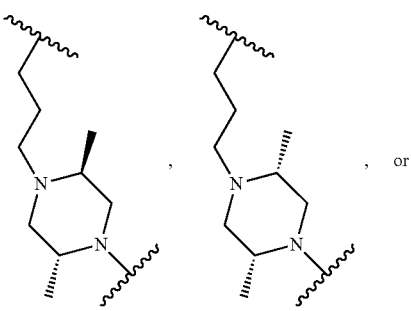

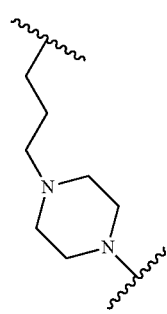

11. The compound of embodiment 8 or a pharmaceutically acceptable salt thereof wherein

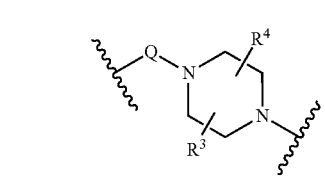

in -Q-X of formula

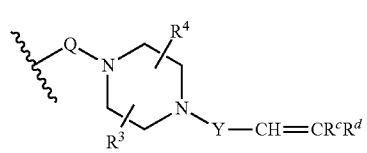

is

-continued

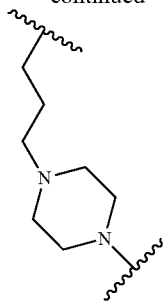

12. The compound of any one of embodiments 2 to 7 or a pharmaceutically acceptable salt thereof wherein Q is alkylene and X is a group of formula (b).

13. The compound of any one of embodiments 2 to 7 or a pharmaceutically acceptable salt thereof wherein Q is alkylene and X is a group of formula (c).

14. The compound of embodiment 13 wherein

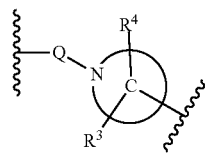

in -Q-X of formula

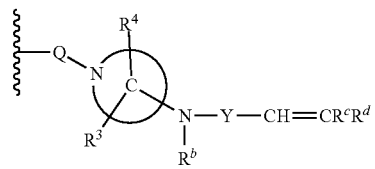

is:

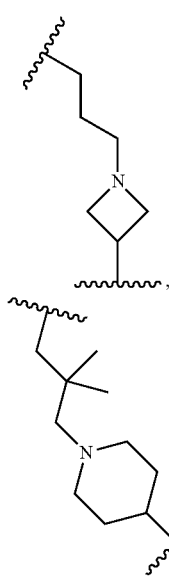 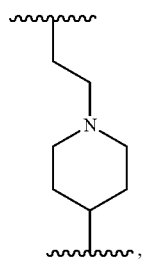 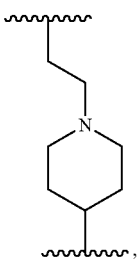

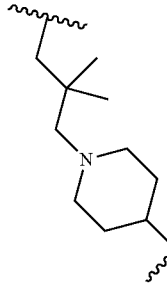 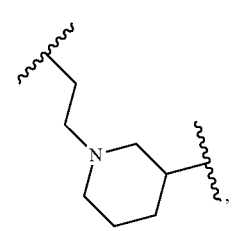, or

-continued

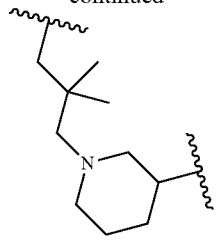

where $R^b$ is hydrogen or methyl, preferably hydrogen.

15. The compound of any one of embodiment 2 to 7 or a pharmaceutically acceptable salt thereof wherein Q is heteroalkylene.

16. The compound of embodiment 15 or a pharmaceutically acceptable salt thereof wherein Q is —(CH$_2$)$_2$—O— and X is a ring of formula (d) where Ar$^1$ is phenylene, 5- or 6-membered heteroarylene or a ring of formula (e) where ring D is azetidinyl, pyrrolidinyl, or piperidinyl.

17. The compound of embodiment 15 or a pharmaceutically acceptable salt thereof wherein

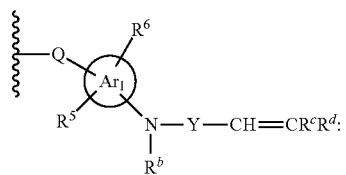

in -Q-X of formula

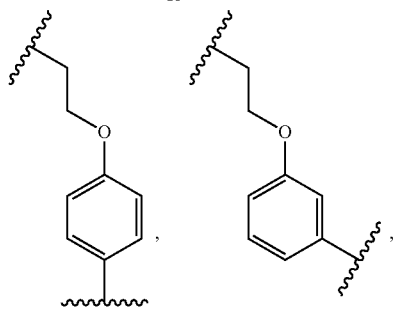

-continued

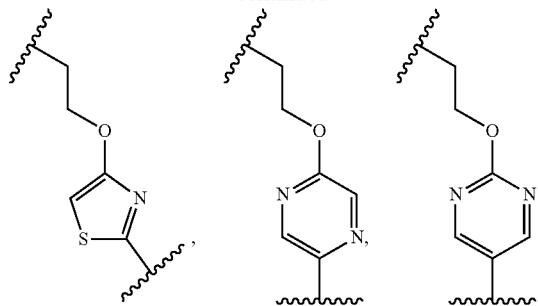

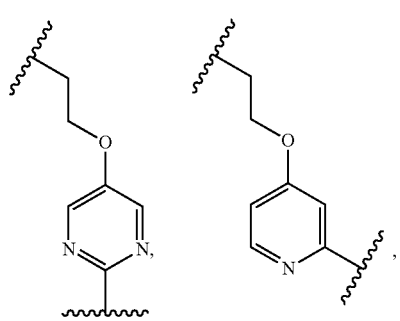

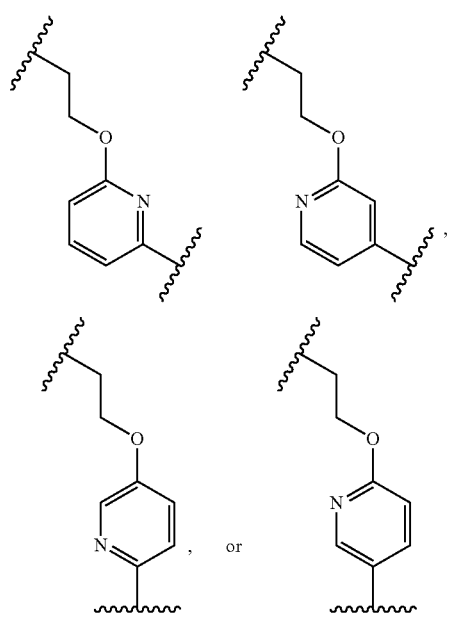

, or where $R^b$ is hydrogen or alkyl, preferably hydrogen.

18. The compound of embodiment 15 or a pharmaceutically acceptable salt thereof wherein

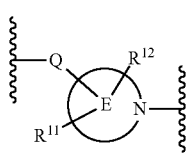

in -Q-X of formula

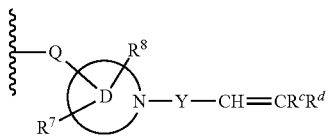

is:

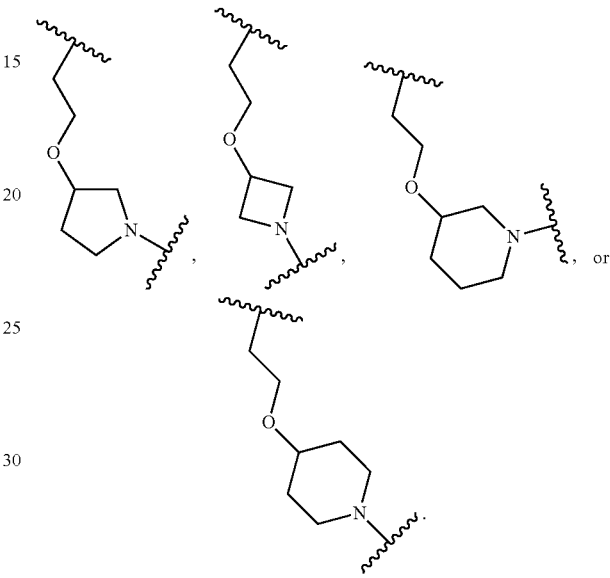

19. The compound of any one of embodiments 2 to 7 or a pharmaceutically acceptable salt thereof wherein Q is -alkylene-cycloalkylene-alkylene-.

20. The compound of embodiment 19 or a pharmaceutically acceptable salt thereof wherein Q is —(CH$_2$)-cyclopropylene-(CH$_2$)— and X is a group of formula (g) where ring E is piperazin-1-yl or piperidin-1-yl where the atom in the 4-position of the above rings is attached to Q, the ring atom attached to —(CH$_2$)-cyclopropylene-(CH$_2$)— being position 1.

21. The compound of embodiment 20 or a pharmaceutically acceptable salt thereof wherein

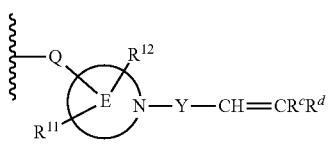

in -Q-X of formula is:

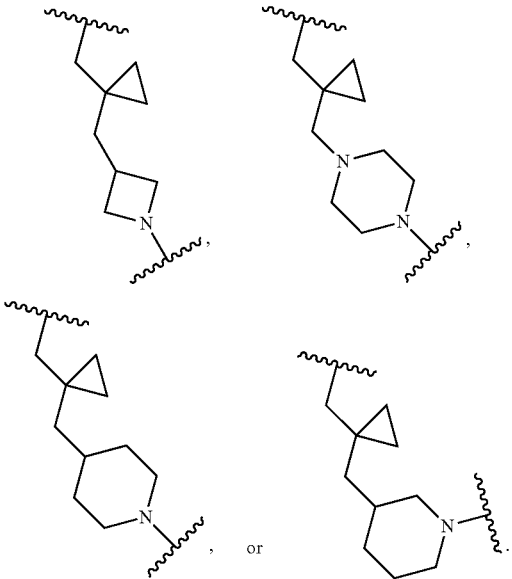

22. The compound of embodiment 19 or a pharmaceutically acceptable salt thereof wherein

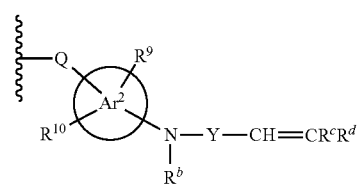

in-Q-X of formula

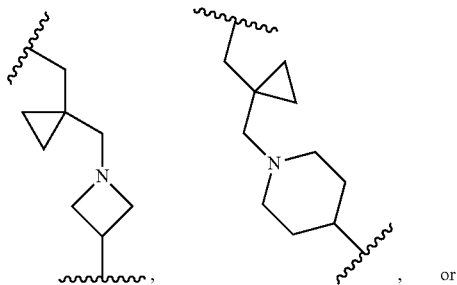

is:

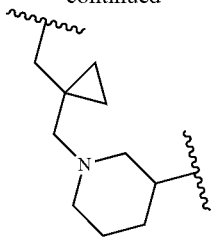

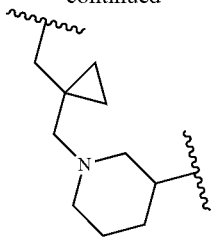

where $R^b$ is hydrogen or alkyl, preferably hydrogen.

23. The compound of any one of embodiments 2 to 22 or a pharmaceutically acceptable salt thereof wherein $R^2$ is alkyl, alkynyl, acyl, alkoxycarbonyl, haloalkyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, or cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

24. The compound of any one of embodiments 2 to 22 or a pharmaceutically acceptable salt thereof wherein $R^2$ is alkyl, cycloalkylalkyl, aminoalkyl, hydroxyalkyl, alkoxyalkyloxyalkyl, or heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl).

25. The compound of any one of embodiments 2 to 22 or a pharmaceutically acceptable salt thereof wherein $R^2$ is alkyl, cycloalkylalkyl, hydroxyalkyl, alkoxyalkyloxyalkyl, or heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, or optionally substituted heterocyclyl).

26. The compound of any one of embodiments 2 to 22 or a pharmaceutically acceptable salt thereof wherein $R^2$ is heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, or optionally substituted heterocyclyl), heteroaralkyl, phenyl, or heteroaryl where phenyl or heteroaryl is optionally substituted with one, two, or three substituents where two substituents are independently selected from alkyl, hydroxy, alkoxy, halo, haloalkyl, haloalkoxy, or cyano and the third substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl.

27. The compound of any one of embodiments 2 to 22 or a pharmaceutically acceptable salt thereof wherein $R^2$ is:

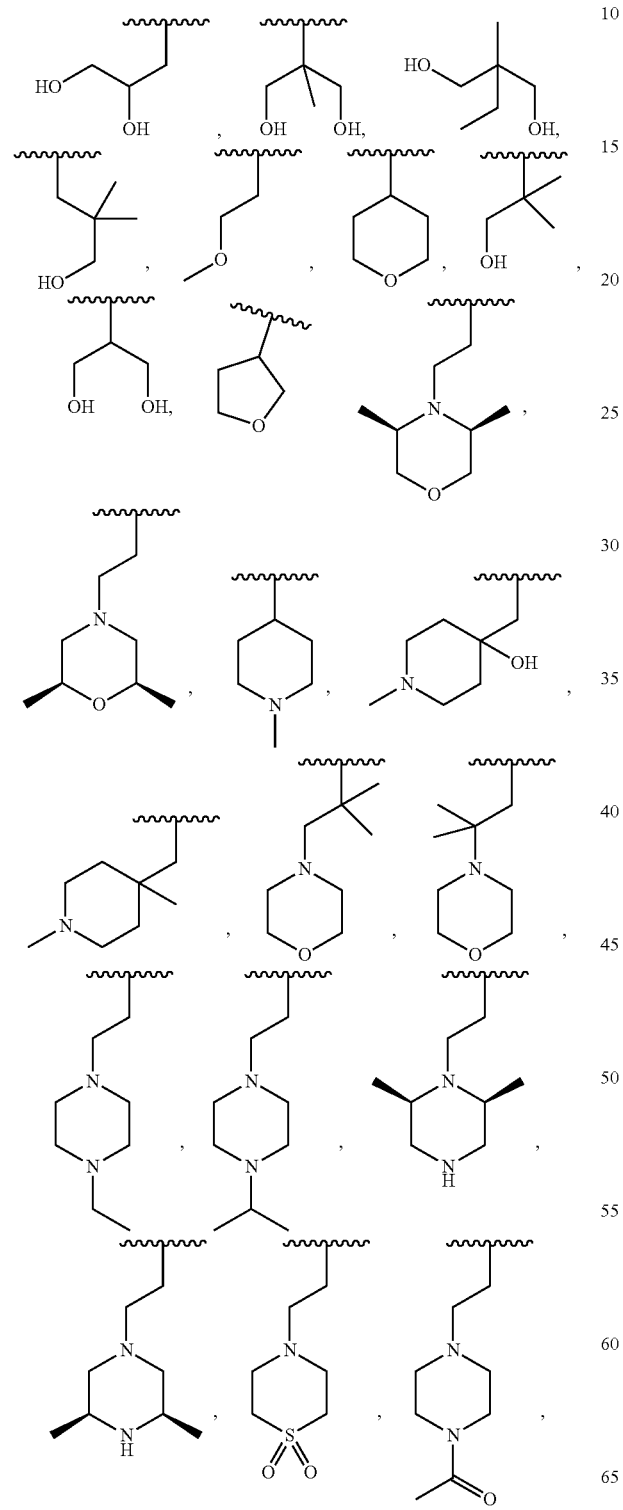

-continued

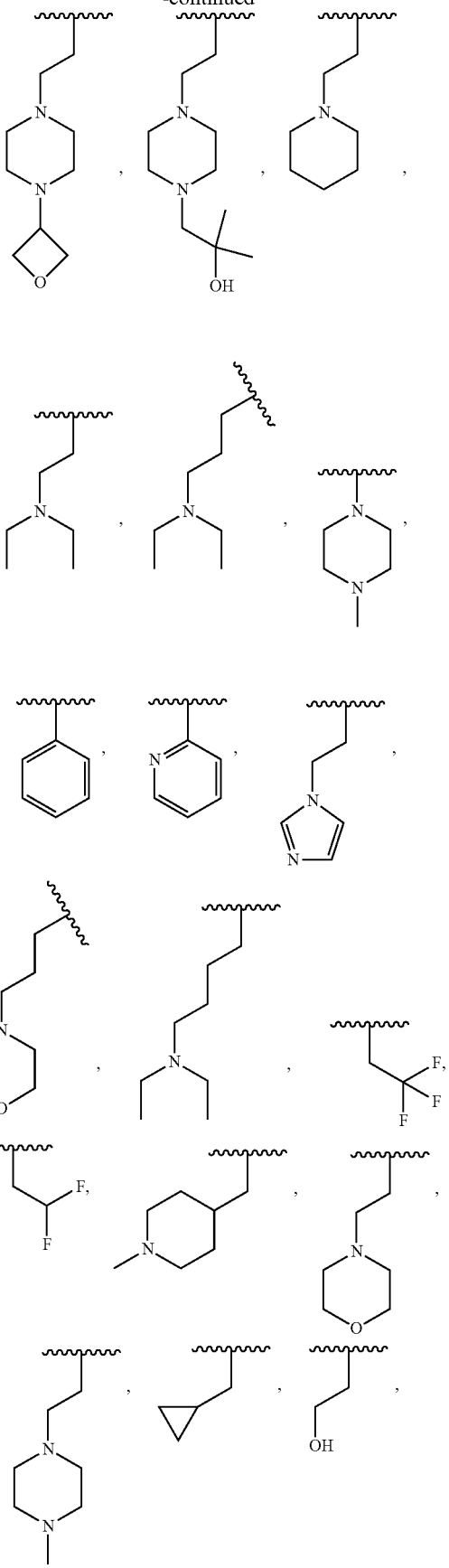

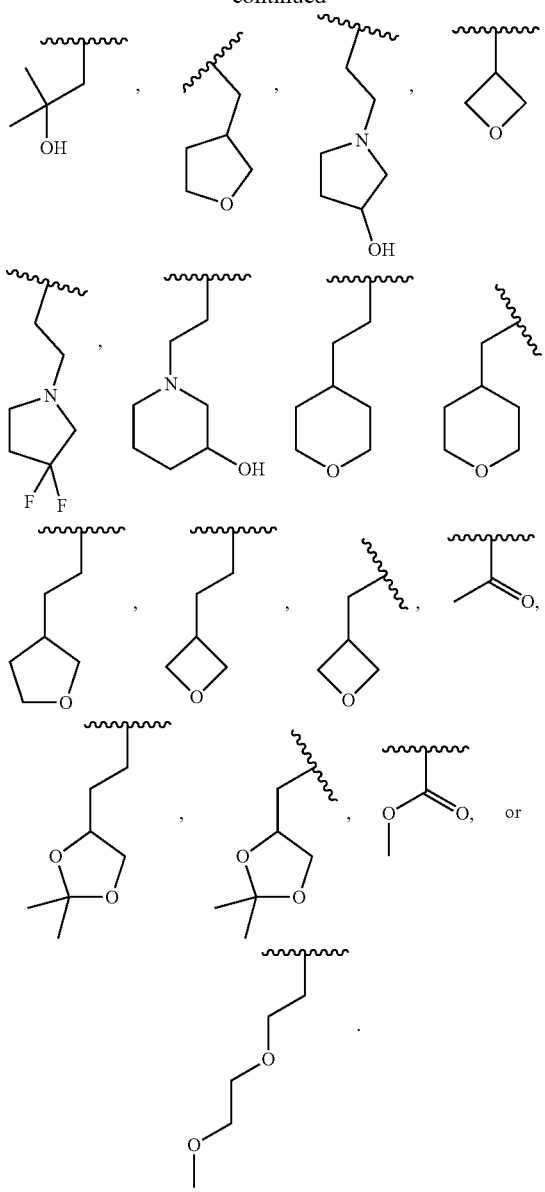

28. The compound of any one of embodiments 2 to 22 or a pharmaceutically acceptable salt thereof wherein R² is:

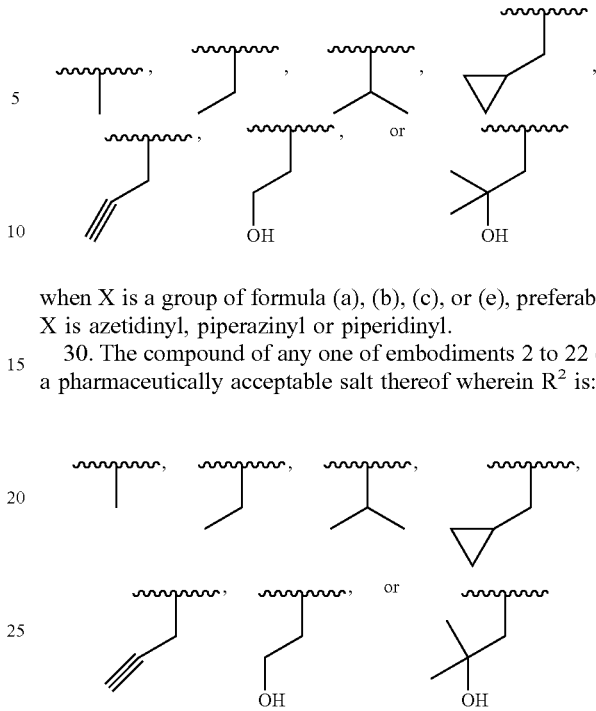

when X is Ar¹ or Ar² where Ar¹ and Ar² are independently phenylene or 5- or 6-membered heteroarylene.

29. The compound of any one of embodiments 2 to 22 or a pharmaceutically acceptable salt thereof wherein R² is:

when X is a group of formula (a), (b), (c), or (e), preferably X is azetidinyl, piperazinyl or piperidinyl.

30. The compound of any one of embodiments 2 to 22 or a pharmaceutically acceptable salt thereof wherein R² is:

when X is piperazinyl or piperidinyl.

31. The compound of any one of embodiments 1 to 30 or a pharmaceutically acceptable salt thereof wherein Y is —CO— and $R^b$ is hydrogen.

32. The compound of any of the embodiments 1 to 30 or a pharmaceutically acceptable salt thereof where $R^c$ and $R^d$ are hydrogen.

33. The compound of any of embodiment 1 to 30 or a pharmaceutically acceptable salt thereof where $R^c$ is alkyl and $R^d$ is hydrogen.

34. The compound of any of embodiments 1 to 30 or a pharmaceutically acceptable salt thereof where $R^c$ is —CH₂NRR', where R is hydrogen, alkyl, hydroxyalkyl, alkoxyalkyl, or heterocyclyl optionally substituted with one or two groups independently selected from alkyl, hydroxyl, alkoxy, or halo and R' is hydrogen, alkyl, or cycloalkyl or R and R' together with the nitrogen atom to which they are attached form heterocycloamino and $R^d$ is hydrogen.

35. The compound of any of embodiments 1 to 30 or a pharmaceutically acceptable salt thereof wherein $R^d$ and $R^f$ and the hydrogen atom on carbon attached to group Y and Z respectively form a bond to give a triple bond.

36. A pharmaceutical composition comprising a compound of any of embodiment 1-35, and/or a pharmaceutically acceptable salt thereof; and a pharmaceutically acceptable excipient 37. A method of treating a disease treatable by inhibition of FGFR in a patient which method comprises administering to the patient in recognized need thereof, a pharmaceutical composition comprising a compound of any of embodiments 1-35 and/or a pharmaceutically acceptable salt thereof, and a pharmaceutically acceptable excipient.

38. The method of embodiment 37 wherein the disease is cancer and the compound and/or a salt thereof of embodiments 1-35 is optionally administered in combination with at least one other anticancer agent.

39. The method of embodiment 38 wherein the cancer is breast cancer, multiple myeloma, bladder cancer, endometrial cancer, gastric cancer, cervical cancer, rhabdomyosarcoma, lung cancer including squamous cell lung cancer, ovarian cancer, cholioangiosarcoma, glioma, or prostate cancers.

40. The method of embodiment 38 or 39 wherein the at least one other anticancer agent is selected from EGFR, MET, VEGFR, PI3K inhibitors, MTOR, MEK, Proteasome, or Ubiquitin Ligase inhibitors.

Embodiment (O)

In further embodiments 41-86 below, the present disclosure includes:

41. A compound of Formula (III):

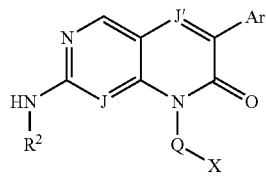

(III)

wherein:

J is N or CH;

J' is N or $CR^1$ where $R^1$ is hydrogen, halo, alkyl, or cycloalkyl;

Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;

$R^2$ is hydrogen, alkyl, alkynyl, acyl, alkoxycarbonyl, haloalkyl, cycloalkyl optionally substituted with amino, alkylamino, dialkylamino, or hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, alkoxy, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, hydroxy, alkoxy, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and (i) Q is alkylene or substituted alkylene; and X is a group of formula (a), (b), (c), or (h):

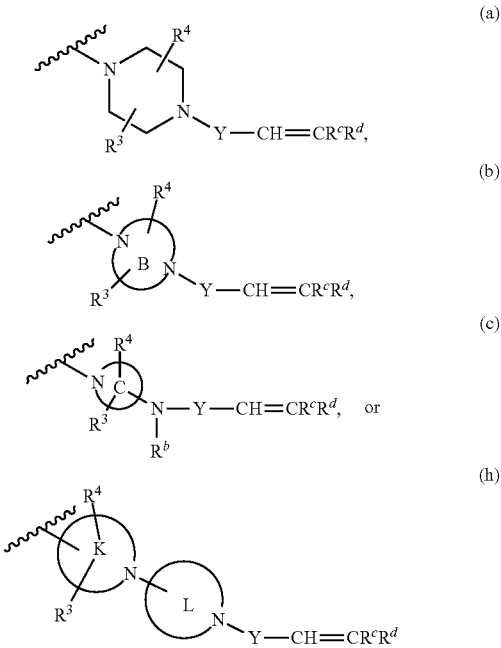

wherein:

ring B is aza bridged heterocycloamino or aza spiroheterocycloamino;

ring C is azetidinyl, pyrrolidinyl, piperidinyl, bridged heterocycloamino, or spiro heterocycloamino;

rings K and L are independently azetidinyl, pyrrolidinyl, piperidinyl, or homopiperidinyl;

each $R^3$ is hydrogen, alkyl, haloalkyl, hydroxy, alkoxy, or halo; and each $R^4$ is hydrogen, alkyl, hydroxy, alkoxy, or halo; or (ii) Q is heteroalkylene, substituted heteroalkylene, or aminoheteroalkylene, and X is a group of formula (d) or (e):

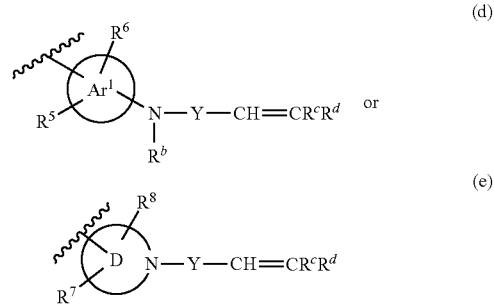

wherein:

$Ar^1$ is 5- or 6-membered cycloalkylene, phenylene, or 5- or 6-membered heteroarylene;

ring D is heterocycloamino, bridged heterocycloamino, or spiroheterocycloamino;

$R^5$ is hydrogen, alkyl, hydroxy, alkoxy, halo, haloalkyl, haloalkoxy, or cyano;

$R^6$ is hydrogen, alkyl, cycloalkyl, hydroxy, alkoxy, halo, haloalkyl, haloalkoxy, or cyano; and $R^7$ and $R^8$ are independently hydrogen, alkyl, hydroxy, alkoxy, or halo; or (iii) Q is -alkylene-cycloalkylene-alkylene-, and
X is a group of formula (f) or (g):

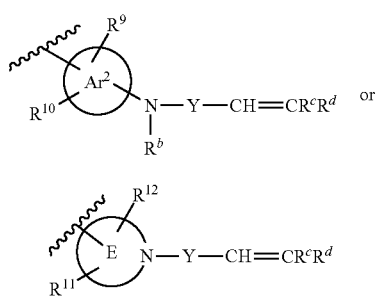

wherein:
$Ar^2$ is 5- or 6-membered cycloalkylene, phenylene, 5- or 6-membered heteroarylene, azetidinyl, pyrrolidinyl, or piperidinyl wherein the ring nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo;
each Y is —CO— or —SO$_2$—;
each $R^b$ is hydrogen or alkyl;
each $R^c$ is hydrogen, alkyl, or substituted alkyl; and
each $R^d$ is hydrogen or alkyl; or
each $R^d$ and the hydrogen atom on carbon attached to group Y can form a bond to give a triple bond

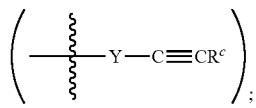

and/or a pharmaceutically acceptable salt thereof;
provided that: (1) when (i) $Ar^1$ is phenylene or 6-membered heteroarylene or (ii) $Ar^2$ is phenylene, 6-membered heteroarylene or piperidinyl or (iii) ring C is piperidinyl, then Q and —$NR^b$—Y—CH=$CR^cR^d$ are meta or para to each other; (2) when ring D or E is piperidinyl, then Q and —Y—CH=$CR^cR^d$ are meta or para to each other; (3) when ring D or E is piperazinyl, then Q and —Y—CH=$CR^cR^d$ are para to each other; and (4) when ring C, D, or E is pyrrolidinyl or azetidinyl, then Q and —$NR^b$—Y—CH=$CR^cR^d$ or Q and —Y—CH=$CR^cR^d$ are (1,3) to each other.

42. The compound of embodiment 41 or a pharmaceutically acceptable salt thereof wherein J is CH and J' is $CR^1$.

43. The compound of embodiment 41 or a pharmaceutically acceptable salt thereof wherein J is N and J' is $CR^1$.

44. The compound of embodiment 43 or a pharmaceutically acceptable salt thereof wherein:

$R^1$ is hydrogen, halo, or alkyl;
$R^2$ is hydrogen, alkyl, acyl, alkoxycarbonyl, alkynyl, haloalkyl, cycloalkyl substituted with amino, alkylamino, or dialkylamino, cycloalkylalkyl, hydroxyalkyl, alkoxyalkyl, alkoxyalkyloxyalkyl, aminoalkyl, heterocyclyl (wherein heterocyclyl is optionally substituted with one two, or three substituents independently selected from alkyl, hydroxy, halo, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl in aralkyl, heteroaryl ring in heteroaralkyl, phenyl, and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl); and (i) Q is alkylene; and
X is a group of formula (a), (b), or (c):

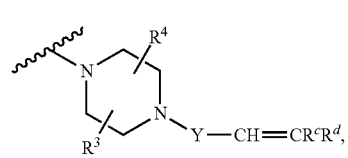

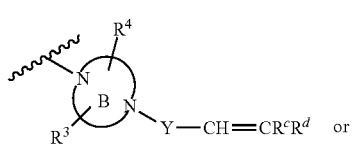

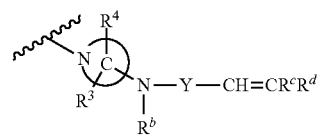

wherein:
ring B is a aza bridged heterocycloamino or aza spiroheterocycloamino;
ring C is azetidinyl-1-1, pyrrolidin-1-yl, piperidin-1-yl, bridged heterocycloamino, or spiro heterocycloamino wherein the nitrogen atom in aforementioned (a), (b) and (c) rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or (ii) Q is heteroalkylene, and
X is a group of formula (d) or (e):

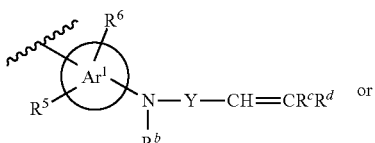 (d)

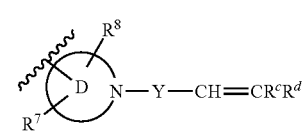 (e)

wherein:
Ar$^1$ is 5- or 6-membered cycloalkylene, phenylene, or 5- or 6-membered heteroarylene;
ring D is heterocycloamino, bridged heterocycloamino, or spiroheterocycloamino;
R$^5$ is hydrogen, alkyl, hydroxy, alkoxy, halo, haloalkyl, haloalkoxy, or cyano;
R$^6$ is hydrogen, alkyl, cycloalkyl, hydroxy, alkoxy, halo, haloalkyl, haloalkoxy, or cyano; and
R$^7$ and R$^8$ are independently hydrogen, alkyl, hydroxy, alkoxy, or halo; and (iii) Q is -alkylene-cycloalkylene-alkylene- and
X is a group of formula (f) or (g):

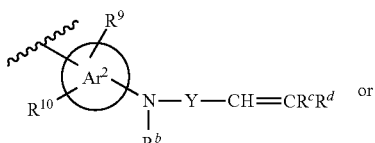 (f)

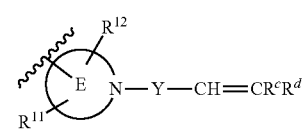 (g)

wherein:
Ar$^2$ is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
R$^9$ is hydrogen, alkyl, hydroxy, alkoxy, halo, haloalkyl, haloalkoxy, or cyano;
R$^{10}$ is hydrogen, alkyl, cycloalkyl, hydroxy, alkoxy, halo, haloalkyl, haloalkoxy, or cyano; and
R$^{11}$ and R$^{12}$ are independently hydrogen, alkyl, hydroxy, alkoxy, or halo;
each Y is —CO— or —SO$_2$—;
each R$^b$ is hydrogen or alkyl;
each R$^c$ is hydrogen, alkyl, or substituted alkyl; and
each R$^d$ is hydrogen or alkyl; or
each R$^d$ and the hydrogen atom on carbon attached to group Y can form a bond to give a triple bond.

45. The compound of any of embodiments 41-44 a pharmaceutically acceptable salt thereof wherein R$^1$ is hydrogen.

46. The compound of any of embodiments 41-44 or a pharmaceutically acceptable salt thereof wherein Ar is phenyl optionally substituted with one, two, three, or four substituents independently selected from alkyl, hydroxy, alkoxy, halo, haloalkyl, haloalkoxy, and cyano.

47. The compound of any of embodiments 41-44 or a pharmaceutically acceptable salt thereof wherein Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl 48. The compound of any of embodiments 41-44 or a pharmaceutically acceptable salt thereof wherein Ar is 2-chloro-3,5-dimethoxy-phenyl, 3,5-dimethoxyphenyl, 2-chlorophenyl, or 2,6-dichloro-3,5-dimethoxyphenyl.

49. The compound of any of embodiments 41-44 or a pharmaceutically acceptable salt thereof wherein Ar is heteroaryl ring optionally substituted with one, two, or three substituents independently selected from alkyl, hydroxy, alkoxy, halo, haloalkyl, haloalkoxy, or cyano.

50. The compound of any one of embodiments 42 to 49 or a pharmaceutically acceptable salt thereof wherein Q is alkylene and X is a group of formula (a).

51. The compound of any one of embodiments 42 to 49 or a pharmaceutically acceptable salt thereof wherein Q is n-propylene and X is a group of formula (a).

52. The compound of embodiment 50 or a pharmaceutically acceptable salt thereof wherein

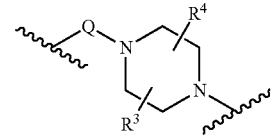

in -Q-X of formula

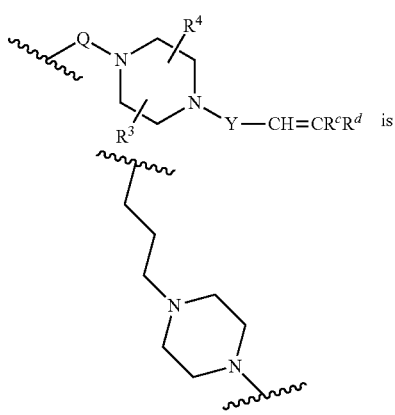 is

53. The compound of any one of embodiments 42 to 49 or a pharmaceutically acceptable salt thereof wherein Q is alkylene and X is a group of formula (c).

54. The compound of any one of embodiments 42 to 49 or a pharmaceutically acceptable salt thereof wherein Q is heteroalkylene.

55. The compound of embodiments embodiment 44 or a pharmaceutically acceptable salt thereof wherein Q is —(CH$_2$)$_2$—O— and X is a ring of formula (d) where Ar$^1$ is phenylene, 5- or 6-membered heteroarylene or a ring of formula (e) where ring D is azetidinyl, pyrrolidinyl, or piperidinyl.

56. The compound of embodiment 45 or a pharmaceutically acceptable salt thereof wherein

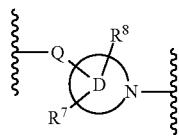

in -Q-X of formula

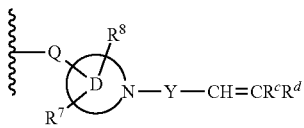

is:

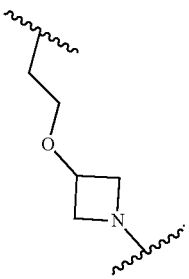

57. The compound of embodiment 54 or a pharmaceutically acceptable salt thereof wherein X is a ring of formula (e) where

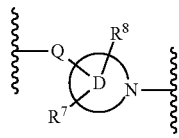

in -Q-X of formula

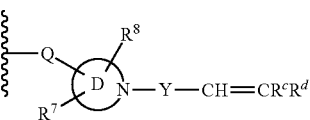

is:

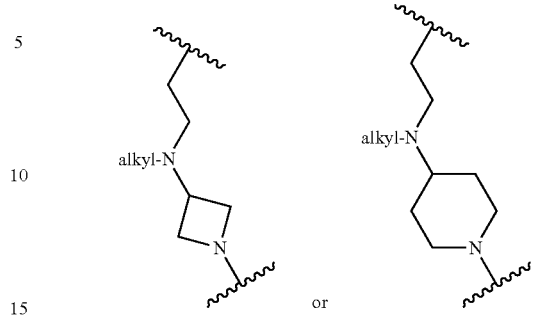

58. The compound of any one of embodiments 41-43, and 45 to 49 or a pharmaceutically acceptable salt thereof wherein Q is a alkylene and X is a group of formula (h).

59. The compound of embodiment 58 or a pharmaceutically acceptable salt thereof wherein -Q-X— is

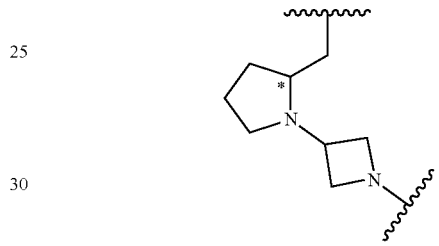

where *C is (R) or (S) or a mixture thereof.

60. The compound of any one of embodiments 41-43 and 45 to 49 or a pharmaceutically acceptable salt thereof wherein Q is a aminoheteroalkylene and X is a group of formula (e).

61. The compound of embodiment 60 or a pharmaceutically acceptable salt thereof wherein -Q-X— is

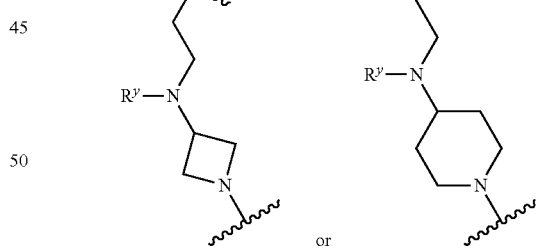

where $R^y$ is hydroxyalkyl, alkoxyalkyl, alkoxyalkyloxyalkyl, or -(alkylene)-NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo).

62. The compound of embodiment 61 or a pharmaceutically acceptable salt thereof wherein $R^y$ is hydroxyalkyl, alkoxyalkyl, or aminoalkyl, preferably $R^y$ is 2-hydroxyethyl or 2-alkoxyethyl.

63. The compound of any one of embodiments 41 to 62 or a pharmaceutically acceptable salt thereof wherein $R^2$ is hydrogen, alkyl, alkynyl, acyl, alkoxycarbonyl, haloalkyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl and heteroaryl in aralkyl, heteroaralkyl, phenyl, and heteroaryl are optionally substituted with one, two, or three substituents where two substituents are independently selected from alkyl, hydroxy, alkoxy, halo, haloalkyl, haloalkoxy, or cyano and the third substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

64. The compound of any one of embodiments 42 to 62 or a pharmaceutically acceptable salt thereof wherein $R^2$ is alkyl, cycloalkylalkyl, aminoalkyl, hydroxyalkyl, alkoxyalkyloxyalkyl, or heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl).

65. The compound of any one of embodiments 42 to 62 or a pharmaceutically acceptable salt thereof wherein $R^2$ is hydrogen, alkyl, acyl, alkoxyalkyl, or alkoxyalkyloxyalkyl.

66. The compound of any one of embodiments 42 to 62 or a pharmaceutically acceptable salt thereof wherein $R^2$ is hydrogen, methylcarbonyl, methoxyethyloxyethyl, or —*CH(CH$_3$)CH$_2$—OCH$_3$ where the stereochemistry at *C is (R) or (S).

67. The compound of any one of embodiments 41 to 66 or a pharmaceutically acceptable salt thereof wherein Y is —CO— and $R^b$ is hydrogen.

68. The compound of any of embodiments 41 to 67 or a pharmaceutically acceptable salt thereof where Y is —CO— and $R^c$ and $R^d$ are hydrogen.

69. The compound of any of the embodiments 41 to 67 or a pharmaceutically acceptable salt thereof where Y is —CO—, $R^c$ is alkyl and $R^d$ is hydrogen.

70. The compound of any of embodiments 41 to 67 or a pharmaceutically acceptable salt thereof where Y is —CO—, $R^c$ is —CH$_2$NRR', where R is hydrogen, alkyl, hydroxyalkyl, alkoxyalkyl, or heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino and $R^d$ is hydrogen.

71. The compound of any of embodiments 41 to 67 or a pharmaceutically acceptable salt thereof wherein $R^d$ and the hydrogen atom on carbon attached to group Y form a bond to give a triple bond.

72. A compound selected from 8-(3-(4-acryloylpiperazin-1-yl)propyl)-2-amino-6-(2,6-dichloro-3,5-dimethoxyphenyl)pyrido[2,3-d]pyrimidin-7(8H)-one and/or a pharmaceutically acceptable salt thereof.

73. A compound selected from 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one and/or a pharmaceutically acceptable salt thereof.

74. A compound selected from:
8-(2-((1-acryloylazetidin-3-yl)(2-methoxyethyl)amino)-ethyl)-6-(2,6-dichloro-3,5-dimethoxyphenyl)-2-(methylamino)pyrido[2,3-d]pyrimidin-7(8H)-one;
8-(2-((1-acryloylazetidin-3-yl)(methyl)amino)ethyl)-6-(2,6-dichloro-3,5-dimethoxy-phenyl)-2-(methylamino)pyrido[2,3-d]pyrimidin-7(8H)-one; or
8-(2-((1-acryloylazetidin-3-yl)(ethyl)amino)ethyl)-6-(2,6-dichloro-3,5-dimethoxyphenyl)-2-(methylamino)pyrido[2,3-d]pyrimidin-7(8H)-one;
and/or a pharmaceutically acceptable salt thereof.

75. A compound selected from (R)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one or (S)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one;
or an R or S mixture of 8-((1-(1-acryloylazetidin-3-yl) pyrrolidin-2-yl)methyl)-6-(2,6-dichloro-3,5-dimethoxyphenyl)-2-(methylamino)pyrido[2,3-d]pyrimidin-7(8H)-one; and/or a pharmaceutically acceptable salt thereof.

76. A compound selected from 8-(2-((1-acryloylpiperidin-4-yl)(methyl)amino)ethyl)-6-(2,6-dichloro-3,5-dimethoxyphenyl)-2-(methylamino)pyrido[2,3-d]pyrimidin-7(8H)-one and/or a pharmaceutically acceptable salt thereof.

77. A compound selected from (S)-8-(2-((1-acryloylazetidin-3-yl)(methyl)amino)-ethyl)-6-(2,6-dichloro-3,5-dimethoxyphenyl)-2-((1-methoxypropan-2-yl)amino)pyrido[2,3-d]pyrimidin-7(8H)-one or 8-(2-((1-acryloylazetidin-3-yl)(2-methoxyethyl)amino)ethyl)-6-(2,6-dichloro-3,5-dimethoxyphenyl)-2-(ethylamino)pyrido[2,3-d]pyrimidin-7(8H)-one; and/or a pharmaceutically acceptable salt thereof.

78. A pharmaceutical composition comprising a compound of any of the embodiments 41-77, and/or a pharmaceutically acceptable salt thereof; and a pharmaceutically acceptable excipient 79. A method of treating a disease treatable by inhibition of FGFR in a patient which method comprises administering to the patient in recognized need thereof, a pharmaceutical composition comprising a compound of any of the embodiments 41-77 and/or a pharmaceutically acceptable salt thereof, and a pharmaceutically acceptable excipient.

80. The method of Claim 79 wherein the disease is cancer and the compound and/or a salt thereof of embodiments 41-77 is optionally administered in combination with at least one other anticancer agent.

81. The method of embodiment 80 wherein the cancer is breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholangiosarcoma, glioma, cholangiocarcinoma, 8,11 myeloproliferative syndrome, myeloproliferative disorders involving FGFR translocations/fusions, alveolar rhabdomyosarcoma, malignant rhabdoid tumors, glioblastoma, muscle invasive bladder or renal cancer or prostate cancers.

82. The method of embodiments 80 or 81 wherein the at least one other anticancer agent is selected from EGFR, MET, VEGFR, PI3K, MTOR, MEK, Proteasome, or Ubiquitin Ligase inhibitors.

83. An intermediate of Formula (II):

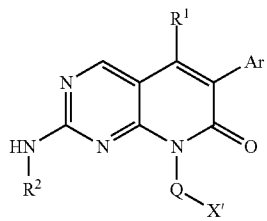

(II)

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, or cyano;
$R^1$ is hydrogen, halo, alkyl, or cycloalkyl;
$R^2$ is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxy, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl, and heteroaryl are optionally substituted with one, two, or three substituents where two of the optional substituents are independently selected from alkyl, hydroxy, alkoxy, halo, haloalkyl, haloalkoxy, and cyano and the one of the optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and (i) Q is alkylene; and
X' is a group of formula (a'), (b'), or (c'):

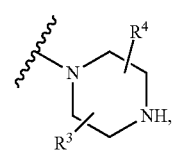

(a')

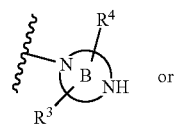

(b')

or

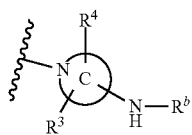

(c')

wherein:
ring B is a aza bridged heterocycloamino or aza spiroheterocycloamino;
ring C is azetidinyl, pyrrolidinyl, piperidinyl, bridged heterocycloamino, or spiro heterocycloamino wherein the nitrogen atom in aforementioned (a'), (b'), and (c') rings is attached to the Q group;
each $R^3$ is hydrogen, alkyl, haloalkyl, hydroxy, alkoxy, or halo; and
each $R^4$ is hydrogen, alkyl, hydroxy, alkoxy, or halo; or (ii) Q is heteroalkylene, and
X' is a group of formula (d') or (e'):

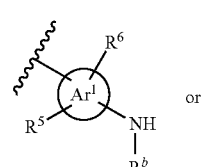

(d')

or

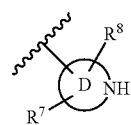

(e')

wherein:
$Ar^1$ is 5- or 6-membered cycloalkylene, phenylene, 5- or 6-membered heteroarylene;
ring D is heterocycloamino, bridged heterocycloamino, or spiroheterocycloamino;
$R^5$ is hydrogen, alkyl, hydroxy, alkoxy, halo, haloalkyl, haloalkoxy, or cyano;
$R^6$ is hydrogen, alkyl, cycloalkyl, hydroxy, alkoxy, halo, haloalkyl, haloalkoxy, or cyano; and
$R^7$ and $R^8$ are independently hydrogen, alkyl, hydroxy, alkoxy, or halo; or (iii) Q is -alkylene-cycloalkylene-alkylene-, and
X' is a group of formula (f') or (g'):

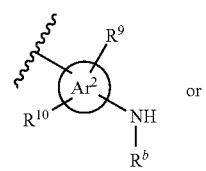

(f')

or

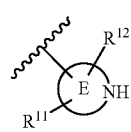

(g')

wherein:
Ar² is 5- or 6-membered cycloalkylene, phenylene, 5- or 6-membered heteroarylene, azetidinyl, pyrrolidinyl, or piperidinyl wherein the nitrogen atom in azetidinyl, pyrrolidinyl, or piperidinyl is attached to the Q group;
ring E is heterocycloamino, bridged heterocycloamino, or spiroheterocycloamino;
$R^9$ is hydrogen, alkyl, hydroxy, alkoxy, halo, haloalkyl, haloalkoxy, or cyano;
$R^{10}$ is hydrogen, alkyl, cycloalkyl, hydroxy, alkoxy, halo, haloalkyl, haloalkoxy, or cyano; and
$R^{11}$ and $R^{12}$ are independently hydrogen, alkyl, hydroxy, alkoxy, or halo; and
$R^b$ is hydrogen or alkyl;
and/or a salt thereof,
provided that: (1) when (i) Ar¹ is phenylene or 6-membered heteroarylene or (ii) Ar² is phenylene, 6-membered heteroarylene or piperidin-1-yl or (iii) ring C is piperidinyl, then Q and —NHR$^b$ in piperidinyl ring are meta or para to each other; (2) when ring C, D, or E is piperidinyl, then Q and the NH group in the piperidinyl ring are meta or para to each other; (3) when ring E is piperazinyl, then Q and the NH group in the piperazinyl ring are para to each other; and (4) when ring C, D, or E is pyrrolidinyl or azetidinyl, then Q and the NH group in the pyrrolidinyl and azetidinyl rings are (1,3) to each other.

84. The intermediate of embodiment 83 wherein R¹ is hydrogen, R² is hydrogen, alkyl, acyl, alkoxyalkyloxyalkyl, or alkoxyalkyl, (preferably R² is hydrogen, methyl, methylcarbonyl, methoxyethyloxyethyl, or —*CH(CH₃)CH₂—OCH₃ where the stereochemistry at *C is (R) or (S)), Ar is 2-chloro-3,5-dimethoxyphenyl or 2,6-dichloro-3,5-dimethoxyphenyl, and -Q-X' is

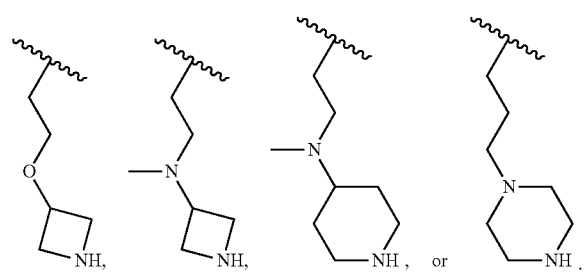

85. A process of making a compound of embodiment 44 comprising reacting a compound of formula (II):

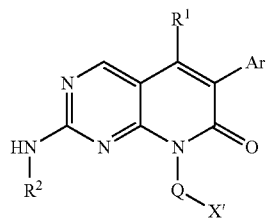

where:
R¹ is hydrogen, alkyl, or halo;
R² is hydrogen, alkyl, alkynyl, acyl, alkoxycarbonyl, haloalkyl, cycloalkyl substituted with amino, alkylamino, or dialkylamino, cycloalkylalkyl, hydroxyalkyl, alkoxyalkyl, alkoxyalkyloxy, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl, and heteroaryl are optionally substituted with one, two, or three substituents where two of the optional substituents are independently selected from alkyl, hydroxy, alkoxy, halo, haloalkyl, haloalkoxy, and cyano and the one of the optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and
Ar, Q, and X' are as defined in the compound of Formula (II) in embodiment 83 above;
(i) with a compound of formula R$^c$R$^d$C=CHYLG or R$^c$C=CYLG where Y is —CO— or —SO₂— and R$^c$ and R$^d$ are as defined in embodiment 44 above and LG is a leaving group under acylating reaction conditions; or
(ii) with a compound of formula R$^c$R$^d$C=CHCOOH where R$^c$ and R$^d$ are as defined in embodiment 4 above under amino acid reaction conditions to give a compound of embodiment 4 where Y is —CO—;
(iii) optionally converting the compound obtained from step (i) or (ii) to an acid addition salt; or
(iv) optionally converting the compound obtained from step (i) or (ii) to the free base.

86. The process of embodiment 85 wherein the compound of Formula (II) is where R² is hydrogen, alkyl, acyl, alkoxyalkyloxyalkyl, or alkoxyalkyl, (preferably R² is hydrogen, methyl, acetyl, methoxyethyloxyethyl, or —*CH(CH₃)CH₂—OCH₃ where the stereochemistry at *C is (R) or (S)), Ar is 2-chloro-3,5-dimethoxyphenyl or 2,6-dichloro-3,5-dimethoxyphenyl, and -Q-X' is

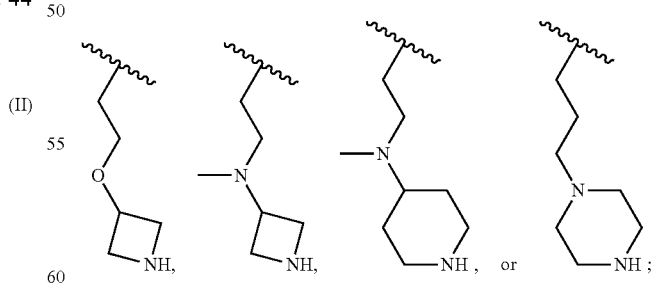

is reacted with
(i) with a compound of formula CH₂=CHCOLG where LG is a leaving group under acylating reaction conditions; or
(ii) with a compound of formula CH₂=CHCOOH under amino acid reaction conditions; to give a compound of embodiment 4 where R¹ is hydrogen, alkyl, acyl, alkoxyalkyloxyalkyl, or alkoxyalkyl, (preferably R² is hydrogen, methyl, methylcarbonyl, methoxyethyloxyethyl, or —*CH(CH₃)CH₂—OCH₃ where the stereochemistry at *C is (R) or (S)), Ar is 2-chloro-3,5-dimethoxyphenyl or 2,6-dichloro-3,5-dimethoxyphenyl, -Q-X' is

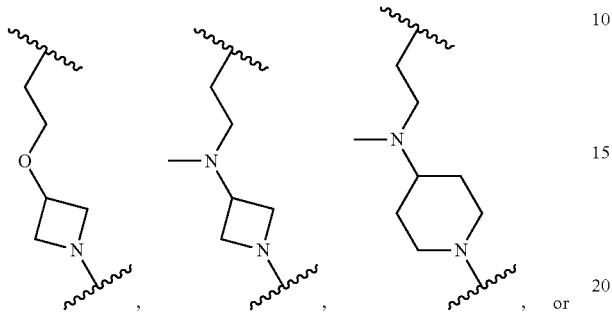

-continued

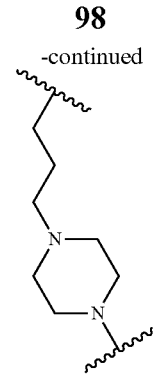

Y is CO and $R^c$ and $R^d$ are hydrogen;

(iii) optionally converting the compound obtained from step (i) or (ii) to an acid addition salt; or (iv) optionally converting the compound obtained from step (i) or (ii) to the free base.

Compounds of the disclosure made are disclosed in Table 1 below:

TABLE 1

| Cpd # | Names |
|---|---|
| 1 | 8-(2-(4-acryloylpiperazin-1-yl)ethyl)-6-(2-chloro-3,5-dimethoxyphenyl)-2-(methylamino)pyrido[2,3-d]pyrimidin-7(8H)-one; |
| 2 | 8-(2-(4-acryloylpiperazin-1-yl)ethyl)-6-(2,6-dichloro-3,5-dimethoxyphenyl)-2-(methylamino)pyrido[2,3-d]pyrimidin-7(8H)-one; |
| 3 | N-(1-(2-(6-(2-chloro-3,5-dimethoxyphenyl)-2-(methylamino)-7-oxopyrido[2,3-d]pyrimidin-8(7H)-yl)ethyl)piperidin-4-yl)acrylamide; |
| 4 | 8-(3-(4-acryloylpiperazin-1-yl)propyl)-6-(2-chloro-3,5-dimethoxyphenyl)-2-(methylamino)pyrido[2,3-d]pyrimidin-7(8H)-one; |
| 5 | 8-(2-((3aR,6aS)-5-acryloylhexahydropyrrolo[3,4-c]pyrrol-2(1H)-yl)ethyl)-6-(2-chloro-3,5-dimethoxyphenyl)-2-(methylamino)pyrido[2,3-d]pyrimidin-7(8H)-one; |
| 6 | 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one; |
| 7 | 8-(3-(4-acryloylpiperazin-1-yl)propyl)-2-((cyclopropylmethyl)amino)-6-(2,6-dichloro-3,5-dimethoxyphenyl)pyrido[2,3-d]pyrimidin-7(8H)-one; |
| 8 | 8-(2-((1-acryloylpiperidin-4-yl)oxy)ethyl)-6-(2,6-dichloro-3,5-dimethoxyphenyl)-2-((2-hydroxy-2-methylpropyl)amino)pyrido[2,3-d]pyrimidin-7(8H)-one; |
| 9 | 8-(2-((1-acryloylpiperidin-4-yl)oxy)ethyl)-6-(2,6-dichloro-3,5-dimethoxyphenyl)-2-(ethylamino)pyrido[2,3-d]pyrimidin-7(8H)-one; |
| 10 | 8-(2-((1-acryloylpiperidin-4-yl)oxy)ethyl)-2-((cyclopropylmethyl)amino)-6-(2,6-dichloro-3,5-dimethoxyphenyl)pyrido[2,3-d]pyrimidin-7(8H)-one; |
| 11 | 8-(3-(4-acryloylpiperazin-1-yl)propyl)-6-(2,6-dichloro-3,5-dimethoxyphenyl)-2-(ethylamino)pyrido[2,3-d]pyrimidin-7(8H)-one; |
| 12 | 8-(3-(4-acryloylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one; |
| 13 | 8-(3-(4-acryloylpiperazin-1-yl)propyl)-6-(2,6-dichloro-3,5-dimethoxyphenyl)-2-((2-hydroxyethyl)amino)pyrido[2,3-d]pyrimidin-7(8H)-one; |
| 14 | 8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one; |
| 15 | 8-(2-((1-acryloylpiperidin-3-yl)oxy)ethyl)-6-(2,6-dichloro-3,5-dimethoxyphenyl)-2-(methylamino)pyrido[2,3-d]pyrimidin-7(8H)-one; |
| 16 | 8-(3-(4-acryloylpiperazin-1-yl)propyl)-6-(2,6-dichloro-3,5-dimethoxyphenyl)-2-(isopropylamino)pyrido[2,3-d]pyrimidin-7(8H)-one; |
| 17 | 8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one; |
| 18 | 8-(3-(4-acryloylpiperazin-1-yl)propyl)-6-(2,6-dichloro-3,5-dimethoxyphenyl)-2-(prop-2-yn-1-ylamino)pyrido[2,3-d]pyrimidin-7(8H)-one; |
| 19 | 8-(3-(4-acryloylpiperazin-1-yl)propyl)-6-(2-chloro-3,5-dimethoxyphenyl)-2-((2-hydroxy-2-methylpropyl)amino)pyrido[2,3-d]pyrimidin-7(8H)-one; |
| 20 | 8-(3-(4-acryloylpiperazin-1-yl)propyl)-6-(2-chloro-3,5-dimethoxyphenyl)-2-(prop-2-yn-1-ylamino)pyrido[2,3-d]pyrimidin-7(8H)-one; |
| 21 | 8-(3-(4-acryloylpiperazin-1-yl)propyl)-2-((cyclopropylmethyl)amino)-6-(2-chloro-3,5-dimethoxyphenyl)pyrido[2,3-d]pyrimidin-7(8H)-one; |
| 22 | 8-(3-(4-acryloylpiperazin-1-yl)propyl)-6-(2-chloro-3,5-dimethoxyphenyl)-2-((2-hydroxyethyl)amino)pyrido[2,3-d]pyrimidin-7(8H)-one; |
| 23 | 8-(3-((2R,6S)-4-acryloyl-2,6-dimethylpiperazin-1-yl)propyl)-6-(2-chloro-3,5-dimethoxyphenyl)-2-(methylamino)pyrido[2,3-d]pyrimidin-7(8H)-one; |
| 24 | 8-(3-((3S,5R)-4-acryloyl-3,5-dimethylpiperazin-1-yl)propyl)-6-(2-chloro-3,5-dimethoxyphenyl)-2-(methylamino)pyrido[2,3-d]pyrimidin-7(8H)-one; |
| 25 | 8-(3-((3S,5R)-4-acryloyl-3,5-dimethylpiperazin-1-yl)propyl)-6-(2,6-dichloro-3,5-dimethoxyphenyl)-2-(methylamino)pyrido[2,3-d]pyrimidin-7(8H)-one; |

TABLE 1-continued

| Cpd # | Names |
|---|---|
| 26 | 8-(3-(4-acryloylpiperazin-1-yl)propyl)-6-(2-chloro-3,5-dimethoxyphenyl)-2-(phenylamino)pyrido[2,3-d]pyrimidin-7(8H)-one; |
| 27 | 8-((1-((4-acryloylpiperazin-1-yl)methyl)cyclopropyl)methyl)-6-(2,6-dichloro-3,5-dimethoxyphenyl)-2-(methylamino)pyrido[2,3-d]pyrimidin-7(8H)-one; |
| 28 | 8-((1-((4-acryloylpiperazin-1-yl)methyl)cyclopropyl)methyl)-6-(2-chloro-3,5-dimethoxyphenyl)-2-(methylamino)pyrido[2,3-d]pyrimidin-7(8H)-one; |
| 29 | 8-(3-((2R,6S)-4-acryloyl-2,6-dimethylpiperazin-1-yl)propyl)-6-(2,6-dichloro-3,5-dimethoxyphenyl)-2-(methylamino)pyrido[2,3-d]pyrimidin-7(8H)-one; |
| 30 | 8-(3-(4-acryloylpiperazin-1-yl)-2,2-dimethylpropyl)-6-(2,6-dichloro-3,5-dimethoxyphenyl)-2-(methylamino)pyrido[2,3-d]pyrimidin-7(8H)-one; |
| 31 | 8-(3-(4-acryloylpiperazin-1-yl)-2,2-dimethylpropyl)-6-(2-chloro-3,5-dimethoxyphenyl)-2-(methylamino)pyrido[2,3-d]pyrimidin-7(8H)-one; |
| 32 | 8-(3-(4-acryloylpiperazin-1-yl)propyl)-6-(2,6-dichloro-3,5-dimethoxyphenyl)-2-(phenylamino)pyrido[2,3-d]pyrimidin-7(8H)-one; |
| 33 | 8-(3-(4-acryloylpiperazin-1-yl)propyl)-6-(2,6-dichloro-3,5-dimethoxyphenyl)-2-(pyridin-2-ylamino)pyrido[2,3-d]pyrimidin-7(8H)-one; |
| 34 | 8-(3-(4-acryloylpiperazin-1-yl)propyl)-6-(2-chloro-3,5-dimethoxyphenyl)-2-(pyridin-2-ylamino)pyrido[2,3-d]pyrimidin-7(8H)-one; |
| 35 | 8-(3-(4-acryloylpiperazin-1-yl)propyl)-6-(2-chloro-3,5-dimethoxyphenyl)-2-((2,2-difluoroethyl)amino)pyrido[2,3-d]pyrimidin-7(8H)-one; |
| 36 | 8-(3-(4-acryloylpiperazin-1-yl)propyl)-6-(2-chloro-3,5-dimethoxyphenyl)-2-((tetrahydro-2H-pyran-4-yl)amino)pyrido[2,3-d]pyrimidin-7(8H)-one; |
| 37 | 8-(3-(4-acryloylpiperazin-1-yl)propyl)-6-(2,6-dichloro-3,5-dimethoxyphenyl)-2-((tetrahydro-2H-pyran-4-yl)amino)pyrido[2,3-d]pyrimidin-7(8H)-one; |
| 38 | (S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one; |
| 39 | 8-(3-(4-acryloylpiperazin-1-yl)propyl)-6-(2-chloro-3,5-dimethoxyphenyl)-2-((2-isopropoxyethyl)amino)pyrido[2,3-d]pyrimidin-7(8H)-one; |
| 40 | 8-(3-(4-acryloylpiperazin-1-yl)propyl)-6-(2-chloro-3,5-dimethoxyphenyl)-2-(((tetrahydrofuran-2-yl)methyl)amino)pyrido[2,3-d]pyrimidin-7(8H)-one; |
| 41 | (R)-8-(3-(4-acryloylpiperazin-1-yl)propyl)-6-(2-chloro-3,5-dimethoxyphenyl)-2-((tetrahydrofuran-3-yl)amino)pyrido[2,3-d]pyrimidin-7(8H)-one; |
| 42 | (S)-8-(3-(4-acryloylpiperazin-1-yl)propyl)-6-(2-chloro-3,5-dimethoxyphenyl)-2-((1-methoxypropan-2-yl)amino)pyrido[2,3-d]pyrimidin-7(8H)-one; |
| 43 | 8-(3-(4-acryloylpiperazin-1-yl)propyl)-6-(2-chloro-3,5-dimethoxyphenyl)-2-((2-morpholinoethyl)amino)pyrido[2,3-d]pyrimidin-7(8H)-one; |
| 44 | 8-(3-(4-acryloylpiperazin-1-yl)propyl)-6-(2,6-dichloro-3,5-dimethoxyphenyl)-2-((2,2-difluoroethyl)amino)pyrido[2,3-d]pyrimidin-7(8H)-one; |
| 45 | 8-(3-(4-acryloylpiperazin-1-yl)propyl)-6-(2,6-dichloro-3,5-dimethoxyphenyl)-2-((2-methoxyethyl)amino)pyrido[2,3-d]pyrimidin-7(8H)-one; |
| 46 | 8-(3-(4-acryloylpiperazin-1-yl)propyl)-6-(2,6-dichloro-3,5-dimethoxyphenyl)-2-((2-isopropoxyethyl)amino)pyrido[2,3-d]pyrimidin-7(8H)-one; |
| 47 | 8-(3-(4-acryloylpiperazin-1-yl)propyl)-6-(2-chloro-3,5-dimethoxyphenyl)-2-((2,2,2-trifluoroethyl)amino)pyrido[2,3-d]pyrimidin-7(8H)-one; |
| 48 | 8-(3-(4-acryloylpiperazin-1-yl)propyl)-6-(2-chloro-3,5-dimethoxyphenyl)-2-((2-methoxyethyl)amino)pyrido[2,3-d]pyrimidin-7(8H)-one; |
| 49 | 8-(3-(4-acryloylpiperazin-1-yl)propyl)-6-(2-chloro-3,5-dimethoxyphenyl)-2-((2-ethoxyethyl)amino)pyrido[2,3-d]pyrimidin-7(8H)-one; |
| 50 | 8-(3-(4-acryloylpiperazin-1-yl)propyl)-6-(2-chloro-3,5-dimethoxyphenyl)-2-((1,3-dimethoxypropan-2-yl)amino)pyrido[2,3-d]pyrimidin-7(8H)-one; |
| 51 | (S)-8-(3-(4-acryloylpiperazin-1-yl)propyl)-6-(2-chloro-3,5-dimethoxyphenyl)-2-((tetrahydrofuran-3-yl)amino)pyrido[2,3-d]pyrimidin-7(8H)-one; |
| 52 | 8-(3-(4-acryloylpiperazin-1-yl)propyl)-6-(2-chloro-3,5-dimethoxyphenyl)-2-(((tetrahydro-2H-pyran-4-yl)methyl)amino)pyrido[2,3-d]pyrimidin-7(8H)-one; |
| 53 | 8-(3-(4-acryloylpiperazin-1-yl)propyl)-6-(2,6-dichloro-3,5-dimethoxyphenyl)-2-((2-ethoxyethyl)amino)pyrido[2,3-d]pyrimidin-7(8H)-one; |
| 54 | 8-(3-(4-acryloylpiperazin-1-yl)propyl)-6-(2,6-dichloro-3,5-dimethoxyphenyl)-2-(((tetrahydro-2H-pyran-4-yl)methyl)amino)pyrido[2,3-d]pyrimidin-7(8H)-one; |
| 55 | 8-(3-(4-acryloylpiperazin-1-yl)propyl)-6-(2,6-dichloro-3,5-dimethoxyphenyl)-2-((2,2,2-trifluoroethyl)amino)pyrido[2,3-d]pyrimidin-7(8H)-one; |
| 56 | (R)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one; |
| 57 | 8-(3-(4-acryloylpiperazin-1-yl)propyl)-6-(2,6-dichloro-3,5-dimethoxyphenyl)-2-((1,3-dimethoxypropan-2-yl)amino)pyrido[2,3-d]pyrimidin-7(8H)-one; |
| 58 | (S)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one; |
| 59 | 8-(3-(4-acryloylpiperazin-1-yl)propyl)-6-(2,6-dichloro-3,5-dimethoxyphenyl)-2-(((tetrahydrofuran-2-yl)methyl)amino)pyrido[2,3-d]pyrimidin-7(8H)-one; |
| 60 | 8-(3-(4-acryloylpiperazin-1-yl)propyl)-6-(2,6-dichloro-3,5-dimethoxyphenyl)-2-((3-(2-oxopyrrolidin-1-yl)propyl)amino)pyrido[2,3-d]pyrimidin-7(8H)-one; |
| 61 | 8-(3-(4-acryloylpiperazin-1-yl)propyl)-2-amino-6-(2,6-dichloro-3,5-dimethoxyphenyl)pyrido[2,3-d]pyrimidin-7(8H)-one; |
| 62 | N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide; |
| 63 | 8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one; |
| 64 | 8-(3-(4-acryloylpiperazin-1-yl)propyl)-6-(2,6-dichloro-3,5-dimethoxyphenyl)-2-((((1r,4r)-4-hydroxycyclohexyl)amino)pyrido[2,3-d]pyrimidin-7(8H)-one; |

TABLE 1-continued

| Cpd # | Names |
|---|---|
| 65 | 8-(3-(4-acryloylpiperazin-1-yl)propyl)-6-(2,6-dichloro-3,5-dimethoxyphenyl)-2-((2-(2-oxopyrrolidin-1-yl)ethyl)amino)pyrido[2,3-d]pyrimidin-7(8H)-one; |
| 66 | 8-(3-(4-acryloylpiperazin-1-yl)propyl)-6-(2,6-dichloro-3,5-dimethoxyphenyl)-2-(oxetan-3-ylamino)pyrido[2,3-d]pyrimidin-7(8H)-one; |
| 67 | (R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one; |
| 68 | 8-(3-(4-acryloylpiperazin-1-yl)propyl)-6-(2-chloro-6-fluoro-3,5-dimethoxyphenyl)-2-(methylamino)pyrido[2,3-d]pyrimidin-7(8H)-one; |
| 69 | (E)-6-(2,6-dichloro-3,5-dimethoxyphenyl)-8-(2-((1-(4-(dimethylamino)but-2-enoyl)azetidin-3-yl)oxy)ethyl)-2-(methylamino)pyrido[2,3-d]pyrimidin-7(8H)-one; |
| 70 | 8-(2-((1-acryloylazetidin-3-yl)oxy)ethyl)-6-(2,6-dichloro-3,5-dimethoxyphenyl)-2-((2-morpholinoethyl)amino)pyrido[2,3-d]pyrimidin-7(8H)-one; |
| 71 | 8-(2-((1-acryloylazetidin-3-yl)oxy)ethyl)-6-(2-chloro-3,5-dimethoxyphenyl)-2-(methylamino)pyrido[2,3-d]pyrimidin-7(8H)-one; |
| 72 | 8-(2-((1-acryloylazetidin-3-yl)oxy)ethyl)-6-(2-chloro-3,5-dimethoxyphenyl)-2-((2-morpholinoethyl)amino)pyrido[2,3-d]pyrimidin-7(8H)-one; |
| 73 | (S)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one; |
| 74 | 8-(2-((1-acryloylazetidin-3-yl)oxy)ethyl)-6-(2,6-dichloro-3,5-dimethoxyphenyl)-2-((2-(4-methylpiperazin-1-yl)ethyl)amino)pyrido[2,3-d]pyrimidin-7(8H)-one; |
| 75 | (R)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one; |
| 76 | 8-(2-((1-acryloylazetidin-3-yl)oxy)ethyl)-2-amino-6-(2,6-dichloro-3,5-dimethoxyphenyl)pyrido[2,3-d]pyrimidin-7(8H)-one; |
| 77 | 8-(2-((1-acryloylazetidin-3-yl)oxy)ethyl)-6-(2,6-dichloro-3,5-dimethoxyphenyl)-2-((2-methoxyethyl)amino)pyrido[2,3-d]pyrimidin-7(8H)-one; |
| 78 | (S)-8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one; |
| 79 | (R)-8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one; |
| 80 | 8-(2-((1-acryloylazetidin-3-yl)(methyl)amino)ethyl)-6-(2,6-dichloro-3,5-dimethoxyphenyl)-2-(methylamino)pyrido[2,3-d]pyrimidin-7(8H)-one; |
| 81 | 8-(3-(4-acryloylpiperazin-1-yl)propyl)-6-(2-fluoro-3,5-dimethoxyphenyl)-2-(methylamino)pyrido[2,3-d]pyrimidin-7(8H)-one; |
| 82 | methyl (8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)carbamate; |
| 83 | (S)-8-(3-(4-acryloylpiperazin-1-yl)propyl)-6-(2,6-dichloro-3,5-dimethoxyphenyl)-2-((1-hydroxypropan-2-yl)amino)pyrido[2,3-d]pyrimidin-7(8H)-one; |
| 84 | 8-(3-(4-acryloylpiperazin-1-yl)propyl)-6-(2,6-difluoro-3,5-dimethoxyphenyl)-2-(methylamino)pyrido[2,3-d]pyrimidin-7(8H)-one; |
| 85 | (S)-8-(3-(4-acryloylpiperazin-1-yl)propyl)-6-(2,6-dichloro-3,5-dimethoxyphenyl)-2-((1-ethoxypropan-2-yl)amino)pyrido[2,3-d]pyrimidin-7(8H)-one; |
| 86 | (E)-8-(3-(4-(but-2-enoyl)piperazin-1-yl)propyl)-6-(2,6-dichloro-3,5-dimethoxyphenyl)-2-(methylamino)pyrido[2,3-d]pyrimidin-7(8H)-one; |
| 87 | (E)-2-amino-8-(3-(4-(but-2-enoyl)piperazin-1-yl)propyl)-6-(2,6-dichloro-3,5-dimethoxyphenyl)pyrido[2,3-d]pyrimidin-7(8H)-one; |
| 88 | methyl (8-(2-((1-acryloylazetidin-3-yl)oxy)ethyl)-6-(2,6-dichloro-3,5-dimethoxyphenyl)-7-oxo-7,8-dihydropyrido[2,3-d]pyrimidin-2-yl)carbamate; |
| 89 | 8-(2-((1-acryloyl-3-methylazetidin-3-yl)oxy)ethyl)-6-(2,6-dichloro-3,5-dimethoxyphenyl)-2-(methylamino)pyrido[2,3-d]pyrimidin-7(8H)-one; |
| 90 | (E)-8-(2-((1-(but-2-enoyl)azetidin-3-yl)oxy)ethyl)-6-(2,6-dichloro-3,5-dimethoxyphenyl)-2-(methylamino)pyrido[2,3-d]pyrimidin-7(8H)-one; |
| 91 | 8-(2-((1-acryloylazetidin-3-yl)oxy)ethyl)-6-(2,6-dichloro-3,5-dimethoxyphenyl)-2-((3-(4-ethylpiperazin-1-yl)propyl)amino)pyrido[2,3-d]pyrimidin-7(8H)-one; |
| 92 | 8-(2-((1-acryloylazetidin-3-yl)oxy)ethyl)-6-(2,6-dichloro-3,5-dimethoxyphenyl)-2-((2-(dimethylamino)ethyl)amino)pyrido[2,3-d]pyrimidin-7(8H)-one; |
| 93 | 8-(2-((1-acryloylazetidin-3-yl)oxy)ethyl)-6-(2,6-dichloro-3,5-dimethoxyphenyl)-2-((2-(pyrrolidin-1-yl)ethyl)amino)pyrido[2,3-d]pyrimidin-7(8H)-one; |
| 94 | 8-(2-((1-acryloylazetidin-3-yl)oxy)ethyl)-6-(2,6-dichloro-3,5-dimethoxyphenyl)-2-((2-(4-ethylpiperazin-1-yl)ethyl)amino)pyrido[2,3-d]pyrimidin-7(8H)-one; |
| 95 | 8-(2-((1-acryloylazetidin-3-yl)oxy)ethyl)-6-(2,6-dichloro-3,5-dimethoxyphenyl)-2-(((1-ethylpiperidin-4-yl)methyl)amino)pyrido[2,3-d]pyrimidin-7(8H)-one; |
| 96 | 8-(2-((1-acryloylazetidin-3-yl)oxy)ethyl)-6-(2,6-dichloro-3,5-dimethoxyphenyl)-2-((3-morpholinopropyl)amino)pyrido[2,3-d]pyrimidin-7(8H)-one; |
| 97 | 8-(2-((1-acryloylazetidin-3-yl)oxy)ethyl)-6-(2,6-dichloro-3,5-dimethoxyphenyl)-2-((3-(4-methylpiperazin-1-yl)propyl)amino)pyrido[2,3-d]pyrimidin-7(8H)-one; |
| 98 | 8-(2-((1-acryloylazetidin-3-yl)oxy)ethyl)-6-(2,6-dichloro-3,5-dimethoxyphenyl)-2-((1-methylpiperidin-4-yl)amino)pyrido[2,3-d]pyrimidin-7(8H)-one; |
| 99 | 8-(2-((1-acryloylazetidin-3-yl)oxy)ethyl)-6-(2,6-dichloro-3,5-dimethoxyphenyl)-2-((3-(pyrrolidin-1-yl)propyl)amino)pyrido[2,3-d]pyrimidin-7(8H)-one; |
| 100 | 8-(2-((1-acryloylazetidin-3-yl)oxy)ethyl)-6-(2,6-dichloro-3,5-dimethoxyphenyl)-2-((2-(diethylamino)ethyl)amino)pyrido[2,3-d]pyrimidin-7(8H)-one; |
| 101 | 8-(2-((1-acryloylazetidin-3-yl)oxy)ethyl)-6-(2,6-dichloro-3,5-dimethoxyphenyl)-2-((3-(diethylamino)propyl)amino)pyrido[2,3-d]pyrimidin-7(8H)-one; |
| 102 | 8-(2-((1-acryloylazetidin-3-yl)oxy)ethyl)-6-(2,6-dichloro-3,5-dimethoxyphenyl)-2-((2-(2-methoxyethoxy)ethyl)amino)pyrido[2,3-d]pyrimidin-7(8H)-one; |
| 103 | 8-(2-((1-acryloylazetidin-3-yl)oxy)ethyl)-6-(2,6-dichloro-3,5-dimethoxyphenyl)-2-((4-(diethylamino)butyl)amino)pyrido[2,3-d]pyrimidin-7(8H)-one; |

TABLE 1-continued

| Cpd # | Names |
|---|---|
| 104 | 8-(2-((1-acryloylazetidin-3-yl)oxy)ethyl)-6-(2,6-dichloro-3,5-dimethoxyphenyl)-2-((3-(dimethylamino)propyl)amino)pyrido[2,3-d]pyrimidin-7(8H)-one; |
| 105 | 8-(2-((1-acryloylazetidin-3-yl)oxy)ethyl)-6-(2,6-dichloro-3,5-dimethoxyphenyl)-2-(((1-methylpiperidin-4-yl)methyl)amino)pyrido[2,3-d]pyrimidin-7(8H)-one; |
| 106 | 8-(2-((1-acryloylazetidin-3-yl)oxy)ethyl)-2-amino-6-(2-chloro-3,5-dimethoxyphenyl)pyrido[2,3-d]pyrimidin-7(8H)-one; |
| 107 | 8-(2-((1-acryloylazetidin-3-yl)oxy)-2-methylpropyl)-6-(2-chloro-3,5-dimethoxyphenyl)-2-(methylamino)pyrido[2,3-d]pyrimidin-7(8H)-one; |
| 108 | 8-(2-((1-acryloylazetidin-3-yl)oxy)-2-methylpropyl)-6-(2,6-dichloro-3,5-dimethoxyphenyl)-2-(methylamino)pyrido[2,3-d]pyrimidin-7(8H)-one; |
| 109 | 8-(2-((1-acryloylazetidin-3-yl)oxy)ethyl)-6-(2,6-dichloro-3,5-dimethoxyphenyl)-2-(((1r,4r)-4-hydroxycyclohexyl)amino)pyrido[2,3-d]pyrimidin-7(8H)-one; |
| 110 | 8-(2-((1-acryloylazetidin-3-yl)(methyl)amino)ethyl)-6-(2,6-dichloro-3,5-dimethoxyphenyl)-2-(ethylamino)pyrido[2,3-d]pyrimidin-7(8H)-one; |
| 111 | 8-(2-((1-acryloylazetidin-3-yl)(ethyl)amino)ethyl)-6-(2,6-dichloro-3,5-dimethoxyphenyl)-2-(methylamino)pyrido[2,3-d]pyrimidin-7(8H)-one; |
| 112 | (R)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one; |
| 113 | (S)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one; |
| 114 | 8-(2-((1-acryloylazetidin-3-yl)(methyl)amino)ethyl)-2-amino-6-(2,6-dichloro-3,5-dimethoxyphenyl)pyrido[2,3-d]pyrimidin-7(8H)-one; |
| 115 | (E)-8-(2-((1-(but-2-enoyl)azetidin-3-yl)(methyl)amino)ethyl)-6-(2,6-dichloro-3,5-dimethoxyphenyl)-2-(methylamino)pyrido[2,3-d]pyrimidin-7(8H)-one; |
| 116 | (R)-8-(2-((1-acryloylazetidin-3-yl)(methyl)amino)ethyl)-6-(2,6-dichloro-3,5-dimethoxyphenyl)-2-((1-methoxypropan-2-yl)amino)pyrido[2,3-d]pyrimidin-7(8H)-one; |
| 117 | 8-(2-((1-acryloylazetidin-3-yl)amino)ethyl)-6-(2,6-dichloro-3,5-dimethoxyphenyl)-2-(methylamino)pyrido[2,3-d]pyrimidin-7(8H)-one; |
| 118 | (S)-8-(2-((1-acryloylazetidin-3-yl)(methyl)amino)ethyl)-6-(2,6-dichloro-3,5-dimethoxyphenyl)-2-((1-methoxypropan-2-yl)amino)pyrido[2,3-d]pyrimidin-7(8H)-one; |
| 119 | 8-(2-((1-acryloylazetidin-3-yl)(methyl)amino)ethyl)-6-(2,6-dichloro-3,5-dimethoxyphenyl)-2-((2-morpholinoethyl)amino)pyrido[2,3-d]pyrimidin-7(8H)-one; |
| 120 | 8-(2-((1-acryloylazetidin-3-yl)(2-methoxyethyl)amino)ethyl)-6-(2,6-dichloro-3,5-dimethoxyphenyl)-2-(methylamino)pyrido[2,3-d]pyrimidin-7(8H)-one; |
| 121 | 8-(2-((1-acryloylazetidin-3-yl)(2-methoxyethyl)amino)ethyl)-6-(2,6-dichloro-3,5-dimethoxyphenyl)-2-(ethylamino)pyrido[2,3-d]pyrimidin-7(8H)-one; |
| 122 | 8-(2-((1-acryloylazetidin-3-yl)(isopropyl)amino)ethyl)-6-(2,6-dichloro-3,5-dimethoxyphenyl)-2-(methylamino)pyrido[2,3-d]pyrimidin-7(8H)-one; |
| 123 | (S)-8-(2-((1-acryloylazetidin-3-yl)(methyl)amino)propyl)-6-(2,6-dichloro-3,5-dimethoxyphenyl)-2-(methylamino)pyrido[2,3-d]pyrimidin-7(8H)-one; |
| 124 | 8-(2-((1-acryloylazetidin-3-yl)(2-methoxyethyl)amino)ethyl)-2-amino-6-(2,6-dichloro-3,5-dimethoxyphenyl)pyrido[2,3-d]pyrimidin-7(8H)-one; |
| 125 | (R)-8-(2-((1-acryloylazetidin-3-yl)(methyl)amino)propyl)-6-(2,6-dichloro-3,5-dimethoxyphenyl)-2-(methylamino)pyrido[2,3-d]pyrimidin-7(8H)-one; |
| 126 | (S)-8-(2-((1-acryloylazetidin-3-yl)(methyl)amino)-3-methylbutyl)-6-(2,6-dichloro-3,5-dimethoxyphenyl)-2-(methylamino)pyrido[2,3-d]pyrimidin-7(8H)-one; |
| 127 | 8-(2-((1-acryloylpiperidin-4-yl)(methyl)amino)ethyl)-6-(2,6-dichloro-3,5-dimethoxyphenyl)-2-(methylamino)pyrido[2,3-d]pyrimidin-7(8H)-one; |
| 128 | 8-(2-((1-acryloylpiperidin-4-yl)(methyl)amino)ethyl)-2-amino-6-(2,6-dichloro-3,5-dimethoxyphenyl)pyrido[2,3-d]pyrimidin-7(8H)-one; |
| 129 | 8-(2-((1-acryloylpiperidin-4-yl)(methyl)amino)ethyl)-6-(2,6-dichloro-3,5-dimethoxyphenyl)-2-(ethylamino)pyrido[2,3-d]pyrimidin-7(8H)-one; |
| 130 | 8-(2-((1-acryloylpiperidin-4-yl)(methyl)amino)ethyl)-6-(2,6-dichloro-3,5-dimethoxyphenyl)-2-(isopropylamino)pyrido[2,3-d]pyrimidin-7(8H)-one; |
| 131 | 8-(2-((1-acryloylpiperidin-4-yl)(ethyl)amino)ethyl)-6-(2,6-dichloro-3,5-dimethoxyphenyl)-2-(methylamino)pyrido[2,3-d]pyrimidin-7(8H)-one; |
| 132 | 8-(2-((1-acryloylpiperidin-4-yl)(ethyl)amino)ethyl)-6-(2,6-dichloro-3,5-dimethoxyphenyl)-2-(ethylamino)pyrido[2,3-d]pyrimidin-7(8H)-one; |
| 133 | 8-(2-((1-acryloylpiperidin-4-yl)(ethyl)amino)ethyl)-6-(2,6-dichloro-3,5-dimethoxyphenyl)-2-(isopropylamino)pyrido[2,3-d]pyrimidin-7(8H)-one; |
| 134 | (R)-N-(1-(2-(6-(2,6-dichloro-3,5-dimethoxyphenyl)-2-(methylamino)-7-oxopyrido[2,3-d]pyrimidin-8(7H)-yl)ethyl)piperidin-3-yl)acrylamide; |
| 135 | (R)-N-(1-(2-(6-(2,6-dichloro-3,5-dimethoxyphenyl)-2-(ethylamino)-7-oxopyrido[2,3-d]-pyrimidin-8(7H)-yl)ethyl)piperidin-3-yl)acrylamide; |
| 136 | (S)-N-(1-(2-(6-(2,6-dichloro-3,5-dimethoxyphenyl)-2-(methylamino)-7-oxopyrido-[2,3-d]pyrimidin-8(7H)-yl)ethyl)piperidin-3-yl)acrylamide; |
| 137 | (S)-N-(1-(2-(6-(2,6-dichloro-3,5-dimethoxyphenyl)-2-(ethylamino)-7-oxopyrido[2,3-d]-pyrimidin-8(7H)-yl)ethyl)piperidin-3-yl)acrylamide; |
| 138 | (S)-N-(1-(2-(6-(2,6-dichloro-3,5-dimethoxyphenyl)-2-(methylamino)-7-oxopyrido[2,3-d]pyrimidin-8(7H)-yl)ethyl)pyrrolidin-3-yl)acrylamide; |
| 139 | (S)-N-(1-(2-(6-(2,6-dichloro-3,5-dimethoxyphenyl)-2-(ethylamino)-7-oxopyrido[2,3-d]-pyrimidin-8(7H)-yl)ethyl)pyrrolidin-3-yl)acrylamide; |
| 140 | (R)-N-(1-(2-(6-(2,6-dichloro-3,5-dimethoxyphenyl)-2-(methylamino)-7-oxopyrido[2,3-d]pyrimidin-8(7H)-yl)ethyl)pyrrolidin-3-yl)acrylamide; |
| 141 | (R)-N-(1-(2-(6-(2,6-dichloro-3,5-dimethoxyphenyl)-2-(ethylamino)-7-oxopyrido[2,3-d]pyrimidin-8(7H)-yl)ethyl)pyrrolidin-3-yl)acrylamide; |

TABLE 1-continued

| Cpd # | Names |
|---|---|
| 142 | 1-(3-(4-acryloylpiperazin-1-yl)propyl)-3-(2,6-dichloro-3,5-dimethoxyphenyl)-7-(methylamino)-1,6-naphthyridin-2(1H)-one; |
| 143 | (S)-1-(3-(4-acryloylpiperazin-1-yl)propyl)-3-(2,6-dichloro-3,5-dimethoxyphenyl)-7-((1-methoxypropan-2-yl)amino)-1,6-naphthyridin-2(1H)-one; |
| 144 | 1-(2-((1-acryloylazetidin-3-yl)oxy)ethyl)-3-(2,6-dichloro-3,5-dimethoxyphenyl)-7-(methylamino)-1,6-naphthyridin-2(1H)-one; |
| 145 | 1-(2-((1-acryloylazetidin-3-yl)oxy)ethyl)-3-(2,6-dichloro-3,5-dimethoxyphenyl)-7-((2-morpholinoethyl)amino)-1,6-naphthyridin-2(1H)-one; |
| 146 | (S)-1-(2-((1-acryloylazetidin-3-yl)oxy)ethyl)-3-(2,6-dichloro-3,5-dimethoxyphenyl)-7-((1-methoxypropan-2-yl)amino)-1,6-naphthyridin-2(1H)-one; |
| 147 | 1-(3-(4-acryloylpiperazin-1-yl)propyl)-3-(2,6-dichloro-3,5-dimethoxyphenyl)-7-(ethylamino)-1,6-naphthyridin-2(1H)-one; |
| 148 | 1-(3-(4-acryloylpiperazin-1-yl)propyl)-7-amino-3-(2,6-dichloro-3,5-dimethoxyphenyl)-1,6-naphthyridin-2(1H)-one; |
| 149 | 1-(3-(4-acryloylpiperazin-1-yl)propyl)-3-(2,6-dichloro-3,5-dimethoxyphenyl)-7-((2-methoxyethyl)amino)-1,6-naphthyridin-2(1H)-one; |
| 150 | 1-(3-(4-acryloylpiperazin-1-yl)propyl)-3-(2,6-dichloro-3,5-dimethoxyphenyl)-7-((2-(2-methoxyethoxy)ethyl)amino)-1,6-naphthyridin-2(1H)-one; |
| 151 | 1-(2-((1-acryloylazetidin-3-yl)(methyl)amino)ethyl)-3-(2,6-dichloro-3,5-dimethoxyphenyl)-7-(ethylamino)-1,6-naphthyridin-2(1H)-one; |
| 152 | 1-(2-((1-acryloylazetidin-3-yl)(ethyl)amino)ethyl)-3-(2,6-dichloro-3,5-dimethoxyphenyl)-7-(ethylamino)-1,6-naphthyridin-2(1H)-one; |
| 153 | 1-(2-((1-acryloylazetidin-3-yl)(2-methoxyethyl)amino)ethyl)-3-(2,6-dichloro-3,5-dimethoxyphenyl)-7-(methylamino)-1,6-naphthyridin-2(1H)-one; |
| 154 | (S)-N-(1-(3-(3-(2,6-dichloro-3,5-dimethoxyphenyl)-7-(methylamino)-2-oxo-1,6-naphthyridin-1(2H)-yl)propyl)pyrrolidin-3-yl)acrylamide; |
| 155 | 1-(2-((1-acryloylazetidin-3-yl)(2-methoxyethyl)amino)ethyl)-3-(2,6-dichloro-3,5-dimethoxyphenyl)-7-(ethylamino)-1,6-naphthyridin-2(1H)-one; |
| 156 | 1-(2-((1-acryloylpiperidin-4-yl)(methyl)amino)ethyl)-3-(2,6-dichloro-3,5-dimethoxyphenyl)-7-(methylamino)-1,6-naphthyridin-2(1H)-one; |
| 157 | 1-(2-((1-acryloylpiperidin-4-yl)(methyl)amino)ethyl)-3-(2,6-dichloro-3,5-dimethoxyphenyl)-7-(ethylamino)-1,6-naphthyridin-2(1H)-one; |
| 158 | (R)-N-(1-(3-(6-(2,6-dichloro-3,5-dimethoxyphenyl)-2-(methylamino)-7-oxopyrido[2,3-d]pyrimidin-8(7H)-yl)propyl)pyrrolidin-3-yl)acrylamide; |
| 159 | (S)-N-(1-(3-(6-(2,6-dichloro-3,5-dimethoxyphenyl)-2-(methylamino)-7-oxopyrido[2,3-d]pyrimidin-8(7H)-yl)propyl)piperidin-3-yl)acrylamide; |
| 160 | 1-(2-((1-acryloylpiperidin-4-yl)(2-methoxyethyl)amino)ethyl)-3-(2,6-dichloro-3,5-dimethoxyphenyl)-7-(methylamino)-1,6-naphthyridin-2(1H)-one; |
| 161 | 1-(2-((1-acryloylpiperidin-4-yl)(2-methoxyethyl)amino)ethyl)-3-(2,6-dichloro-3,5-dimethoxyphenyl)-7-(ethylamino)-1,6-naphthyridin-2(1H)-one; |
| 162 | (R)-N-(1-(3-(6-(2,6-dichloro-3,5-dimethoxyphenyl)-2-(methylamino)-7-oxopyrido[2,3-d]pyrimidin-8(7H)-yl)propyl)piperidin-3-yl)acrylamide; |
| 163 | 8-(3-(4-acryloylpiperazin-1-yl)propyl)-6-(2,6-dichloro-3-hydroxy-5-methoxyphenyl)-2-(methylamino)pyrido[2,3-d]pyrimidin-7(8H)-one; |
| 164 | 8-(3-(4-acryloylpiperazin-1-yl)propyl)-6-(2,6-dichloro-3-hydroxy-5-methoxyphenyl)-2-aminopyrido[2,3-d]pyrimidin-7(8H)-one; | an individual E or Z isomer thereof, and/or a pharmaceutically acceptable salt of any of the above compounds.

In one embodiment, the compound is:

8-(3-(4-acryloylpiperazin-1-yl)propyl)-6-(2,6-dichloro-3,5-dimethoxyphenyl)-2-(methylamino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one;

8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-methoxyethyl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

8-(3-(4-acryloylpiperazin-1-yl)propyl)-2-amino-6-(2,6-dichloro-3,5-dimethoxy-phenyl)pyrido[2,3-d]pyrimidin-7(8H)-one;

N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide;

8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one;

(S)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one;

8-(2-((1-acryloylazetidin-3-yl)oxy)ethyl)-2-amino-6-(2,6-dichloro-3,5-dimethoxyphenyl)pyrido[2,3-d]pyrimidin-7(8H)-one;

8-(2-((1-acryloylazetidin-3-yl)oxy)ethyl)-6-(2,6-dichloro-3,5-dimethoxyphenyl)-2-((2-methoxyethyl)amino)pyrido[2,3-d]pyrimidin-7(8H)-one; or 8-(2-((1-acryloylazetidin-3-yl)(methyl)amino)ethyl)-6-(2,6-dichloro-3,5-dimethoxyphenyl)-2-(methylamino)pyrido[2,3-d]pyrimidin-7(8H)-one;

and/or a pharmaceutically acceptable salt of any of the above compounds.

In another embodiment the compound is:

8-(3-(4-acryloylpiperazin-1-yl)propyl)-6-(2,6-dichloro-3,5-dimethoxyphenyl)-2-(methylamino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one;

8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-methoxyethyl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

8-(3-(4-acryloylpiperazin-1-yl)propyl)-2-amino-6-(2,6-dichloro-3,5-dimethoxy-phenyl)pyrido[2,3-d]pyrimidin-7(8H)-one;

N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide;

8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one;

(S)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one;

8-(2-((1-acryloylazetidin-3-yl)oxy)ethyl)-2-amino-6-(2,6-dichloro-3,5-dimethoxyphenyl)pyrido[2,3-d]pyrimidin-7(8H)-one;

8-(2-((1-acryloylazetidin-3-yl)oxy)ethyl)-6-(2,6-dichloro-3,5-dimethoxyphenyl)-2-((2-methoxyethyl)amino)pyrido[2,3-d]pyrimidin-7(8H)-one; or 8-(2-((1-acryloylazetidin-3-yl)(methyl)amino)ethyl)-6-(2,6-dichloro-3,5-dimethoxyphenyl)-2-(methylamino)pyrido[2,3-d]pyrimidin-7(8H)-one;

and/or a pharmaceutically acceptable salt of any of the above compounds.

In another embodiment, the compound is:

8-(3-(4-acryloylpiperazin-1-yl)propyl)-6-(2,6-dichloro-3,5-dimethoxyphenyl)-2-(methylamino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one;

8-(3-(4-acryloylpiperazin-1-yl)propyl)-6-(2,6-dichloro-3,5-dimethoxyphenyl)-2-((2-methoxyethyl)amino)pyrido[2,3-d]pyrimidin-7(8H)-one;

(R)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

(S)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one;

8-(3-(4-acryloylpiperazin-1-yl)propyl)-2-amino-6-(2,6-dichloro-3,5-dimethoxy-phenyl)pyrido[2,3-d]pyrimidin-7(8H)-one;

N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide; or 8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one;

and/or a pharmaceutically acceptable salt of any of the above compounds.

In another embodiment the compound is:

8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one;

(S)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one;

8-(2-((1-acryloylazetidin-3-yl)oxy)ethyl)-2-amino-6-(2,6-dichloro-3,5-dimethoxyphenyl)pyrido[2,3-d]pyrimidin-7(8H)-one;

8-(2-((1-acryloylazetidin-3-yl)oxy)ethyl)-6-(2,6-dichloro-3,5-dimethoxyphenyl)-2-((2-methoxyethyl)amino)pyrido[2,3-d]pyrimidin-7(8H)-one; or 8-(2-((1-acryloylazetidin-3-yl)(methyl)amino)ethyl)-6-(2,6-dichloro-3,5-dimethoxyphenyl)-2-(methylamino)pyrido[2,3-d]pyrimidin-7(8H)-one;

and/or a pharmaceutically acceptable salt of any of the above compounds.

In another embodiment the compound is 8-(3-(4-acryloylpiperazin-1-yl)propyl)-2-amino-6-(2,6-dichloro-3,5-dimethoxyphenyl)pyrido[2,3-d]pyrimidin-7(8H)-one and/or a pharmaceutically acceptable salt thereof.

In another embodiment the compound is 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one and/or a pharmaceutically acceptable salt thereof.

In another embodiment the compound is 8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one and/or a pharmaceutically acceptable salt thereof.

In another embodiment the compound is (S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one and/or a pharmaceutically acceptable salt thereof.

In another embodiment the compound is (R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one and/or a pharmaceutically acceptable salt thereof.

In another embodiment the compound is N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide and/or a pharmaceutically acceptable salt thereof.

In another embodiment the compound is 8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one and/or a pharmaceutically acceptable salt thereof.

In another embodiment the compound is 8-(2-((1-acryloylazetidin-3-yl)(methyl)amino)-ethyl)-6-(2,6-dichloro-3,5-dimethoxyphenyl)-2-(methylamino)pyrido[2,3-d]pyrimidin-7(8H)-one and/or a pharmaceutically acceptable salt thereof.

Other representative compounds of the disclosure are disclosed in Table 2 below:

TABLE 2

| | Name |
|---|---|
| 1 | 8-(2-((1-acryloylazetidin-3-yl)oxy)ethyl)-6-(2,6-dichloro-3,5-dimethoxyphenyl)-2-((2-(4,4-difluoropiperidin-1-yl)ethyl)amino)pyrido[2,3-d]pyrimidin-7(8H)-one |
| 2 | 8-(2-((1-acryloylpyrrolidin-3-yl)oxy)ethyl)-6-(2,6-dichloro-3,5-dimethoxyphenyl)-2-((2-morpholinoethyl)amino)pyrido[2,3-d]pyrimidin-7(8H)-one |
| 3 | (E)-6-(2,6-dichloro-3,5-dimethoxyphenyl)-8-(2-((1-(4-(dimethylamino)but-2-enoyl)pyrrolidin-3-yl)oxy)ethyl)-2-((2-methoxyethyl)amino)pyrido[2,3-d]pyrimidin-7(8H)-one |
| 4 | 8-(2-((1-acryloylazetidin-3-yl)oxy)-2-methylpropyl)-6-(2,6-dichloro-3,5-dimethoxyphenyl)-2-((2-morpholinoethyl)amino)pyrido[2,3-d]pyrimidin-7(8H)-one |
| 5 | 6-(2,6-dichloro-3,5-dimethoxyphenyl)-8-(2-((1-(3-methylbut-2-enoyl)azetidin-3-yl)oxy)ethyl)-2-((2-morpholinoethyl)amino)pyrido[2,3-d]pyrimidin-7(8H)-one |
| 6 | 8-(2-((1-acryloylazetidin-3-yl)oxy)ethyl)-6-(2,6-dichloro-3,5-dimethoxyphenyl)-2-((2-(diethylamino)ethyl)amino)pyrido[2,3-d]pyrimidin-7(8H)-one |
| 7 | 8-(2-((1-acryloylazetidin-3-yl)oxy)-2-methylpropyl)-6-(2,6-dichloro-3,5-dimethoxyphenyl)-2-((2-(diethylamino)ethyl)amino)pyrido[2,3-d]pyrimidin-7(8H)-one |
| 8 | 8-(2-((1-acryloylpyrrolidin-3-yl)oxy)ethyl)-6-(2,6-dichloro-3,5-dimethoxyphenyl)-2-((2-(4-ethylpiperazin-1-yl)ethyl)amino)pyrido[2,3-d]pyrimidin-7(8H)-one |
| 9 | 8-(2-((1-acryloylazetidin-3-yl)oxy)ethyl)-6-(2,6-dichloro-3,5-dimethoxyphenyl)-2-((2-(4-ethylpiperazin-1-yl)ethyl)amino)pyrido[2,3-d]pyrimidin-7(8H)-one |
| 10 | 8-(2-((1-acryloylpyrrolidin-3-yl)oxy)ethyl)-6-(2-chloro-3,5-dimethoxyphenyl)-2-((4-(4-methylpiperazin-1-yl)phenyl)amino)pyrido[2,3-d]pyrimidin-7(8H)-one |
| 11 | 8-(2-((1-acryloylazetidin-3-yl)oxy)ethyl)-6-(2-chloro-3,5-dimethoxyphenyl)-2-((4-(4-methylpiperazin-1-yl)phenyl)amino)pyrido[2,3-d]pyrimidin-7(8H)-one |
| 12 | 8-(2-((1-acryloylpyrrolidin-3-yl)oxy)ethyl)-6-(2-chloro-3,5-dimethoxyphenyl)-2-((2-(4,4-difluoropiperidin-1-yl)ethyl)amino)pyrido[2,3-d]pyrimidin-7(8H)-one |
| 13 | 8-(2-((1-acryloylazetidin-3-yl)oxy)ethyl)-6-(2-chloro-3,5-dimethoxyphenyl)-2-((2-(4,4-difluoropiperidin-1-yl)ethyl)amino)pyrido[2,3-d]pyrimidin-7(8H)-one |
| 14 | 8-(2-((1-acryloylpyrrolidin-3-yl)oxy)ethyl)-6-(2-chloro-3,5-dimethoxyphenyl)-2-((2-morpholinoethyl)amino)pyrido[2,3-d]pyrimidin-7(8H)-one |
| 15 | 6-(2,6-dichloro-3,5-dimethoxyphenyl)-2-((2-hydroxy-2-methylpropyl)amino)-8-(3-(4-(3-methylbut-2-enoyl)piperazin-1-yl)propyl)pyrido[2,3-d]pyrimidin-7(8H)-one |
| 16 | 8-(2-((1-acryloylazetidin-3-yl)oxy)-2-methylpropyl)-6-(2-chloro-3,5-dimethoxyphenyl)-2-((2-morpholinoethyl)amino)pyrido[2,3-d]pyrimidin-7(8H)-one |
| 17 | 6-(2-chloro-3,5-dimethoxyphenyl)-8-(2-((1-(3-methylbut-2-enoyl)azetidin-3-yl)oxy)ethyl)-2-((2-morpholinoethyl)amino)pyrido[2,3-d]pyrimidin-7(8H)-one |
| 18 | 8-(2-((1-acryloylazetidin-3-yl)oxy)ethyl)-6-(2-chloro-3,5-dimethoxyphenyl)-2-((2-(diethylamino)ethyl)amino)pyrido[2,3-d]pyrimidin-7(8H)-one |
| 19 | 8-(2-((1-acryloylazetidin-3-yl)oxy)-2-methylpropyl)-6-(2-chloro-3,5-dimethoxyphenyl)-2-((2-(diethylamino)ethyl)amino)pyrido[2,3-d]pyrimidin-7(8H)-one |
| 20 | 8-(2-((1-acryloylpyrrolidin-3-yl)oxy)ethyl)-6-(2-chloro-3,5-dimethoxyphenyl)-2-((2-(4-ethylpiperazin-1-yl)ethyl)amino)pyrido[2,3-d]pyrimidin-7(8H)-one |
| 21 | 8-(2-((1-acryloylazetidin-3-yl)oxy)ethyl)-6-(2-chloro-3,5-dimethoxyphenyl)-2-((2-(4-ethylpiperazin-1-yl)ethyl)amino)pyrido[2,3-d]pyrimidin-7(8H)-one |
| 22 | 8-(2-((1-acryloylazetidin-3-yl)oxy)-2-methylpropyl)-6-(2-chloro-3,5-dimethoxyphenyl)-2-((2-(4-ethylpiperazin-1-yl)ethyl)amino)pyrido[2,3-d]pyrimidin-7(8H)-one |
| 23 | 6-(2-chloro-3,5-dimethoxyphenyl)-2-((2-(4-ethylpiperazin-1-yl)ethyl)amino)-8-(2-((1-(3-methylbut-2-enoyl)azetidin-3-yl)oxy)ethyl)pyrido[2,3-d]pyrimidin-7(8H)-one |
| 24 | N-(1-(2-(2-amino-6-(2-chloro-3,5-dimethoxyphenyl)-7-oxopyrido[2,3-d]pyrimidin-8(7H)-yl)ethyl)azetidin-3-yl)acrylamide |
| 25 | 8-(2-((1-acryloylazetidin-3-yl)amino)ethyl)-2-amino-6-(2-chloro-3,5-dimethoxyphenyl)pyrido[2,3-d]pyrimidin-7(8H)-one |
| 26 | 8-(2-((1-acryloylazetidin-3-yl)amino)ethyl)-6-(2-chloro-3,5-dimethoxyphenyl)-2-(methylamino)pyrido[2,3-d]pyrimidin-7(8H)-one |
| 27 | N-(1-(2-(6-(2-chloro-3,5-dimethoxyphenyl)-2-(methylamino)-7-oxopyrido[2,3-d]pyrimidin-8(7H)-yl)ethyl)azetidin-3-yl)acrylamide |
| 28 | 2-amino-6-(2-chloro-3,5-dimethoxyphenyl)-8-(2-((1-(3-methylbut-2-enoyl)azetidin-3-yl)amino)ethyl)pyrido[2,3-d]pyrimidin-7(8H)-one |
| 29 | N-(1-(2-(2-amino-6-(2-chloro-3,5-dimethoxyphenyl)-7-oxopyrido[2,3-d]pyrimidin-8(7H)-yl)ethyl)piperidin-4-yl)acrylamide |
| 30 | 8-(2-((1-acryloylpiperidin-4-yl)amino)ethyl)-2-amino-6-(2-chloro-3,5-dimethoxyphenyl)pyrido[2,3-d]pyrimidin-7(8H)-one |
| 31 | 8-(3-(4-acryloylpiperazin-1-yl)propyl)-2-amino-6-(2-chloro-3,5-dimethoxyphenyl)pyrido[2,3-d]pyrimidin-7(8H)-one |
| 32 | 8-(2-((1-acryloylazetidin-3-yl)amino)ethyl)-2-amino-6-(2,6-dichloro-3,5-dimethoxyphenyl)pyrido[2,3-d]pyrimidin-7(8H)-one |
| 33 | N-(1-(2-(2-amino-6-(2,6-dichloro-3,5-dimethoxyphenyl)-7-oxopyrido[2,3-d]pyrimidin-8(7H)-yl)ethyl)azetidin-3-yl)acrylamide |
| 34 | 6-(2-chloro-3,5-dimethoxyphenyl)-2-(methylamino)-8-(2-((1-(3-methylbut-2-enoyl)azetidin-3-yl)amino)ethyl)pyrido[2,3-d]pyrimidin-7(8H)-one |
| 35 | 8-(2-((1-acryloylpiperidin-4-yl)amino)ethyl)-6-(2-chloro-3,5-dimethoxyphenyl)-2-(methylamino)pyrido[2,3-d]pyrimidin-7(8H)-one |

TABLE 2-continued

| | Name |
|---|---|
| 36 | 8-(2-((1-acryloylpyrrolidin-3-yl)amino)ethyl)-2-amino-6-(2,6-dichloro-3,5-dimethoxyphenyl)pyrido[2,3-d]pyrimidin-7(8H)-one |
| 37 | N-(1-(2-(6-(2,6-dichloro-3,5-dimethoxyphenyl)-2-(methylamino)-7-oxopyrido[2,3-d]pyrimidin-8(7H)-yl)ethyl)azetidin-3-yl)acrylamide |
| 38 | 8-(2-((1-acryloylazetidin-3-yl)amino)ethyl)-6-(2,6-dichloro-3,5-dimethoxyphenyl)-2-(methylamino)pyrido[2,3-d]pyrimidin-7(8H)-one |
| 39 | N-(1-(2-(6-(2-chloro-3,5-dimethoxyphenyl)-2-(oxetan-3-ylamino)-7-oxopyrido[2,3-d]pyrimidin-8(7H)-yl)ethyl)azetidin-3-yl)acrylamide |
| 40 | 8-(2-((1-acryloylazetidin-3-yl)amino)ethyl)-6-(2-chloro-3,5-dimethoxyphenyl)-2-(oxetan-3-ylamino)pyrido[2,3-d]pyrimidin-7(8H)-one |
| 41 | 8-(3-(4-acryloyl-2,6-dimethylpiperazin-1-yl)propyl)-2-amino-6-(2-chloro-3,5-dimethoxyphenyl)pyrido[2,3-d]pyrimidin-7(8H)-one |
| 42 | N-(1-(2-(6-(2-chloro-3,5-dimethoxyphenyl)-2-((2-methoxyethyl)amino)-7-oxopyrido[2,3-d]pyrimidin-8(7H)-yl)ethyl)azetidin-3-yl)acrylamide |
| 43 | 8-(2-((1-acryloylazetidin-3-yl)amino)ethyl)-6-(2-chloro-3,5-dimethoxyphenyl)-2-((2-methoxyethyl)amino)pyrido[2,3-d]pyrimidin-7(8H)-one |
| 44 | (E)-2-amino-6-(2-chloro-3,5-dimethoxyphenyl)-8-(2-((1-(4-(dimethylamino)but-2-enoyl)azetidin-3-yl)oxy)ethyl)pyrido[2,3-d]pyrimidin-7(8H)-one |
| 45 | 8-(2-((1-acryloylpyrrolidin-3-yl)amino)ethyl)-6-(2,6-dichloro-3,5-dimethoxyphenyl)-2-(methylamino)pyrido[2,3-d]pyrimidin-7(8H)-one |
| 46 | 8-(3-(4-acryloyl-2,6-dimethylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one |
| 47 | 8-(2-((1-acryloylpiperidin-4-yl)amino)ethyl)-2-amino-6-(2,6-dichloro-3,5-dimethoxyphenyl)pyrido[2,3-d]pyrimidin-7(8H)-one |
| 48 | N-(1-(2-(2-amino-6-(2,6-dichloro-3,5-dimethoxyphenyl)-7-oxopyrido[2,3-d]pyrimidin-8(7H)-yl)ethyl)piperidin-4-yl)acrylamide |
| 49 | 2-amino-6-(2,6-dichloro-3,5-dimethoxyphenyl)-8-(2-((1-(3-methylbut-2-enoyl)azetidin-3-yl)amino)ethyl)pyrido[2,3-d]pyrimidin-7(8H)-one |
| 50 | N-(8-(3-(4-acryloylpiperazin-1-yl)propyl)-6-(2-chloro-3,5-dimethoxyphenyl)-7-oxo-7,8-dihydropyrido[2,3-d]pyrimidin-2-yl)acetamide |
| 51 | 8-(2-((1-acryloylazetidin-3-yl)amino)ethyl)-6-(2-chloro-3,5-dimethoxyphenyl)-2-((oxetan-3-ylmethyl)amino)pyrido[2,3-d]pyrimidin-7(8H)-one |
| 52 | N-(1-(2-(6-(2-chloro-3,5-dimethoxyphenyl)-2-((oxetan-3-ylmethyl)amino)-7-oxopyrido[2,3-d]pyrimidin-8(7H)-yl)ethyl)azetidin-3-yl)acrylamide |
| 53 | N-(1-(2-(6-(2-chloro-3,5-dimethoxyphenyl)-7-oxo-2-((tetrahydrofuran-3-yl)amino)pyrido[2,3-d]pyrimidin-8(7H)-yl)ethyl)azetidin-3-yl)acrylamide |
| 54 | 8-(2-((1-acryloylazetidin-3-yl)amino)ethyl)-6-(2-chloro-3,5-dimethoxyphenyl)-2-((tetrahydrofuran-3-yl)amino)pyrido[2,3-d]pyrimidin-7(8H)-one |
| 55 | 8-(3-(4-acryloyl-2,6-dimethylpiperazin-1-yl)propyl)-6-(2-chloro-3,5-dimethoxyphenyl)-2-(methylamino)pyrido[2,3-d]pyrimidin-7(8H)-one |
| 56 | (E)-6-(2-chloro-3,5-dimethoxyphenyl)-8-(2-((1-(4-(dimethylamino)but-2-enoyl)azetidin-3-yl)oxy)ethyl)-2-(methylamino)pyrido[2,3-d]pyrimidin-7(8H)-one |
| 57 | (E)-2-amino-6-(2-chloro-3,5-dimethoxyphenyl)-8-(2-((1-(4-(dimethylamino)but-2-enoyl)pyrrolidin-3-yl)oxy)ethyl)pyrido[2,3-d]pyrimidin-7(8H)-one |
| 58 | 8-(2-((1-acryloylazetidin-3-yl)amino)ethyl)-6-(2-chloro-3,5-dimethoxyphenyl)-2-(phenylamino)pyrido[2,3-d]pyrimidin-7(8H)-one |
| 59 | N-(1-(2-(6-(2-chloro-3,5-dimethoxyphenyl)-7-oxo-2-(phenylamino)pyrido[2,3-d]pyrimidin-8(7H)-yl)ethyl)azetidin-3-yl)acrylamide |
| 60 | 8-(2-((1-acryloylpiperidin-4-yl)amino)ethyl)-6-(2,6-dichloro-3,5-dimethoxyphenyl)-2-(methylamino)pyrido[2,3-d]pyrimidin-7(8H)-one |
| 61 | 6-(2,6-dichloro-3,5-dimethoxyphenyl)-2-(methylamino)-8-(2-((1-(3-methylbut-2-enoyl)azetidin-3-yl)amino)ethyl)pyrido[2,3-d]pyrimidin-7(8H)-one |
| 62 | N-(1-(2-(6-(2,6-dichloro-3,5-dimethoxyphenyl)-2-(methylamino)-7-oxopyrido[2,3-d]pyrimidin-8(7H)-yl)ethyl)piperidin-4-yl)acrylamide |
| 63 | 8-(2-((1-acryloylazetidin-3-yl)amino)ethyl)-6-(2-chloro-3,5-dimethoxyphenyl)-2-(((tetrahydrofuran-3-yl)methyl)amino)pyrido[2,3-d]pyrimidin-7(8H)-one |
| 64 | 8-(2-((1-acryloylazetidin-3-yl)amino)ethyl)-6-(2-chloro-3,5-dimethoxyphenyl)-2-((2-(oxetan-3-yl)ethyl)amino)pyrido[2,3-d]pyrimidin-7(8H)-one |
| 65 | N-(1-(2-(6-(2-chloro-3,5-dimethoxyphenyl)-2-((2-(oxetan-3-yl)ethyl)amino)-7-oxopyrido[2,3-d]pyrimidin-8(7H)-yl)ethyl)azetidin-3-yl)acrylamide |
| 66 | N-(1-(2-(6-(2-chloro-3,5-dimethoxyphenyl)-7-oxo-2-(((tetrahydrofuran-3-yl)methyl)amino)pyrido[2,3-d]pyrimidin-8(7H)-yl)ethyl)azetidin-3-yl)acrylamide |
| 67 | 8-(2-((1-acryloylazetidin-3-yl)amino)ethyl)-6-(2-chloro-3,5-dimethoxyphenyl)-2-((tetrahydro-2H-pyran-4-yl)amino)pyrido[2,3-d]pyrimidin-7(8H)-one |
| 68 | 8-(3-(4-acryloylpiperazin-1-yl)propyl)-6-(2-chloro-3,5-dimethoxyphenyl)-2-(oxetan-3-ylamino)pyrido[2,3-d]pyrimidin-7(8H)-one |
| 69 | N-(1-(2-(6-(2-chloro-3,5-dimethoxyphenyl)-7-oxo-2-((tetrahydro-2H-pyran-4-yl)amino)pyrido[2,3-d]pyrimidin-8(7H)-yl)ethyl)azetidin-3-yl)acrylamide |
| 70 | 8-(2-((1-acryloylpiperidin-4-yl)amino)ethyl)-6-(2-chloro-3,5-dimethoxyphenyl)-2-(oxetan-3-ylamino)pyrido[2,3-d]pyrimidin-7(8H)-one |
| 71 | 6-(2-chloro-3,5-dimethoxyphenyl)-2-((2-methoxyethyl)amino)-8-(2-((1-(3-methylbut-2-enoyl)azetidin-3-yl)amino)ethyl)pyrido[2,3-d]pyrimidin-7(8H)-one |
| 72 | 8-(2-((1-acryloylpiperidin-4-yl)amino)ethyl)-6-(2-chloro-3,5-dimethoxyphenyl)-2-((2-methoxyethyl)amino)pyrido[2,3-d]pyrimidin-7(8H)-one |

TABLE 2-continued

| | Name |
|---|---|
| 73 | (E)-6-(2,6-dichloro-3,5-dimethoxyphenyl)-8-(2-((1-(4-(dimethylamino)but-2-enoyl)pyrrolidin-3-yl)oxy)ethyl)-2-(oxetan-3-ylamino)pyrido[2,3-d]pyrimidin-7(8H)-one |
| 74 | 8-(2-((1-acryloylazetidin-3-yl)amino)ethyl)-6-(2,6-dichloro-3,5-dimethoxyphenyl)-2-(oxetan-3-ylamino)pyrido[2,3-d]pyrimidin-7(8H)-one |
| 75 | N-(1-(2-(6-(2,6-dichloro-3,5-dimethoxyphenyl)-2-(oxetan-3-ylamino)-7-oxopyrido[2,3-d]pyrimidin-8(7H)-yl)ethyl)azetidin-3-yl)acrylamide |
| 76 | 8-(3-(4-acryloyl-2,6-dimethylpiperazin-1-yl)propyl)-2-amino-6-(2,6-dichloro-3,5-dimethoxyphenyl)pyrido[2,3-d]pyrimidin-7(8H)-one |
| 77 | 2-amino-6-(2,6-dichloro-3,5-dimethoxyphenyl)-8-(3-(4-(3-methylbut-2-enoyl)piperazin-1-yl)propyl)pyrido[2,3-d]pyrimidin-7(8H)-one |
| 78 | (E)-2-amino-6-(2,6-dichloro-3,5-dimethoxyphenyl)-8-(2-((1-(4-(dimethylamino)but-2-enoyl)azetidin-3-yl)oxy)ethyl)pyrido[2,3-d]pyrimidin-7(8H)-one |
| 79 | N-(1-(2-(6-(2,6-dichloro-3,5-dimethoxyphenyl)-2-((2-methoxyethyl)amino)-7-oxopyrido[2,3-d]pyrimidin-8(7H)-yl)ethyl)azetidin-3-yl)acrylamide |
| 80 | 8-(2-((1-acryloylazetidin-3-yl)amino)ethyl)-6-(2,6-dichloro-3,5-dimethoxyphenyl)-2-((2-methoxyethyl)amino)pyrido[2,3-d]pyrimidin-7(8H)-one |
| 81 | N-(1-(2-(6-(2-chloro-3,5-dimethoxyphenyl)-7-oxo-2-(((tetrahydro-2H-pyran-4-yl)methyl)amino)pyrido[2,3-d]pyrimidin-8(7H)-yl)ethyl)azetidin-3-yl)acrylamide |
| 82 | N-(1-(2-(6-(2-chloro-3,5-dimethoxyphenyl)-7-oxo-2-((tetrahydrofuran-3-yl)amino)pyrido[2,3-d]pyrimidin-8(7H)-yl)ethyl)piperidin-4-yl)acrylamide |
| 83 | N-(1-(2-(6-(2-chloro-3,5-dimethoxyphenyl)-2-((oxetan-3-ylmethyl)amino)-7-oxopyrido[2,3-d]pyrimidin-8(7H)-yl)ethyl)piperidin-4-yl)acrylamide |
| 84 | 8-(3-(4-acryloylpiperazin-1-yl)propyl)-6-(2-chloro-3,5-dimethoxyphenyl)-2-((oxetan-3-ylmethyl)amino)pyrido[2,3-d]pyrimidin-7(8H)-one |
| 85 | N-(1-(2-(6-(2-chloro-3,5-dimethoxyphenyl)-7-oxo-2-((2-(tetrahydrofuran-3-yl)ethyl)amino)pyrido[2,3-d]pyrimidin-8(7H)-yl)ethyl)azetidin-3-yl)acrylamide |
| 86 | 8-(3-(4-acryloylpiperazin-1-yl)propyl)-6-(2-chloro-3,5-dimethoxyphenyl)-2-((tetrahydrofuran-3-yl)amino)pyrido[2,3-d]pyrimidin-7(8H)-one |
| 87 | N-(8-(3-(4-acryloyl-2,6-dimethylpiperazin-1-yl)propyl)-6-(2-chloro-3,5-dimethoxyphenyl)-7-oxo-7,8-dihydropyrido[2,3-d]pyrimidin-2-yl)acetamide |
| 88 | 8-(2-((1-acryloylpiperidin-4-yl)amino)ethyl)-6-(2-chloro-3,5-dimethoxyphenyl)-2-((oxetan-3-ylmethyl)amino)pyrido[2,3-d]pyrimidin-7(8H)-one |
| 89 | 8-(2-((1-acryloylpyrrolidin-3-yl)amino)ethyl)-6-(2-chloro-3,5-dimethoxyphenyl)-2-((tetrahydro-2H-pyran-4-yl)amino)pyrido[2,3-d]pyrimidin-7(8H)-one |
| 90 | 8-(2-((1-acryloylazetidin-3-yl)amino)ethyl)-6-(2-chloro-3,5-dimethoxyphenyl)-2-(((tetrahydro-2H-pyran-4-yl)methyl)amino)pyrido[2,3-d]pyrimidin-7(8H)-one |
| 91 | 8-(2-((1-acryloylazetidin-3-yl)amino)ethyl)-6-(2-chloro-3,5-dimethoxyphenyl)-2-((2-(tetrahydrofuran-3-yl)ethyl)amino)pyrido[2,3-d]pyrimidin-7(8H)-one |
| 92 | 8-(2-((1-acryloylpiperidin-4-yl)amino)ethyl)-6-(2-chloro-3,5-dimethoxyphenyl)-2-((tetrahydrofuran-3-yl)amino)pyrido[2,3-d]pyrimidin-7(8H)-one |
| 93 | 6-(2-chloro-3,5-dimethoxyphenyl)-2-((2-hydroxyethyl)amino)-8-(3-(4-(3-methylbut-2-enoyl)piperazin-1-yl)propyl)pyrido[2,3-d]pyrimidin-7(8H)-one |
| 94 | 8-(3-(4-acryloyl-2,6-dimethylpiperazin-1-yl)propyl)-6-(2-chloro-3,5-dimethoxyphenyl)-2-((2-hydroxyethyl)amino)pyrido[2,3-d]pyrimidin-7(8H)-one |
| 95 | N-(1-(2-(6-(2-chloro-3,5-dimethoxyphenyl)-7-oxo-2-(phenylamino)pyrido[2,3-d]pyrimidin-8(7H)-yl)ethyl)piperidin-4-yl)acrylamide |
| 96 | 8-(2-((1-acryloylpiperidin-4-yl)amino)ethyl)-6-(2-chloro-3,5-dimethoxyphenyl)-2-(phenylamino)pyrido[2,3-d]pyrimidin-7(8H)-one |
| 97 | 6-(2-chloro-3,5-dimethoxyphenyl)-8-(2-((1-(3-methylbut-2-enoyl)azetidin-3-yl)amino)ethyl)-2-(phenylamino)pyrido[2,3-d]pyrimidin-7(8H)-one |
| 98 | 8-(2-((1-acryloylazetidin-3-yl)amino)ethyl)-6-(2,6-dichloro-3,5-dimethoxyphenyl)-2-((oxetan-3-ylmethyl)amino)pyrido[2,3-d]pyrimidin-7(8H)-one |
| 99 | N-(1-(2-(6-(2,6-dichloro-3,5-dimethoxyphenyl)-2-((oxetan-3-ylmethyl)amino)-7-oxopyrido[2,3-d]pyrimidin-8(7H)-yl)ethyl)azetidin-3-yl)acrylamide |
| 100 | (E)-6-(2,6-dichloro-3,5-dimethoxyphenyl)-8-(2-((1-(4-(dimethylamino)but-2-enoyl)azetidin-3-yl)oxy)ethyl)-2-((tetrahydrofuran-3-yl)amino)pyrido[2,3-d]pyrimidin-7(8H)-one |
| 101 | 8-(2-((1-acryloylpyrrolidin-3-yl)amino)ethyl)-6-(2,6-dichloro-3,5-dimethoxyphenyl)-2-(oxetan-3-ylamino)pyrido[2,3-d]pyrimidin-7(8H)-one |
| 102 | N-(1-(2-(6-(2,6-dichloro-3,5-dimethoxyphenyl)-7-oxo-2-((tetrahydrofuran-3-yl)amino)pyrido[2,3-d]pyrimidin-8(7H)-yl)ethyl)azetidin-3-yl)acrylamide |
| 103 | 8-(2-((1-acryloylazetidin-3-yl)amino)ethyl)-6-(2,6-dichloro-3,5-dimethoxyphenyl)-2-((tetrahydrofuran-3-yl)amino)pyrido[2,3-d]pyrimidin-7(8H)-one |
| 104 | 8-(3-(4-acryloyl-2,6-dimethylpiperazin-1-yl)propyl)-6-(2,6-dichloro-3,5-dimethoxyphenyl)-2-(methylamino)pyrido[2,3-d]pyrimidin-7(8H)-one |
| 105 | 6-(2,6-dichloro-3,5-dimethoxyphenyl)-2-(methylamino)-8-(3-(4-(3-methylbut-2-enoyl)piperazin-1-yl)propyl)pyrido[2,3-d]pyrimidin-7(8H)-one |
| 106 | (E)-2-amino-6-(2,6-dichloro-3,5-dimethoxyphenyl)-8-(2-((1-(4-(dimethylamino)but-2-enoyl)pyrrolidin-3-yl)oxy)ethyl)pyrido[2,3-d]pyrimidin-7(8H)-one |
| 107 | 8-(2-((1-acryloylpyrrolidin-3-yl)amino)ethyl)-6-(2,6-dichloro-3,5-dimethoxyphenyl)-2-((2-methoxyethyl)amino)pyrido[2,3-d]pyrimidin-7(8H)-one |
| 108 | (E)-6-(2,6-dichloro-3,5-dimethoxyphenyl)-8-(2-((1-(4-(dimethylamino)but-2-enoyl)azetidin-3-yl)oxy)ethyl)-2-((oxetan-3-ylmethyl)amino)pyrido[2,3-d]pyrimidin-7(8H)-one |

TABLE 2-continued

| | Name |
|---|---|
| 109 | N-(1-(2-(6-(2,6-dichloro-3,5-dimethoxyphenyl)-7-oxo-2-(phenylamino)pyrido[2,3-d]pyrimidin-8(7H)-yl)ethyl)azetidin-3-yl)acrylamide |
| 110 | 8-(2-((1-acryloylazetidin-3-yl)amino)ethyl)-6-(2,6-dichloro-3,5-dimethoxyphenyl)-2-(phenylamino)pyrido[2,3-d]pyrimidin-7(8H)-one |
| 111 | 6-(2-chloro-3,5-dimethoxyphenyl)-8-(2-((1-(3-methylbut-2-enoyl)azetidin-3-yl)amino)ethyl)-2-((tetrahydro-2H-pyran-4-yl)amino)pyrido[2,3-d]pyrimidin-7(8H)-one |
| 112 | 8-(3-(4-acryloyl-2,6-dimethylpiperazin-1-yl)propyl)-6-(2,6-dichloro-3,5-dimethoxyphenyl)-2-((oxetan-3-ylmethyl)amino)pyrido[2,3-d]pyrimidin-7(8H)-one |
| 113 | 8-(3-(4-acryloylpiperazin-1-yl)propyl)-6-(2-chloro-3,5-dimethoxyphenyl)-2-(((tetrahydrofuran-3-yl)methyl)amino)pyrido[2,3-d]pyrimidin-7(8H)-one |
| 114 | N-(1-(2-(6-(2-chloro-3,5-dimethoxyphenyl)-7-oxo-2-(((tetrahydrofuran-3-yl)methyl)amino)pyrido[2,3-d]pyrimidin-8(7H)-yl)ethyl)piperidin-4-yl)acrylamide |
| 115 | N-(1-(2-(6-(2-chloro-3,5-dimethoxyphenyl)-7-oxo-2-((2-(tetrahydro-2H-pyran-4-yl)ethyl)amino)pyrido[2,3-d]pyrimidin-8(7H)-yl)ethyl)azetidin-3-yl)acrylamide |
| 116 | N-(1-(2-(6-(2-chloro-3,5-dimethoxyphenyl)-2-((2-(oxetan-3-yl)ethyl)amino)-7-oxopyrido[2,3-d]pyrimidin-8(7H)-yl)ethyl)piperidin-4-yl)acrylamide |
| 117 | 6-(2-chloro-3,5-dimethoxyphenyl)-8-(2-((1-(3-methylbut-2-enoyl)azetidin-3-yl)amino)ethyl)-2-((2-(oxetan-3-yl)ethyl)amino)pyrido[2,3-d]pyrimidin-7(8H)-one |
| 118 | 6-(2-chloro-3,5-dimethoxyphenyl)-8-(3-(4-(3-methylbut-2-enoyl)piperazin-1-yl)propyl)-2-(oxetan-3-ylamino)pyrido[2,3-d]pyrimidin-7(8H)-one |
| 119 | 8-(2-((1-acryloylazetidin-3-yl)amino)ethyl)-6-(2-chloro-3,5-dimethoxyphenyl)-2-((2-(tetrahydro-2H-pyran-4-yl)ethyl)amino)pyrido[2,3-d]pyrimidin-7(8H)-one |
| 120 | 8-(2-((1-acryloylpiperidin-4-yl)amino)ethyl)-6-(2-chloro-3,5-dimethoxyphenyl)-2-(((tetrahydrofuran-3-yl)methyl)amino)pyrido[2,3-d]pyrimidin-7(8H)-one |
| 121 | 8-(2-((1-acryloylpiperidin-4-yl)amino)ethyl)-6-(2-chloro-3,5-dimethoxyphenyl)-2-((2-(oxetan-3-yl)ethyl)amino)pyrido[2,3-d]pyrimidin-7(8H)-one |
| 122 | 8-(2-((1-acryloylpiperidin-4-yl)amino)ethyl)-6-(2-chloro-3,5-dimethoxyphenyl)-2-((tetrahydro-2H-pyran-4-yl)amino)pyrido[2,3-d]pyrimidin-7(8H)-one |
| 123 | (E)-6-(2-chloro-3,5-dimethoxyphenyl)-8-(2-((1-(4-(dimethylamino)but-2-enoyl)azetidin-3-yl)oxy)ethyl)-2-(oxetan-3-ylamino)pyrido[2,3-d]pyrimidin-7(8H)-one |
| 124 | 8-(3-(4-acryloyl-2,6-dimethylpiperazin-1-yl)propyl)-6-(2-chloro-3,5-dimethoxyphenyl)-2-((2-methoxyethyl)amino)pyrido[2,3-d]pyrimidin-7(8H)-one |
| 125 | (E)-6-(2-chloro-3,5-dimethoxyphenyl)-8-(2-((1-(4-(dimethylamino)but-2-enoyl)azetidin-3-yl)oxy)ethyl)-2-((2-methoxyethyl)amino)pyrido[2,3-d]pyrimidin-7(8H)-one |
| 126 | N-(1-(2-(6-(2,6-dichloro-3,5-dimethoxyphenyl)-2-(oxetan-3-ylamino)-7-oxopyrido[2,3-d]pyrimidin-8(7H)-yl)ethyl)piperidin-4-yl)acrylamide |
| 127 | 6-(2,6-dichloro-3,5-dimethoxyphenyl)-8-(2-((1-(3-methylbut-2-enoyl)azetidin-3-yl)amino)ethyl)-2-(oxetan-3-ylamino)pyrido[2,3-d]pyrimidin-7(8H)-one |
| 128 | N-(1-(2-(6-(2,6-dichloro-3,5-dimethoxyphenyl)-7-oxo-2-((tetrahydro-2H-pyran-4-yl)amino)pyrido[2,3-d]pyrimidin-8(7H)-yl)ethyl)azetidin-3-yl)acrylamide |
| 129 | N-(1-(2-(6-(2,6-dichloro-3,5-dimethoxyphenyl)-7-oxo-2-(((tetrahydrofuran-3-yl)methyl)amino)pyrido[2,3-d]pyrimidin-8(7H)-yl)ethyl)azetidin-3-yl)acrylamide |
| 130 | 8-(2-((1-acryloylpiperidin-4-yl)amino)ethyl)-6-(2,6-dichloro-3,5-dimethoxyphenyl)-2-(((tetrahydro-2H-pyran-4-yl)methyl)amino)pyrido[2,3-d]pyrimidin-7(8H)-one |
| 131 | N-(1-(2-(6-(2,6-dichloro-3,5-dimethoxyphenyl)-2-((2-(oxetan-3-yl)ethyl)amino)-7-oxopyrido[2,3-d]pyrimidin-8(7H)-yl)ethyl)azetidin-3-yl)acrylamide |
| 132 | 8-(2-((1-acryloylazetidin-3-yl)amino)ethyl)-6-(2,6-dichloro-3,5-dimethoxyphenyl)-2-((2-(oxetan-3-yl)ethyl)amino)pyrido[2,3-d]pyrimidin-7(8H)-one |
| 133 | 8-(2-((1-acryloylpiperidin-4-yl)amino)ethyl)-6-(2,6-dichloro-3,5-dimethoxyphenyl)-2-(oxetan-3-ylamino)pyrido[2,3-d]pyrimidin-7(8H)-one |
| 134 | 8-(2-((1-acryloylazetidin-3-yl)amino)ethyl)-6-(2,6-dichloro-3,5-dimethoxyphenyl)-2-(((tetrahydrofuran-3-yl)methyl)amino)pyrido[2,3-d]pyrimidin-7(8H)-one |
| 135 | 8-(2-((1-acryloylazetidin-3-yl)amino)ethyl)-6-(2,6-dichloro-3,5-dimethoxyphenyl)-2-((tetrahydro-2H-pyran-4-yl)amino)pyrido[2,3-d]pyrimidin-7(8H)-one |
| 136 | 8-(2-((1-acryloylpyrrolidin-3-yl)amino)ethyl)-6-(2,6-dichloro-3,5-dimethoxyphenyl)-2-((oxetan-3-ylmethyl)amino)pyrido[2,3-d]pyrimidin-7(8H)-one |
| 137 | N-(1-(2-(6-(2,6-dichloro-3,5-dimethoxyphenyl)-2-((2-methoxyethyl)amino)-7-oxopyrido[2,3-d]pyrimidin-8(7H)-yl)ethyl)piperidin-4-yl)acrylamide |
| 138 | 6-(2,6-dichloro-3,5-dimethoxyphenyl)-2-((2-methoxyethyl)amino)-8-(2-((1-(3-methylbut-2-enoyl)azetidin-3-yl)amino)ethyl)pyrido[2,3-d]pyrimidin-7(8H)-one |
| 139 | 8-(2-((1-acryloylpiperidin-4-yl)amino)ethyl)-6-(2,6-dichloro-3,5-dimethoxyphenyl)-2-((2-methoxyethyl)amino)pyrido[2,3-d]pyrimidin-7(8H)-one |
| 140 | 8-(2-((1-acryloylpiperidin-4-yl)amino)ethyl)-6-(2,6-dichloro-3,5-dimethoxyphenyl)-2-((2-(tetrahydrofuran-3-yl)ethyl)amino)pyrido[2,3-d]pyrimidin-7(8H)-one |
| 141 | (E)-6-(2,6-dichloro-3,5-dimethoxyphenyl)-8-(2-((1-(4-(dimethylamino)but-2-enoyl)pyrrolidin-3-yl)oxy)ethyl)-2-(methylamino)pyrido[2,3-d]pyrimidin-7(8H)-one |
| 142 | 8-(3-(4-acryloyl-2,6-dimethylpiperazin-1-yl)propyl)-6-(2-chloro-3,5-dimethoxyphenyl)-2-((oxetan-3-ylmethyl)amino)pyrido[2,3-d]pyrimidin-7(8H)-one |
| 143 | N-(1-(2-(6-(2-chloro-3,5-dimethoxyphenyl)-7-oxo-2-((2-(tetrahydrofuran-3-yl)ethyl)amino)pyrido[2,3-d]pyrimidin-8(7H)-yl)ethyl)piperidin-4-yl)acrylamide |

TABLE 2-continued

| | Name |
|---|---|
| 144 | 6-(2-chloro-3,5-dimethoxyphenyl)-8-(2-((1-(3-methylbut-2-enoyl)azetidin-3-yl)amino)ethyl)-2-((2-(tetrahydrofuran-3-yl)ethyl)amino)pyrido[2,3-d]pyrimidin-7(8H)-one |
| 145 | 8-(3-(4-acryloylpiperazin-1-yl)propyl)-6-(2-chloro-3,5-dimethoxyphenyl)-2-((2-(tetrahydrofuran-3-yl)ethyl)amino)pyrido[2,3-d]pyrimidin-7(8H)-one |
| 146 | 6-(2-chloro-3,5-dimethoxyphenyl)-8-(2-((1-(3-methylbut-2-enoyl)azetidin-3-yl)amino)ethyl)-2-(((tetrahydro-2H-pyran-4-yl)methyl)amino)pyrido[2,3-d]pyrimidin-7(8H)-one |
| 147 | (E)-6-(2-chloro-3,5-dimethoxyphenyl)-8-(2-((1-(4-(dimethylamino)but-2-enoyl)azetidin-3-yl)oxy)ethyl)-2-((tetrahydrofuran-3-yl)amino)pyrido[2,3-d]pyrimidin-7(8H)-one |
| 148 | (E)-6-(2-chloro-3,5-dimethoxyphenyl)-8-(2-((1-(4-(dimethylamino)but-2-enoyl)azetidin-3-yl)oxy)ethyl)-2-((oxetan-3-ylmethyl)amino)pyrido[2,3-d]pyrimidin-7(8H)-one |
| 149 | (E)-6-(2-chloro-3,5-dimethoxyphenyl)-8-(2-((1-(4-(dimethylamino)but-2-enoyl)pyrrolidin-3-yl)oxy)ethyl)-2-(oxetan-3-ylamino)pyrido[2,3-d]pyrimidin-7(8H)-one |
| 150 | 8-(3-(4-acryloyl-2,6-dimethylpiperazin-1-yl)propyl)-6-(2-chloro-3,5-dimethoxyphenyl)-2-((2-hydroxy-2-methylpropyl)amino)pyrido[2,3-d]pyrimidin-7(8H)-one |
| 151 | (E)-6-(2-chloro-3,5-dimethoxyphenyl)-8-(2-((1-(4-(dimethylamino)but-2-enoyl)pyrrolidin-3-yl)oxy)ethyl)-2-((2-methoxyethyl)amino)pyrido[2,3-d]pyrimidin-7(8H)-one |
| 152 | 8-(3-(4-acryloylpiperazin-1-yl)propyl)-6-(2-chloro-3,5-dimethoxyphenyl)-2-((2-(2-methoxyethoxy)ethyl)amino)pyrido[2,3-d]pyrimidin-7(8H)-one |
| 153 | 8-(3-(4-acryloyl-2,6-dimethylpiperazin-1-yl)propyl)-6-(2-chloro-3,5-dimethoxyphenyl)-2-(phenylamino)pyrido[2,3-d]pyrimidin-7(8H)-one |
| 154 | N-(1-(2-(6-(2,6-dichloro-3,5-dimethoxyphenyl)-2-((oxetan-3-ylmethyl)amino)-7-oxopyrido[2,3-d]pyrimidin-8(7H)-yl)ethyl)piperidin-4-yl)acrylamide |
| 155 | N-(1-(2-(6-(2,6-dichloro-3,5-dimethoxyphenyl)-7-oxo-2-(((tetrahydro-2H-pyran-4-yl)methyl)amino)pyrido[2,3-d]pyrimidin-8(7H)-yl)ethyl)azetidin-3-yl)acrylamide |
| 156 | N-(6-(2,6-dichloro-3,5-dimethoxyphenyl)-8-(3-(4-(3-methylbut-2-enoyl)piperazin-1-yl)propyl)-7-oxo-7,8-dihydropyrido[2,3-d]pyrimidin-2-yl)acetamide |
| 157 | N-(8-(3-(4-acryloyl-2,6-dimethylpiperazin-1-yl)propyl)-6-(2,6-dichloro-3,5-dimethoxyphenyl)-7-oxo-7,8-dihydropyrido[2,3-d]pyrimidin-2-yl)acetamide |
| 158 | N-(1-(2-(6-(2,6-dichloro-3,5-dimethoxyphenyl)-7-oxo-2-((tetrahydrofuran-3-yl)amino)pyrido[2,3-d]pyrimidin-8(7H)-yl)ethyl)piperidin-4-yl)acrylamide |
| 159 | N-(1-(2-(6-(2,6-dichloro-3,5-dimethoxyphenyl)-7-oxo-2-((2-(tetrahydrofuran-3-yl)ethyl)amino)pyrido[2,3-d]pyrimidin-8(7H)-yl)ethyl)azetidin-3-yl)acrylamide |
| 160 | 8-(2-((1-acryloylpyrrolidin-3-yl)amino)ethyl)-6-(2,6-dichloro-3,5-dimethoxyphenyl)-2-(((tetrahydrofuran-3-yl)methyl)amino)pyrido[2,3-d]pyrimidin-7(8H)-one |
| 161 | 8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one |
| 162 | 8-(2-((1-acryloylpiperidin-4-yl)amino)ethyl)-6-(2,6-dichloro-3,5-dimethoxyphenyl)-2-((tetrahydrofuran-3-yl)amino)pyrido[2,3-d]pyrimidin-7(8H)-one |
| 163 | 8-(2-((1-acryloylazetidin-3-yl)amino)ethyl)-6-(2,6-dichloro-3,5-dimethoxyphenyl)-2-(((tetrahydro-2H-pyran-4-yl)methyl)amino)pyrido[2,3-d]pyrimidin-7(8H)-one |
| 164 | 6-(2,6-dichloro-3,5-dimethoxyphenyl)-8-(2-((1-(3-methylbut-2-enoyl)azetidin-3-yl)amino)ethyl)-2-((tetrahydrofuran-3-yl)amino)pyrido[2,3-d]pyrimidin-7(8H)-one |
| 165 | 8-(2-((1-acryloylpiperidin-4-yl)amino)ethyl)-6-(2,6-dichloro-3,5-dimethoxyphenyl)-2-((oxetan-3-ylmethyl)amino)pyrido[2,3-d]pyrimidin-7(8H)-one |
| 166 | 6-(2,6-dichloro-3,5-dimethoxyphenyl)-8-(2-((1-(3-methylbut-2-enoyl)azetidin-3-yl)amino)ethyl)-2-((oxetan-3-ylmethyl)amino)pyrido[2,3-d]pyrimidin-7(8H)-one |
| 167 | 8-(3-(4-acryloylpiperazin-1-yl)propyl)-6-(2,6-dichloro-3,5-dimethoxyphenyl)-2-((oxetan-3-ylmethyl)amino)pyrido[2,3-d]pyrimidin-7(8H)-one |
| 168 | 8-(2-((1-acryloylpyrrolidin-3-yl)amino)ethyl)-6-(2,6-dichloro-3,5-dimethoxyphenyl)-2-((tetrahydro-2H-pyran-4-yl)amino)pyrido[2,3-d]pyrimidin-7(8H)-one |
| 169 | 8-(2-((1-acryloylazetidin-3-yl)amino)ethyl)-6-(2,6-dichloro-3,5-dimethoxyphenyl)-2-((2-(tetrahydrofuran-3-yl)ethyl)amino)pyrido[2,3-d]pyrimidin-7(8H)-one |
| 170 | (E)-6-(2-chloro-3,5-dimethoxyphenyl)-8-(2-((1-(4-(dimethylamino)but-2-enoyl)azetidin-3-yl)oxy)ethyl)-2-(phenylamino)pyrido[2,3-d]pyrimidin-7(8H)-one |
| 171 | 8-(3-(4-acryloyl-2,6-dimethylpiperazin-1-yl)propyl)-6-(2,6-dichloro-3,5-dimethoxyphenyl)-2-((2-hydroxyethyl)amino)pyrido[2,3-d]pyrimidin-7(8H)-one |
| 172 | 8-(2-((1-acryloylpiperidin-4-yl)amino)ethyl)-6-(2,6-dichloro-3,5-dimethoxyphenyl)-2-(phenylamino)pyrido[2,3-d]pyrimidin-7(8H)-one |
| 173 | N-(1-(2-(6-(2,6-dichloro-3,5-dimethoxyphenyl)-7-oxo-2-(phenylamino)pyrido[2,3-d]pyrimidin-8(7H)-yl)ethyl)piperidin-4-yl)acrylamide |
| 174 | 8-(3-(4-acryloyl-2,6-dimethylpiperazin-1-yl)propyl)-6-(2-chloro-3,5-dimethoxyphenyl)-2-((2-(oxetan-3-yl)ethyl)amino)pyrido[2,3-d]pyrimidin-7(8H)-one |
| 175 | 6-(2-chloro-3,5-dimethoxyphenyl)-8-(3-(4-(3-methylbut-2-enoyl)piperazin-1-yl)propyl)-2-((2-(oxetan-3-yl)ethyl)amino)pyrido[2,3-d]pyrimidin-7(8H)-one |

TABLE 2-continued

| | Name |
|---|---|
| 176 | 8-(3-(4-acryloyl-2,6-dimethylpiperazin-1-yl)propyl)-6-(2-chloro-3,5-dimethoxyphenyl)-2-((tetrahydro-2H-pyran-4-yl)amino)pyrido[2,3-d]pyrimidin-7(8H)-one |
| 177 | 8-(2-((1-acryloylpiperidin-4-yl)amino)ethyl)-6-(2-chloro-3,5-dimethoxyphenyl)-2-((2-(tetrahydro-2H-pyran-4-yl)ethyl)amino)pyrido[2,3-d]pyrimidin-7(8H)-one |
| 178 | (E)-6-(2-chloro-3,5-dimethoxyphenyl)-8-(2-((1-(4-(dimethylamino)but-2-enoyl)azetidin-3-yl)oxy)ethyl)-2-((2-(oxetan-3-yl)ethyl)amino)pyrido[2,3-d]pyrimidin-7(8H)-one |
| 179 | (E)-6-(2-chloro-3,5-dimethoxyphenyl)-8-(2-((1-(4-(dimethylamino)but-2-enoyl)pyrrolidin-3-yl)oxy)ethyl)-2-((tetrahydrofuran-3-yl)amino)pyrido[2,3-d]pyrimidin-7(8H)-one |
| 180 | (E)-6-(2-chloro-3,5-dimethoxyphenyl)-8-(2-((1-(4-(dimethylamino)but-2-enoyl)azetidin-3-yl)oxy)ethyl)-2-(((tetrahydrofuran-3-yl)methyl)amino)pyrido[2,3-d]pyrimidin-7(8H)-one |
| 181 | (E)-6-(2-chloro-3,5-dimethoxyphenyl)-8-(2-((1-(4-(dimethylamino)but-2-enoyl)pyrrolidin-3-yl)oxy)ethyl)-2-((oxetan-3-ylmethyl)amino)pyrido[2,3-d]pyrimidin-7(8H)-one |
| 182 | (E)-6-(2-chloro-3,5-dimethoxyphenyl)-8-(2-((1-(4-(dimethylamino)but-2-enoyl)azetidin-3-yl)oxy)ethyl)-2-((tetrahydro-2H-pyran-4-yl)amino)pyrido[2,3-d]pyrimidin-7(8H)-one |
| 183 | 8-(3-(4-acryloylpiperazin-1-yl)propyl)-6-(2-chloro-3,5-dimethoxyphenyl)-2-(((2,2-dimethyl-1,3-dioxolan-4-yl)methyl)amino)pyrido[2,3-d]pyrimidin-7(8H)-one |
| 184 | 8-(2-((1-acryloylpyrrolidin-3-yl)amino)ethyl)-6-(2,6-dichloro-3,5-dimethoxyphenyl)-2-((2-(tetrahydrofuran-3-yl)ethyl)amino)pyrido[2,3-d]pyrimidin-7(8H)-one |
| 185 | 6-(2,6-dichloro-3,5-dimethoxyphenyl)-8-(2-((1-(3-methylbut-2-enoyl)azetidin-3-yl)amino)ethyl)-2-((tetrahydro-2H-pyran-4-yl)amino)pyrido[2,3-d]pyrimidin-7(8H)-one |
| 186 | N-(1-(2-(6-(2,6-dichloro-3,5-dimethoxyphenyl)-7-oxo-2-((2-(tetrahydro-2H-pyran-4-yl)ethyl)amino)pyrido[2,3-d]pyrimidin-8(7H)-yl)ethyl)azetidin-3-yl)acrylamide |
| 187 | 8-(2-((1-acryloylazetidin-3-yl)amino)ethyl)-6-(2,6-dichloro-3,5-dimethoxyphenyl)-2-((2-(tetrahydro-2H-pyran-4-yl)ethyl)amino)pyrido[2,3-d]pyrimidin-7(8H)-one |
| 188 | N-(1-(2-(6-(2,6-dichloro-3,5-dimethoxyphenyl)-7-oxo-2-((tetrahydro-2H-pyran-4-yl)amino)pyrido[2,3-d]pyrimidin-8(7H)-yl)ethyl)piperidin-4-yl)acrylamide |
| 189 | 8-(2-((1-acryloylpiperidin-4-yl)amino)ethyl)-6-(2,6-dichloro-3,5-dimethoxyphenyl)-2-((tetrahydro-2H-pyran-4-yl)amino)pyrido[2,3-d]pyrimidin-7(8H)-one |
| 190 | 8-(3-(4-acryloylpiperazin-1-yl)propyl)-6-(2,6-dichloro-3,5-dimethoxyphenyl)-2-((2-(tetrahydrofuran-3-yl)ethyl)amino)pyrido[2,3-d]pyrimidin-7(8H)-one |
| 191 | 8-(3-(4-acryloylpiperazin-1-yl)propyl)-6-(2,6-dichloro-3,5-dimethoxyphenyl)-2-((2-(oxetan-3-yl)ethyl)amino)pyrido[2,3-d]pyrimidin-7(8H)-one |
| 192 | 8-(3-(4-acryloyl-2,6-dimethylpiperazin-1-yl)propyl)-6-(2,6-dichloro-3,5-dimethoxyphenyl)-2-(oxetan-3-ylamino)pyrido[2,3-d]pyrimidin-7(8H)-one |
| 193 | 8-(2-((1-acryloylpyrrolidin-3-yl)amino)ethyl)-6-(2,6-dichloro-3,5-dimethoxyphenyl)-2-(((tetrahydro-2H-pyran-4-yl)methyl)amino)pyrido[2,3-d]pyrimidin-7(8H)-one |
| 194 | N-(1-(2-(6-(2,6-dichloro-3,5-dimethoxyphenyl)-2-((2-(oxetan-3-yl)ethyl)amino)-7-oxopyrido[2,3-d]pyrimidin-8(7H)-yl)ethyl)piperidin-4-yl)acrylamide |
| 195 | N-(1-(2-(6-(2,6-dichloro-3,5-dimethoxyphenyl)-7-oxo-2-(((tetrahydrofuran-3-yl)methyl)amino)pyrido[2,3-d]pyrimidin-8(7H)-yl)ethyl)piperidin-4-yl)acrylamide |
| 196 | 8-(2-((1-acryloylpiperidin-4-yl)amino)ethyl)-6-(2,6-dichloro-3,5-dimethoxyphenyl)-2-(((tetrahydrofuran-3-yl)methyl)amino)pyrido[2,3-d]pyrimidin-7(8H)-one |
| 197 | 6-(2,6-dichloro-3,5-dimethoxyphenyl)-8-(2-((1-(3-methylbut-2-enoyl)azetidin-3-yl)amino)ethyl)-2-((2-(oxetan-3-yl)ethyl)amino)pyrido[2,3-d]pyrimidin-7(8H)-one |
| 198 | 8-(3-(4-acryloylpiperazin-1-yl)propyl)-6-(2,6-dichloro-3,5-dimethoxyphenyl)-2-(((tetrahydrofuran-3-yl)methyl)amino)pyrido[2,3-d]pyrimidin-7(8H)-one |
| 199 | (E)-6-(2,6-dichloro-3,5-dimethoxyphenyl)-8-(2-((1-(4-(dimethylamino)but-2-enoyl)azetidin-3-yl)oxy)ethyl)-2-(oxetan-3-ylamino)pyrido[2,3-d]pyrimidin-7(8H)-one |
| 200 | 8-(3-(4-acryloyl-2,6-dimethylpiperazin-1-yl)propyl)-6-(2,6-dichloro-3,5-dimethoxyphenyl)-2-((2-methoxyethyl)amino)pyrido[2,3-d]pyrimidin-7(8H)-one |
| 201 | (E)-6-(2,6-dichloro-3,5-dimethoxyphenyl)-8-(2-((1-(4-(dimethylamino)but-2-enoyl)azetidin-3-yl)oxy)ethyl)-2-((2-methoxyethyl)amino)pyrido[2,3-d]pyrimidin-7(8H)-one |
| 202 | 6-(2-chloro-3,5-dimethoxyphenyl)-8-(3-(4-(3-methylbut-2-enoyl)piperazin-1-yl)propyl)-2-((2-(tetrahydrofuran-3-yl)ethyl)amino)pyrido[2,3-d]pyrimidin-7(8H)-one |
| 203 | 6-(2-chloro-3,5-dimethoxyphenyl)-8-(3-(4-(3-methylbut-2-enoyl)piperazin-1-yl)propyl)-2-(((tetrahydro-2H-pyran-4-yl)methyl)amino)pyrido[2,3-d]pyrimidin-7(8H)-one |
| 204 | (E)-6-(2-chloro-3,5-dimethoxyphenyl)-8-(2-((1-(4-(dimethylamino)but-2-enoyl)pyrrolidin-3-yl)oxy)ethyl)-2-((tetrahydro-2H-pyran-4-yl)amino)pyrido[2,3-d]pyrimidin-7(8H)-one |
| 205 | (E)-6-(2-chloro-3,5-dimethoxyphenyl)-8-(2-((1-(4-(dimethylamino)but-2-enoyl)azetidin-3-yl)oxy)ethyl)-2-(((tetrahydro-2H-pyran-4-yl)methyl)amino)pyrido[2,3-d]pyrimidin-7(8H)-one |

TABLE 2-continued

| | Name |
|---|---|
| 206 | (E)-6-(2-chloro-3,5-dimethoxyphenyl)-8-(2-((1-(4-(dimethylamino)but-2-enoyl)pyrrolidin-3-yl)oxy)ethyl)-2-(((tetrahydrofuran-3-yl)methyl)amino)pyrido[2,3-d]pyrimidin-7(8H)-one |
| 207 | (E)-6-(2-chloro-3,5-dimethoxyphenyl)-8-(2-((1-(4-(dimethylamino)but-2-enoyl)pyrrolidin-3-yl)oxy)ethyl)-2-((2-(oxetan-3-yl)ethyl)amino)pyrido[2,3-d]pyrimidin-7(8H)-one |
| 208 | 6-(2-chloro-3,5-dimethoxyphenyl)-2-((2-(2-methoxyethoxy)ethyl)amino)-8-(3-(4-(3-methylbut-2-enoyl)piperazin-1-yl)propyl)pyrido[2,3-d]pyrimidin-7(8H)-one |
| 209 | 8-(3-(4-acryloyl-2,6-dimethylpiperazin-1-yl)propyl)-6-(2-chloro-3,5-dimethoxyphenyl)-2-((2-(2-methoxyethoxy)ethyl)amino)pyrido[2,3-d]pyrimidin-7(8H)-one |
| 210 | N-(1-(2-(6-(2,6-dichloro-3,5-dimethoxyphenyl)-7-oxo-2-(((tetrahydro-2H-pyran-4-yl)methyl)amino)pyrido[2,3-d]pyrimidin-8(7H)-yl)ethyl)piperidin-4-yl)acrylamide |
| 211 | N-(1-(2-(6-(2,6-dichloro-3,5-dimethoxyphenyl)-7-oxo-2-((2-(tetrahydrofuran-3-yl)ethyl)amino)pyrido[2,3-d]pyrimidin-8(7H)-yl)ethyl)piperidin-4-yl)acrylamide |
| 212 | 6-(2,6-dichloro-3,5-dimethoxyphenyl)-8-(2-((1-(3-methylbut-2-enoyl)azetidin-3-yl)amino)ethyl)-2-((2-(tetrahydrofuran-3-yl)ethyl)amino)pyrido[2,3-d]pyrimidin-7(8H)-one |
| 213 | 8-(3-(4-acryloyl-2,6-dimethylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one |
| 214 | 6-(2,6-dichloro-3,5-dimethoxyphenyl)-8-(2-((1-(3-methylbut-2-enoyl)azetidin-3-yl)amino)ethyl)-2-(((tetrahydro-2H-pyran-4-yl)methyl)amino)pyrido[2,3-d]pyrimidin-7(8H)-one |

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of the present disclosure such as compound of Formula (I) where Q is as defined above and X is a group of formula (a) can be prepared as illustrated and described in Scheme 1 below.

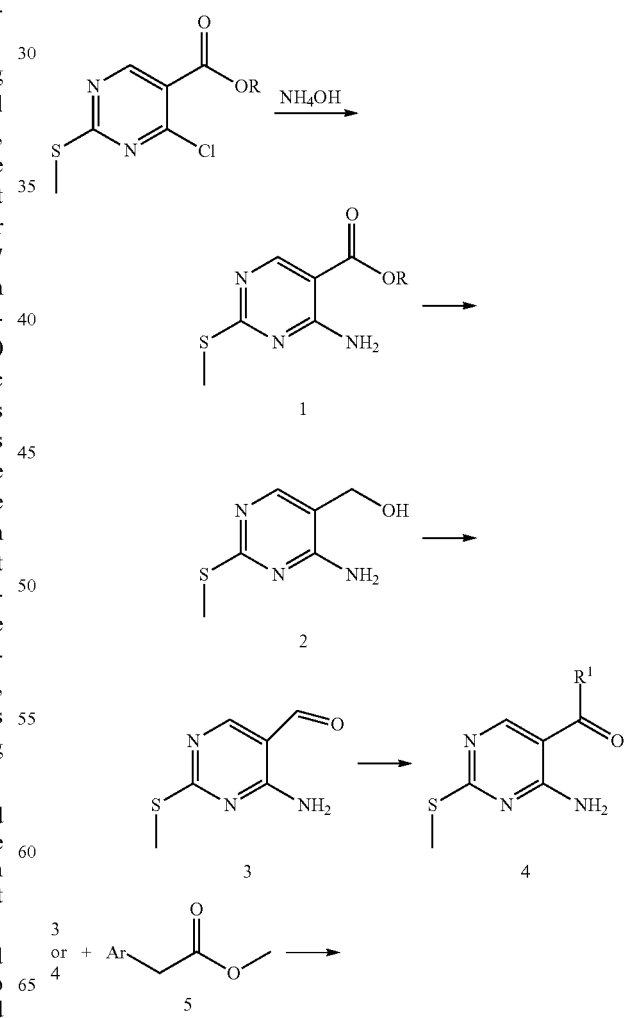

Scheme 1

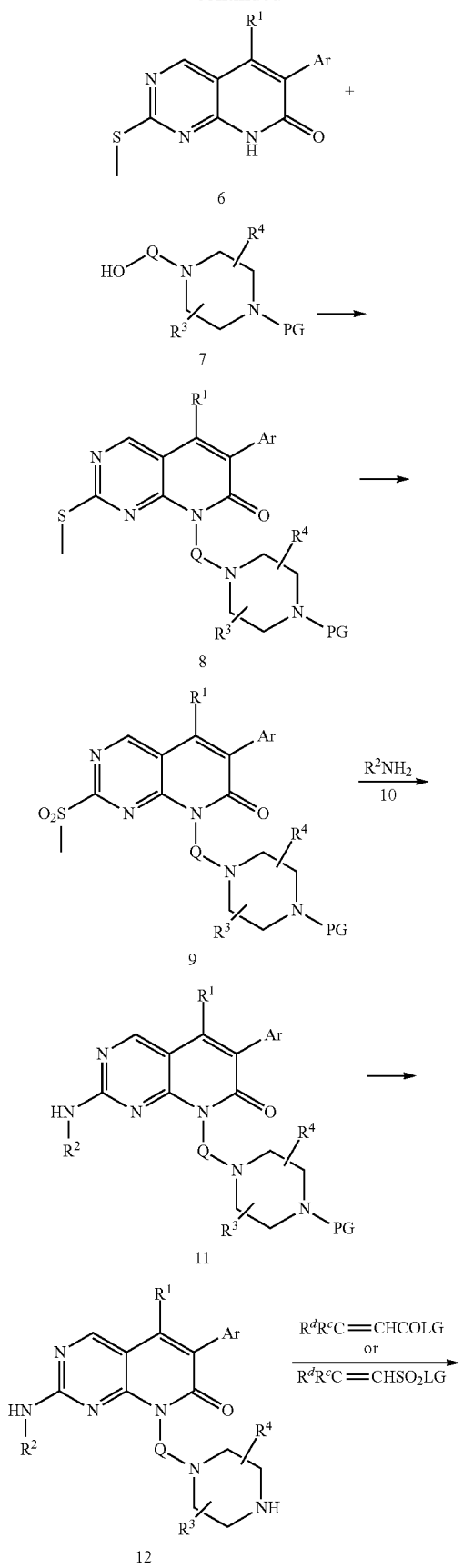

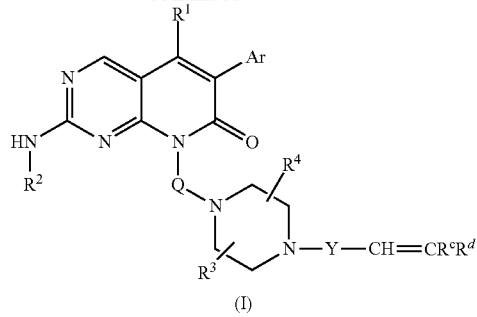

Substitution of the chlorine atom in ethyl 4-chloro-2-methylthiopyrimidine-5-carboxylate (R is ethyl) with ammonia in an organic solvent such as dichloromethane, tetrahydrofuran (THF), N,N-dimethylformamide (DMF), N-methylpyrrolidine (NMP), methyl alcohol, and the like, provides an amino compound of formula 1. Reduction of the ester group in compound 1 to an alcohol with a reducing agent such as lithium aluminum hydride in a solvent such as THF or diethyl ether at 0° C. to room temperature provides a compound of formula 2.

Oxidation of the alcohol group in 2 provides an aldehyde of formula 3. The reaction is carried out under standard oxidation conditions well known in the art such as manganese dioxide ($MnO_2$) in solvents such as dichloromethane at 0° C. to 60° C. For compounds of Formula (I) where $R^1$ is alkyl, compound 3 can be treated with an alkyl lithium or alkyl magnesium halide in a solvent such as THF to generate a secondary alcohol which can then be oxidized under standard oxidation reaction conditions to provide a compound of formula 4.

Coupling of compound 3 or 4 with an ester compound of formula 5 where Ar is as defined in aspect one above provides a quinolone compound of formula 6 where $R^1$ is hydrogen or alkyl, respectively. The coupling reaction is carried out in solvents such as N,N-dimethylformamide (DMF), N-methylpyrrolidine (NMP), and the like, using a base such as sodium hydride, sodium bicarbonate, lithium bicarbonate, potassium bicarbonate or triethylamine, and the like, at room temperature to 150° C. Compounds of formula 5 are either commercially available e.g. methyl 2-phenylacetate, methyl 2-(2-chlorophenyl)acetate, methyl 2-(2,4-dichlorophenyl)acetate, methyl 2-(2,6-dichlorophenyl)acetate, methyl 2-(3-methoxyphenyl)acetate and methyl 2-(3,5-dimethoxyphenyl)acetate are commercially available or can be readily prepared by methods well known in the art such as esterification of an aryl acetic acid to an aryl acetic ester under methanolic or ethanolic acidic (e.g. hydrogen chloride or sulfuric acid) conditions. and Reaction of a compound of formula 6 with a compound of formula 7 where Q, $R^3$, and $R^4$ are as defined in aspect one above and PG is a suitable nitrogen protecting group under standard Mitsunobu reaction conditions (e.g. triphenylphosphine, diisopropylazo-dicarboxylate in solvents such as THF, DCM or DMF provides a compound of formula 8. Compounds of formula 7 are either commercially available e.g 3-(piperazin-1-yl)propan-1-ol and tert-butyl 4-(3-hydroxypropyl)piperazine-1-carboxylate or how they can be made or can be readily prepared by methods well known in the art. Alternatively, the hydroxy group in 7 can be converted to a suitable leaving group such as tosylate, mesylate, or halo and then reacted with compound 6 in the presence of an organic base such as triethylamine, pyridine, and the like, to give a compound of formula 8.

Oxidation of the methylthio group in compound 8 provides sulfone of formula 9, utilizing oxidizing agents such as 3-chloroperbenzoic acid (MCPBA) in dichloromethane or Oxone© in methanol, aqueous ethanol or aqueous tetrahydrofuran at 0° C. to room temperature. Alternatively, the oxidation may be carried out under catalytic conditions with rhenium/peroxide reagents, see ("Oxidation of Sulfoxides by Hydrogen Peroxide, Catalyzed by Methyltrioxorhenium (VII)", Lahi, David W.; Espenson, James H, Inorg. Chem (2000) 39(10) pp. 2164-2167; "Rhenium oxo complexes in catalytic oxidations, Catal. Today (2000) 55(4), pp 317-363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, J. Org. Chem. (1998) 63(5), pp 1740-1741).

Coupling of the sulfone compound 9 with an amine of formula 10 where $R^2$ is as defined in aspect one above in a solvent such as DMF or NMP at temperatures of 80° C. to 150° C. provides a compound of formula 11. Compounds of formula 10 are either commercially available e.g., methylamine, N',N'-diethylbutane-1,4-diamine, 2-aminoethanol, 1-amino-2-methylpropan-2-ol, 2-morpholinoethanamine and 2-(4-methylpiperazin-1-yl)ethanamine or can be readily prepared by methods well known in the art.

Removal of the amino protecting group provides a compound of formula 12. The reaction conditions depend on nature of the amino protecting group. For example, when PG is Boc, it can be removed by treating a compound of formula 11 with an acid e.g. hydrogen chloride or trifluoroacetic acid in solvents such as DCM.

Compound 12 can be then converted to a compound of Formula (I) by methods well known in the art. For example, reacting 12 with an acyl halide of formula $R^dR^cC=CHCOLG$ or $R^dR^cC=CHSO_2X$ where $R^c$ and $R^d$ are as defined in the Summary and LG is halo under standard acylating or sulfonylating conditions i.e., in the presence of a base such as TEA or DIEA in solvents such as THF or DCM provides a compound of Formula (I).

It will be apparent to a person of ordinary skill in the art that compounds of Formula (I) where X is a group of formula (b), (c), (d), (e), (f), or (g) can be readily prepared by a method disclosed above but substituting a compound 7 with a compound of formula respectively. Representative examples of such preparations are provided in Working Examples below. Compounds of formula (b), (c), (d), (e), (f), or (g) such as tert-butyl 4-(2-hydroxyethyl)-piperazine-1-carboxylate, tert-butyl 4-(3-hydroxypropyl)piperazine-1-carboxylate, tert-butyl 3-(2-hydroxyethoxy)pyrrolidine-1-carboxylate, and tert-butyl 3-(2-hydroxyethoxy)-azetidine-1-carboxylate are commercially available.

Compounds of Formula (IC) can be prepared by methods well known in the art. For example, compounds of Formula (IC) where Q is as defined above, X is a group of formula (a) and $R^2$ phenyl or heteroaryl substituted with at least —NH(alkylene)$_n$-Z—CH=CR$^e$R$^f$ can be prepared as illustrated and described in Scheme 2 below.

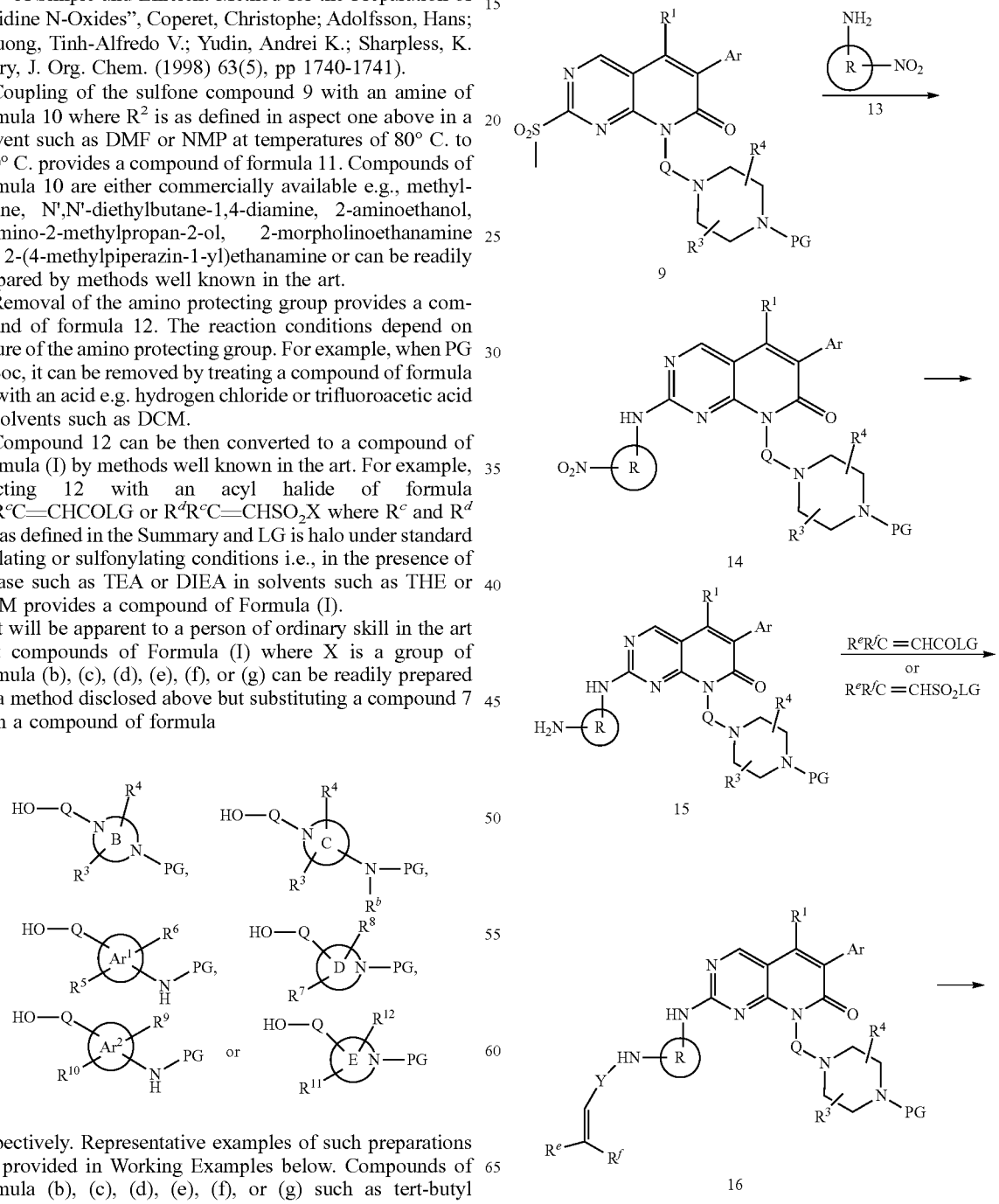

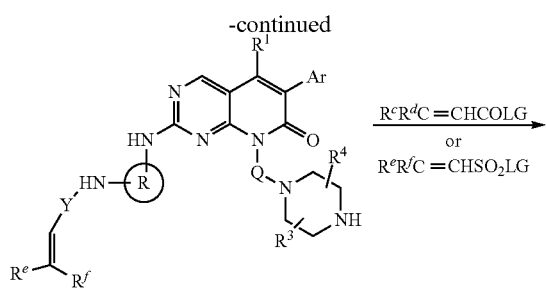

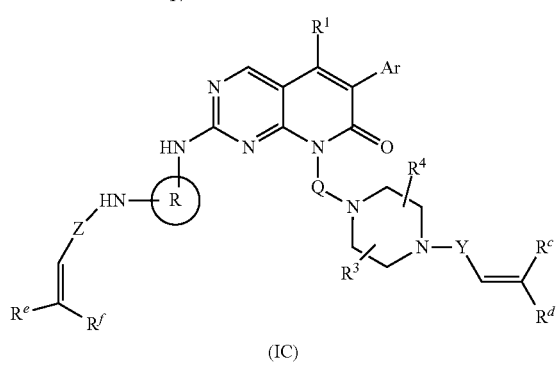

Coupling of the sulfone compound 9 with an amine of formula 13 where R is phenyl or heteroaryl in a solvent such as DMF or THF and a base such as tert-BuOK or NaH at temperatures of 0° C. to 100° C. provides a compound of formula 14. Compounds of formula 13 are either commercially available e.g., 2-nitroaniline, 4-methyl-2-nitroaniline, 4-chloro-2-nitroaniline, 4-methoxy-2-nitroaniline, 2-methyl-6-nitroaniline, 4-fluoro-2-nitroaniline, 3-nitropyridin-4-amine, 2-nitropyridin-3-amine, 6-methyl-3-nitropyridin-2-amine, 4-chloro-3-nitropyridin-2-amine, 6-methoxy-3-nitropyridin-2-amine, 6-chloro-5-nitropyrimidin-4-amine and 2-methyl-5-nitropyrimidin-4-amine or can be readily prepared by methods well known in the art.

Reduction of the nitro group in 14 provides an amine of formula 15. The reduction reaction is carried out in solvents such as methanol, ethyl acetate, tetrahydrofuran and the like using reducing agents such as tin(II)chloride, zinc and iron. Alternatively, the reduction can be done with hydrogen gas and a catalyst such as palladium, palladium hydroxide, platinum oxide or Raney nickel and the like. Treatment of compound 15 with acyl halide of formula $R^eR^fC=CHCOLG$ or $R^eR^fC=CHSO_2X$ where $R^d$ and $R^f$ are as defined in the Summary and LG is halo under standard acylating or sulfonylating conditions i.e., in the presence of a base such as TEA or DIEA in solvents such as THF or DCM provides a compound of formula 16.

Removal of the amino protecting group in 16 provides a compound of formula 17. The reaction conditions depend on nature of the amino protecting group. For example, when PG is Boc, it can be removed by treating a compound of formula 16 with an acid e.g. hydrogen chloride or trifluoroacetic acid in solvents such as DCM.

Compound 17 can be then converted to a compound of Formula (IC) by methods well known in the art. For example, reacting 17 with an acyl halide of formula $R^dR^cC=CHCOLG$ or $R^dR^cC=CHSO_2X$ where $R^c$ and $R^d$ are as defined in the Summary and LG is halo under standard acylating or sulfonylating conditions i.e., in the presence of a base such as TEA or DIEA in solvents such as THF or DCM provides a compound of Formula (IC).

It will be apparent to a person of ordinary skill in the art, that using above methodology and using appropriate starting materials, other compounds of Formula (IC) and also compounds of Formula (IB) can be synthesized.

Testing

The FGFR kinase inhibitory activity of the compounds of the present disclosure can be tested using the in vitro and in vivo assays described in Biological Examples 1-4 and 8 below. A determination of kinase inhibitory activity by any of those assays is considered to be kinase inhibitory activity within the scope of this disclosure even if any or all of the other assays do not result in a determination of kinase inhibitory activity. The ability of the compound of the disclosure to form an irreversible covalent bond can be determined by the assays described in Biological Examples 5-7, 9, or 10 and the ability of the compound of the disclosure to form an irreversible covalent bond with Cys488 of FGFR1 (UniprotKB Sequence ID P11362), Cys491 (UniprotKB Sequence ID P21802) of FGFR2, Cys482 (UniprotKB Sequence ID P22607) of FGFR3, and Cys477 (UniprotKB Sequence ID P22455) or Cys552 of FGFR4 and the olefinic bond in the compound of the disclosure, can be determined by the assays described in Biological Examples 7, Method B below. A determination of the irreversibility of the covalent bond between the FGFRs and the olefinic bond of the compound of the disclosure by any of Biological Examples 5, 6, 7, 9 or 10 below is considered within the scope of this disclosure even if one or more of the other methods does not result in a determination of binding irreversibility of the covalent bond.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; and proteasome inhibitor such as carfilzomib, MLN9708, delanzomib, or bortezomib.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure such as 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one used to determine the anti-tumor activity in HGS and RT4 tumor models (Example 4 below: In HGS model, vehicle dosed group reached tumor size 645 dosing at day 42 after inoculation whereas for animals treated with 20/kg of compound, the tumor size was 55 mm3 showing significant antitumor activity and induced tumor regression), include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat;

masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+-123-iethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., —125-iethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39·HCl), AC-7700 (Ajinomoto, also known as AVE-8062, AVE-8062A, CS-39-L-Ser·HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

EXAMPLES

The following preparations of compounds of Formula (III) and intermediates (References) are given to enable those skilled in the art to more clearly understand and to practice the present disclosure. They should not be considered as limiting the scope of the disclosure, but merely as being illustrative and representative thereof.
Reference 1

Synthesis of 6-(2-chlorophenyl)-2-(methylthio) pyrido[2,3-d]pyrimidin-7(8H)-one

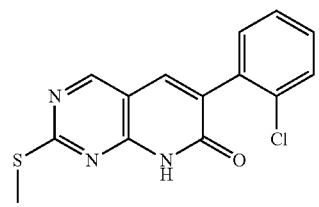 [SMILES: CSc1ncc2cc(-c3ccccc3Cl)c(=O)[nH]c2n1]

Step 1
To a solution of ethyl 4-chloro-2-(methylthio)pyrimidine-5-carboxylate (30 g, 129.3 mmol, 1.00 equiv) and Et$_3$N (51 mL) in THF (225 mL) was added NH$_3$·H$_2$O (300 mL). The resulting mixture was stirred at rt overnight. The mixture was concentrated and diluted with EtOAc. The organic phase was washed with sat. NaHCO$_3$ solution and brine, dried over anhydrous sodium sulfate. The solids were filtered and concentrated under vacuum to give 26.8 g (97%) of ethyl 4-amino-2-(methylthio)pyrimidine-5-carboxylate as a white solid.
Step 2
To a suspension of LiAlH4 (10.53 g, 277.0 mmol, 2.2 equiv) in THF (500 mL) was added drop wise ethyl 4-amino-2-(methylthio)pyrimidine-5-carboxylate (26.8 g, 126.0 mmol, 1.0 equiv) in THF (500 mL) at 0° C. The resulting mixture was stirred at 0° C. for 5 h. The reaction was quenched with 15% NaOH solution. The mixture was stirred for 1 h. The white precipitate was removed by filtration, washing with EtOAc. The filtrate was concentrated under vacuum to give 22 g (crude) of (4-amino-2-(methylthio)pyrimidin-5-yl)methanol as a white solid.
Step 3
To a solution of (4-amino-2-(methylthio)pyrimidin-5-yl) methanol (11 g, 63 mmol, 1.0 equiv) in CHCl$_3$ (900 mL) was added MnO$_2$ (43.85 g, 504 mmol, 8.0 equiv). The suspension was stirred overnight at rt. The resulting mixture was filtration and washing with CHCl$_3$. The filtrate was concentrated under vacuum to give 10 g (94%) of 4-amino-2-(methylthio)pyrimidine-5-carbaldehyde as a white solid.
Step 4
A solution of 4-amino-2-(methylthio)pyrimidine-5-carbaldehyde (20 g, 119 mmol, 1.0 equiv), K$_2$CO$_3$ (49.26 g, 357 mmol, 3.0 equiv) and methyl 2-(2-chlorophenyl)acetate (32.84 g, 178.5 mmol, 1.5 equiv) in NMP (130 ml) was stirred at 110° C. overnight. The reaction was diluted with EtOAc and water and extracted with EtOAc. The organic phase washed with brine, dried and concentrated. The residue was purified by column chromatography using EtOAc/PE (1/3) to give. 19 g (53%) of 6-(2-chlorophenyl)-2-(methylthio)pyrido[2,3-d]pyrimidin-7(8H)-one as a yellow solid.
Reference 2

Synthesis of 6-(2,6-dichloro-3,5-dimethoxy-phenyl)-2-(methylsulfanyl)-7H,8H-pyrido[2,3-d]pyrimidin-7-one

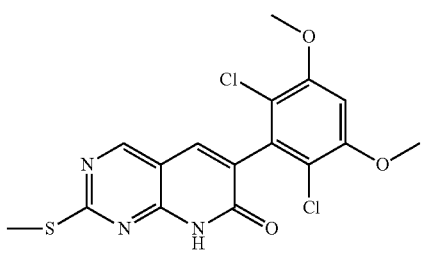

Step 1
Into a 500-mL 3-necked round-bottom flask, which was purged and maintained with an inert atmosphere of nitrogen, was placed a solution of 1,3-dimethoxy-5-methylbenzene (5 g, 32.85 mmol, 1.00 equiv) in dichloromethane (150 mL). This was followed by the addition of sulfuroyl dichloride (8.869 g, 65.71 mmol, 2.00 equiv) drop wise with stirring at 0° C. The resulting solution was stirred overnight at room temperature. The pH value of the solution was adjusted to 8 with sodium carbonate (sat. aq.). The resulting solution was extracted with dichloromethane, and the combined organic layers were concentrated under vacuum. The resulting mixture was washed with hexane to give 5.36 g (74%) of 2,4-dichloro-1,5-dimethoxy-3-methylbenzene as a white solid.

Step 2

Into a 1 L round-bottom flask, was placed a solution of 2,4-dichloro-1,5-dimethoxy-3-methylbenzene (35 g, 158.31 mmol, 1.00 equiv) in tetrachloromethane (600 mL). NBS (31 g, 174.18 mmol, 1.10 equiv) and AIBN (3.5 g, 21.31 mmol, 0.13 equiv) were added to the reaction mixture. The resulting solution was heated to reflux for 3 h. The reaction was then quenched by the addition of sodium carbonate (sat. aq.). The organic layer was washed with sodium chloride (sat.). The resulting mixture was concentrated under vacuum to give 38 g (80%) of 3-(bromo-methyl)-2,4-dichloro-1,5-dimethoxybenzene as a yellow solid.

Step 3

Into a 1 L round-bottom flask, was placed a solution of 3-(bromomethyl)-2,4-dichloro-1,5-dimethoxybenzene (47 g, 156.68 mmol, 1.00 equiv) in DMSO (500 mL). Sodium cyanide (8.445 g, 172.32 mmol, 1.10 equiv) was added to the reaction mixture. The resulting solution was stirred overnight at 35° C. The reaction was then quenched with sodium bicarbonate (sat. aq.). The resulting solution was extracted with ethyl acetate, The combined organic layers were washed with water and concentrated. The residue was applied onto a silica gel column with ethyl acetate/petroleum ether (1:10) as eluent to yield 20 g (52%) of 2-(2,6-dichloro-3,5-dimethoxy-phenyl)acetonitrile as a white solid.

Step 4

Into a 100-mL round-bottom flask, was placed a solution of 4-amino-2-(methylsulfanyl)-pyrimidine-5-carbaldehyde (2.0 g, 11.82 mmol, 1.00 equiv) in DMF (40 mL). 2-(2,6-Dichloro-3,5-Dimethoxyphenyl)acetonitrile (4.08 g, 16.58 mmol, 1.40 equiv), and potassium carbonate (4.90 g, 35.20 mmol, 3.00 equiv) were added and the resulting solution was stirred for 12 h at 100° C. in an oil bath, and then it was quenched with water. The resulting solution was extracted with ethyl acetate, and the combined organic layers were dried over anhydrous sodium sulfate and concentrated under vacuum. The residue was applied onto a silica gel column with ethyl acetate/petroleum ether (1:2) as eluent to yield 1.65 g (35%) of 6-(2,6-dichloro-3,5-dimethoxy-phenyl)-2-(methylsulfanyl)-7H,8H-pyrido[2,3-d]pyrimidin-7-imine as a yellow solid.

Step 5

Into a 50-mL round-bottom flask, was placed a solution of 6-(2,6-dichloro-3,5-dimethoxy-phenyl)-2-(methylsulfanyl)-7H,8H-pyrido[2,3-d]pyrimidin-7-imine (1.60 g, 4.03 mmol, 1.00 equiv) in acetic acid (40 mL). NaNO₂ (1.50 g, 21.74 mmol, 5.00 equiv) was added to the reaction mixture. The resulting solution was stirred for 2 h at 70° C., and then it was quenched with water. The solids were collected by filtration to give 1.25 g (78%) of 6-(2,6-dichloro-3,5-dimethoxy-phenyl)-2-(methylsulfanyl)-7H,8H-pyrido[2,3-d]pyrimidin-7-one as a yellow solid.

Reference 3

Synthesis of 6-(3,5-dimethoxyphenyl)-2-(methylthio)pyrido[2,3-d]pyrimidin-7(8H)-one

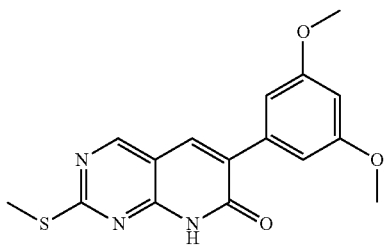

Step 1

To a solution of 2-(3,5-dimethoxyphenyl)acetic acid (7.5 g, 38.2 mmol) in MeOH (30 mL) was added SOCl₂ (1 mL) at 0° C. The mixture was stirred at room temperature for 2 h, and then it was concentrated under vacuum to give a residue. The residue was re-dissolved in EtOAc (100 mL), and the mixture was washed NaHCO₃, the organic layer was dried over Na₂SO₄, filtered and concentrated to give methyl 2-(3,5-dimethoxyphenyl)acetate (8.1 g, 100%) as a colorless oil.

Step 2

To a solution of methyl 2-(3,5-dimethoxyphenyl)acetate (3.38 g, 20 mmol), and 4-amino-2-(methylthio)pyrimidine-5-carbaldehyde (6.3 g, 30 mmol) in NMP (20 mL) was added K₂CO₃ (5.5 g, 40 mmol) and the mixture was stirred at 70° C. overnight. H₂O (50 mL) was added and the mixture was filtered, the filtered cake was washed with EtOAc and dried to give 6-(3,5-dimethoxyphenyl)-2-(methylthio)pyrido[2,3-d]pyrimidin-7(8H)-one (6.5 g, 99%) as a light yellow solid.

Reference 4

Synthesis of 6-(2-chloro-3,5-dimethoxyphenyl)-2-(methylthio)pyrido[2,3-d]pyrimidin-7(8H)-one

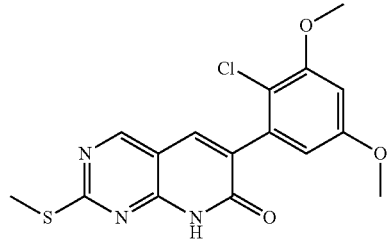

Step 1

To a solution of 2-(3,5-dimethoxyphenyl)acetic acid (25 g, 127.6 mmol) in H₂O/MeCN (200/200 mL) was added Oxone (78.5 g, 127.6 mmol) and KCl (9.5 g, 127.6 mmol), and the mixture was stirred at room temperature for 2 h. The mixture was filtered, EtOAc was added to the filtrate, and the H₂O layer was separated. The organic layer was concentrated to give a residue, which was dissolved in NaOH, washed with EtOAc, then the H₂O layer was adjusted to pH=5-6 with concentrated HCl (aq). The solid was filtered and the filtered cake was dried to give 2-(2-chloro-3,5-dimethoxyphenyl)acetic acid (26.5 g, 90%) as a light yellow solid.

Step 2

To a solution of 2-(2-chloro-3,5-dimethoxyphenyl)acetic acid (26.5 g, 114.9 mmol) in MeOH (100 mL) was added SOCl₂ (2 mL) at 0° C. The mixture was stirred at room temperature for 2 h, and then concentrated under vacuum to give a residue. The residue was re-dissolved in EtOAc, and the mixture was washed NaHCO₃. The organic layer was dried over Na₂SO₄, filtered and concentrated to give methyl 2-(2-chloro-3,5-dimethoxyphenyl)acetate (28.1 g, 100%) as a white solid.

Step 3

To a solution of 4-amino-2-(methylthio)pyrimidine-5-carbaldehyde (12.5 g, 74 mmol), and methyl 2-(2-chloro-3,5-dimethoxyphenyl)acetate (28 g, 114.5 mmol) in NMP (30 mL) was added K₂CO₃ (20.5 g, 148 mmol) and the mixture was stirred at 70° C. overnight. H₂O was added, the mixture was filtered and the filtered cake was washed with EtOAc. The filtered cake was dried to give 6-(2-chloro-3,5-dimethoxyphenyl)-2-(methylthio)pyrido[2,3-d]pyrimidin-7(8H)-one (14.8 g, 55%) as an off-white solid.

Example 1

Synthesis of 8-(2-(4-acryloylpiperazin-1-yl)ethyl)-6-(2-chloro-3,5-dimethoxyphenyl)-2-(methylamino) pyrido[2,3-d]pyrimidin-7(8H)-one

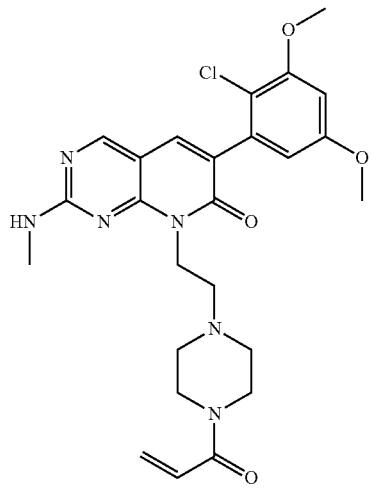

Step 1

To a solution of tert-butyl 4-(2-hydroxyethyl)piperazine-1-carboxylate (2.30 g, 10 mmol) in dichloromethane (100 mL) was added DIPEA (2.58 g, 20 mmol) and MsCl (1.72 g, 15 mmol) at 0° C. The reaction mixture was stirred at ambient temperature for 1 h before quenching with water. The reaction mixture was exacted with DCM, washed with brine and the organic layer was dried over anhydrous sodium sulfate, filtered, evaporated to provide tert-butyl 4-(2-((methylsulfonyl)oxy)ethyl)piperazine-1-carboxylate as a colorless oil (3.08 g, crude).

Step 2

To a solution of 6-(2-chloro-3,5-dimethoxyphenyl)-2-(methylthio)pyrido[2,3-d]pyrimidin-7(8H)-one (1.5 g, 4.3 mmol) in DMF (10 mL) was added $K_2CO_3$ (1.79 g, 13 mmol) and tert-butyl 4-(2-((methylsulfonyl)oxy)ethyl)piperazine-1-carboxylate (2 g, 6.5 mmol). The reaction mixture was stirred at 75° C. for 1 h and then poured into water, exacted with ethyl acetate and washed with brine. The organic layer was dried over anhydrous sodium sulfate, filtered and evaporated under vacuum to provide tert-butyl 4-(2-(6-(2-chloro-3,5-dimethoxyphenyl)-2-(methylthio)-7-oxopyrido[2,3-d]pyrimidin-8(7H)-yl)ethyl)piperazine-1-carboxylate as a white solid (2.5 g, crude).

Step 3

To a solution of tert-butyl 4-(2-(6-(2-chloro-3,5-dimethoxyphenyl)-2-(methylthio)-7-oxopyrido[2,3-d]pyrimidin-8(7H)-yl)ethyl)piperazine-1-carboxylate (2.30 g, 4.3 mmol) in DCM (30 mL) was added m-CPBA (1.50 g, 8.6 mmol). The reaction mixture was stirred at ambient temperature for 1 h before diluting with DCM (60 mL). The reaction mixture was washed with sat. $NaHCO_3$ and the organic layer was dried over anhydrous sodium sulfate, filtered and evaporated to provide tert-butyl 4-(2-(6-(2-chloro-3,5-dimethoxyphenyl)-2-(methylsulfinyl)-7-oxopyrido[2,3-d]pyrimidin-8 (7H)-yl)ethyl)piperazine-1-carboxylate as a white solid (2.50 g, crude).

Step 4

To a solution of tert-butyl 4-(2-(6-(2-chloro-3,5-dimethoxyphenyl)-2-(methylsulfinyl)-7-oxopyrido[2,3-d]pyrimidin-8(7H)-yl)ethyl)piperazine-1-carboxylate (2.50 g, 4.3 mmol) in DMSO (10 mL) was added DIPEA (1.66 g, 17.2 mmol) and methylamine hydrochloride (0.58 g, 8.6 mmol). The reaction mixture was stirred at 85° C. for 1 h and then poured into water, exacted with ethyl acetate and washed with brine. The organic layer was dried over anhydrous sodium sulfate, filtered and evaporated to provide tert-butyl 4-(2-(6-(2-chloro-3,5-dimethoxyphenyl)-2-(methylamino)-7-oxopyrido[2,3-d]pyrimidin-8(7H)-yl)ethyl)-piperazine-1-carboxylate as a yellow oil (2.40 g, crude).

Step 5

To a solution of tert-butyl 4-(2-(6-(2-chloro-3,5-dimethoxyphenyl)-2-(methylamino)-7-oxopyrido[2,3-d]pyrimidin-8(7H)-yl)ethyl)piperazine-1-carboxylate (2.4 g, 4.3 mmol) in DCM (10 mL) was added TFA (4 mL). The reaction mixture was stirred at ambient temperature overnight and then concentrated. The residue was dissolved in DCM (200 mL) and IPA (100 mL), washed with sat. $NaHCO_3$. The organic layer was dried over anhydrous sodium sulfate, filtered and evaporated to provide 6-(2-chloro-3,5-dimethoxyphenyl)-2-(methylamino)-8-(2-(piperazin-1-yl)ethyl)pyrido[2,3-d]pyrimidin-7(8H)-one as a gray solid (1.2 g, 70%) after flash chromatography (DCM/MeOH/$NH_4OH$=200:10:1).

Step 6

To a solution of 6-(2-chloro-3,5-dimethoxyphenyl)-2-(methylamino)-8-(2-(piperazin-1-yl)ethyl)pyrido[2,3-d]pyrimidin-7(8H)-one (230 mg, 0.5 mmol) in DCM (5 mL) was added TEA (156 mg, 1.5 mmol) and acryloyl chloride (46 mg, 0.5 mmol) in DCM (5 mL) at 0° C. The reaction mixture was stirred at 0° C. for 30 min before quenching with water. The residue was exacted with DCM, washed with brine and the organic layer was dried over anhydrous sodium sulfate, filtered and evaporated to provide 8-(2-(4-acryloylpiperazin-1-yl)ethyl)-6-(2-chloro-3,5-dimethoxyphenyl)-2-(methylamino)pyrido[2,3-d]pyrimidin-7(8H)-one as a white solid (60 mg, 23%) after flash chromatography (DCM/MeOH=30:1). MS (ESI, pos. ion) m/z: 513.1 (M+1).

Example 2

Synthesis of 8-(2-(4-acryloylpiperazin-1-yl)ethyl)-6-(2,6-dichloro-3,5-dimethoxyphenyl)-2-(methylamino)pyrido[2,3-d]pyrimidin-7(8H)-one

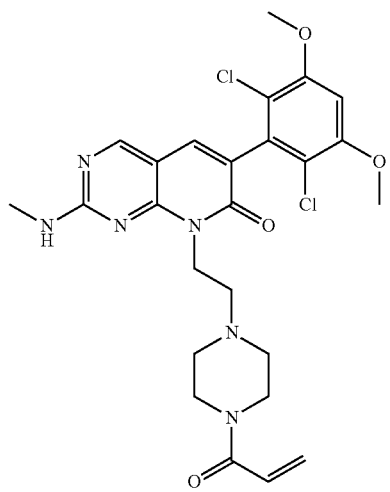

Step 1

To a solution of tert-butyl 4-(2-hydroxyethyl)piperazine-1-carboxylate (4 g, 17.37 mmol, 1.00 equiv), PPh₃ (14 g, 53.38 mmol, 3.07 equiv) and 4H-imidazole (3.5 g, 51.41 mmol, 2.96 equiv) in ether/ACN (300/100 mL) was added I2 (13 g) in portions at 0° C. over 10 min. The resulting solution was stirred overnight at room temperature and then extracted with ethyl acetate. The organic layer was dried over anhydrous sodium sulfate and concentrated. The residue was purified by chromatography (ethyl acetate/pet ether) to provide 2 g (34%) of tert-butyl 4-(2-iodoethyl)piperazine-1-carboxylate as a colorless oil.

Step 2

To a solution of 6-(2,6-dichloro-3,5-dimethoxyphenyl)-2-(methylsulfanyl)-7H,8H-pyrido[2,3-d]pyrimidin-7-one (800 mg, 2.01 mmol, 1.00 equiv) in acetone (100 mL) was added tert-butyl 4-(2-iodoethyl)piperazine-1-carboxylate (700 mg, 2.06 mmol, 1.02 equiv) and K₂CO₃ (800 mg, 5.75 mmol, 2.86 equiv). The resulting solution was stirred overnight at 60° C. The resulting reaction mixture was concentrated and the residue was purified by chromatography (ethyl acetate/pet. ether (1:4)) to provide 0.5 g (41%) of tert-butyl 4-[2-[6-(2,6-dichloro-3,5-dimethoxyphenyl)-2-(methylsulfanyl)-7-oxo-7H,8H-pyrido[2,3-d]pyrimidin-8-yl]-ethyl]piperazine-1-carboxylate as a light yellow solid.

Step 3

A solution of tert-butyl 4-[2-[6-(2,6-dichloro-3,5-dimethoxyphenyl)-2-(methylsulfanyl)-7-oxo-7H,8H-pyrido[2,3-d]pyrimidin-8-yl]ethyl]piperazine-1-carboxylate (500 mg, 0.82 mmol, 1.00 equiv) and mCPBA (300 mg, 1.74 mmol, 2.00 equiv). in chloroform (100 mL) was stirred for 2 h at room temperature and then diluted with ethyl acetate. The organic layer was washed with brine and then dried over anhydrous sodium sulfate, filtered and concentrated to give 0.5 g (95%) of 4-(tert-butoxycarbonyl)-1-(2-(6-(2,6-dichloro-3,5-dimethoxyphenyl)-2-(methylsulfinyl)-7-oxopyrido[2,3-d]pyrimidin-8(7H)-yl)ethyl)piperazine 1-oxide.

Step 4

To a solution of 4-(tert-butoxycarbonyl)-1-(2-(6-(2,6-dichloro-3,5-dimethoxyphenyl)-2-(methylsulfinyl)-7-oxopyrido[2,3-d]pyrimidin-8(7H)-yl)ethyl)piperazine 1-oxide (500 mg, 0.78 mmol, 1.00 equiv) in tert-butanol (100 mL) was added MeNH₂ (2M in THF) (2 mL). The reaction mixture was stirred overnight at 50° C. The resulting reaction mixture was concentrated to provide 0.4 g (84%) of 4-(tert-butoxycarbonyl)-1-(2-(6-(2,6-dichloro-3,5-dimethoxyphenyl)-2-(methylamino)-7-oxopyrido[2,3-d]pyrimidin-8(7H)-yl)ethyl)piperazine 1-oxide as a light yellow solid.

Step 5

To a solution of 4-(tert-butoxycarbonyl)-1-(2-(6-(2,6-dichloro-3,5-dimethoxyphenyl)-2-(methylamino)-7-oxopyrido[2,3-d]pyrimidin-8(7H)-yl)ethyl)piperazine 1-oxide (400 mg, 0.66 mmol, 1.00 equiv) in DMF (80 mL) was added PPh₃ (800 mg, 3.05 mmol, 5.00 equiv). The resulting solution was stirred overnight at 80° C. and then extracted with of ethyl acetate and the organic layers combined and washed with sat NaCl. The organic layer was dried over anhydrous sodium sulfate, filtered and concentrated to provide 0.3 g (77%) of tert-butyl 4-(2-(6-(2,6-dichloro-3,5-dimethoxyphenyl)-2-(methylamino)-7-oxopyrido[2,3-d]pyrimidin-8(7H)-yl)ethyl)piperazine-1-carboxylate as a light yellow solid.

Step 6

To a solution of tert-butyl 4-(2-(6-(2,6-dichloro-3,5-dimethoxyphenyl)-2-(methylamino)-7-oxopyrido[2,3-d]pyrimidin-8(7H)-yl)ethyl)piperazine-1-carboxylate (100 mg, 0.17 mmol, 1.00 equiv) in DCM (10 mL) was added trifluoroacetic acid (5 mL). The resulting solution was stirred for 2 h at room temperature. The pH was adjusted to 8 with aq. NaHCO₃. The resulting solution was extracted with DCM and the organic layers combined and dried over anhydrous sodium sulfate, filtered and concentrated to provide 80 mg (96%) of 6-(2,6-dichloro-3,5-dimethoxyphenyl)-2-(methylamino)-8-(2-(piperazin-1-yl)ethyl)pyrido[2,3-d]pyrimidin-7(8H)-one as a light brown solid.

Step 7

To a solution of 6-(2,6-dichloro-3,5-dimethoxyphenyl)-2-(methylamino)-8-(2-(piperazin-1-yl)ethyl)pyrido[2,3-d]pyrimidin-7(8H)-one (50 mg, 0.10 mmol, 1.00 equiv) in DMF (10 mL) was added prop-2-enoic acid (11 mg, 0.15 mmol, 1.51 equiv), HATU (58 mg, 0.15 mmol, 1.51 equiv) and TEA (31 mg, 0.31 mmol, 3.02 equiv). The resulting solution was stirred for 2 h at room temperature and then extracted with ethyl acetate) and the organic layers combined. The organic layer was washed with brine and then dried over anhydrous sodium sulfate, filtered and concentrated. The crude product was purified by Prep-HPLC ((Prep-HPLC-010): Column, XSelect CSH Prep C18 OBD Column, 5 um, 19*150 mm; mobile phase, water with 0.05% TFA and MeCN (15.0% MeCN up to 29.0% in 10 min);) to provide 17 mg (31%) of 8-(2-(4-acryloylpiperazin-1-yl)ethyl)-6-(2,6-dichloro-3,5-dimethoxyphenyl)-2-(methylamino)pyrido[2,3-d]pyrimidin-7(8H)-one as a light yellow solid. MS (ESI, pos. ion) m/z: 547.1 (M+1).

Example 3

Synthesis of N-(1-(2-(6-(2-chloro-3,5-dimethoxyphenyl)-2-(methylamino)-7-oxopyrido[2,3-d]pyrimidin-8(7H)-yl)ethyl)piperidin-4-yl)acrylamide

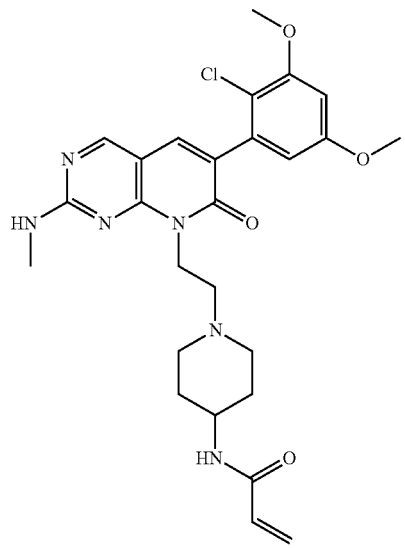

Step 1

To a solution of tert-butyl piperidin-4-ylcarbamate (2.5 g, 12.5 mmol) in MeOH (25 mL) was added K₂CO₃ (6.9 g, 50 mmol) and 2-bromoethanol (3.1 g, 25 mmol). The reaction mixture was stirred at ambient temperature overnight and then concentrated. The residue was diluted with water and exacted with ethyl acetate. The organic layer was dried over anhydrous sodium sulfate, filtered and evaporated to provide tert-butyl (1-(2-hydroxyethyl)piperidin-4-yl)carbamate as a light yellow oil (1.9 g, 61%) after flash chromatography (pet. ether/ethyl acetate=5:1).

Step 2

To a solution of tert-butyl (1-(2-hydroxyethyl)piperidin-4-yl)carbamate (1.8 g, 7.5 mmol) in DCM (10 mL) was added DIPEA (1.9 g, 15 mmol) and MsCl (1.2 g, 10 mmol) at 0° C. The reaction mixture was stirred at ambient temperature for 1 h before quenching with water. The reaction mixture was exacted with DCM (100 mL), washed with aq NaHCO₃ and brine. The organic layer was dried over anhydrous sodium sulfate, filtered and evaporated to provide 2-(4-((tert-butoxycarbonyl)amino)piperidin-1-yl)ethyl methanesulfonate as a yellow solid (2.40 g, crude).

Step 3

To a solution of 6-(2-chloro-3,5-dimethoxyphenyl)-2-(methylthio)pyrido[2,3-d]pyrimidin-7(8H)-one (1.8 g, 5.0 mmol) and 2-(4-((tert-butoxycarbonyl)amino)piperidin-1-yl)ethyl methanesulfonate (1.8 g, 7.5 mmol) in DMF (10 mL) was added K₂CO₃ (2.1 g, 15 mmol). The reaction mixture was stirred at 85° C. for 2 h and then diluted with ethyl acetate. The reaction mixture was washed with aq. NaHCO₃ and brine. The organic layer was dried over anhydrous sodium sulfate, filtered and evaporated to provide tert-butyl (1-(2-(6-(2-chloro-3,5-dimethoxyphenyl)-2-(methylthio)-7-oxopyrido[2,3-d]pyrimidin-8(7H)-yl)ethyl)piperidin-4-yl)carbamate as a white solid (2.3 g, 80%) after flash chromatography (DCM/MeOH=30:1).

Step 4

To a solution of tert-butyl (1-(2-(6-(2-chloro-3,5-dimethoxyphenyl)-2-(methylthio)-7-oxopyrido[2,3-d]pyrimidin-8(7H)-yl)ethyl)piperidin-4-yl)carbamate (2.3 g, 4.0 mmol) in DCM (40 mL) was added m-CPBA (1.3 g, 5.9 mmol). The reaction mixture was stirred at room temperature for 0.5 h and then washed with aq. NaHSO₃ (50 mL) and aq. NaHCO₃ (50 mL). The organic phase was dried and concentrated to provide tert-butyl (1-(2-(6-(2-chloro-3,5-dimethoxyphenyl)-2-(methylsulfinyl)-7-oxopyrido[2,3-d]pyrimidin-8(7H)-yl)ethyl)piperidin-4-yl)carbamate as a light yellow oil (1.8 g, 75%).

Step 5

To a solution of tert-butyl (1-(2-(6-(2-chloro-3,5-dimethoxyphenyl)-2-(methylsulfinyl)-7-oxopyrido[2,3-d]pyrimidin-8(7H)-yl)ethyl)piperidin-4-yl)carbamate (1.8 g, 3.0 mmol) in DMSO (20 mL) was added methylamine hydrochloride (612 mg, 9.0 mmol). The reaction mixture was stirred at 85° C. for 30 min and then cooled to ambient temperature, poured into water and exacted with ethyl acetate. The organic layer was washed with brine, dried over anhydrous sodium sulfate, filtered and evaporated to provide tert-butyl (1-(2-(6-(2-chloro-3,5-dimethoxyphenyl)-2-(methylamino)-7-oxopyrido[2,3-d]pyrimidin-8(7H)-yl)ethyl)piperidin-4-yl)carbamate as a yellow oil (856 mg, 50%).

Step 6

To a solution of tert-butyl (1-(2-(6-(2-chloro-3,5-dimethoxyphenyl)-2-(methylamino)-7-oxopyrido[2,3-d]pyrimidin-8(7H)-yl)ethyl)piperidin-4-yl)carbamate (850 mg, 1.5 mmol) in dioxane (10 mL) was added con. HCl (5 mL) and the reaction mixture were stirred at ambient temperature for 3 h before diluting with DCM and washing with aq NaHCO₃. The organic layer was dried over anhydrous sodium sulfate, filtered and evaporated to provide 8-(2-(4-aminopiperidin-1-yl)ethyl)-6-(2-chloro-3,5-dimethoxyphenyl)-2-(methylamino)pyrido[2,3-d]pyrimidin-7(8H)-one as a pale yellow oil (210 mg, 30%) after flash chromatography (DCM/MeOH=10:1).

Step 7

To a solution of 8-(2-(4-aminopiperidin-1-yl)ethyl)-6-(2-chloro-3,5-dimethoxyphenyl)-2-(methylamino)pyrido[2,3-d]pyrimidin-7(8H)-one (100 mg, 0.21 mmol) in DCM (5 mL) at −40° C. was added TEA (64 mg, 0.63 mmol) and acryloyl chloride (29 mg, 0.32 mmol). The reaction mixture was stirred for 30 min and then poured into water and exacted with DCM. The organic layer was dried over anhydrous sodium sulfate, filtered and evaporated to provide N-(1-(2-(6-(2-chloro-3,5-dimethoxyphenyl)-2-(methylamino)-7-oxopyrido[2,3-d]pyrimidin-8(7H)-yl)ethyl)piperidin-4-yl)acrylamide as a white solid (20 mg, 18%) after prep-TLC (DCM/MeOH=20:1). MS (ESI, pos. ion) m/z: 527.2 (M+1).

Example 4

Synthesis of 8-(3-(4-acryloylpiperazin-1-yl)propyl)-6-(2-chloro-3,5-dimethoxyphenyl)-2-(methylamino)pyrido[2,3-d]pyrimidin-7(8H)-one

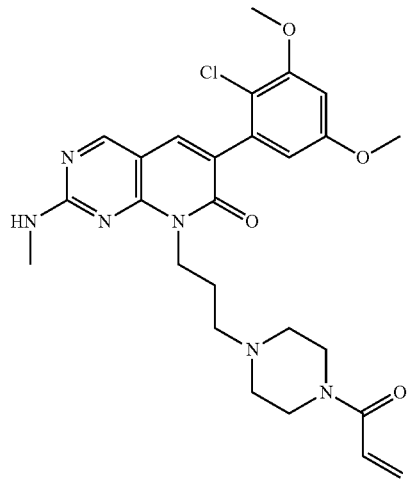 [SMILES: C=CC(=O)N1CCN(CCCn2c(=O)c(-c3cc(OC)cc(OC)c3Cl)cc3cnc(NC)nc32)CC1]

Step 1

A mixture of 3-(piperazin-1-yl)propan-1-ol (1.44 g, 10 mmol), Boc₂O (3.3 g, 15 mmol) and DIPEA (1.80 g, 15 mmol) in DCM (100 mL) was stirred at room temperature until reaction completion and then diluted with DCM (200 mL). The organic layer was washed with brine, dried over anhydrous sodium sulfate, filtered and evaporated. The residue was purified by chromatography (DCM:MeOH=20:1) to provide tert-butyl 4-(3-hydroxypropyl)piperazine-1-carboxylate as a colorless oil (2.4 g, 97%).

Step 2

A mixture of tert-butyl 4-(3-hydroxypropyl)piperazine-1-carboxylate (1.52 g, 6.2 mmol), Ph₃P (2.46 g, 9.4 mmol), I₂ (2.40 g, 9.4 mmol) and imidazole (1.28 g, 18.6 mmol) in DCM (100 mL) was stirred at room temperature for 5 h and then diluted with DCM (200 mL). The organic layer was washed with brine, dried over anhydrous sodium sulfate, filtered and evaporated. The residue was purified by chromatography (PE:EtOAc=5:1) to provide tert-butyl 4-(3-iodopropyl)piperazine-1-carboxylate (1.10 g, 50%) as a colorless oil.

Step 3

A mixture of tert-butyl 4-(3-iodopropyl)piperazine-1-carboxylate (0.93 g, 2.64 mmol), 6-(2-chloro-3,5-dimethoxyphenyl)-2-(methylthio)pyrido[2,3-d]pyrimidin-7(8H)-one (0.80 g, 2.2 mmol), K$_2$CO$_3$ (0.61 g, 4.4 mmol) in DMF (10 mL) was stirred at 80° C. for 1 h and then cooled to room temperature and diluted with EtOAc. The organic layer was washed with brine, dried over anhydrous sodium sulfate, filtered, and evaporated to provide give tert-butyl 4-(3-(6-(2-chloro-3,5-dimethoxyphenyl)-2-(methylthio)-7-oxopyrido[2,3-d]pyrimidin-8(7H)-yl)propyl)piperazine-1-carboxylate (1.30 g, crude) as a yellow oil.

Step 4

A mixture of tert-butyl 4-(3-(6-(2-chloro-3,5-dimethoxyphenyl)-2-(methylthio)-7-oxopyrido[2,3-d]pyrimidin-8(7H)-yl)propyl)piperazine-1-carboxylate (1.30 g, 2.2 mmol) and m-CPBA (0.62 g, 6.6 mmol) in DCM (50 mL) was stirred at room temperature for 30 min before diluting with DCM (200 mL). The organic layer was washed with brine, dried over anhydrous sodium sulfate, filtered, and evaporated to provide tert-butyl 4-(3-(6-(2-chloro-3,5-dimethoxyphenyl)-2-(methylsulfinyl)-7-oxopyrido[2,3-d]pyrimidin-8(7H)-yl)propyl)piperazine-1-carboxylate (1.33 g, crude) as a yellow oil.

Step 5

A mixture of tert-butyl 4-(3-(6-(2-chloro-3,5-dimethoxyphenyl)-2-(methylsulfinyl)-7-oxopyrido[2,3-d]pyrimidin-8(7H)-yl)propyl)piperazine-1-carboxylate (1.33 g, 2.2 mmol), MeNH$_2$·HCl (300 mg, 5.4 mmol) and DIPEA (851 mg, 6.6 mmol) in DMSO (10 mL) was stirred at 85° C. for 1 h and then cooled to room temperature and diluted with EtOAc. The organic layer was washed with brine), dried over anhydrous sodium sulfate, filtered and evaporated to provide tert-butyl 4-(3-(6-(2-chloro-3,5-dimethoxyphenyl)-2-(methylamino)-7-oxopyrido[2,3-d]pyrimidin-8(7H)-yl)propyl)piperazine-1-carboxylate give (1.26 g, crude) as a yellow oil.

Step 6

A mixture of tert-butyl 4-(3-(6-(2-chloro-3,5-dimethoxyphenyl)-2-(methylamino)-7-oxopyrido[2,3-d]pyrimidin-8(7H)-yl)propyl)piperazine-1-carboxylate (1.26 g, 2.3 mmol) in conc. HCl (5 mL) and dioxane (10 mL) was stirred at room temperature for 10 h and then the pH was adjusted to 8 with 1N NaOH. The reaction mixture was diluted with DCM and $^i$PrOH. The organic layer was washed with brine, dried over anhydrous sodium sulfate, filtered and evaporated. The residue was purified by chromatography (DCM:MeOH=5:1) to provide 6-(2-chloro-3,5-dimethoxyphenyl)-2-(methylamino)-8-(3-(piperazin-1-yl)propyl)pyrido[2,3-d]pyrimidin-7(8H)-one (0.40 g, 38%) as a white solid.

Step 7

To a solution of 6-(2-chloro-3,5-dimethoxyphenyl)-2-(methylamino)-8-(3-(piperazin-1-yl)propyl)pyrido[2,3-d]pyrimidin-7(8H)-one (140 mg, 0.3 mmol) and TEA (66 mg, 0.6 mol) at −78° C. in DCM (50 mL) was added acryloyl chloride (54.3 mg, 0.6 mmol) in DCM (1 mL). The reaction mixture was stirred at −78° C. for 10 min before diluting with DCM. The organic layer was washed with brine, dried over anhydrous sodium sulfate, filtered and evaporated. The residue was purified by Prep-TLC (DCM:MeOH=30:1) to provide 8-(3-(4-acryloylpiperazin-1-yl)propyl)-6-(2-chloro-3,5-dimethoxyphenyl)-2-(methylamino)pyrido[2,3-d]pyrimidin-7(8H)-on (75 mg, 68%) as a white solid. MS (ESI, pos. ion) m/z: 527.0 (M+1).

Example 5

Synthesis of 8-(2-((3aR,6aS)-5-acryloylhexahydropyrrolo[3,4-c]pyrrol-2(1H)-yl)ethyl)-6-(2-chloro-3,5-dimethoxyphenyl)-2-(methylamino)pyrido[2,3-d]pyrimidin-7(8H)-one

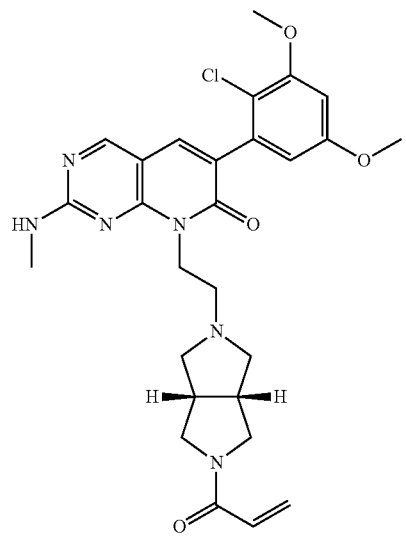

Step 1

To a solution of 1H-pyrrole-2,5-dione (12.6 g, 130 mmol) in DCM (150 mL) at 0° C. was added TFA (1.1 mL) and a solution of N-benzyl-1-methoxy-N-((trimethylsilyl)methyl)-methanamine (33.9 g, 143 mmol) in DCM (50 mL). The reaction mixture was then stirred at ambient temperature for 35 h. The organic layer was washed with sat. NaHCO$_3$ and brine. The organic layer was dried over anhydrous sodium sulfate, filtered and evaporated. The residue was stirred at ethyl acetate/heptane (10%, 150 mL) overnight. The solid was collected and MeOHI/NH$_2$OH (aq. 50%) (2.1 mL) was added. The reaction mixture was stirred at ambient temperature overnight and then concentrated and the residue was dissolved in ethyl acetate, filtered to remove some insoluble materials. The filtrated was concentrated to provide (3aR,6aS)-5-benzyltetrahydropyrrolo[3,4-c]pyrrole-1,3(2H,3aH)-dione as a light yellow solid (13 g, 39%).

Step 2

To a suspension of LiAlH$_4$ (4.3 g, 113 mmol) in THF (50 mL) was added a solution of (3aR,6aS)-5-benzyltetrahydropyrrolo[3,4-c]pyrrole-1,3(2H,3aH)-dione (13 g, 56.5 mmol) in THF (150 mL) at 0° C. under an N$_2$ atmosphere. After addition, the reaction mixture was stirred at 0° C. for 0.5 h and then refluxed for 3 h before cooling to ambient temperature. The reaction mixture was quenched by aq. NaOH (15%) (5.2 mL), filtered and the filtrated was evaporated to provide (3aR,6aS)-2-benzyloctahydropyrrolo[3,4-c]pyrrole as a yellow oil (10 g, 88%).

Step 3

To a solution of (3aR,6aS)-2-benzyloctahydropyrrolo[3,4-c]pyrrole (10 g, 49.5 mmol) in THF (100 mL) was added DIPEA (12.8 g, 99 mmol) and Boc$_2$O (10.8 g, 49.5 mmol). The reaction mixture was stirred at ambient temperature for 5 h before diluting with ethyl acetate. The reaction mixture was washed with aq. NaHCO$_3$ and brine. The organic layer was dried over anhydrous sodium sulfate, filtered and evaporated to provide (3aR,6aS)-tert-butyl 5-benzylhexahydropyrrolo[3,4-c]pyrrole-2(1H)-carboxylate as a yellow oil (12 g, 80%).

Step 4

To a solution of (3aR,6aS)-tert-butyl 5-benzylhexahydropyrrolo[3,4-c]pyrrole-2(1H)-carboxylate (5 g, 16.5 mmol) in MeOH (50 mL) was added Pd(OH)$_2$/C (10%) (0.5 g). The reaction mixture was stirred at 60° C. overnight under an H$_2$ atmosphere at 60 psi and then cooled to ambient temperature. The reaction mixture was filtered through Celite and the filtrate was evaporated to provide (3aR,6aS)-tert-butyl hexahydropyrrolo[3,4-c]pyrrole-2(1H)-carboxylate get as a colorless oil (2.3 g, 66%).

Step 5

To a solution of (3aR,6aS)-tert-butyl hexahydropyrrolo[3,4-c]pyrrole-2(1H)-carboxylate (2.3 g, 10.8 mmol) in DMF (30 mL) was added K$_2$CO$_3$ (3 g, 21.6 mmol) and 2-bromoethanol (2.0 g, 16.2 mmol). The reaction mixture was stirred at ambient temperature for 8 h and then diluted with ethyl acetate. The reaction mixture was washed with water and the organic layer was dried over anhydrous sodium sulfate, filtered and evaporated to provide (3aR,6aS)-tert-butyl 5-(2-hydroxyethyl)hexahydropyrrolo[3,4-c]pyrrole-2(1H)-carboxylate as a yellow oil (1.7 g, 61%).

Step 6

To a solution of (3aR,6aS)-tert-butyl 5-(2-hydroxyethyl)hexahydropyrrolo[3,4-c]pyrrole-2(1H)-carboxylate (1.0 g, 3.9 mmol) in DCM (20 mL) at 0° C. was added DIPEA (1.51 g, 11.7 mmol) and MsCl (1.56 g, 4.7 mmol). The resulting mixture was stirred at ambient temperature for 30 min before quenching with sat. NaHCO$_3$. The mixture was exacted with ethyl acetate and washed with brine. The organic layer was dried over anhydrous sodium sulfate, filtered and evaporated to provide (3aR,6aS)-tert-butyl 5-(2-((methylsulfonyl)oxy)ethyl)hexahydropyrrolo-[3,4-c]pyrrole-2(1H)-carboxylate as a yellow solid (1.2 g, 92%).

Step 7

To a solution of 6-(2-chloro-3,5-dimethoxyphenyl)-2-(methylthio)pyrido[2,3-d]pyrimidin-7(8H)-one (1.09 g, 3 mmol) in DMF (10 mL) was added K$_2$CO$_3$ (1.3 g, 9 mmol) and (3aR,6aS)-tert-butyl 5-(2-((methylsulfonyl)oxy)ethyl) hexahydropyrrolo[3,4-c]pyrrole-2(1H)-carboxylate (1.2 g, 3.6 mmol). The reaction mixture was stirred at 85° C. for 1 h before cooling to ambient temperature. The reaction mixture was poured into water, filtered and the filtered cake was washed with water and dried to provide (3aR,6aS)-tert-butyl 5-(2-(6-(2-chloro-3,5-dimethoxy-phenyl)-2-(methylthio)-7-oxopyrido[2,3-d]pyrimidin-8(7H)-yl)ethyl)-hexahydropyrrolo[3,4-c]pyrrole-2(1H)-carboxylate as a white solid (1.3 g, 67%).

Step 8

To a solution of (3aR,6aS)-tert-butyl 5-(2-(6-(2-chloro-3,5-dimethoxyphenyl)-2-(methylthio)-7-oxopyrido[2,3-d]pyrimidin-8(7H)-yl)ethyl)hexahydropyrrolo[3,4-c]pyrrole-2(1H)-carboxylate (1.3 g, 2.2 mmol) in DCM (20 mL) was added m-CPBA (1.5 g, 8.8 mmol). The reaction mixture was stirred at ambient temperature for 2 h before quenching with sat. Na$_2$SO$_3$. The mixture was exacted with DCM, washed with sat. NaHCO$_3$ and brine. The organic layer was dried over anhydrous sodium sulfate, filtered and evaporated to provide (3aR,6aS)-tert-butyl 5-(2-(6-(2-chloro-3,5-dimethoxyphenyl)-2-(methylsulfonyl)-7-oxopyrido[2,3-d]pyrimidin-8(7H)-yl)ethyl)hexahydropyrrolo[3,4-c]pyrrole-2(1H)-carboxylate as a yellow solid (1.3 g, crude).

Step 9

To a solution of (3aR,6aS)-tert-butyl 5-(2-(6-(2-chloro-3,5-dimethoxyphenyl)-2-(methylsulfonyl)-7-oxopyrido[2,3-d]pyrimidin-8(7H)-yl)ethyl)hexahydropyrrolo[3,4-c]pyrrole-2(1H)-carboxylate (1.3 g, 2.0 mmol) in DMSO (20 mL) was added DIPEA (0.77 g, 6.0 mmol) and methylamine hydrochloride (0.67 g, 10 mmol). The reaction mixture was stirred at 85° C. for 30 min before cooling to ambient temperature. The residue was diluted with ethyl acetate and washed with brine. The organic layer was dried over anhydrous sodium sulfate, filtered and evaporated to provide (3aR,6aS)-tert-butyl 5-(2-(6-(2-chloro-3,5-dimethoxyphenyl)-2-(methylamino)-7-oxopyrido[2,3-d]pyrimidin-8(7H)-yl)ethyl)hexahydropyrrolo[3,4-c]pyrrole-2(1H)-carboxylate as a light yellow oil (0.85 g, crude).

Step 10

To a solution of (3aR,6aS)-tert-butyl 5-(2-(6-(2-chloro-3,5-dimethoxyphenyl)-2-(methylamino)-7-oxopyrido[2,3-d]pyrimidin-8(7H)-yl)ethyl)hexahydropyrrolo[3,4-c]pyrrole-2(1H)-carboxylate (0.9 g, 1.5 mmol) in dioxane (10 mL) was added conc. HCl (5 mL). The reaction mixture was stirred at ambient temperature for 3 h before evaporating. The residue was adjusted to pH=7 with sat. NaHCO$_3$ and exacted with ethyl acetate and washed with brine. The organic layer was dried over anhydrous sodium sulfate, filtered and evaporated to provide 6-(2-chloro-3,5-dimethoxyphenyl)-8-(2-((3aR,6aS)-hexahydropyrrolo[3,4-c]pyrrol-2(1H)-yl)ethyl)-2-(methylamino)pyrido[2,3-d]pyrimidin-7(8H)-one as a yellow oil (0.38 g, crude).

Step 11

To a solution of 6-(2-chloro-3,5-dimethoxyphenyl)-8-(2-((3aR,6aS)-hexahydropyrrolo[3,4-c]pyrrol-2(1H)-yl)ethyl)-2-(methylamino)pyrido[2,3-d]pyrimidin-7(8H)-one (350 mg, 0.72 mmol) in DCM (5 mL) at −40° C. was added acryloyl chloride (65 mg, 0.72 mmol). The reaction mixture was stirred at −40° C. for 30 min before warming to 0° C. The reaction mixture was evaporated and the residue was purified by prep-HPLC to provide 8-(2-((3aR,6aS)-5-acryloylhexahydropyrrolo[3,4-c]pyrrol-2(1H)-yl)ethyl)-6-(2-chloro-3,5-dimethoxyphenyl)-2-(methylamino)pyrido[2,3-d]pyrimidin-7(8H)-one as a white solid (5 mg, <5%). MS (ESI, pos. ion) m/z: 538.7 (M+1).

Example 6

Synthesis of 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one

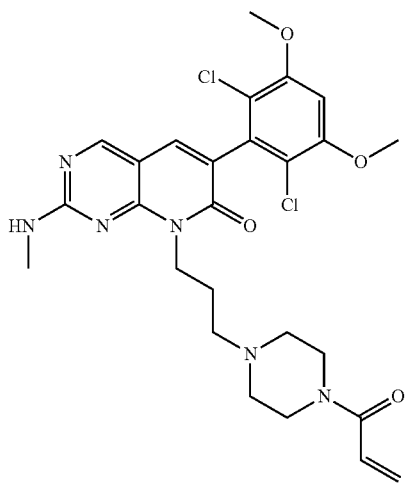 [SMILES: C=CC(=O)N1CCN(CCCn2c(=O)c(-c3c(Cl)c(OC)cc(OC)c3Cl)cc3cnc(NC)nc32)CC1]

Step 1

To a solution of 3-(piperazin-1-yl)propan-1-ol (1 g, 6.93 mmol, 1.00 equiv) in THF (50 mL) and TEA (2 g) was added di-tert-butyl dicarbonate (2.26 g, 10.36 mmol, 1.49 equiv). The resulting solution was stirred for 2 h at room temperature and then concentrated. The residue was purified by chromatography (DCM/MeOH (15:1)) to provide 1.48 g (87%) of tert-butyl 4-(3-hydroxypropyl)piperazine-1-carboxylate as a light yellow liquid.

Step 2

To a solution of tert-butyl 4-(3-hydroxypropyl)piperazine-1-carboxylate (1.48 g, 6.06 mmol, 1.00 equiv) in DCM (60 mL), imidazole (620 mg) and TPP (2.38 g, 9.07 mmol, 1.50 equiv) was added $I_2$ (2.31 g, 9.10 mmol, 1.50 equiv). The resulting solution was stirred for 2 h at room temperature and then concentrated. The residue was purified by chromatography (DCM/MeOH (50:1)) to provide 1.65 g (77%) of tert-butyl 4-(3-iodopropyl)piperazine-1-carboxylate as yellow oil.

Step 3

To a solution of 6-(2,6-dichloro-3,5-dimethoxyphenyl)-2-(methylsulfanyl)-7H,8H-pyrido[2,3-d]pyrimidin-7-one (600 mg, 1.51 mmol, 1.00 equiv) in acetone (50 mL) and $K_2CO_3$ (630 mg) was added tert-butyl 4-(3-iodopropyl)piperazine-1-carboxylate (640 mg, 1.81 mmol, 1.20 equiv). The resulting solution was heated to reflux for 3 h and then the solids were filtered out. The residue was purified by chromatography (DCM/EtOAc (2:1)) to provide 720 mg (77%) of tert-butyl 4-[3-[6-(2,6-dichloro-3,5-dimethoxyphenyl)-2-(methylsulfanyl)-7-oxo-7H,8H-pyrido[2,3-d]pyrimidin-8-yl]propyl]piperazine-1-carboxylate as a yellow solid.

Step 4

To a solution of tert-butyl 4-[3-[6-(2,6-dichloro-3,5-dimethoxyphenyl)-2-(methyl-sulfanyl)-7-oxo-7H,8H-pyrido[2,3-d]pyrimidin-8-yl]propyl]piperazine-1-carboxylate (720 mg, 1.15 mmol, 1.00 equiv) in $CHCl_3$ (50 mL) was added mCPBA (600 mg). The resulting solution was stirred overnight at room temperature and then quenched with sat. $Na_2CO_3$. The resulting solution was extracted DCM/MeOH (10:1) and the organic layer was concentrated. This provided 750 mg (97%) of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]piperazin-1-ium-1-olate as a yellow solid.

Step 5

To a solution of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]piperazin-1-ium-1-olate (750 mg, 1.12 mmol, 1.00 equiv) in tert-BuOH (50 mL), was added $MeNH_2$/THF (2N) (1 mL). The resulting solution was stirred for 2 h at 60° C. and then concentrated. This provided 680 mg (98%) of 4-[(tert-butoxy)carbonyl]-1-[3-[6-(2,6-dichloro-3,5-dimethoxyphenyl)-2-(methylamino)-7-oxo-7H,8H-pyrido[2,3-d]pyrimidin-8-yl]propyl]piperazin-1-ium-1-olate as a yellow solid.

Step 6

To a solution of 4-[(tert-butoxy)carbonyl]-1-[3-[6-(2,6-dichloro-3,5-dimethoxyphenyl)-2-(methylamino)-7-oxo-7H,8H-pyrido[2,3-d]pyrimidin-8-yl]propyl]piperazin-1-ium-1-olate (680 mg, 1.09 mmol, 1.00 equiv) in MeOH (100 mL) was added Zn (1 g) and sat. $NH_4Cl$ (4 mL). The resulting reaction mixture was stirred overnight at room temperature and then solids were filtered out. The residue was purified by chromatography (DCM/MeOH (35:1)) to provide 650 mg (98%) of tert-butyl 4-[3-[6-(2,6-dichloro-3,5-dimethoxyphenyl)-2-(methylamino)-7-oxo-7H,8H-pyrido[2,3-d]pyrimidin-8-yl]propyl]piperazine-1-carboxylate as a yellow solid.

Step 7

To a solution of tert-butyl 4-[3-[6-(2,6-dichloro-3,5-dimethoxyphenyl)-2-(methylamino)-7-oxo-7H,8H-pyrido[2,3-d]pyrimidin-8-yl]propyl]piperazine-1-carboxylate (650 mg, 1.07 mmol, 1.00 equiv) in dioxane (12 mL), was added conc. HCl (3 mL). The resulting solution was stirred for 3 h at room temperature and then concentrated. This provided 550 mg (95%) of 6-(2,6-dichloro-3,5-dimethoxyphenyl)-2-(methylamino)-8-(3-(piperazin-1-yl)propyl)pyrido[2,3-d]pyrimidin-7(8H)-one hydrochloride as an off-white solid.

Step 8

To a solution of 6-(2,6-dichloro-3,5-dimethoxyphenyl)-2-(methylamino)-8-[3-(piperazin-1-yl)propyl]-7H,8H-pyrido[2,3-d]pyrimidin-7-one hydrochloride (250 mg, 0.49 mmol, 1.00 equiv) in DCM (20 mL) was added TEA (120 mg, 1.19 mmol, 2.41 equiv) and prop-2-enoyl chloride (54 mg, 0.60 mmol, 1.21 equiv). The resulting solution was stirred for 2 h at room temperature and then quenched with $H_2O$ (30 mL). The resulting solution was extracted with DCM/MeOH (10:1) and the organic layers combined and concentrated. The crude product was purified by Prep-HPLC (Column, SunFire Prep C18 OBD Column, 150 mm Sum 10 nm; mobile phase, Water with 10 mmol $NH_4HCO_3$ and MeCN (30.0% MeCN up to 80.0% in 10 min); Detector, nm). This provided 112.1 mg (41%) of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one as a white solid. MS (ESI, pos. ion) m/z: 561.1 (M+1).

Example 7

Synthesis of 8-(3-(4-acryloylpiperazin-1-yl)propyl)-2-((cyclopropylmethyl)amino)-6-(2,6-dichloro-3,5-dimethoxyphenyl)pyrido[2,3-d]pyrimidin-7(8H)-one

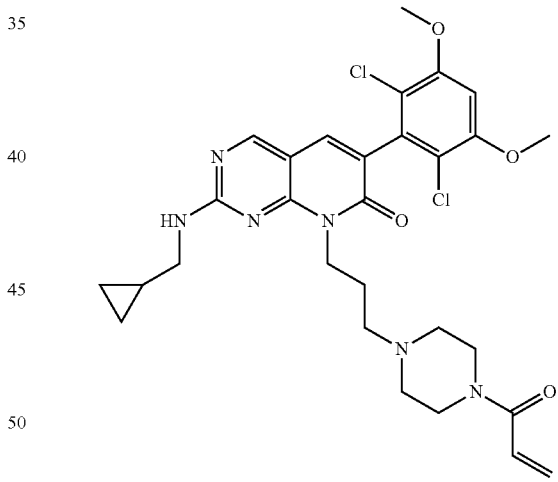

Step 1

To a solution of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]piperazin-1-ium-1-olate (350 mg, 0.52 mmol, 1.00 equiv) in tBuOH (20 mL) and TEA (0.3 mL) was added cyclopropylmethanamine (70 mg, 0.98 mmol, 1.89 equiv). The resulting solution was stirred for 2 h at 60° C. and then diluted with $H_2O$. The resulting solution was extracted with DCM/MeOH (10:1) and the organic layers combined and concentrated. This provided 310 mg (90%) of 4-[(tert-butoxy)carbonyl]-1-(3-[2-[(cyclopropylmethyl)amino]-6-(2,6-dichloro-3,5-dimethoxyphenyl)-7-oxo-7H,8H-pyrido[2,3-d]pyrimidin-8-yl]propyl)piperazin-1-ium-1-olate as a yellow solid.

Step 2

To a solution of 4-[(tert-butoxy)carbonyl]-1-(3-[2-[(cyclopropylmethyl)amino]-6-(2,6-dichloro-3,5-dimethoxyphenyl)-7-oxo-7H,8H-pyrido[2,3-d]pyrimidin-8-yl]propyl)piperazin-1-ium-1-olate (310 mg, 0.47 mmol, 1.00 equiv) in MeOH (60 mL) was added sat. NH$_4$Cl (2 mL) and Zn (2 g). The resulting reaction mixture was stirred overnight at room temperature and then the solids were filtered out. The residue was purified by chromatography (DCM/MeOH (100:8) to provide 270 mg (89%) of tert-butyl 4-(3-[2-[(cyclopropylmethyl)amino]-6-(2,6-dichloro-3,5-dimethoxyphenyl)-7-oxo-7H,8H-pyrido[2,3-d]pyrimidin-8-yl]propyl)piperazine-1-carboxylate as a yellow solid.

Step 3

To a solution of tert-butyl 4-(3-[2-[(cyclopropylmethyl)amino]-6-(2,6-dichloro-3,5-dimethoxyphenyl)-7-oxo-7H,8H-pyrido[2,3-d]pyrimidin-8-yl]propyl)piperazine-1-carboxylate (270 mg, 0.42 mmol, 1.00 equiv) in dioxane (6 mL) was added conc. HCl (2 mL). The resulting solution was stirred for 1 h at room temperature and then concentrated. This provided 220 mg (90%) of 2-[(cyclopropylmethyl)amino]-6-(2,6-dichloro-3,5-dimethoxyphenyl)-8-[3-(piperazin-1-yl)propyl]-7H,8H-pyrido[2,3-d]pyrimidin-7-one hydrochloride as a light yellow solid.

Step 4

To a solution of 2-[(cyclopropylmethyl)amino]-6-(2,6-dichloro-3,5-dimethoxyphenyl)-8-[3-(piperazin-1-yl)propyl]-7H,8H-pyrido[2,3-d]pyrimidin-7-one hydrochloride (220 mg, 0.40 mmol, 1.00 equiv) in DCM (40 mL) was added TEA (0.4 mL) and prop-2-enoyl chloride (0.2 mL). The resulting solution was stirred for 1 h at room temperature and then quenched with H$_2$O (50 mL). The resulting solution was extracted with DCM/MeOH (10:1) (2×80 mL) and the organic layers combined. The crude product was purified by Prep-HPLC (Column, XBridge Prep Shield RP18 OBD Column, 19*150 mm Sum 13 nm; mobile phase, water with 10 mmol NH$_4$HCO$_3$ and MeCN (20.0% MeCN up to 60.0% in 10 min); Detector, 254 nm). This provided 45.1 mg (19%) of 2-[(cyclopropylmethyl)amino]-6-(2,6-dichloro-3,5-dimethoxyphenyl)-8-[3-[4-(prop-2-enoyl)piperazin-1-yl]propyl]-7H,8H-pyrido[2,3-d]pyrimidin-7-one as a white solid. MS (ESI, pos. ion) m/z: 601.0 (M+1).

Example 8

Synthesis of 8-(2-((1-acryloylpiperidin-4-yl)oxy)ethyl)-6-(2,6-dichloro-3,5-dimethoxyphenyl)-2-((2-hydroxy-2-methylpropyl)amino)pyrido[2,3-d]pyrimidin-7(8H)-one

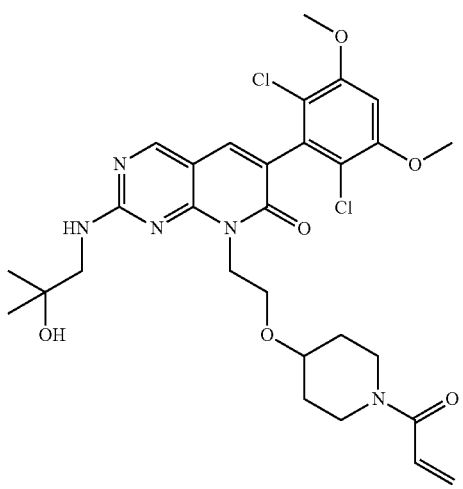 [SMILES: C=CC(=O)N1CCC(OCCn2c(=O)c(-c3c(Cl)c(OC)cc(OC)c3Cl)cc3cnc(NCC(C)(C)O)nc32)CC1]

Step 1

To a mixture of NaH (1 g, 25.00 mmol, 1.00 equiv) in THF (100 mL) was added tert-butyl 4-hydroxypiperidine-1-carboxylate (5 g, 24.84 mmol, 1.00 equiv). The reaction mixture was stirred for 20 min at 0° C. and then methyl 2-bromoacetate (3.8 g, 24.84 mmol, 1.00 equiv) was added. The resulting solution was stirred overnight at room temperature and then quenched with H$_2$O. The resulting solution was extracted with ethyl acetate and the organic layers combined and washed with (sat.) NaCl. The mixture was dried over anhydrous sodium sulfate and concentrated. The residue was purified by chromatography (DCM/MeOH (10:1)) to give 3 g (44%) of tert-butyl 4-(2-methoxy-2-oxoethoxy)piperidine-1-carboxylate as a colorless oil.

Step 2

To a solution of LAH (500 mg, 13.18 mmol, 1.20 equiv) in THF (100 mL) at 0° C. was added tert-butyl 4-(2-methoxy-2-oxoethoxy)piperidine-1-carboxylate (3 g, 10.98 mmol, 1.00 equiv) in THF (50 mL) drop wise. The resulting solution was stirred for 2 h at room temperature and then quenched with 15% NaOH (2 mL). The resulting solution was extracted with ethyl acetate and the organic layers combined and washed with sat. NaCl. The mixture was dried over anhydrous sodium sulfate and concentrated to give 2 g (74%) of tert-butyl 4-(2-hydroxyethoxy)piperidine-1-carboxylate as a colorless oil.

Step 3

To a solution of tert-butyl 4-(2-hydroxyethoxy)piperidine-1-carboxylate (2 g, 8.15 mmol, 1.00 equiv) in DCM (100 mL) was added I$_2$ (3.1 g, 1.50 equiv), imidazole (0.8 g, 1.50 equiv), and PPh$_3$ (3.2 g, 12.20 mmol, 1.50 equiv). The resulting solution was stirred for 2 h at room temperature and then concentrated. The residue was purified by chromatography (EtOAc/pet. ether (4:1)) to give 2 g (69%) of tert-butyl 4-(2-iodoethoxy)piperidine-1-carboxylate as a light yellow oil.

Step 4

To a solution of 6-(2,6-dichloro-3,5-dimethoxyphenyl)-2-(methylsulfanyl)-7H,8H-pyrido[2,3-d]pyrimidin-7-one (1.2 g, 3.01 mmol, 1.00 equiv) in ACN (150 mL) was added tert-butyl 4-(2-iodoethoxy)piperidine-1-carboxylate (1.3 g, 3.66 mmol, 1.20 equiv) and K$_2$CO$_3$ (1.2 g, 8.68 mmol, 3.00 equiv). The resulting solution was stirred overnight at 70° C. and then concentrated. The residue was purified by chromatography applied onto (DCM/EtOAc (40:1)) to give 1.5 g (80%) of tert-butyl 4-[2-[6-(2,6-dichloro-3,5-dimethoxyphenyl)-2-(methylsulfanyl)-7-oxo-7H,8H-pyrido[2,3-d]pyrimidin-8-yl]ethoxy]piperidine-1-carboxylate as a yellow solid.

Step 5

To a solution of tert-butyl 4-[2-[6-(2,6-dichloro-3,5-dimethoxyphenyl)-2-(methylsulfanyl)-7-oxo-7H,8H-pyrido[2,3-d]pyrimidin-8-yl]ethoxy]piperidine-1-carboxylate (1.5 g, 2.40 mmol, 1.00 equiv) in DCM (100 mL) was added mCPBA (1.0 g, 2.50 equiv). The resulting solution was stirred for 2 h at room temperature and then quenched with H$_2$O. The resulting solution was extracted with DCM and the organic layers were combined and washed with sat. NaHCO$_3$. The mixture was dried over anhydrous sodium sulfate and concentrated to give 1.6 g (100%) of tert-butyl 4-[2-[6-(2,6-dichloro-3,5-dimethoxyphenyl)-2-methanesulfonyl-7-oxo-7H,8H-pyrido[2,3-d]pyrimidin-8-yl]ethoxy]piperidine-1-carboxylate as a yellow solid.

Step 6

To a solution of tert-butyl 4-[2-[6-(2,6-dichloro-3,5-dimethoxyphenyl)-2-methanesulfonyl-7-oxo-7H,8H-pyrido[2,3-d]pyrimidin-8-yl]ethoxy]piperidine-1-carboxylate (400 mg, 0.61 mmol, 1.00 equiv) in t-BuOH (50 mL) was added TEA (121 mg, 1.20 mmol, 1.97 equiv), and 1-amino-2-methyl-propan-2-ol (80 mg, 0.90 mmol, 1.48 equiv). The resulting solution was stirred for 2 h at 50° C. and then concentrated. The residue was purified by chromatography (EtOAc/pet. ether (2:1)) to provide 250 mg (62%) of tert-butyl 4-[2-[6-(2,6-dichloro-3,5-dimethoxyphenyl)-2-[(2-hydroxy-2-methylpropyl)amino]-7-oxo-7H,8H-pyrido[2,3-d]pyrimidin-8-yl]ethoxy]piperidine-1-carboxylate as a yellow solid.

Step 7

To a solution of tert-butyl 4-[2-[6-(2,6-dichloro-3,5-dimethoxyphenyl)-2-[(2-hydroxy-2-methylpropyl)amino]-7-oxo-7H,8H-pyrido[2,3-d]pyrimidin-8-yl]ethoxy]piperidine-1-carboxylate (250 mg, 0.38 mmol, 1.00 equiv) in DCM (5 mL) was added TFA (2 mL). The resulting solution was stirred for 1 h at room temperature and then concentrated. The pH was adjusted to 8 with sat. NaHCO$_3$. The resulting solution was extracted with DCM and the organic layers were combined and dried over anhydrous sodium sulfate and concentrated to give 180 mg (85%) of 6-(2,6-dichloro-3,5-dimethoxyphenyl)-2-[(2-hydroxy-2-methylpropyl)amino]-8-[2-(piperidin-4-yloxy)ethyl]-7H,8H-pyrido[2,3-d]pyrimidin-7-one as a light brown solid.

Step 8

To a solution of 6-(2,6-dichloro-3,5-dimethoxyphenyl)-2-[(2-hydroxy-2-methyl-propyl)amino]-8-[2-(piperidin-4-yloxy)ethyl]-7H,8H-pyrido[2,3-d]pyrimidin-7-one (180 mg, 0.32 mmol, 1.00 equiv) in DCM/MeOH (10/10 mL) was added TEA (64 mg, 0.63 mmol, 1.99 equiv) and prop-2-enoyl chloride (29 mg, 0.32 mmol, 1.01 equiv). The resulting solution was stirred for 2 h at room temperature and then concentrated. The crude product was purified by Prep-HPLC (Column, XBridge Prep Shield RP18 OBD Column, 150 mm Sum 13 nm; mobile phase, Water with 10 mmol NH$_4$HCO$_3$ and MeCN (20.0% MeCN up to 65.0% in 8 min); Detector, nm). This provided 87.5 mg (44%) of 6-(2,6-dichloro-3,5-dimethoxyphenyl)-2-[(2-hydroxy-2-methyl-propyl)amino]-8-(2-[[1-(prop-2-enoyl)piperidin-4-yl]oxy]ethyl)-7H,8H-pyrido[2,3-d]pyrimidin-7-one as a white solid. MS (ESI, pos. ion) m/z: 620.4 (M+1).

Example 9

Synthesis of 8-(2-((1-acryloylpiperidin-4-yl)oxy)ethyl)-6-(2,6-dichloro-3,5-dimethoxyphenyl)-2-(ethylamino)pyrido[2,3-d]pyrimidin-7(8H)-one Step 1

To a solution of tert-butyl 4-[2-[6-(2,6-dichloro-3,5-dimethoxyphenyl)-2-methanesulfonyl-7-oxo-7H,8H-pyrido[2,3-d]pyrimidin-8-yl]ethoxy]piperidine-1-carboxylate (400 mg, 0.61 mmol, 1.00 equiv) in t-BuOH (50 mL) and TEA (121 mg, 1.20 mmol, 1.97 equiv) was added ethanamine hydrochloride (80 mg, 0.98 mmol, 1.61 equiv). The resulting solution was stirred for 2 h at 50° C. and then concentrated. The residue was purified by chromatography (EtOAc/pet. ether (2:1)). This provided 200 mg (53%) of tert-butyl 4-[2-[6-(2,6-dichloro-3,5-dimethoxyphenyl)-2-(ethylamino)-7-oxo-7H,8H-pyrido[2,3-d]pyrimidin-8-yl]ethoxy]piperidine-1-carboxylate as a yellow solid.

Step 2

To a solution of tert-butyl 4-[2-[6-(2,6-dichloro-3,5-dimethoxyphenyl)-2-(ethylamino)-7-oxo-7H,8H-pyrido[2,3-d]pyrimidin-8-yl]ethoxy]piperidine-1-carboxylate (200 mg, 0.32 mmol, 1.00 equiv) in DCM (4 mL) was added TFA (2 mL). The resulting solution was stirred for 1 h at room temperature and then concentrated. The pH was adjusted to 8 with sat. NaHCO$_3$ and the resulting solution was extracted with DCM and the organic layers were combined and dried over anhydrous sodium sulfate and concentrated to give 150 mg (89%) of 6-(2,6-dichloro-3,5-dimethoxyphenyl)-2-(ethylamino)-8-[2-(piperidin-4-yloxy)ethyl]-7H,8H-pyrido[2,3-d]pyrimidin-7-one as a light brown solid.

Step 3

To a solution of 6-(2,6-dichloro-3,5-dimethoxyphenyl)-2-(ethylamino)-8-[2-(piperidin-4-yloxy)ethyl]-7H,8H-pyrido[2,3-d]pyrimidin-7-one (150 mg, 0.29 mmol, 1.00 equiv) in DCM/MeOH (10/10 mL) and TEA (53 mg, 0.52 mmol, 2.00 equiv) was added prop-2-enoyl chloride (24 mg, 0.27 mmol, 1.00 equiv). The resulting solution was stirred for 2 h at room temperature and then concentrated. The crude product was purified by Prep-HPLC (Column, XSelect CSH Prep C18 OBD Column, 150 mm Sum 13 nm; mobile phase, H$_2$O with 0.1% FA and MeCN (25.0% MeCN up to 60.0% in 8 min). This provided 79 mg (48%) of 6-(2,6-dichloro-3,5-dimethoxyphenyl)-2-(ethylamino)-8-(2-[[1-(prop-2-enoyl)piperidin-4-yl]oxy]ethyl)-7H,8H-pyrido[2,3-d]pyrimidin-7-one as a white solid. MS (ESI, pos. ion) m/z: 576.3 (M+1).

Example 10

Synthesis of 8-(2-((1-acryloylpiperidin-4-yl)oxy)ethyl)-2-((cyclopropylmethyl)amino)-6-(2,6-dichloro-3,5-dimethoxyphenyl)pyrido[2,3-d]pyrimidin-7(8H)-one

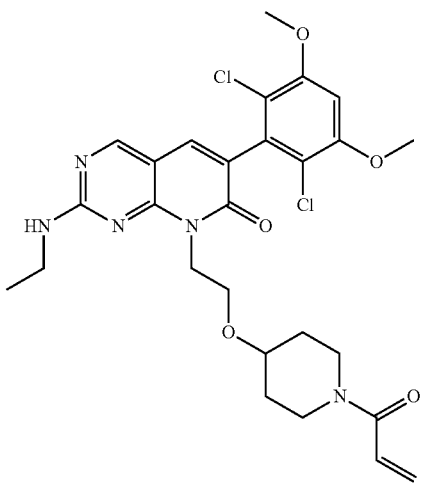 [SMILES: C=CC(=O)N1CCC(OCCn2c(=O)c(-c3c(Cl)c(OC)cc(OC)c3Cl)cc3cnc(NCC)nc32)CC1]

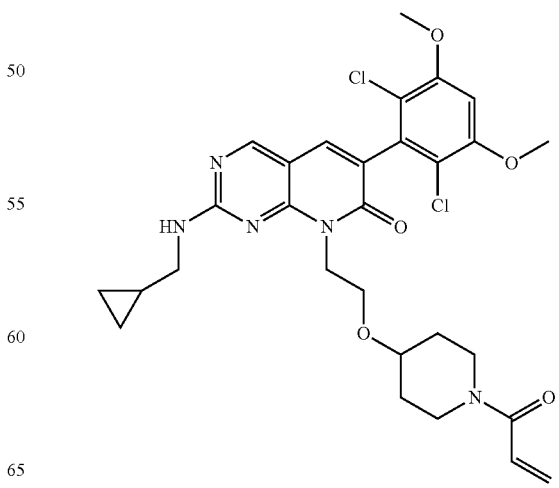

Step 1

To a solution of tert-butyl 4-[2-[6-(2,6-dichloro-3,5-dimethoxyphenyl)-2-methanesulfonyl-7-oxo-7H,8H-pyrido[2,3-d]pyrimidin-8-yl]ethoxy]piperidine-1-carboxylate (400 mg, 0.61 mmol, 1.00 equiv) in t-BuOH (50 mL) and TEA (123 mg, 1.22 mmol, 2.00 equiv) was added cyclopropylmethanamine (65 mg, 0.91 mmol, 1.50 equiv). The resulting solution was stirred for 2 h at 50° C. and then concentrated. The residue was purified by chromatography (EtOAc/pet. ether (1:2)). This provided 150 mg (38%) of tert-butyl 4-(2-[2-[(cyclopropylmethyl)amino]-6-(2,6-dichloro-3,5-dimethoxyphenyl)-7-oxo-7H,8H-pyrido[2,3-d]pyrimidin-8-yl]ethoxy)piperidine-1-carboxylate as a yellow solid which was converted to the title compound as described in Example 9, Steps 2 and 3 above MS (ESI, pos. ion) m/z: 602.3 (M+1).

Example 11

Synthesis of 8-(3-(4-acryloylpiperazin-1-yl)propyl)-6-(2,6-dichloro-3,5-dimethoxyphenyl)-2-(ethylamino)pyrido[2,3-d]pyrimidin-7(8H)-one

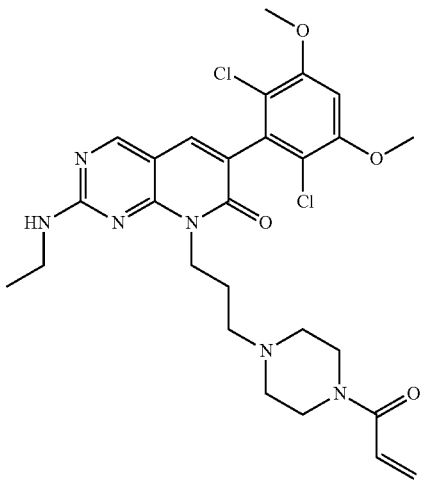 [SMILES: C=CC(=O)N1CCN(CCCn2c(=O)c(-c3c(Cl)c(OC)cc(OC)c3Cl)cc3cnc(NCC)nc32)CC1]

Step 1

To a solution of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]piperazin-1-ium-1-olate (350 mg, 0.52 mmol, 1.00 equiv) in t-BuOH (50 mL) and TEA (0.4 mL) was added EtNH$_2$·HCl (200 mg). The resulting solution was stirred for 2 h at 60° C. and then diluted with H$_2$O. The resulting solution was extracted with DCM/MeOH (10:1) and the organic layers were combined and concentrated to give 320 mg (96%) of 4-[(tert-butoxy)carbonyl]-1-[3-[6-(2,6-dichloro-3,5-dimethoxyphenyl)-2-(ethylamino)-7-oxo-7H,8H-pyrido[2,3-d]pyrimidin-8-yl]propyl]piperazin-1-ium-1-olate as a yellow solid which was converted to 6-(2,6-dichloro-3,5-dimethoxyphenyl)-2-(ethylamino)-8-[3-[4-(prop-2-enoyl)piperazin-1-yl]propyl]-7H,8H-pyrido[2,3-d]pyrimidin-7-one (280 mg) by following the procedures described in Example 6, Steps 6 to 8 above. MS (ESI, pos. ion) m/z: 575.1 (M+1).

Example 12

Synthesis of 8-(3-(4-acryloylpiperazin-1-yl)propyl)-6-(2,6-dichloro-3,5-dimethoxyphenyl)-2-((2-hydroxy-2-methylpropyl)amino)pyrido[2,3-d]pyrimidin-7(8H)-one

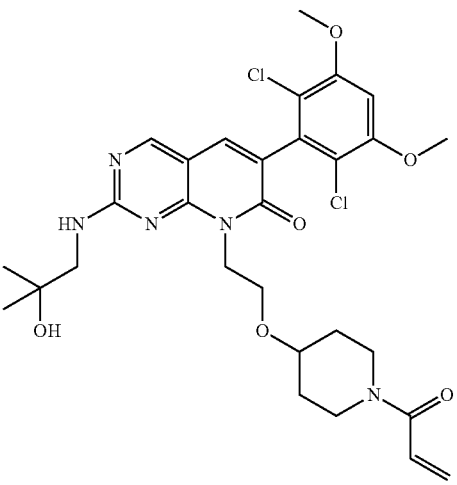 [SMILES: C=CC(=O)N1CCC(OCCn2c(=O)c(-c3c(Cl)c(OC)cc(OC)c3Cl)cc3cnc(NCC(C)(C)O)nc32)CC1]

Step 1

To a solution of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]piperazin-1-ium-1-olate (350 mg, 0.52 mmol, 1.00 equiv) in t-BuOH (25 mL) and TEA (0.3 mL) was added 1-amino-2-methylpropan-2-ol (90 mg, 1.01 mmol, 1.94 equiv). The resulting solution was stirred for 2 h at 60° C. and then with H$_2$O (60 mL). The resulting solution was extracted with DCM/MeOH (10:1) (2×100 mL) and the organic layers were combined and concentrated. This provided 320 mg (90%) of 4-[(tert-butoxy)carbonyl]-1-[3-[6-(2,6-dichloro-3,5-dimethoxyphenyl)-2-[(2-hydroxy-2-methylpropyl)amino]-7-oxo-7H,8H-pyrido[2,3-d]pyrimidin-8-yl]propyl]piperazin-1-ium-1-olate as a yellow solid. 4-[(tert-Butoxy)carbonyl]-1-[3-[6-(2,6-dichloro-3,5-dimethoxyphenyl)-2-[(2-hydroxy-2-methylpropyl)amino]-7-oxo-7H,8H-pyrido[2,3-d]pyrimidin-8-yl]propyl]piperazin-1-ium-1-olate was converted to the title compound by following the procedure described in Example 6, Steps 6 to 8 above. MS (ESI, pos. ion) m/z: 619.1 (M+1).

Example 13

Synthesis of 8-(3-(4-acryloylpiperazin-1-yl)propyl)-6-(2,6-dichloro-3,5-dimethoxyphenyl)-2-((2-hydroxyethyl)amino)pyrido[2,3-d]pyrimidin-7(8H)-one

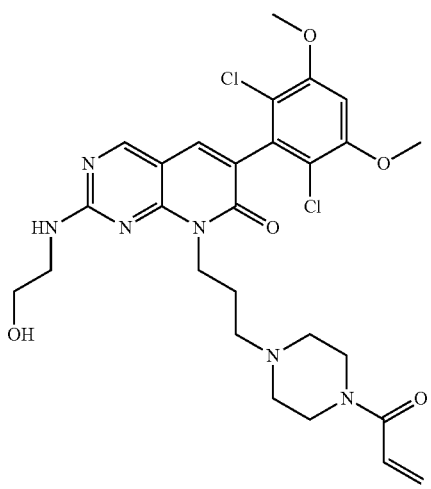 [SMILES: C=CC(=O)N1CCN(CCCn2c(=O)c(-c3c(Cl)c(OC)cc(OC)c3Cl)cc3cnc(NCCO)nc32)CC1]

The title compound was prepared as described in Example 6 except 2-aminoethanol was used in Step 5. MS (ESI, pos. ion) m/z: 591.1 (M+1).

Example 14

Synthesis of 8-(2-((1-acryloylazetidin-3-yl)oxy)ethyl)-6-(2,6-dichloro-3,5-dimethoxyphenyl)-2-(methylamino)pyrido[2,3-d]pyrimidin-7(8H)-one

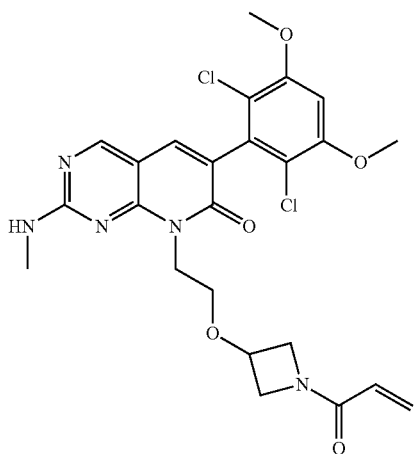 [SMILES: C=CC(=O)N1CC(OCCn2c(=O)c(-c3c(Cl)c(OC)cc(OC)c3Cl)cc3cnc(NC)nc32)C1]

Step 1

To a solution of tert-butyl 3-hydroxyazetidine-1-carboxylate (2 g, 11.55 mmol, 1.00 equiv) and NaH (460 mg, 11.50 mmol, 1.00 equiv) in THF (20 mL) was added a solution of methyl 2-bromoacetate (1.52 g, 9.94 mmol, 1.00 equiv) in THF (10 mL) drop wise with stirring over 2 min. The resulting solution was stirred for 2 h at room temperature and then $H_2O$ was added. The resulting solution was diluted with $H_2O$ and extracted with ethyl acetate and the organic layers were combined and washed with sat. NaCl. The mixture was dried over anhydrous sodium sulfate and concentrated to give 1 g (35%) of tert-butyl 3-(2-methoxy-2-oxoethoxy)azetidine-1-carboxylate as yellow crude oil.

Step 2

To a solution of tert-butyl 3-(2-methoxy-2-oxoethoxy)azetidine-1-carboxylate (2.2 g, 8.97 mmol, 1.00 equiv) in THF (20 mL) at 0° C. was added LAH (400 mg, 10.54 mmol, 1.20 equiv), in 3 portions over 30 min. The resulting solution was stirred for 2 h at room temperature and then quenched by the addition of $H_2O$, 15% NaOH (0.4 mL) and $H_2O$. The solids were filtered out and the resulting mixture was concentrated to give 1.5 g (77%) of tert-butyl 3-(2-hydroxyethoxy)-azetidine-1-carboxylate as light yellow crude oil.

Step 3

To a solution of tert-butyl 3-(2-hydroxyethoxy)azetidine-1-carboxylate (1.4 g, 6.44 mmol, 1.00 equiv), $I_2$ (2.45 g, 1.50 equiv) and imidazole (0.71 g, 1.60 equiv) in DCM (20 mL) was added $PPh_3$ (2.54 g, 9.68 mmol, 1.50 equiv). The resulting solution was stirred for 2 h at room temperature and then the solids were filtered out. The resulting solution was concentrated and the residue was purified by column chromatography (EtOAc/pet. ether (1:5)) to give 1.1 g (52%) of tert-butyl 3-(2-iodoethoxy)azetidine-1-carboxylate as yellow oil.

Step 4

A mixture of 6-(2,6-dichloro-3,5-dimethoxyphenyl)-2-(methylsulfanyl)-7H,8H-pyrido[2,3-d]pyrimidin-7-one (1 g, 2.51 mmol, 1.00 equiv), tert-butyl 3-(2-iodoethoxy)azetidine-1-carboxylate (980 mg, 3.00 mmol, 1.20 equiv) and $K_2CO_3$ (1 g, 7.24 mmol, 3.00 equiv) in acetone (40 mL) was stirred overnight at 70° C. The solids were then filtered out and the resulting solution was concentrated. The residue was purified by chromatography (DCM/MeOH (20:1)) to give 1.4 g (93%) of tert-butyl 3-[2-[6-(2,6-dichloro-3,5-dimethoxyphenyl)-2-(methylsulfanyl)-7-oxo-7H,8H-pyrido[2,3-d]pyrimidin-8-yl]ethoxy]azetidine-1-carboxylate as a yellow solid.

Step 5

To a solution of tert-butyl 3-[2-[6-(2,6-dichloro-3,5-dimethoxyphenyl)-2-(methylsulfanyl)-7-oxo-7H,8H-pyrido[2,3-d]pyrimidin-8-yl]ethoxy]azetidine-1-carboxylate (1.2 g, 2.01 mmol, 1.00 equiv) in DCM (40 mL) was added m-CPBA (1 g, 5.79 mmol, 2.50 equiv). The resulting solution was stirred for 2 h at room temperature and then washed with sat. $NaHCO_3$ and sat. NaCl. The organic layer was dried over anhydrous sodium sulfate and concentrated to give 1.2 g (95%) of tert-butyl 3-[2-[6-(2,6-dichloro-3,5-dimethoxyphenyl)-2-methanesulfonyl-7-oxo-7H,8H-pyrido[2,3-d]pyrimidin-8-yl]ethoxy]-azetidine-1-carboxylate as a yellow crude solid.

Step 6

A solution of tert-butyl 3-[2-[6-(2,6-dichloro-3,5-dimethoxyphenyl)-2-methanesulfonyl-7-oxo-7H,8H-pyrido[2,3-d]pyrimidin-8-yl]ethoxy]azetidine-1-carboxylate (1.2 g, 1.91 mmol, 1.00 equiv) and $CH_3NH_2$ (2M) (1 mL) in t-BuOH (10 mL) was stirred for 40 min at 60° C. The resulting mixture was then concentrated under vacuum to give 1 g (90%) of tert-butyl 3-[2-[6-(2,6-dichloro-3,5-dimethoxyphenyl)-2-(methylamino)-7-oxo-7H,8H-pyrido[2,3-d]pyrimidin-8-yl]ethoxy]azetidine-1-carboxylate as a brown crude solid.

Step 7

A solution of tert-butyl 3-[2-[6-(2,6-dichloro-3,5-dimethoxyphenyl)-2-(methylamino)-7-oxo-7H,8H-pyrido[2,3-d]pyrimidin-8-yl]ethoxy]azetidine-1-carboxylate (1 g, 1.72 mmol, 1.00 equiv) and TFA (8 mL, 1.00 equiv) in DCM (40 mL) was stirred overnight at room temperature. The reaction solution was then quenched with sat. NaHCO$_3$ and the layers were separated. The organic layer and then washed with sat. NaCl, dried over anhydrous sodium sulfate and concentrated. The residue was purified by chromatography (DCM/MeOH (20:1-1:5)) to give 0.6 g (73%) of 8-[2-(azetidin-3-yloxy)ethyl]-6-(2,6-dichloro-3,5-dimethoxyphenyl)-2-(methylamino)-7H,8H-pyrido[2,3-d]pyrimidin-7-one as a yellow solid.

Step 8

To a solution of 8-[2-(azetidin-3-yloxy)ethyl]-6-(2,6-dichloro-3,5-dimethoxyphenyl)-2-(methylamino)-7H,8H-pyrido[2,3-d]pyrimidin-7-one (200 mg, 0.42 mmol, 1.00 equiv) in DCM (4 mL) MeOH (4 mL) and TEA (130 mg, 1.28 mmol, 3.00 equiv) was added prop-2-enoyl chloride (40 mg, 0.44 mmol, 1.06 equiv). The resulting solution was stirred for 4 h at room temperature and then concentrated. The crude product was purified by Prep-HPLC (Column, Sunfire Prep C18 OBD Column, 19*150 mm Sum 10 nm; mobile phase, H$_2$O with 10 mmol NH$_4$HCO$_3$ and MeCN (20.0% MeCN up to 60.0% in 10 min); Detector, nm). This provided 80.8 mg (36%) of 6-(2,6-dichloro-3,5-dimethoxyphenyl)-2-(methylamino)-8-(2-[[1-(prop-2-enoyl)azetidin-3-yl]oxy]ethyl)-7H,8H-pyrido[2,3-d]pyrimidin-7-one as a white solid. MS (ESI, pos. ion) m/z: 534.2 (M+1).

Example 15

Synthesis of 8-(2-((1-acryloylpiperidin-3-yl)oxy)ethyl)-6-(2,6-dichloro-3,5-dimethoxyphenyl)-2-(methylamino)pyrido[2,3-d]pyrimidin-7(8H)-one

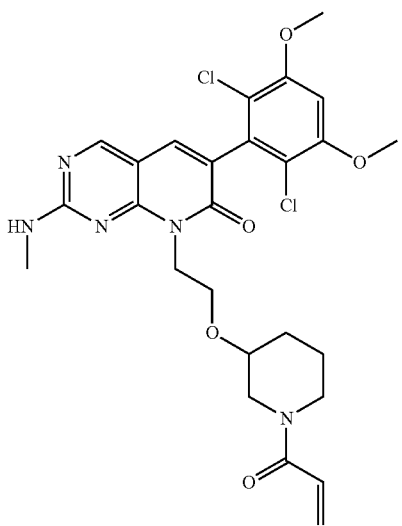 [SMILES: C=CC(=O)N1CCCC(OCCn2c(=O)c(-c3c(Cl)c(OC)cc(OC)c3Cl)cc3cnc(NC)nc32)C1]

Step 1

To a solution of tert-butyl 3-hydroxypiperidine-1-carboxylate (5 g, 24.84 mmol, 1.00 equiv) and NaH (1.00 g, 24.84 mmol, 1.00 equiv) in THF (100 mL) at 0° C. was added methyl 2-bromoacetate (3.78 g, 24.71 mmol, 1.00 equiv) drop wise. The resulting solution was stirred overnight at room temperature and then quenched with H$_2$O. The resulting solution was extracted with ethyl acetate and the organic layers were combined and then washed with sat. NaCl (100 mL). The organic layer was dried over anhydrous sodium sulfate and concentrated to give 5.6 g (82%) of tert-butyl 3-(2-methoxy-2-oxoethoxy)piperidine-1-carboxylate as yellow oil.

Step 2

To a solution of tert-butyl 3-(2-methoxy-2-oxoethoxy)piperidine-1-carboxylate (5.6 g, 20.49 mmol, 1.00 equiv) in THF (50 mL) at 0° C. was added LAH (940 mg, 24.77 mmol, 1.20 equiv) and the resulting solution was stirred for 2 h at room temperature. The reaction was then quenched with H$_2$O, 15% NaOH and H$_2$O. The solids were filtered out and the resulting solution was concentrated to give 1.5 g (30%) of tert-butyl 3-(2-hydroxyethoxy)piperidine-1-carboxylate as yellow oil which was converted to tert-butyl 3-(2-iodoethoxy)piperidine-1-carboxylate as described in Example 8, Step 3 above.

Step 3

A mixture of tert-butyl 3-(2-iodoethoxy)piperidine-1-carboxylate (1.07 g, 3.01 mmol, 1.20 equiv), 6-(2,6-dichloro-3,5-dimethoxyphenyl)-2-(methylsulfanyl)-7H,8H-pyrido[2,3-d]pyrimidin-7-one (1 g, 2.51 mmol, 1.00 equiv) and K$_2$CO$_3$ (2.08 g, 15.05 mmol, 6.00 equiv), in acetone (50 mL) was stirred for 2 days at 60° C. The resulting mixture was concentrated under vacuum and the residue was purified by chromatography (DCM/EtOAc (10:1)) to give 800 mg (51%) of tert-butyl 3-[2-[6-(2,6-dichloro-3,5-dimethoxyphenyl)-2-(methylsulfanyl)-7-oxo-7H,8H-pyrido[2,3-d]pyrimidin-8-yl]ethoxy]piperidine-1-carboxylate as a yellow solid.

Step 4

A solution of tert-butyl 3-[2-[6-(2,6-dichloro-3,5-dimethoxyphenyl)-2-(methylsulfanyl)-7-oxo-7H,8H-pyrido[2,3-d]pyrimidin-8-yl]ethoxy]piperidine-1-carboxylate (800 mg, 1.28 mmol, 1.00 equiv) and mCPBA (551 mg, 3.20 mmol, 2.50 equiv) in DCM (50 mL) was stirred for 2 h at room temperature. The reaction solution was then quenched with sat. NaHCO$_3$ and extracted with DCM. The organic layers were combined, washed with sat. NaCl, dried over anhydrous sodium sulfate and concentrated to give 900 mg (crude) of tert-butyl 3-(2-(6-(2,6-dichloro-3,5-dimethoxyphenyl)-2-(methylsulfonyl)-7-oxopyrido[2,3-d]pyrimidin-8(7H)-yl)ethoxy)piperidine-1-carboxylate as a yellow solid.

Step 5

A solution of tert-butyl 3-(2-(6-(2,6-dichloro-3,5-dimethoxyphenyl)-2-(methylsulfonyl)-7-oxopyrido[2,3-d]pyrimidin-8(7H)-yl)ethoxy)piperidine-1-carboxylate (900 mg, 1.37 mmol, 1.00 equiv) and MeNH$_2$ (2M in THF) (1.0 mL, 1.50 equiv) in t-BuOH (50 mL) was stirred for 2 h at 60° C. The reaction was concentrated and the residue was purified by chromatography (DCM/EtOAc (1:1)) to give 800 mg (96%) of tert-butyl 3-[2-[6-(2,6-dichloro-3,5-dimethoxyphenyl)-2-(methylamino)-7-oxo-7H,8H-pyrido[2,3-d]pyrimidin-8-yl]ethoxy]piperidine-1-carboxylate as a yellow solid which was converted to the title compound as described in Example 8, Steps 7 and 8 above. MS (ESI, pos. ion) m/z: 562.0 (M+1).

Example 16

Synthesis of 8-(3-(4-acryloylpiperazin-1-yl)propyl)-6-(2,6-dichloro-3,5-dimethoxyphenyl)-2-(isopropylamino)pyrido[2,3-d]pyrimidin-7(8H)-one

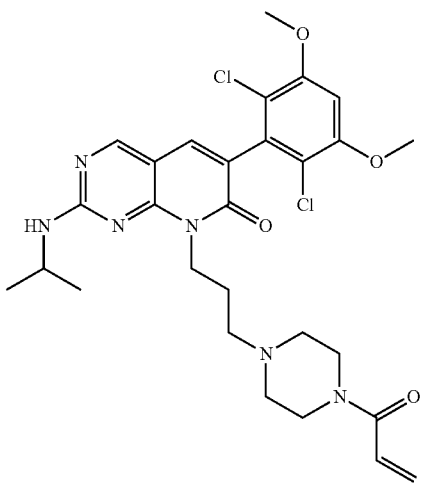 [SMILES: C=CC(=O)N1CCN(CCCn2c(=O)c(-c3c(Cl)c(OC)cc(OC)c3Cl)cc3cnc(NC(C)C)nc32)CC1]

The title compound was prepared as Example 6 except propan-2-amine was used in Step 5. MS (ESI, pos. ion) m/z: 589.1 (M+1).

Example 17

Synthesis of 8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one

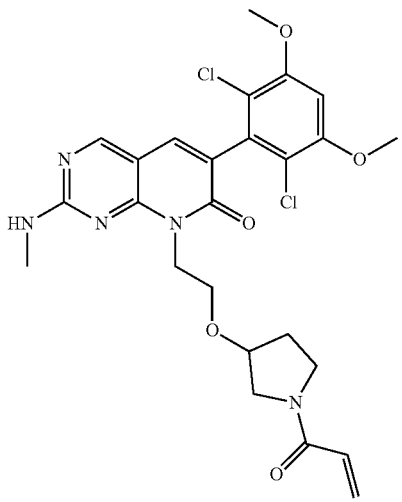 [SMILES: C=CC(=O)N1CCC(OCCn2c(=O)c(-c3c(Cl)c(OC)cc(OC)c3Cl)cc3cnc(NC)nc32)C1]

The title compound was prepared as Example 8 except tert-butyl 3-hydroxypyrrolidine-1-carboxylate is used in step 1 and methylamine was used in Step 6. MS (ESI, pos. ion) m/z: 548.4 (M+1).

Example 18

Synthesis of 8-(3-(4-acryloylpiperazin-1-yl)propyl)-6-(2,6-dichloro-3,5-dimethoxyphenyl)-2-(prop-2-yn-1-ylamino)pyrido[2,3-d]pyrimidin-7(8H)-one

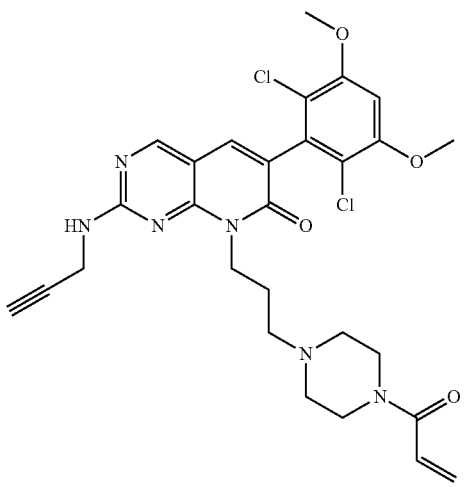 [SMILES: C#CCNc1ncc2cc(-c3c(Cl)c(OC)cc(OC)c3Cl)c(=O)n(CCCN3CCN(C(=O)C=C)CC3)c2n1]

The title compound was prepared as Example 6 except prop-2-yn-1-amine was used in Step 5. MS (ESI, pos. ion) m/z: 585.1 (M+1).

Example 19

Synthesis of 8-(3-(4-acryloylpiperazin-1-yl)propyl)-6-(2-chloro-3,5-dimethoxyphenyl)-2-((2-hydroxy-2-methylpropyl)amino)pyrido[2,3-d]pyrimidin-7(8H)-one

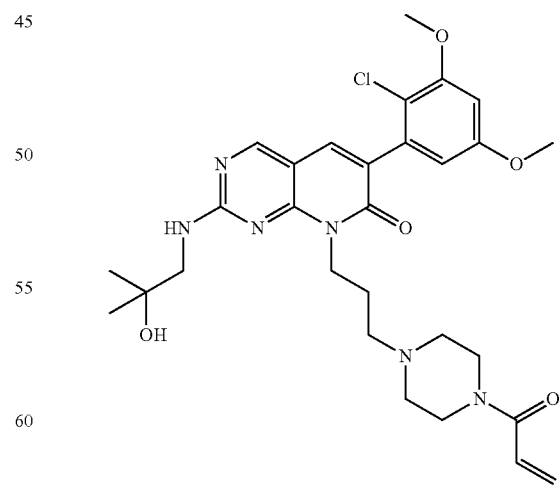

The title compound was prepared as in Example 4 except 1-amino-2-methylpropan-2-ol was used instead in Step 5. MS (ESI, pos. ion) m/z: 585.3 (M+1).

Example 20

Synthesis of 8-(3-(4-acryloylpiperazin-1-yl)propyl)-6-(2-chloro-3,5-dimethoxyphenyl)-2-(prop-2-yn-1-ylamino)pyrido[2,3-d]pyrimidin-7(8H)-one

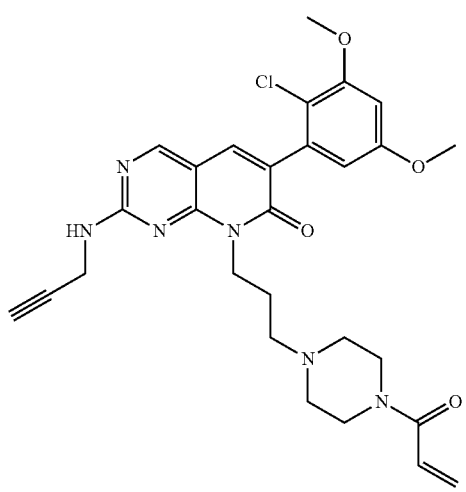 [SMILES: C#CCNc1ncc2cc(-c3cc(OC)cc(OC)c3Cl)c(=O)n(CCCN3CCN(C(=O)C=C)CC3)c2n1]

The title compound was prepared as in Example 4 except prop-2-yn-1-amine was used in step 5. MS (ESI, pos. ion) m/z: 551.1 (M+1).

Example 21

Synthesis of 8-(3-(4-acryloylpiperazin-1-yl)propyl)-2-((cyclopropylmethyl)amino)-6-(2-chloro-3,5-dimethoxyphenyl)pyrido[2,3-d]pyrimidin-7(8H)-one

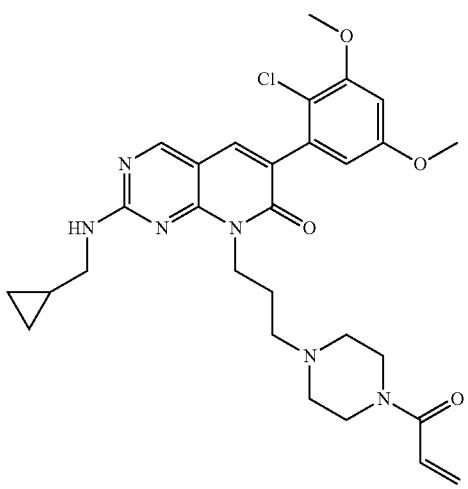 [SMILES: C=CC(=O)N1CCN(CCCn2c(=O)c(-c3cc(OC)cc(OC)c3Cl)cc3cnc(NCC4CC4)nc32)CC1]

The title compound was prepared as in Example 4 except cyclopropylmethanamine was used in Step 5. MS (ESI, pos. ion) m/z: 567.4 (M+1).

Example 22

Synthesis of 8-(3-(4-acryloylpiperazin-1-yl)propyl)-6-(2-chloro-3,5-dimethoxyphenyl)-2-((2-hydroxyethyl)amino)pyrido[2,3-d]pyrimidin-7(8H)-one

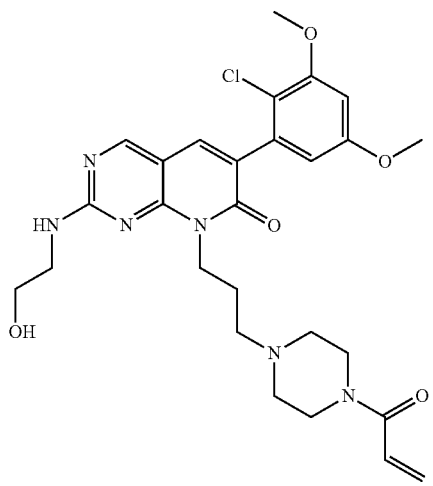 [SMILES: C=CC(=O)N1CCN(CCCn2c(=O)c(-c3cc(OC)cc(OC)c3Cl)cc3cnc(NCCO)nc32)CC1]

The title compound was prepared as in Example 4 except 2-aminoethanol was used in Step 5. MS (ESI, pos. ion) m/z: 557.2 (M+1).

Example 23

Synthesis of 8-(3-((2R,6S)-4-acryloyl-2,6-dimethylpiperazin-1-yl)propyl)-6-(2-chloro-3,5-dimethoxyphenyl)-2-(methylamino)pyrido[2,3-d]pyrimidin-7(8H)-one

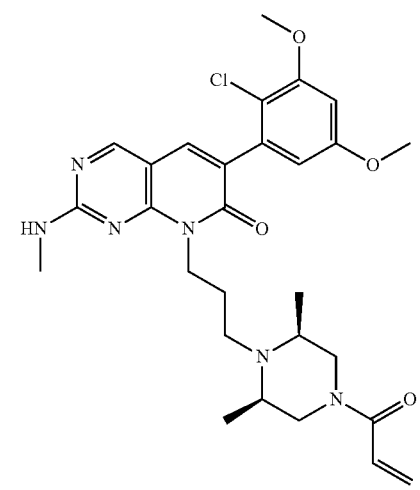 [SMILES: C=CC(=O)N1C[C@@H](C)N(CCCn2c(=O)c(-c3cc(OC)cc(OC)c3Cl)cc3cnc(NC)nc32)[C@@H](C)C1]

Step 1

A mixture of (3S,5R)-tert-butyl 3,5-dimethylpiperazine-1-carboxylate (2.14 g, 10.0 mmol), 3-bromopropan-1-ol (2.76 g, 20 mmol) and $K_2CO_3$ (2.76 g, 20 mmol) in DMF (5.0 mL) was heated to 90° C. for 2 h in a microwave. The reaction mixture was poured into water (30 mL) and extracted with EtOAc. The organic phase was separated, dried and concentrated. The residue was purified by chromatography (DCM:MeOH=30:1) to provide (3R,5S)-tert-butyl 4-(3-hydroxypropyl)-3,5-dimethylpiperazine-1-carboxylate as a yellow liquid (2.14 g, 50%).
Step 2

To a solution of (3R,5S)-tert-butyl 4-(3-hydroxypropyl)-3,5-dimethylpiperazine-1-carboxylate (680 mg, 5.0 mmol) and TEA (505 mg, 5.0 mmol) in DCM (30 mL) at room temperature was added drop wise MsCl (428 mg, 3.75 mmol). The reaction mixture was then washed with water and brine. The organic phase was dried, filtered and concentrated. The residue was purified by chromatography (DCM:MeOH=50:1) to provide (3R,5S)-tert-butyl 3,5-dimethyl-4-(3-((methylsulfonyl)oxy)propyl)piperazine-1-carboxylate as a yellow liquid (700 mg, 80%).
Step 3

A mixture of (3R,5S)-tert-butyl 3,5-dimethyl-4-(3-((methylsulfonyl)oxy)propyl)-piperazine-1-carboxylate (350 mg, 1.0 mmol), $K_2CO_3$ (250 mg, 1.8 mmol) and 6-(2-chloro-3,5-dimethoxyphenyl)-2-(methylthio)pyrido[2,3-d]pyrimidin-7(8H)-one (330 mg, 0.9 mmol) in DMF (20 mL) was heated to 85° C. for 1 h. The reaction mixture was cooled to room temperature and water (50 mL) was added. A white solid appeared and this was collected by filtration. The filtrated cake was washed with water and dried. The white solid was crude (3R,5S)-tert-butyl 4-(3-(6-(2-chloro-3,5-dimethoxyphenyl)-2-(methylthio)-7-oxopyrido[2,3-d]pyrimidin-8(7H)-yl)propyl)-3,5-dimethylpiperazine-1-carboxylate and was used directly (400 mg, 72%) in the next step.
Step 4

To a solution of (3R,5S)-tert-butyl 4-(3-(6-(2-chloro-3,5-dimethoxyphenyl)-2-(methylthio)-7-oxopyrido[2,3-d]pyrimidin-8(7H)-yl)propyl)-3,5-dimethylpiperazine-1-carboxylate (200 mg, 0.32 mmol) in DCM (15 mL) at room temperature was added m-CPBA (75%) (112 mg, 0.486 mmol). The mixture was stirred at ambient temperature for 30 min before quenching with sat. $Na_2SO_3$ (5 mL). The mixture was extracted with DCM, washed with aq. $NaHCO_3$ and brine. The organic layer was dried over anhydrous sodium sulfate, filtered and evaporated to provide (3R,5S)-tert-butyl 4-(3-(6-(2-chloro-3,5-dimethoxyphenyl)-2-(methylsulfinyl)-7-oxopyrido[2,3-d]pyrimidin-8(7H)-yl)propyl)-3,5-dimethylpiperazine-1-carboxylate as a white solid (203 mg, 100%).
Step 5

A solution of (3R,5S)-tert-butyl 4-(3-(6-(2-chloro-3,5-dimethoxyphenyl)-2-(methyl-sulfinyl)-7-oxopyrido[2,3-d]pyrimidin-8(7H)-yl)propyl)-3,5-dimethylpiperazine-1-carboxylate (203 mg, 0.32 mmol), methanamine hydrochloride (68 mg, 1.28 mmol) and TEA (130 mg, 1.28 mmol) in DMSO (15 mL) was heated to 85° C. for 1 h before cooling to ambient temperature. The mixture was poured into water, filtered and the filtrated cake was washed with water and dried to provide (3R,5S)-tert-butyl 4-(3-(6-(2-chloro-3,5-dimethoxyphenyl)-2-(methyl-amino)-7-oxopyrido[2,3-d]pyrimidin-8(7H)-yl)propyl)-3,5-dimethylpiperazine-1-carboxylate (180 mg, crude) which was converted to 6-(2-chloro-3,5-dimethoxyphenyl)-8-(3-((2R,6S)-2,6-dimethylpiperazin-1-yl)propyl)-2-(methylamino)pyrido[2,3-d]pyrimidin-7(8H)-one as described in Example 8, Step 7 above.
Step 6

To a solution of 6-(2-chloro-3,5-dimethoxyphenyl)-8-(3-((2R,6S)-2,6-dimethylpiperazin-1-yl)propyl)-2-(methylamino)pyrido[2,3-d]pyrimidin-7(8H)-one (60 mg, 0.12 mmol) in sat. $NaHCO_3$ (1.0 mL) and THF (10 mL) was added acryloyl chloride (11 mg, 0.12 mmol) in THF (2 mL). The mixture was stirred at room temperature for 5 min before extracting with EtOAc, dried over anhydrous sodium sulfate, filtered and evaporated. The residue was purified by chromatography (DCM:MeOH=30:1) to provide 8-(3-((2R,6S)-4-acryloyl-2,6-dimethylpiperazin-1-yl)propyl)-6-(2-chloro-3,5-dimethoxyphenyl)-2-(methylamino)pyrido[2,3-d]pyrimidin-7(8H)-one (20 mg, 30%) as a white solid. MS (ESI, pos. ion) m/z: 555.2 (M+1).

Example 24

Synthesis of 8-(3-((3S,5R)-4-acryloyl-3,5-dimethylpiperazin-1-yl)propyl)-6-(2-chloro-3,5-dimethoxyphenyl)-2-(methylamino)pyrido[2,3-d]pyrimidin-7(8H)-one

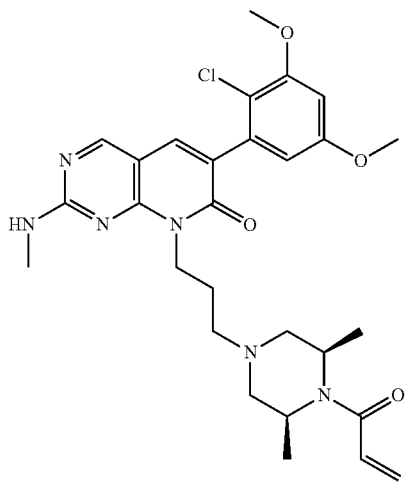 [SMILES: C=CC(=O)N1[C@H](C)CN(CCCn2c(=O)c(-c3cc(OC)cc(OC)c3Cl)cc3cnc(NC)nc32)C[C@@H]1C]

The title compound was prepared as described in Example 23 above, but substituting (3S,5R)-tert-butyl 3,5-dimethylpiperazine-1-carboxylate with (2S,6R)-tert-butyl 2,6-dimethylpiperazine-1-carboxylate. MS (ESI, pos. ion) m/z: 555.3 (M+1).

Example 25

Synthesis of 8-(3-((3S,5R)-4-acryloyl-3,5-dimethylpiperazin-1-yl)propyl)-6-(2,6-dichloro-3,5-dimethoxyphenyl)-2-(methylamino)pyrido[2,3-d]pyrimidin-7(8H)-one

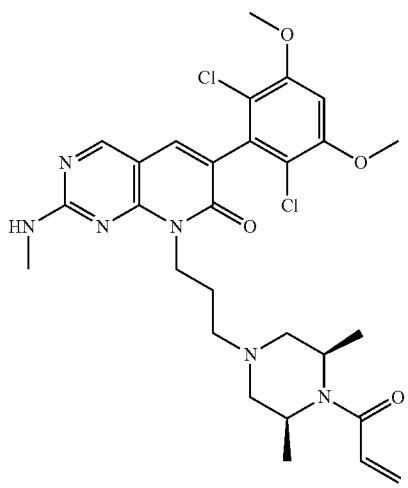 [SMILES: C=CC(=O)N1[C@H](C)CN(CCCn2c(=O)c(-c3c(Cl)c(OC)cc(OC)c3Cl)cc3cnc(NC)nc32)C[C@@H]1C]

The title compound was prepared as described in Example 24 above, but substituting 6-(2-chloro-3,5-dimethoxyphenyl)-2-(methylthio)pyrido[2,3-d]pyrimidin-7(8H)-one with 6-(2,6-dichloro-3,5-dimethoxyphenyl)-2-(methylthio)pyrido[2,3-d]pyrimidin-7(8H)-one. MS (ESI, pos. ion) m/z: 589.0 (M+1).

Example 26

Synthesis of 8-(3-(4-acryloylpiperazin-1-yl)propyl)-6-(2-chloro-3,5-dimethoxyphenyl)-2-(phenylamino)pyrido[2,3-d]pyrimidin-7(8H)-one

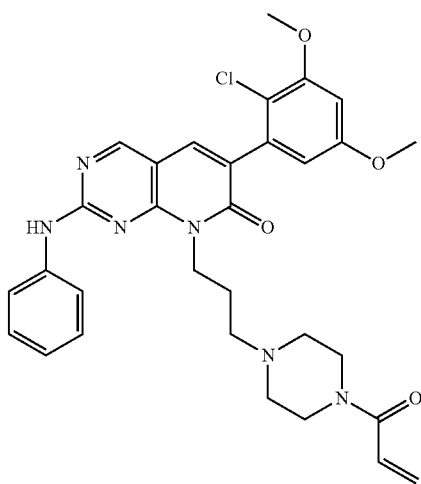 [SMILES: C=CC(=O)N1CCN(CCCn2c(=O)c(-c3cc(OC)cc(OC)c3Cl)cc3cnc(Nc4ccccc4)nc32)CC1]

The title compound was prepared as Example 4 except aniline is used in Step 5. MS (ESI, pos. ion) m/z: 589.2 (M+1).

Example 27

Synthesis of 8-((1-((4-acryloylpiperazin-1-yl)methyl)cyclopropyl)methyl)-6-(2,6-dichloro-3,5-dimethoxyphenyl)-2-(methylamino)pyrido[2,3-d]pyrimidin-7(8H)-one

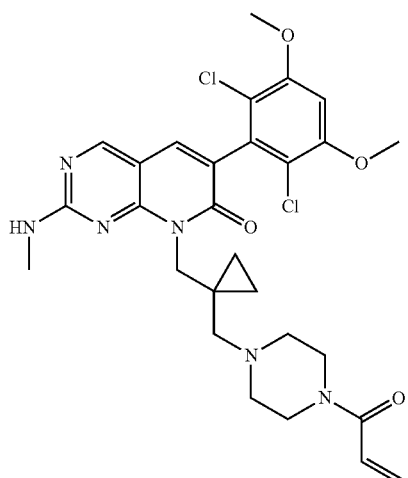

Step 1

Into a solution of [1-(hydroxymethyl)cyclopropyl]methanol (9.5 g, 93.02 mmol,) and $CCl_4$ (15.57 g, 102.43 mmol) in THF (50 mL) at 0° C. was added [bis(dimethylamino)phosphanyl]-dimethylamine (16.70 g, 102.33 mmol). The resulting solution was stirred overnight at room temperature and then quenched by the addition of water. The resulting solution was extracted with DCM and the organic layers combined. The resulting mixture was washed with sat. NaCl and dried over $Na_2SO_4$ and then concentrated. The residue was purified by chromatography (EtOAc/pet. ether (1:1) to afford 5.2 g (46%) of [1-(chloromethyl)cyclopropyl]methanol as yellow oil.

Step 2

A mixture of [1-(chloromethyl)cyclopropyl]methanol (5.2 g, 43.13 mmol), tert-butyl piperazine-1-carboxylate (8.87 g, 47.62 mmol), $K_2CO_3$ (17.94 g, 129.80 mmol) and KI (360 mg, 2.17 mmol) in acetone (100 mL) was stirred overnight at 60° C. The resulting mixture was then cooled and concentrated. The residue was purified by chromatography (EtOAc/pet. ether (2:1) to afford 4 g (34%) of tert-butyl 4-[[1-(hydroxymethyl)cyclopropyl]methyl]piperazine-1-carboxylate as light yellow oil.

Step 3

A solution of tert-butyl 4-[[1-(hydroxymethyl)cyclopropyl]methyl]piperazine-1-carboxylate (1 g, 3.70 mmol), $PPh_3$ (2.91 g, 11.09 mmol), imidazole (760 mg, 11.18 mmol), and $I_2$ (2.82 g, 11.10 mmol, 3.00 equiv) in DCM (50 mL) was stirred for 2 h at room temperature. The solids were filtered and the resulting mixture was concentrated. The residue was purified by chromatography (DCM/EtOAc (10:1) to afford 800 mg (57%) of tert-butyl 4-[[1-(iodomethyl)-cyclopropyl]methyl]piperazine-1-carboxylate as brown oil which was converted to the title compound as described in Example 6 above. MS (ESI, pos. ion) m/z: 587.1 (M+1).

Example 28

Synthesis of 8-((1-((4-acryloylpiperazin-1-yl)methyl)cyclopropyl)methyl)-6-(2-chloro-3,5-dimethoxyphenyl)-2-(methylamino)pyrido[2,3-d]pyrimidin-7(8H)-one

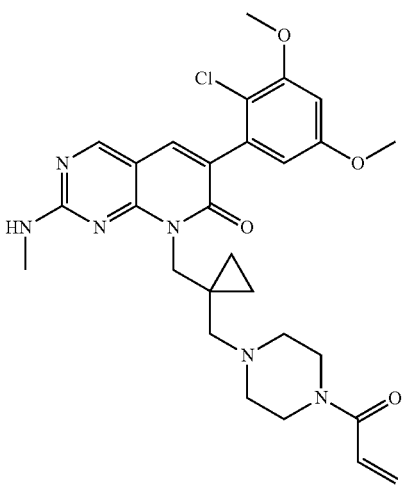 [SMILES: C=CC(=O)N1CCN(CC2(Cn3c(=O)c(-c4cc(OC)cc(OC)c4Cl)cc4cnc(NC)nc43)CC2)CC1]

Prepared as described in Example 27 above except 6-(2-chloro-3,5-dimethoxy-phenyl)-2-(methylthio)pyrido[2,3-d]pyrimidin-7(8H)-one was used. MS (ESI, pos. ion) m/z: 553.1 (M+1).

Example 29

Synthesis of 8-(3-((2R,6S)-4-acryloyl-2,6-dimethylpiperazin-1-yl)propyl)-6-(2,6-dichloro-3,5-dimethoxyphenyl)-2-(methylamino)pyrido[2,3-d]pyrimidin-7(8H)-one

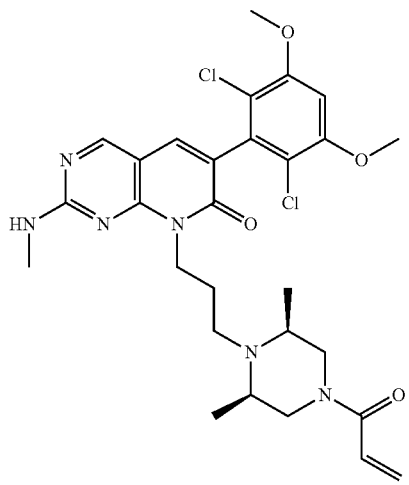 [SMILES: C=CC(=O)N1C[C@@H](C)N(CCCn2c(=O)c(-c3c(Cl)c(OC)cc(OC)c3Cl)cc3cnc(NC)nc32)[C@@H](C)C1]

Prepared as described in Example 23, except 6-(2,6-dichloro-3,5-dimethoxy-phenyl)-2-(methylthio)pyrido[2,3-d]pyrimidin-7(8H)-one was used. MS (ESI, pos. ion) m/z: 589.2 (M+1).

Example 30

Synthesis of 8-(3-(4-acryloylpiperazin-1-yl)-2,2-dimethylpropyl)-6-(2,6-dichloro-3,5-dimethoxyphenyl)-2-(methylamino)pyrido[2,3-d]pyrimidin-7(8H)-one

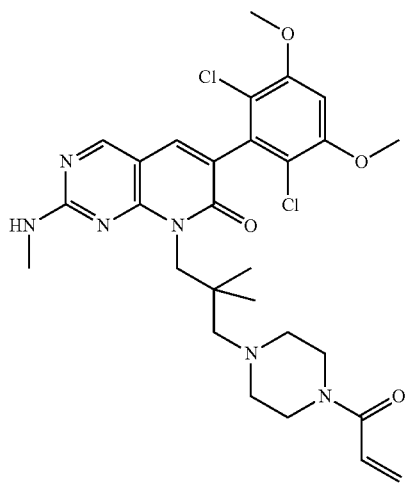 [SMILES: C=CC(=O)N1CCN(CC(C)(C)Cn2c(=O)c(-c3c(Cl)c(OC)cc(OC)c3Cl)cc3cnc(NC)nc32)CC1]

Step 1

To a solution of tert-butyl piperazine-1-carboxylate (2.9 g, 15.57 mmol) in AcOH (8 mL) was added formalin (35% wt. (1.5 mL)). The resulting solution was stirred at RT for 30 min and then 2-methylpropanal (1.5 mL) was added. The resulting solution was stirred for 12 h at 50° C. and then concentrated. The resulting solution was extracted with EtOAc and the organic layers combined. The organic layer was washed with sat. NaHCO₃ and then concentrated to afford 3.6 g (86%) of tert-butyl 4-(2,2-dimethyl-3-oxopropyl)piperazine-1-carboxylate as a colorless semi-solid.

Step 2

A solution of tert-butyl 4-(2,2-dimethyl-3-oxopropyl)piperazine-1-carboxylate (3.6 g, 13.32 mmol) and NaBH₄ (0.5 g) in isopropanol (10 mL) was stirred for 4 h at room temperature. The reaction was then quenched with water. The resulting mixture was concentrated and the residue was purified by chromatography (DCM/EtOAc (10:1) to afford 3 g (83%) of tert-butyl 4-(3-hydroxy-2,2-dimethylpropyl)piperazine-1-carboxylate as a white solid.

Step 3

To a solution of tert-butyl 4-(3-hydroxy-2,2-dimethylpropyl)piperazine-1-carboxylate (1.2 g, 4.41 mmol) and TEA (2 mL) in DCM (10 mL) was added MsCl (700 mg, 6.14 mmol) drop wise. The resulting solution was stirred for 3 h at room temperature and then concentrated. The residue was purified by chromatography (DCM/Acetone (1:50)) to afford 0.4 g (26%) of tert-butyl 4-[3-(methanesulfonyloxy)-2,2-dimethylpropyl]piperazine-1-carboxylate as yellow oil which was converted to the title compound as described in Example 6 above. MS (ESI, pos. ion) m/z: 589.2 (M+1).

Example 31

Synthesis of 8-(3-(4-acryloylpiperazin-1-yl)-2,2-dimethylpropyl)-6-(2-chloro-3,5-dimethoxyphenyl)-2-(methylamino)pyrido[2,3-d]pyrimidin-7(8H)-one

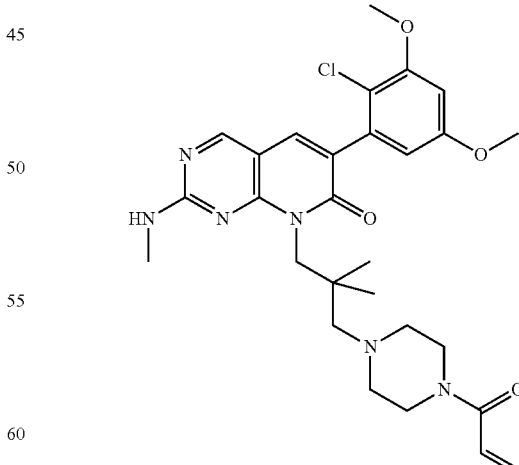

Prepared as described in Example 30 above except 6-(2-chloro-3,5-dimethoxyphenyl)-2-(methylthio)pyrido[2,3-d]pyrimidin-7(8H)-one was used. MS (ESI, pos. ion) m/z: 555.4 (M+1).

Example 32

Synthesis of 8-(3-(4-acryloylpiperazin-1-yl)propyl)-6-(2,6-dichloro-3,5-dimethoxyphenyl)-2-(phenylamino)pyrido[2,3-d]pyrimidin-7(8H)-one

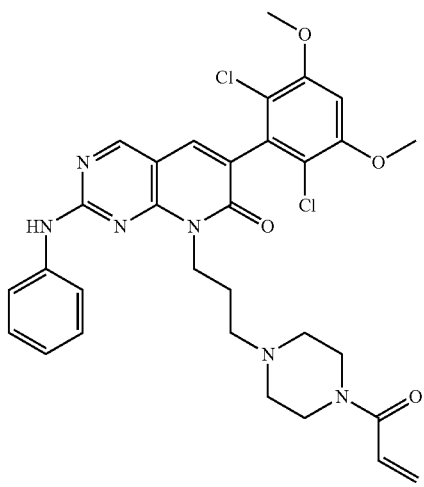 [SMILES: C=CC(=O)N1CCN(CCCn2c(=O)c(-c3c(Cl)c(OC)cc(OC)c3Cl)cc3cnc(Nc4ccccc4)nc32)CC1]

Prepared as described in Example 6 above except aniline was in Step 5. MS (ESI, pos. ion) m/z: 623.1 (M+1).

Example 33

Synthesis of 8-(3-(4-acryloylpiperazin-1-yl)propyl)-6-(2,6-dichloro-3,5-dimethoxyphenyl)-2-(pyridin-2-ylamino)pyrido[2,3-d]pyrimidin-7(8H)-one

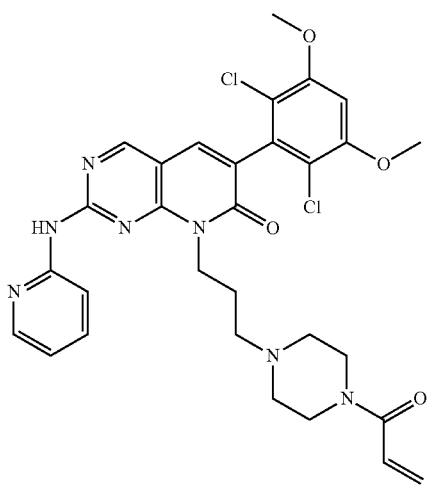 [SMILES: C=CC(=O)N1CCN(CCCn2c(=O)c(-c3c(Cl)c(OC)cc(OC)c3Cl)cc3cnc(Nc4ccccn4)nc32)CC1]

Prepared as described in Example 6 above except pyridin-2-amine was used in Step 5. MS (ESI, pos. ion) m/z: 624.1 (M+1).

Example 34

Synthesis of 8-(3-(4-acryloylpiperazin-1-yl)propyl)-6-(2-chloro-3,5-dimethoxyphenyl)-2-(pyridin-2-ylamino)pyrido[2,3-d]pyrimidin-7(8H)-one

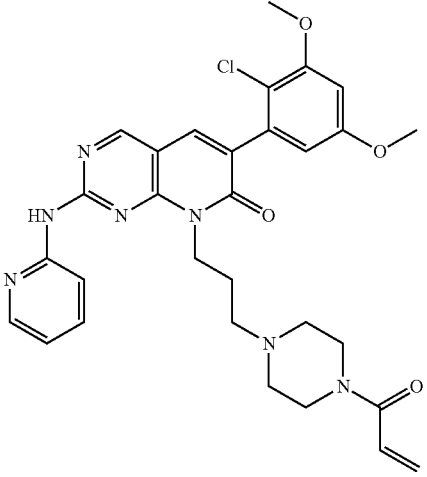 [SMILES: C=CC(=O)N1CCN(CCCn2c(=O)c(-c3cc(OC)cc(OC)c3Cl)cc3cnc(Nc4ccccn4)nc32)CC1]

Prepared as described in Example 4 above except pyridin-2-amine was used in Step 5. MS (ESI, pos. ion) m/z: 590.1 (M+1).

Example 35

Synthesis of 8-(3-(4-acryloylpiperazin-1-yl)propyl)-6-(2-chloro-3,5-dimethoxyphenyl)-2-((2,2-difluoroethyl)amino)pyrido[2,3-d]pyrimidin-7(8H)-one

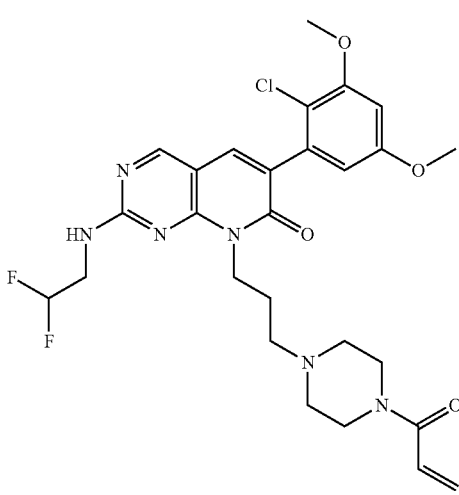 [SMILES: C=CC(=O)N1CCN(CCCn2c(=O)c(-c3cc(OC)cc(OC)c3Cl)cc3cnc(NCC(F)F)nc32)CC1]

Prepared as described in Example 4 above except 2,2-difluoroethanamine was used in Step 5. MS (ESI, pos. ion) m/z: 577.3 (M+1).

Example 36

Synthesis of 8-(3-(4-acryloylpiperazin-1-yl)propyl)-6-(2-chloro-3,5-dimethoxyphenyl)-2-((tetrahydro-2H-pyran-4-yl)amino)pyrido[2,3-d]pyrimidin-7(8H)-one

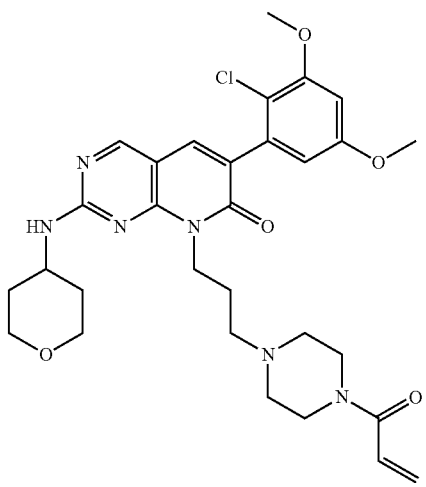 [SMILES: C=CC(=O)N1CCN(CCCn2c(=O)c(-c3cc(OC)cc(OC)c3Cl)cc3cnc(NC4CCOCC4)nc32)CC1]

Prepared as described in Example 4 above except tetrahydro-2H-pyran-4-amine was used in Step 5. MS (ESI, pos. ion) m/z: 597.1 (M+1).

Example 37

Synthesis of 8-(3-(4-acryloylpiperazin-1-yl)propyl)-6-(2,6-dichloro-3,5-dimethoxyphenyl)-2-((tetrahydro-2H-pyran-4-yl)amino)pyrido[2,3-d]pyrimidin-7(8H)-one

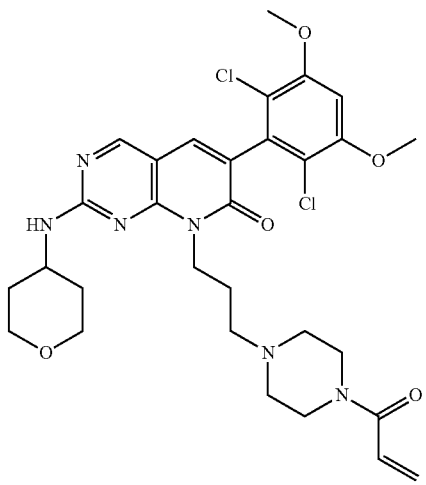 [SMILES: C=CC(=O)N1CCN(CCCn2c(=O)c(-c3c(Cl)c(OC)cc(OC)c3Cl)cc3cnc(NC4CCOCC4)nc32)CC1]

Prepared as described in Example 6 above except tetrahydro-2H-pyran-4-amine was used in Step 5. MS (ESI, pos. ion) m/z: 631.1 (M+1).

Example 38

Synthesis of (S)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one

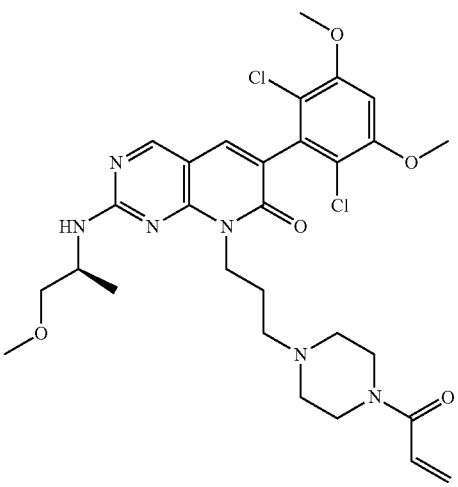 [SMILES: C=CC(=O)N1CCN(CCCn2c(=O)c(-c3c(Cl)c(OC)cc(OC)c3Cl)cc3cnc(N[C@@H](C)COC)nc32)CC1]

Prepared as described in Example 6 above except (S)-1-methoxypropan-2-amine was used in Step 5. MS (ESI, pos. ion) m/z: 619.1 (M+1).

Example 39

Synthesis of 8-(3-(4-acryloylpiperazin-1-yl)propyl)-6-(2-chloro-3,5-dimethoxyphenyl)-2-((2-isopropoxyethyl)amino)pyrido[2,3-d]pyrimidin-7(8H)-one

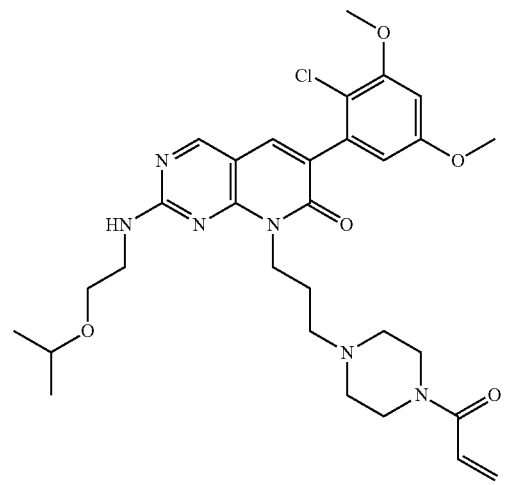 [SMILES: C=CC(=O)N1CCN(CCCn2c(=O)c(-c3cc(OC)cc(OC)c3Cl)cc3cnc(NCCOC(C)C)nc32)CC1]

Prepared as described in Example 4 above except 2-isopropoxyethanamine was used in Step 5. MS (ESI, pos. ion) m/z: 599.4 (M+1).

Example 40

Synthesis of 8-(3-(4-acryloylpiperazin-1-yl)propyl)-6-(2-chloro-3,5-dimethoxyphenyl)-2-(((tetrahydrofuran-2-yl)methyl)amino)pyrido[2,3-d]pyrimidin-7(8H)-one

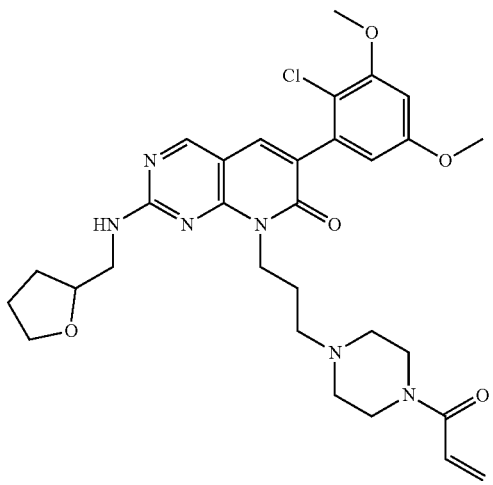 [SMILES: C=CC(=O)N1CCN(CCCn2c(=O)c(-c3cc(OC)cc(OC)c3Cl)cc3cnc(NCC4CCCO4)nc32)CC1]

Prepared as described in Example 4 above except (tetrahydrofuran-2-yl)methanamine was used in Step 5. MS (ESI, pos. ion) m/z: 597.2 (M+1).

Example 41

Synthesis of (R)-8-(3-(4-acryloylpiperazin-1-yl)propyl)-6-(2-chloro-3,5-dimethoxyphenyl)-2-((tetrahydrofuran-3-yl)amino)pyrido[2,3-d]pyrimidin-7(8H)-one

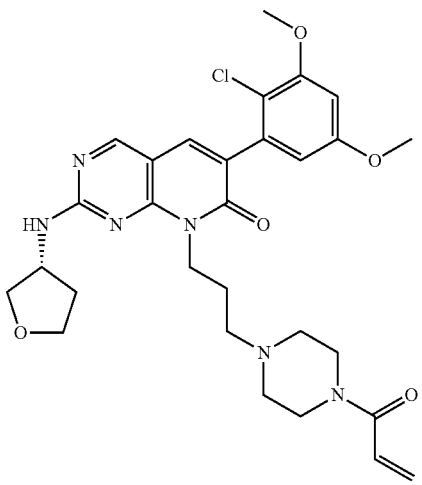 [SMILES: C=CC(=O)N1CCN(CCCn2c(=O)c(-c3cc(OC)cc(OC)c3Cl)cc3cnc(N[C@@H]4CCOC4)nc32)CC1]

Prepare as described in Example 4 above except (R)-tetrahydrofuran-3-amine was used in Step 5. MS (ESI, pos. ion) m/z: 583.1 (M+1).

Example 42

Synthesis of (S)-8-(3-(4-acryloylpiperazin-1-yl)propyl)-6-(2-chloro-3,5-dimethoxyphenyl)-2-((1-methoxypropan-2-yl)amino)pyrido[2,3-d]pyrimidin-7(8H)-one

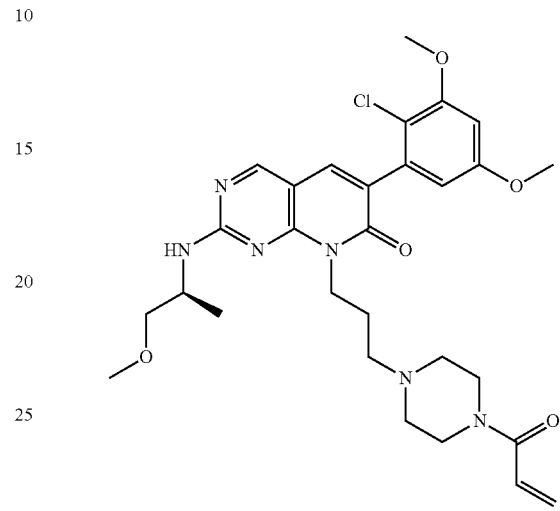

Prepared as described in Example 4 above except (S)-1-methoxypropan-2-amine was used in Step 5. MS (ESI, pos. ion) m/z: 585.3 (M+1).

Example 43

Synthesis of 8-(3-(4-acryloylpiperazin-1-yl)propyl)-6-(2-chloro-3,5-dimethoxyphenyl)-2-((2-morpholinoethyl)amino)pyrido[2,3-d]pyrimidin-7(8H)-one

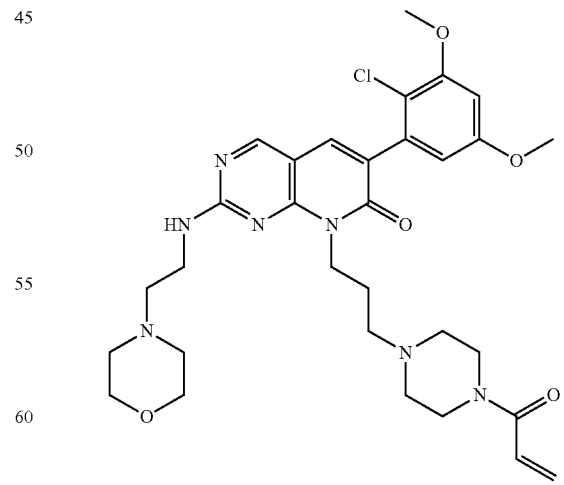

Prepared as described in Example 4 above except 2-morpholinoethanamine was used in Step 5. MS (ESI, pos. ion) m/z: 626.6 (M+1).

Example 44

Synthesis of 8-(3-(4-acryloylpiperazin-1-yl)propyl)-6-(2,6-dichloro-3,5-dimethoxyphenyl)-2-((2,2-difluoroethyl)amino)pyrido[2,3-d]pyrimidin-7(8H)-one

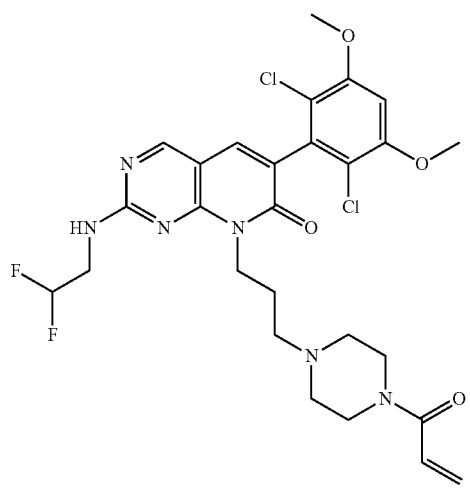 [SMILES: C=CC(=O)N1CCN(CCCn2c(=O)c(-c3c(Cl)c(OC)cc(OC)c3Cl)cc3cnc(NCC(F)F)nc32)CC1]

Prepared as described in Example 6 above except 2,2-difluoroethanamine was used in Step 5. MS (ESI, pos. ion) m/z: 611.1 (M+1).

Example 45

Synthesis of 8-(3-(4-acryloylpiperazin-1-yl)propyl)-6-(2,6-dichloro-3,5-dimethoxyphenyl)-2-((2-methoxyethyl)amino)pyrido[2,3-d]pyrimidin-7(8H)-one

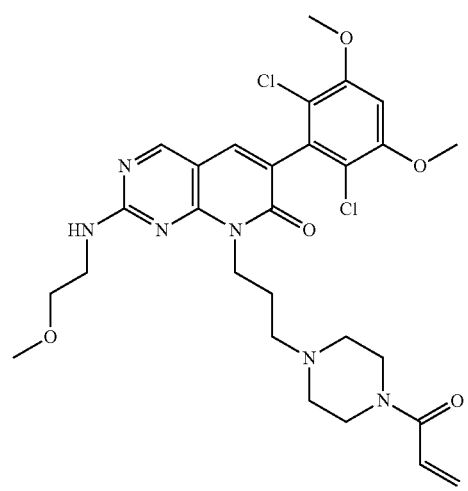 [SMILES: C=CC(=O)N1CCN(CCCn2c(=O)c(-c3c(Cl)c(OC)cc(OC)c3Cl)cc3cnc(NCCOC)nc32)CC1]

Prepared as described in Example 6 above except 2-methoxyethanamine was used in Step 5. MS (ESI, pos. ion) m/z: 605.1 (M+1).

Example 46

Synthesis of 8-(3-(4-acryloylpiperazin-1-yl)propyl)-6-(2,6-dichloro-3,5-dimethoxyphenyl)-2-((2-isopropoxyethyl)amino)pyrido[2,3-d]pyrimidin-7(8H)-one

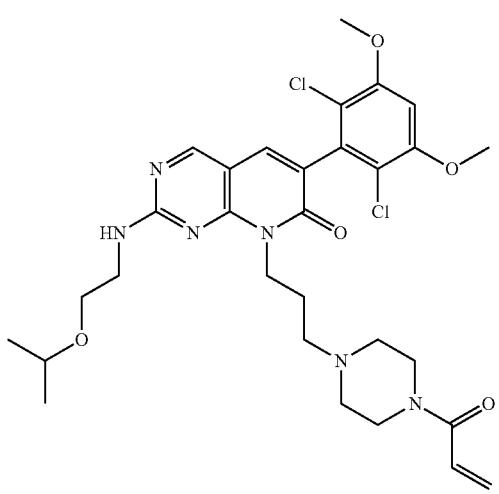 [SMILES: C=CC(=O)N1CCN(CCCn2c(=O)c(-c3c(Cl)c(OC)cc(OC)c3Cl)cc3cnc(NCCOC(C)C)nc32)CC1]

Prepared as described in Example 6 above except 2-isopropoxyethanamine was used in Step 5. MS (ESI, pos. ion) m/z: 633.1 (M+1).

Example 47

Synthesis of 8-(3-(4-acryloylpiperazin-1-yl)propyl)-6-(2-chloro-3,5-dimethoxyphenyl)-2-((2,2,2-trifluoroethyl)amino)pyrido[2,3-d]pyrimidin-7(8H)-one

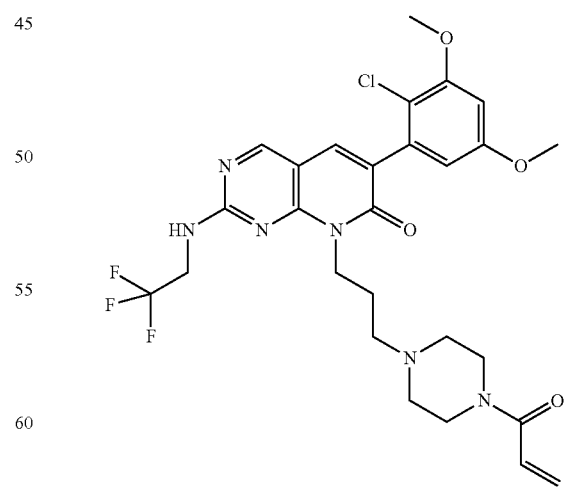

Prepared as described in Example 4 above except 2,2,2-trifluoroethanamine was used in Step 5. MS (ESI, pos. ion) m/z: 595.1 (M+1).

Example 48

Synthesis of 8-(3-(4-acryloylpiperazin-1-yl)propyl)-6-(2-chloro-3,5-dimethoxyphenyl)-2-((2-methoxyethyl)amino)pyrido[2,3-d]pyrimidin-7(8H)-one

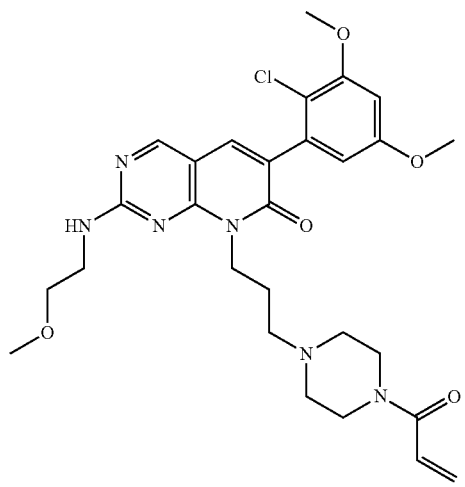 [SMILES: C=CC(=O)N1CCN(CCCn2c(=O)c(-c3cc(OC)cc(OC)c3Cl)cc3cnc(NCCOC)nc32)CC1]

Prepared as described in Example 4 above except 2-methoxyethanamine was used in Step 5. MS (ESI, pos. ion) m/z: 571.1 (M+1).

Example 49

Synthesis of 8-(3-(4-acryloylpiperazin-1-yl)propyl)-6-(2-chloro-3,5-dimethoxyphenyl)-2-((2-ethoxyethyl)amino)pyrido[2,3-d]pyrimidin-7(8H)-one

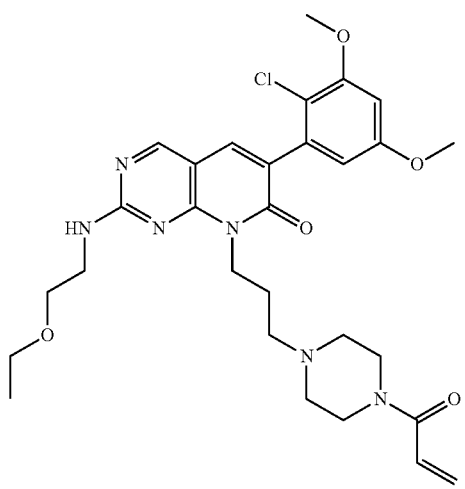 [SMILES: C=CC(=O)N1CCN(CCCn2c(=O)c(-c3cc(OC)cc(OC)c3Cl)cc3cnc(NCCOCC)nc32)CC1]

Prepared as described in Example 4 above except 2-ethoxyethanamine was used in Step 5.
MS (ESI, pos. ion) m/z: 585.3 (M+1).

Example 50

Synthesis of 8-(3-(4-acryloylpiperazin-1-yl)propyl)-6-(2-chloro-3,5-dimethoxyphenyl)-2-((1,3-dimethoxypropan-2-yl)amino)pyrido[2,3-d]pyrimidin-7(8H)-one

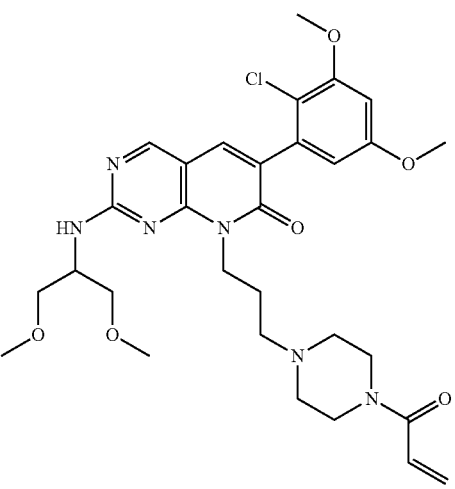 [SMILES: C=CC(=O)N1CCN(CCCn2c(=O)c(-c3cc(OC)cc(OC)c3Cl)cc3cnc(NC(COC)COC)nc32)CC1]

Prepared as described in Example 4 above except 1,3-dimethoxypropan-2-amine was used in Step 5. MS (ESI, pos. ion) m/z: 615.2 (M+1).

Example 51

Synthesis of (S)-8-(3-(4-acryloylpiperazin-1-yl)propyl)-6-(2-chloro-3,5-dimethoxyphenyl)-2-((tetrahydrofuran-3-yl)amino)pyrido[2,3-d]pyrimidin-7(8H)-one

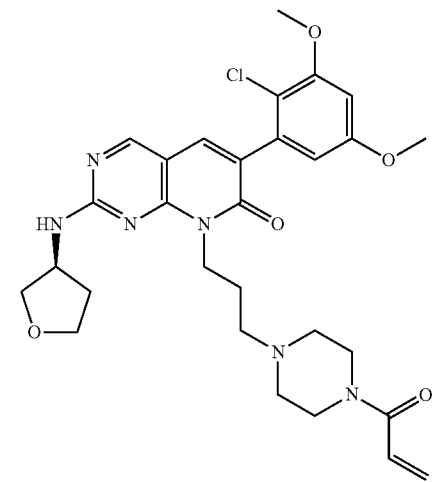 [SMILES: C=CC(=O)N1CCN(CCCn2c(=O)c(-c3cc(OC)cc(OC)c3Cl)cc3cnc(N[C@H]4CCOC4)nc32)CC1]

Prepared as described in Example 4 above except (S)-tetrahydrofuran-3-amine was used in Step 5. MS (ESI, pos. ion) m/z: 583.3 (M+1).

Example 52

Synthesis of 8-(3-(4-acryloylpiperazin-1-yl)propyl)-6-(2-chloro-3,5-dimethoxyphenyl)-2-(((tetrahydro-2H-pyran-4-yl)methyl)amino)pyrido[2,3-d]pyrimidin-7(8H)-one

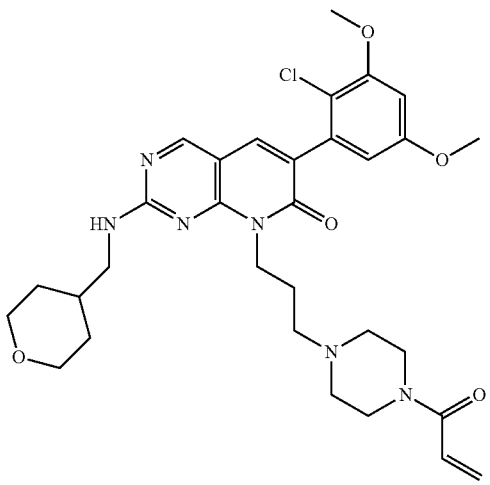 [SMILES: C=CC(=O)N1CCN(CCCn2c(=O)c(-c3cc(OC)cc(OC)c3Cl)cc3cnc(NCC4CCOCC4)nc32)CC1]

Prepared as described in Example 4 above except (tetrahydro-2H-pyran-4-yl)methanamine was used in Step 5. MS (ESI, pos. ion) m/z: 611.4 (M+1).

Example 53

Synthesis of 8-(3-(4-acryloylpiperazin-1-yl)propyl)-6-(2,6-dichloro-3,5-dimethoxyphenyl)-2-((2-ethoxyethyl)amino)pyrido[2,3-d]pyrimidin-7(8H)-one

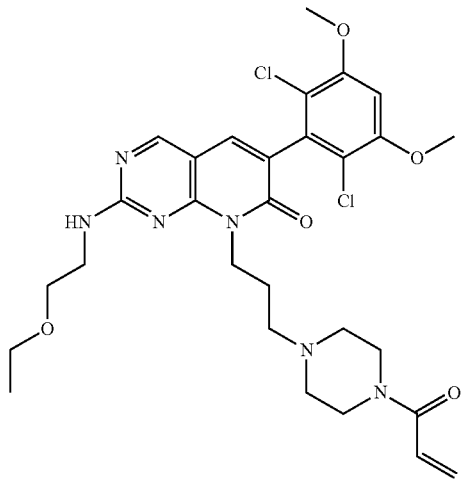 [SMILES: C=CC(=O)N1CCN(CCCn2c(=O)c(-c3c(Cl)c(OC)cc(OC)c3Cl)cc3cnc(NCCOCC)nc32)CC1]

Prepared as described in Example 6 above except 2-ethoxyethanamine was used in Step 5. MS (ESI, pos. ion) m/z: 619.3 (M+1).

Example 54

Synthesis of 8-(3-(4-acryloylpiperazin-1-yl)propyl)-6-(2,6-dichloro-3,5-dimethoxyphenyl)-2-(((tetrahydro-2H-pyran-4-yl)methyl)amino)pyrido[2,3-d]pyrimidin-7(8H)-one

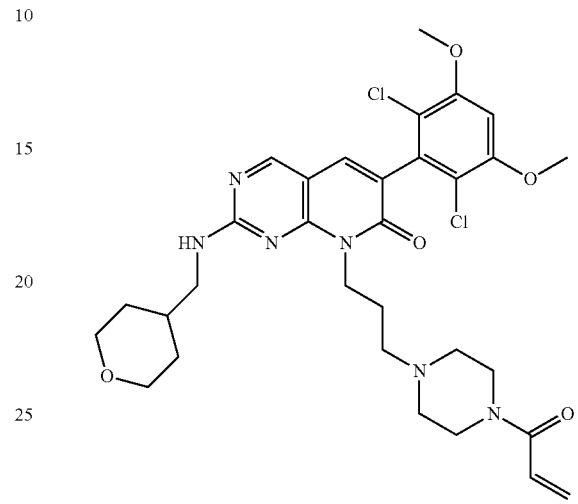

Prepared as described in Example 6 above except (tetrahydro-2H-pyran-4-yl)methanamine was used in Step 5. MS (ESI, pos. ion) m/z: 645.4 (M+1).

Example 55

Synthesis of 8-(3-(4-acryloylpiperazin-1-yl)propyl)-6-(2,6-dichloro-3,5-dimethoxyphenyl)-2-((2,2,2-trifluoroethyl)amino)pyrido[2,3-d]pyrimidin-7(8H)-one

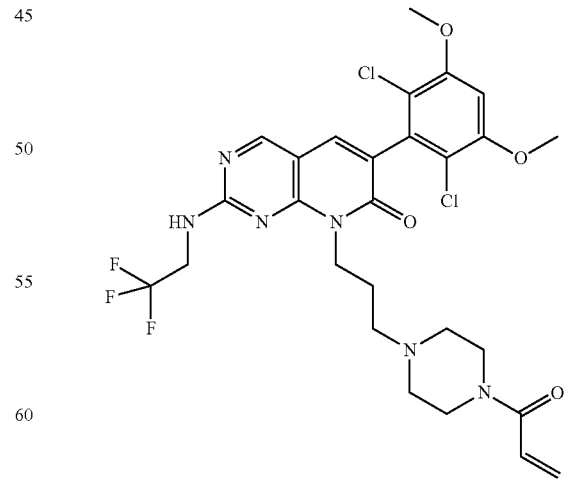

Prepared as described in Example 6 above except 2,2,2-trifluoroethanamine was used in Step 5. MS (ESI, pos. ion) m/z: 629.1 (M+1).

Example 56

Synthesis of (R)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one

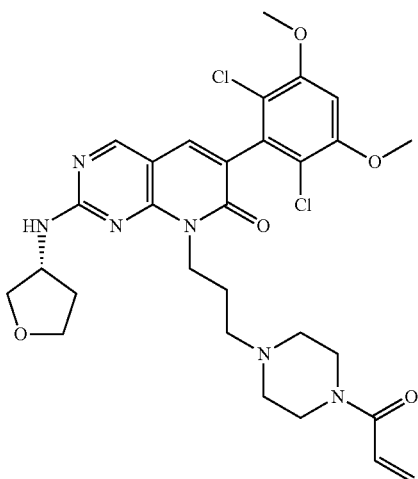

Prepared as described in Example 6 above except (R)-tetrahydrofuran-3-amine was used in Step 5. MS (ESI, pos. ion) m/z: 617.2 (M+1).

Example 57

Synthesis of 8-(3-(4-acryloylpiperazin-1-yl)propyl)-6-(2,6-dichloro-3,5-dimethoxyphenyl)-2-((1,3-dimethoxypropan-2-yl)amino)pyrido[2,3-d]pyrimidin-7(8H)-one

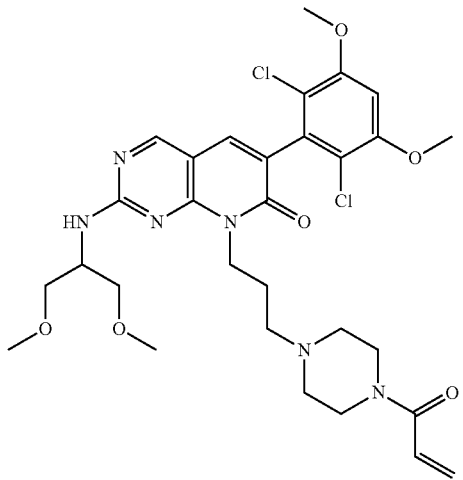 [SMILES: C=CC(=O)N1CCN(CCCn2c(=O)c(-c3c(Cl)c(OC)cc(OC)c3Cl)cc3cnc(NC(COC)COC)nc32)CC1]

Prepared as described in Example 6 above except 1,3-dimethoxypropan-2-amine was used in Step 5. MS (ESI, pos. ion) m/z: 649.6 (M+1).

Example 58

Synthesis of (S)-8-(3-(4-acryloylpiperazin-1-yl)propyl)-6-(2,6-dichloro-3,5-dimethoxyphenyl)-2-((tetrahydrofuran-3-yl)amino)pyrido[2,3-d]pyrimidin-7(8H)-one

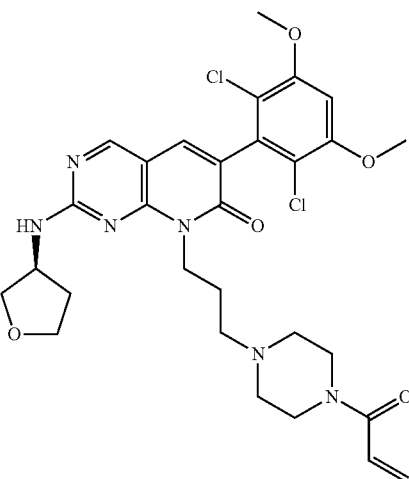

Prepared as described in Example 6 above except (S)-tetrahydrofuran-3-amine was used in Step 5. MS (ESI, pos. ion) m/z: 617.1 (M+1).

Example 59

Synthesis of 8-(3-(4-acryloylpiperazin-1-yl)propyl)-6-(2,6-dichloro-3,5-dimethoxyphenyl)-2-(((tetrahydrofuran-2-yl)methyl)amino)pyrido[2,3-d]pyrimidin-7(8H)-one

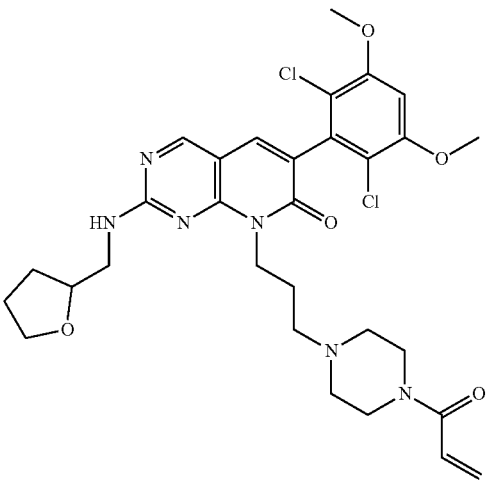 [SMILES: C=CC(=O)N1CCN(CCCn2c(=O)c(-c3c(Cl)c(OC)cc(OC)c3Cl)cc3cnc(NCC4CCCO4)nc32)CC1]

Prepared as described in Example 6 above except (tetrahydrofuran-2-yl)methanamine was used in Step 5. MS (ESI, pos. ion) m/z: 631.2 (M+1).

Example 60

Synthesis of 8-(3-(4-acryloylpiperazin-1-yl)propyl)-6-(2,6-dichloro-3,5-dimethoxyphenyl)-2-((3-(2-oxopyrrolidin-1-yl)propyl)amino)pyrido[2,3-d]pyrimidin-7(8H)-one

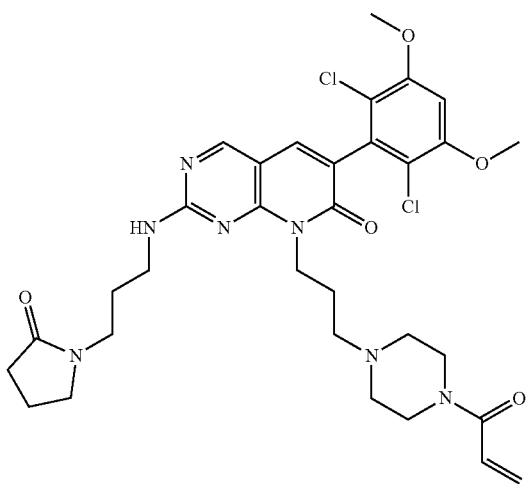 [SMILES: C=CC(=O)N1CCN(CCCn2c(=O)c(-c3c(Cl)c(OC)cc(OC)c3Cl)cc3cnc(NCCCN4CCCC4=O)nc32)CC1]

Prepared as described in Example 6 above except 1-(3-aminopropyl)pyrrolidin-2-one was used in Step 5. MS (ESI, pos. ion) m/z: 672.2 (M+1).

Example 61

Synthesis of 8-(3-(4-acryloylpiperazin-1-yl)propyl)-2-amino-6-(2,6-dichloro-3,5-dimethoxyphenyl)pyrido[2,3-d]pyrimidin-7(8H)-one

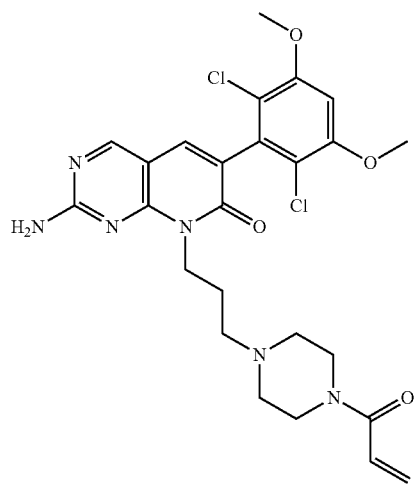 [SMILES: C=CC(=O)N1CCN(CCCn2c(=O)c(-c3c(Cl)c(OC)cc(OC)c3Cl)cc3cnc(N)nc32)CC1]

Prepared as described in Example 6 above except ammonia was used in Step 5. MS (ESI, pos. ion) m/z: 547.2 (M+1).

Example 62

Synthesis of N-(8-(3-(4-acryloylpiperazin-1-yl)propyl)-6-(2,6-dichloro-3,5-dimethoxyphenyl)-7-oxo-7,8-dihydropyrido[2,3-d]pyrimidin-2-yl)acetamide

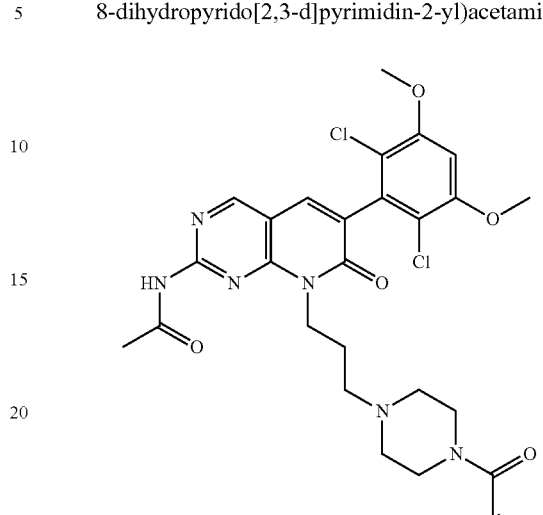

Step 1

A solution of tert-butyl 4-[3-[2-amino-6-(2,6-dichloro-3,5-dimethoxyphenyl)-7-oxo-7H,8H-pyrido[2,3-d]pyrimidin-8-yl]propyl]piperazine-1-carboxylate (200 mg, 0.34 mmol) and pyridine (0.08 mL) in acetyl chloride (5 mL) was stirred for 36 h at room temperature. The resulting mixture was concentrated and then purified by chromatography (DCM/MeOH (12:1)) to afford 180 mg (84%) of tert-butyl 4-[3-[6-(2,6-dichloro-3,5-dimethoxyphenyl)-2-acetamido-7-oxo-7H,8H-pyrido[2,3-d]pyrimidin-8-yl]propyl]piperazine-1-carboxylate as a yellow solid which was converted to the title compound as described in Example 6, Steps 7 and 8. MS (ESI, pos. ion) m/z: 589.3 (M+1).

Example 63

Synthesis of 8-(3-(4-acryloylpiperazin-1-yl)propyl)-6-(2,6-dichloro-3,5-dimethoxyphenyl)-2-((2-(2-methoxyethoxy)ethyl)amino)pyrido[2,3-d]pyrimidin-7(8H)-one

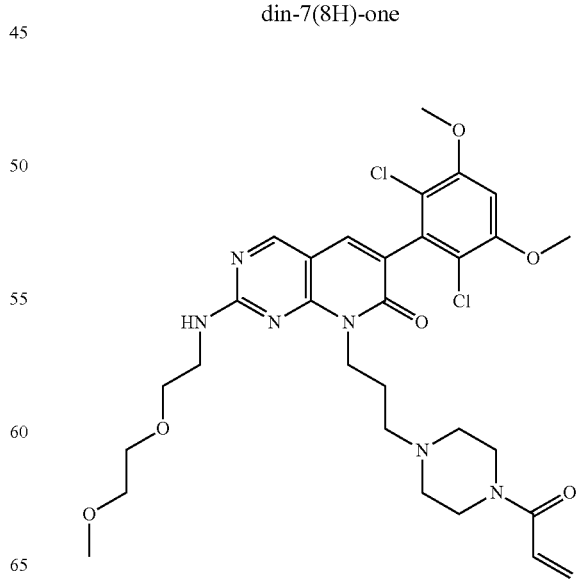

Prepared as described in Example 6 above except 2-(2-methoxyethoxy)ethanamine was used in Step 5. MS (ESI, pos. ion) m/z: 649.4 (M+1).

Example 64

Synthesis of 8-(3-(4-acryloylpiperazin-1-yl)propyl)-6-(2,6-dichloro-3,5-dimethoxyphenyl)-2-(((1r,4r)-4-hydroxycyclohexyl)amino)pyrido[2,3-d]pyrimidin-7(8H)-one

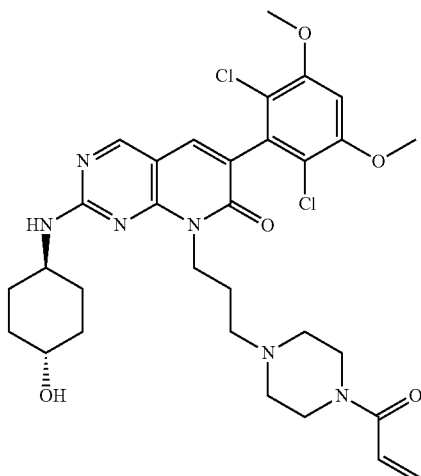

Prepared as described in Example 6 above except (1r,4r)-4-aminocyclohexanol was used in Step 5. MS (ESI, pos. ion) m/z: 645.4 (M+1).

Example 65

Synthesis of 8-(3-(4-acryloylpiperazin-1-yl)propyl)-6-(2,6-dichloro-3,5-dimethoxyphenyl)-2-((2-(2-oxopyrrolidin-1-yl)ethyl)amino)pyrido[2,3-d]pyrimidin-7(8H)-one

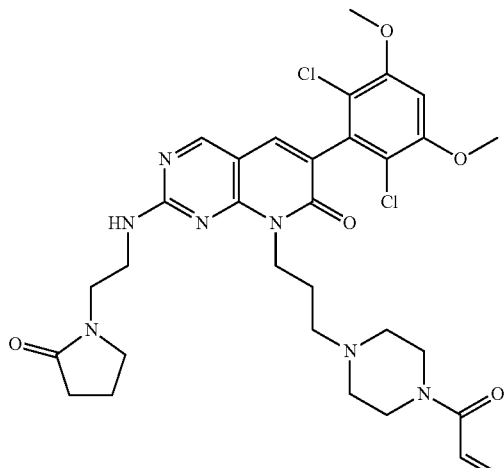

Prepared as described in Example 6 except 1-(2-aminoethyl)pyrrolidin-2-one was used in Step 5. MS (ESI, pos. ion) m/z: 649.4 (M+1).

Example 66

Synthesis of 8-(3-(4-acryloylpiperazin-1-yl)propyl)-6-(2,6-dichloro-3,5-dimethoxyphenyl)-2-(oxetan-3-ylamino)pyrido[2,3-d]pyrimidin-7(8H)-one

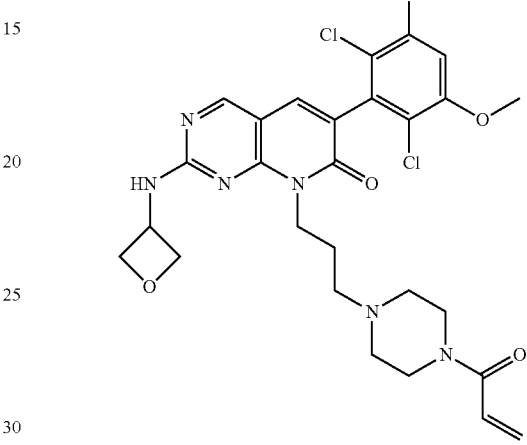

Prepared as described in Example 6 above except oxetan-3-amine was used in Step 5. MS (ESI, pos. ion) m/z: 603.1 (M+1).

Example 67

Synthesis of (R)-8-(3-(4-acryloylpiperazin-1-yl)propyl)-6-(2,6-dichloro-3,5-dimethoxyphenyl)-2-((1-methoxypropan-2-yl)amino)pyrido[2,3-d]pyrimidin-7(8H)-one

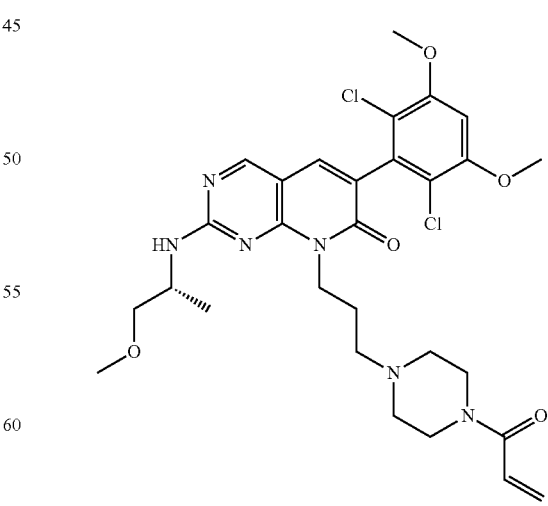

Prepared as described in Example 6 above except (R)-1-methoxypropan-2-amine was used in Step 5. MS (ESI, pos. ion) m/z: 619.2 (M+1).

Example 68

Synthesis of 8-(3-(4-acryloylpiperazin-1-yl)propyl)-6-(2-chloro-6-fluoro-3,5-dimethoxyphenyl)-2-(methylamino)pyrido[2,3-d]pyrimidin-7(8H)-one

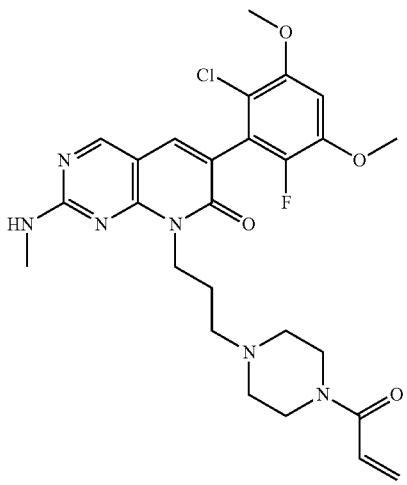 [SMILES: C=CC(=O)N1CCN(CCCn2c(=O)c(-c3c(F)c(OC)cc(OC)c3Cl)cc3cnc(NC)nc32)CC1]

Step 1

To a solution of 1,3-dimethoxy-5-methylbenzene (4 g, 26.28 mmol) in ACN (60 mL) at 0° C. was added Selectfluor (8.4 g, 23.73 mmol) drop wise with stirring. The resulting solution was stirred overnight at room temperature and then quenched with water. The resulting solution was extracted with DCM and the organic layers combined and concentrated. The residue was purified by chromatography (ethyl acetate/pet. ether (1:20)) to afford 1.5 g (34%) of 2-fluoro-1,5-dimethoxy-3-methylbenzene as colorless oil.

Step 2

To a solution of 2-fluoro-1,5-dimethoxy-3-methylbenzene (1.5 g, 8.81 mmol) in DCM (30 mL) was added a solution of sulfuroyl dichloride (1.19 g, 8.82 mmol) in DCM (20 mL) drop wise with stirring at 0° C. The resulting solution was stirred for 1 h at room temperature. The pH value of the solution was adjusted to 9 with sat. NaHCO$_3$. The resulting solution was extracted with DCM and the organic layers were combined and concentrated. The residue was purified by chromatography (EtOAc/pet. ether (1:7)) to afford 1.2 g (67%) of 2-chloro-4-fluoro-1,5-dimethoxy-3-methylbenzene as a white solid.

Step 3

A solution of 2-chloro-4-fluoro-1,5-dimethoxy-3-methylbenzene (1.2 g, 5.86 mmol), NBS (1.04 g, 5.84 mmol) and AIBN (380 mg, 2.31 mmol). in CCl4 (40 mL) was heated to reflux for 4 hr. The reaction was quenched with sat. NaHCO$_3$ and extracted with DCM. The organic layers were combined and concentrated to afford 1.4 g (84%) of 3-(bromomethyl)-2-chloro-4-fluoro-1,5-dimethoxybenzene as a yellow solid.

Step 4

To a solution of 3-(bromomethyl)-2-chloro-4-fluoro-1,5-dimethoxybenzene (1.4 g, 4.94 mmol) in DMSO (30 mL) was added NaCN (240 mg, 4.90 mmol). The resulting solution was stirred overnight at 35° C. and then quenched with sat. NaHCO$_3$. The solution was extracted with DCM and the organic layers combined and washed with water and then concentrated. The residue was purified by chromatography (DCM/pet. ether (75:100)) to afford 510 mg (45%) of 2-(2-chloro-6-fluoro-3,5-dimethoxyphenyl)acetonitrile as a white solid.

Step 5

To a solution of 2-(2-chloro-6-fluoro-3,5-dimethoxyphenyl)acetonitrile (510 mg, 2.22 mmol) in DMF (40 mL) was added K$_2$CO$_3$ (920 mg, 6.66 mmol), Cs$_2$CO$_3$ (720 mg, 2.21 mmol) and 4-amino-2-(methylsulfanyl)pyrimidine-5-carbaldehyde (380 mg, 2.25 mmol). The resulting solution was stirred for 3 h at 85° C. and then diluted with water. The resulting solution was extracted with DCM and the organic layers combined, washed with sat. NaCl and then concentrated. The residue was purified by chromatography (EA/DCM (1:5)) to afford 500 mg (59%) of 6-(2-chloro-6-fluoro-3,5-dimethoxyphenyl)-2-(methylsulfanyl)-7H,8H-pyrido[2,3-d]pyrimidin-7-imine as a yellow solid.

Step 6

To a solution of 6-(2-chloro-6-fluoro-3,5-dimethoxyphenyl)-2-(methylsulfanyl)-7H,8H-pyrido[2,3-d]pyrimidin-7-imine (500 mg, 1.31 mmol) in AcOH (15 mL) was added NaNO$_2$ (450 mg, 6.52 mmol). The resulting solution was stirred for 2 h at 85° C. and then the pH was adjusted to 9 with sat. Na$_2$CO$_3$. The resulting solution was extracted with DCM and the organic layers were combined and concentrated to afford 410 mg (82%) of 6-(2-chloro-6-fluoro-3,5-dimethoxyphenyl)-2-(methylsulfanyl)-7H,8H-pyrido[2,3-d]pyrimidin-7-one as a yellow solid which was converted to the title compound as described in Example 6 above.

MS (ESI, pos. ion) m/z: 545.2 (M+1).

Example 69

Synthesis of (E)-6-(2,6-dichloro-3,5-dimethoxyphenyl)-8-(2-((1-(4-(dimethylamino)but-2-enoyl)azetidin-3-yl)oxy)ethyl)-2-(methylamino)pyrido[2,3-d]pyrimidin-7(8H)-one

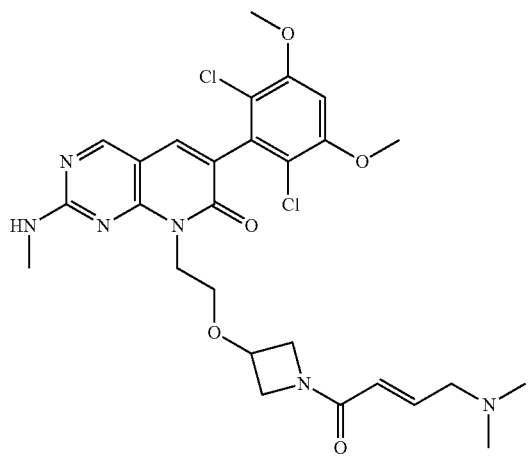 [SMILES: CNc1ncc2cc(-c3c(Cl)c(OC)cc(OC)c3Cl)c(=O)n(CCOC3CN(C(=O)/C=C/CN(C)C)C3)c2n1]

A solution of 8-[2-(azetidin-3-yloxy)ethyl]-6-(2,6-dichloro-3,5-dimethoxyphenyl)-2-(methylamino)-7H,8H-pyrido[2,3-d]pyrimidin-7-one (100 mg, 0.21 mmol), HATU (127 mg, 0.33 mmol), TEA (0.09 mL) and (2E)-4-(dimethylamino)but-2-enoic acid (35 mg, 0.27 mmol) in DMF (15 mL) was stirred overnight at room temperature. The resulting solution was diluted with water and the solids were collected by filtration. The residue was purified by chromatography (DCM/MeOH (15:1) to afford 22 mg (17.86%) of 6-(2,6-dichloro-3,5-dimethoxyphenyl)-8-[2-([1-[(2E)-4-(dimethylamino)but-2-enoyl]azetidin-3-yl]oxy)ethyl]-2-(methylamino)-7H,8H-pyrido[2,3-d]pyrimidin-7-one as a white solid.

MS (ESI, pos. ion) m/z: 591.3 (M+1).

Example 70

Synthesis of 8-(2-((1-acryloylazetidin-3-yl)oxy)ethyl)-6-(2,6-dichloro-3,5-dimethoxyphenyl)-2-((2-morpholinoethyl)amino)pyrido[2,3-d]pyrimidin-7(8H)-one

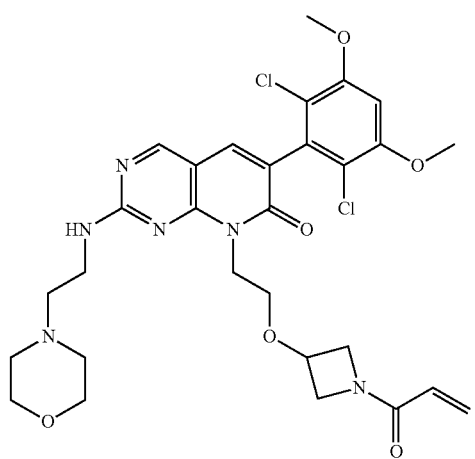 [SMILES: C=CC(=O)N1CC(OCCn2c(=O)c(-c3c(Cl)c(OC)cc(OC)c3Cl)cc3cnc(NCCN4CCOCC4)nc32)C1]

Prepared as described in Example 14 above except 2-morpholinoethanamine was used in Step 5. MS (ESI, pos. ion) m/z: 633.5 (M+1).

Example 71

Synthesis of 8-(2-((1-acryloylazetidin-3-yl)oxy)ethyl)-6-(2-chloro-3,5-dimethoxyphenyl)-2-(methylamino)pyrido[2,3-d]pyrimidin-7(8H)-one

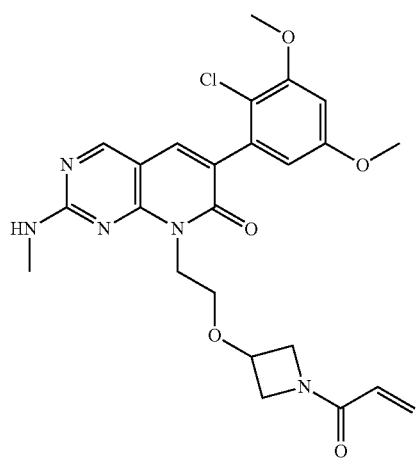 [SMILES: C=CC(=O)N1CC(OCCn2c(=O)c(-c3cc(OC)cc(OC)c3Cl)cc3cnc(NC)nc32)C1]

Prepared as described in Example 14 above except 6-(2-chloro-3,5-dimethoxy-phenyl)-2-(methylthio)pyrido[2,3-d]pyrimidin-7(8H)-one was used in Step 4. MS (ESI, pos. ion) m/z: 500.1 (M+1).

Example 72

Synthesis of 8-(2-((1-acryloylazetidin-3-yl)oxy)ethyl)-6-(2-chloro-3,5-dimethoxyphenyl)-2-((2-morpholinoethyl)amino)pyrido[2,3-d]pyrimidin-7(8H)-one

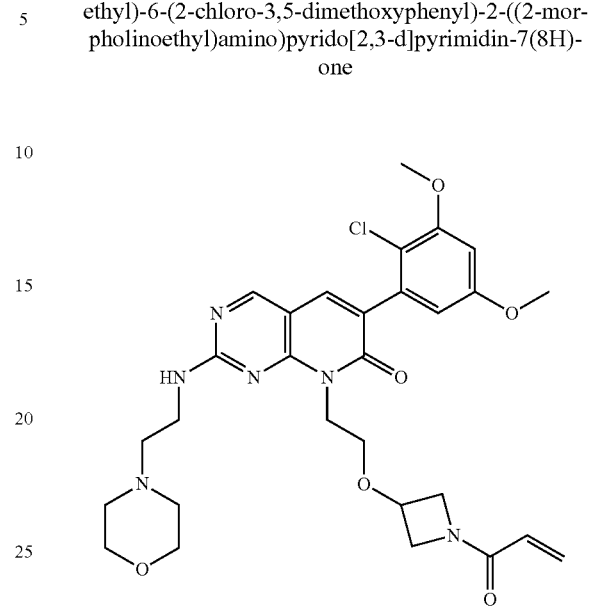

Prepared as described in Example 14 except 6-(2-chloro-3,5-dimethoxy-phenyl)-2-(methylthio)pyrido[2,3-d]pyrimidin-7(8H)-one was used in Step 4 and 2-morpholinoethanamine was used in Step 6. MS (ESI, pos. ion) m/z: 599.3 (M+1).

Example 73

Synthesis of (S)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one

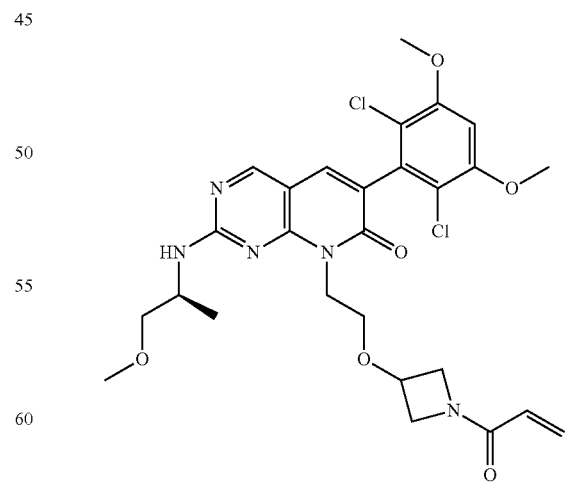

Prepared as described in Example 14 above except (S)-1-methoxypropan-2-amine was used in Step 6. MS (ESI, pos. ion) m/z: 592.2 (M+1).

Example 74

Synthesis of 8-(2-((1-acryloylazetidin-3-yl)oxy)ethyl)-6-(2,6-dichloro-3,5-dimethoxyphenyl)-2-((2-(4-methylpiperazin-1-yl)ethyl)amino)pyrido[2,3-d]pyrimidin-7(8H)-one

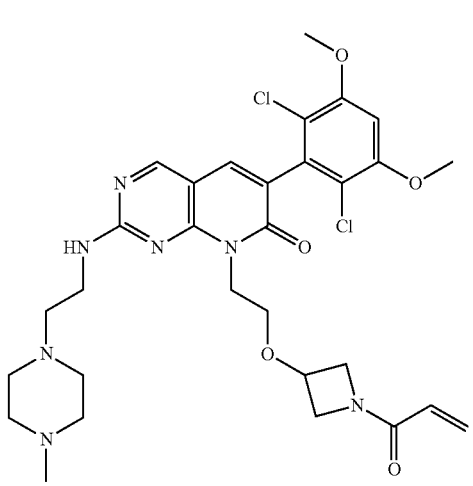 [SMILES: C=CC(=O)N1CC(OCCn2c(=O)c(-c3c(Cl)c(OC)cc(OC)c3Cl)cc3cnc(NCCN4CCN(C)CC4)nc32)C1]

Prepared as described in Example 14 above except 2-(4-methylpiperazin-1-yl)ethanamine was used in Step 6. MS (ESI, pos. ion) m/z: 646.2 (M+1).

Example 75

Synthesis of (R)-8-(2-((1-acryloylazetidin-3-yl)oxy)ethyl)-6-(2,6-dichloro-3,5-dimethoxyphenyl)-2-((1-methoxypropan-2-yl)amino)pyrido[2,3-d]pyrimidin-7(8H)-one

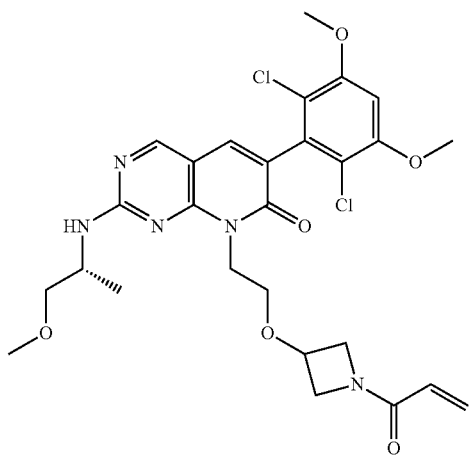 [SMILES: C=CC(=O)N1CC(OCCn2c(=O)c(-c3c(Cl)c(OC)cc(OC)c3Cl)cc3cnc(N[C@H](C)COC)nc32)C1]

Prepared as described in Example 14 above except (R)-1-methoxypropan-2-amine was used in Step 6. MS (ESI, pos. ion) m/z: 592.2 (M+1).

Example 76

Synthesis of 8-(2-((1-acryloylazetidin-3-yl)oxy)ethyl)-2-amino-6-(2,6-dichloro-3,5-dimethoxyphenyl)pyrido[2,3-d]pyrimidin-7(8H)-one

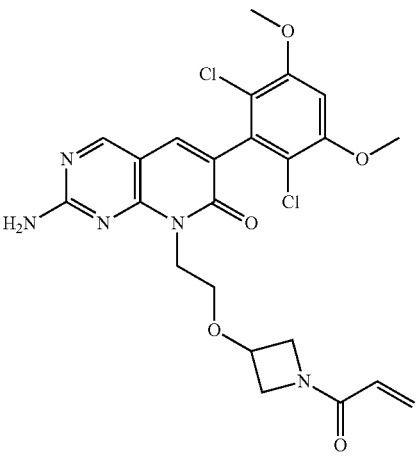 [SMILES: C=CC(=O)N1CC(OCCn2c(=O)c(-c3c(Cl)c(OC)cc(OC)c3Cl)cc3cnc(N)nc32)C1]

Prepared as in Example 14 except ammonia was used in Step 6. MS (ESI, pos. ion) m/z: 520.1 (M+1).

Example 77

Synthesis of 8-(2-((1-acryloylazetidin-3-yl)oxy)ethyl)-6-(2,6-dichloro-3,5-dimethoxyphenyl)-2-((2-methoxyethyl)amino)pyrido[2,3-d]pyrimidin-7(8H)-one

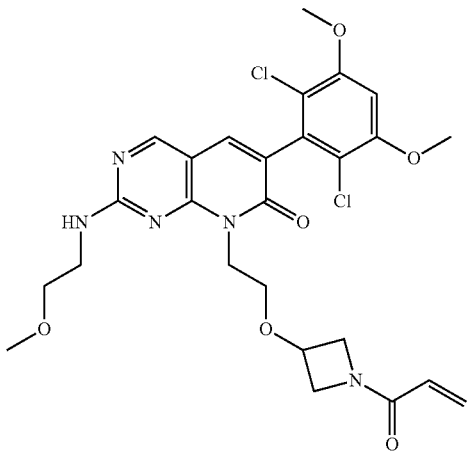 [SMILES: C=CC(=O)N1CC(OCCn2c(=O)c(-c3c(Cl)c(OC)cc(OC)c3Cl)cc3cnc(NCCOC)nc32)C1]

Prepared as described in Example 14 above except 2-methoxyethanamine was used in Step 6. MS (ESI, pos. ion) m/z: 578.1 (M+1).

Example 78

Synthesis of (S)-8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one

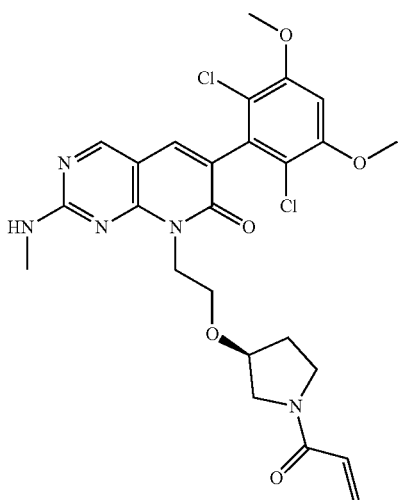 [SMILES: C=CC(=O)N1CC[C@H](OCCn2c(=O)c(-c3c(Cl)c(OC)cc(OC)c3Cl)cc3cnc(NC)nc32)C1]

Prepared as described in Example 14 above except (S)-tert-butyl 3-hydroxypyrrolidine-1-carboxylate was used in Step 1. MS (ESI, pos. ion) m/z: 548.3 (M+1).

Example 79

Synthesis of (R)-8-(2-((1-acryloylpyrrolidin-3-yl)oxy)ethyl)-6-(2,6-dichloro-3,5-dimethoxyphenyl)-2-(methylamino)pyrido[2,3-d]pyrimidin-7(8H)-one

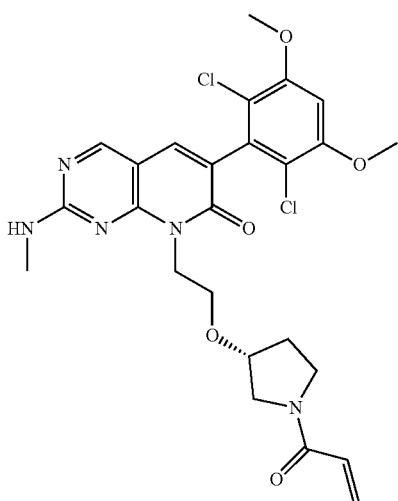 [SMILES: C=CC(=O)N1CC[C@@H](OCCn2c(=O)c(-c3c(Cl)c(OC)cc(OC)c3Cl)cc3cnc(NC)nc32)C1]

Prepared as described in Example 14 above except (R)-tert-butyl 3-hydroxypyrrolidine-1-carboxylate was used in Step 1. MS (ESI, pos. ion) m/z: 548.2 (M+1).

Example 80

Synthesis of 8-(2-((1-acryloylazetidin-3-yl)(methyl)amino)ethyl)-6-(2,6-dichloro-3,5-dimethoxyphenyl)-2-(methylamino)pyrido[2,3-d]pyrimidin-7(8H)-one

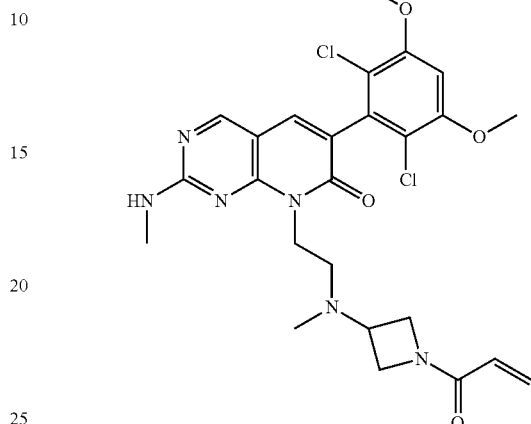

Step 1
To a solution of tert-butyl N-(2-hydroxyethyl)-N-methylcarbamate (2 g, 11.41 mmol) in THF (15 mL) at 0° C. was added NaH (450 mg, 18.75 mmol). The resulting solution was stirred for 2 h at 0° C. and then benzyl bromide (2 g, 11.69 mmol) was added dropwise with stirring at 0° C. The resulting solution was stirred for 4 h at room temperature and then quenched with sat. NH$_4$Cl. The resulting solution was extracted with ethyl acetate and the organic layers were combined, washed with sat. NaCl, dried over Na$_2$SO$_4$, filtered and concentrated. The residue was purified by chromatography (ethyl acetate/petroleum ether (1:10)) to afford 2.2 g (73%) of tert-butyl N-[2-(benzyloxy)ethyl]-N-methylcarbamate as a colorless oil.

Step 2
A solution of tert-butyl N-[2-(benzyloxy)ethyl]-N-methylcarbamate (2 g, 7.54 mmol), TFA (4 mL) and DCM (10 mL) was stirred for 4 h at room temperature and then sat. NaHCO$_3$ was added. The resulting solution was diluted with DCM, washed with sat. NaCl, dried over Na$_2$SO$_4$, filtered and concentrated to afford 1.5 g (crude) of [2-(benzyloxy)ethyl](methyl)amine as a colorless oil.

Step 3
A solution of [2-(benzyloxy)ethyl](methyl)amine (1.5 g, 9.08 mmol) and tert-butyl 3-oxoazetidine-1-carboxylate (1.7 g, 9.93 mmol) in DCM (20 mL) was stirred overnight at rt and then NaBH$_3$CN (800 mg, 12.73 mmol) was added. The resulting solution was stirred for 6 h at room temperature and then water was added. The resulting solution was diluted with DCM, washed with sat. NaCl, dried over Na$_2$SO$_4$, filtered and concentrated. The residue was purified by chromatography (ethyl acetate/petroleum ether (1:20-1:1)) to afford 1 g (34%) of tert-butyl 3-[[2-(benzyloxy)ethyl](methyl)amino]azetidine-1-carboxylate as a brown oil.

Step 4
A mixture of tert-butyl 3-[[2-(benzyloxy)ethyl](methyl)amino]azetidine-1-carboxylate (1.1 g, 1.00 equiv) and Pd on carbon (0.4 g) in MeOH (20 mL) was stirred overnight at room temperature under 1 atm of H$_2$. The solids were then filtered and the solvent was evaporated. The residue was purified by chromatography (DCM/MeOH (25:1)) to afford 0.5 g (63%) of tert-butyl 3-[(2-hydroxyethyl)(methyl)amino]azetidine-1-carboxylate as a light yellow oil.

Step 5

A solution of tert-butyl 3-[(2-hydroxyethyl)(methyl)amino]azetidine-1-carboxylate (310 mg, 1.35 mmol), PPh$_3$ (520 mg, 1.98 mmol), imidazole (135 mg) and I$_2$ (500 mg) in DCM (100 mL) was stirred for 4 h at room temperature. The resulting mixture was then concentrated and the residue was purified by chromatography (DCM/ethyl acetate (20:1)) to afford 430 mg (94%) of tert-butyl 3-[(2-iodoethyl)(methyl)amino]azetidine-1-carboxylate as a light yellow oil.

Step 6

A mixture of tert-butyl 3-[(2-iodoethyl)(methyl)amino]azetidine-1-carboxylate (470 mg, 1.38 mmol), K$_2$CO$_3$ (497 mg, 3.60 mmol) and 6-(2,6-dichloro-3,5-dimethoxyphenyl)-2-(methylsulfanyl)-7H,8H-pyrido[2,3-d]pyrimidin-7-one (400 mg, 1.00 mmol) in acetone (20 mL) was stirred overnight at 60° C. The resulting mixture was then concentrated and the residue was purified by chromatography (DCM/MeOH (25:1)) to afford 500 mg (59%) of tert-butyl 3-([2-[6-(2,6-dichloro-3,5-dimethoxyphenyl)-2-(methylsulfanyl)-7-oxo-7H,8H-pyrido[2,3-d]pyrimidin-8-yl]ethyl](methyl)amino)azetidine-1-carboxylate as a brown solid.

Step 7

A solution of tert-butyl 3-([2-[6-(2,6-dichloro-3,5-dimethoxyphenyl)-2-(methylsulfanyl)-7-oxo-7H,8H-pyrido[2,3-d]pyrimidin-8-yl]ethyl](methyl)amino)azetidine-1-carboxylate (500 mg, 0.82 mmol) and mCPBA (415 mg) in DCM (20 mL) was stirred overnight at room temperature and then sat. NaHCO$_3$ was added. The resulting solution was extracted with DCM and the organic layer was washed with sat. NaCl, dried over Na$_2$SO$_4$ and concentrated to afford 510 mg (94%) of 1-(tert-butoxycarbonyl)-N-(2-(6-(2,6-dichloro-3,5-dimethoxyphenyl)-2-(methylsulfinyl)-7-oxopyrido[2,3-d]pyrimidin-8(7H)-yl-ethyl)-N-methylazetidin-3-amine oxide as a yellow crude solid.

Step 8

A solution of 1-(tert-butoxycarbonyl)-N-(2-(6-(2,6-dichloro-3,5-dimethoxyphenyl)-2-(methylsulfinyl)-7-oxopyrido[2,3-d]pyrimidin-8(7H)-yl)ethyl)-N-methylazetidin-3-amine oxide (510 mg, 0.77 mmol) and methanamine (0.8 mL, 2M in THF) in DCM (10 mL) was stirred for 1 h at room temperature. The resulting mixture was then concentrated to afford 420 mg (890%) of 1-(tert-butoxycarbonyl)-N-(2-(6-(2,6-dichloro-3,5-dimethoxyphenyl)-2-(methylamino)-7-oxopyrido[2,3-d]pyrimidin-8(7H)-yl)ethyl)-N-methylazetidin-3-amine oxide as a yellow crude solid Step 9

A mixture of 1-(tert-butoxycarbonyl)-N-(2-(6-(2,6-dichloro-3,5-dimethoxyphenyl)-2-(methylamino)-7-oxopyrido[2,3-d]pyrimidin-8(7H)-yl)ethyl)-N-methylazetidin-3-amine oxide (420 mg, 0.69 mmol), Zn (500 mg, 7.69 mmol) and NH$_4$Cl (sat. 2 mL) in MeOH (20 mL) was stirred for 2 h at 60° C. The resulting mixture was then concentrated and the residue was purified by chromatography (DCM/MeOH (15:1)) to afford 380 mg (93%) of tert-butyl 3-([2-[6-(2,6-dichloro-3,5-dimethoxyphenyl)-2-(methylamino)-7-oxo-7H,8H-pyrido[2,3-d]pyrimidin-8-yl]ethyl]-(methyl)amino)azetidine-1-carboxylate as a brown solid.

Step 10

A solution of tert-butyl 3-([2-[6-(2,6-dichloro-3,5-dimethoxyphenyl)-2-(methylamino)-7-oxo-7H,8H-pyrido[2,3-d]pyrimidin-8-yl]ethyl](methyl)amino)azetidine-1-carboxylate (300 mg, 0.51 mmol), TFA (2 mL) and DCM (10 mL) was stirred for 2 h at room temperature and then sat NaHCO$_3$ was added. The resulting solution was extracted with DCM and the organic layers were combined, washed with sat. NaCl, dried over Na$_2$SO$_4$ and concentrated to afford 200 mg (80%) of 8-[2-[(azetidin-3-yl)(methyl)amino]ethyl]-6-(2,6-dichloro-3,5-dimethoxyphenyl)-2-(methylamino)-7H,8H-pyrido[2,3-d]pyrimidin-7-one as a light yellow crude solid.

Step 11

A solution of 8-[2-[(azetidin-3-yl)(methyl)amino]ethyl]-6-(2,6-dichloro-3,5-dimethoxy-phenyl)-2-(methylamino)-7H,8H-pyrido[2,3-d]pyrimidin-7-one (200 mg, 0.41 mmol), prop-2-enoyl chloride (58 mg, 0.64 mmol), MeOH (10 mL), TEA (123 mg, 3.00 equiv) and DCM (10 mL) was stirred overnight at room temperature and then concentrated. The crude product was purified by Prep-HPLC to afford 81.3 g (36%) of the title compound as an off-white solid. MS (ESI, pos. ion) m/z: 547.1 (M+1).

Example 81

Synthesis of 8-(3-(4-acryloylpiperazin-1-yl)propyl)-6-(2-fluoro-3,5-dimethoxyphenyl)-2-(methylamino)pyrido[2,3-d]pyrimidin-7(8H)-one

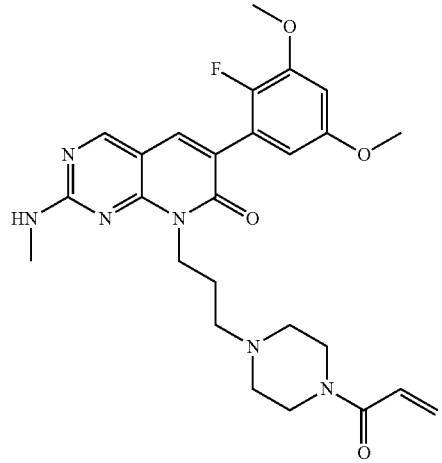 [SMILES: C=CC(=O)N1CCN(CCCn2c(=O)c(-c3cc(OC)cc(OC)c3F)cc3cnc(NC)nc32)CC1]

Step 1

To a solution of methyl 2-(3,5-dimethoxyphenyl)acetate (8.5 g, 40.5 mmol) in MeCN (200 mL) at 0° C. was added select-Fluor (20.1 g, 56.7 mmol). The reaction was stirred overnight at 0° C. and then warmed to rt. The reaction was poured into aq. NaHCO$_3$ and extracted with EtOAc. The organic layer was dried over Na$_2$SO$_4$, filtered and concentrated. The residue was purified by chromatography (silica gel, PE:EtOAc=10:1) to afford methyl 2-(2-fluoro-3,5-dimethoxyphenyl)acetate (3.9 g, 42%) as a yellow oil.

Step 2

A mixture of methyl 2-(2-fluoro-3,5-dimethoxyphenyl)acetate (1.8 g, 7.9 mmol), K$_2$CO$_3$ (2.3 g, 16.5 mmol) and 4-amino-2-(methylthio)pyrimidine-5-carbaldehyde (1.1 g, 6.6 mmol) in NMP (30 mL) was stirred overnight at 100° C. The reaction was cooled and then water was added and the mixture was filtered. The filtered cake was washed with EtOAc and dried to afford 6-(2-fluoro-3,5-dimethoxyphenyl)-2-(methylthio)pyrido[2,3-d]pyrimidin-7(8H)-one (650 mg, 28%) as a yellow solid which was converted to the title compounds as described in Example 4 above.

MS (ESI, pos. ion) m/z: 511.2 (M+1).

Example 82

Synthesis of methyl (8-(3-(4-acryloylpiperazin-1-yl)propyl)-6-(2,6-dichloro-3,5-dimethoxy-phenyl)-7-oxo-7,8-dihydropyrido[2,3-d]pyrimidin-2-yl)carbamate

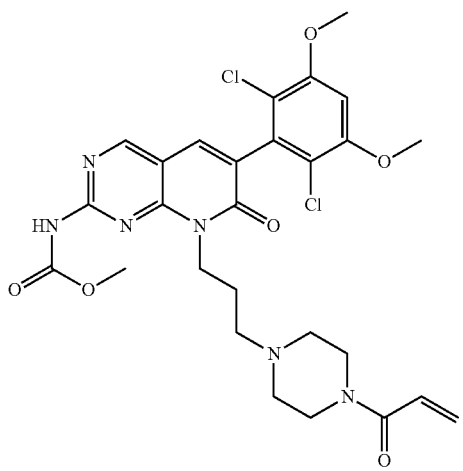 [SMILES: C=CC(=O)N1CCN(CCCn2c(=O)c(-c3c(Cl)c(OC)cc(OC)c3Cl)cc3cnc(NC(=O)OC)nc32)CC1]

Step 1

To a solution of tert-butyl 4-[3-[2-amino-6-(2,6-dichloro-3,5-dimethoxyphenyl)-7-oxo-7H,8H-pyrido[2,3-d]pyrimidin-8-yl]propyl]piperazine-1-carboxylate (200 mg, 0.34 mmol) in THF (20 mL) was added dimethyl carbonate (61 mg, 0.68 mmol,) and t-BuOK (94 mg, 0.84 mmol, 2.49 equiv). The resulting solution was stirred overnight at room temperature, and then extracted with DCM. The organic layer was dried over $Na_2SO_4$ and then concentrated to afford 200 mg (91%) of tert-butyl 4-[3-[6-(2,6-dichloro-3,5-dimethoxyphenyl)-2-[(methoxycarbonyl)-amino]-7-oxo-7H,8H-pyrido[2,3-d]pyrimidin-8-yl]propyl]piperazine-1-carboxylate as a yellow solid. This material was then converted to the title compound as described in Example 6, steps 7 and 8. MS (ESI, pos. ion) m/z: 605.1 (M+1).

Example 83

Synthesis of (S)-8-(3-(4-acryloylpiperazin-1-yl)propyl)-6-(2,6-dichloro-3,5-dimethoxyphenyl)-2-((1-hydroxypropan-2-yl)amino)pyrido[2,3-d]pyrimidin-7(8H)-one

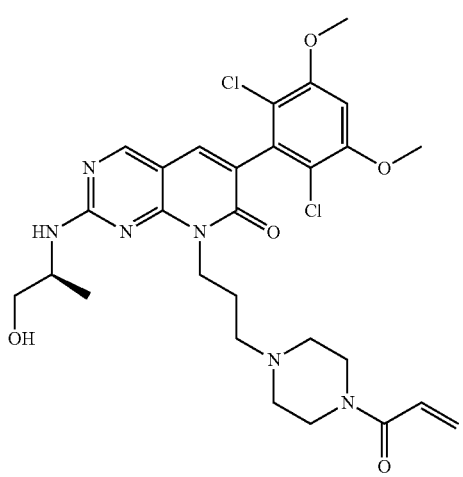 [SMILES: C=CC(=O)N1CCN(CCCn2c(=O)c(-c3c(Cl)c(OC)cc(OC)c3Cl)cc3cnc(N[C@@H](C)CO)nc32)CC1]

The title compound was prepared as described in Example 6 except (S)-2-aminopropan-1-ol was used in Step 5. MS (ESI, pos. ion) m/z: 605.1 (M+1).

Example 84

Synthesis of 8-(3-(4-acryloylpiperazin-1-yl)propyl)-6-(2,6-difluoro-3,5-dimethoxyphenyl)-2-(methylamino)pyrido[2,3-d]pyrimidin-7(8H)-one

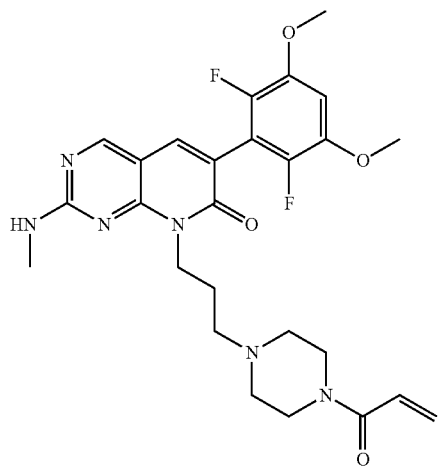 [SMILES: C=CC(=O)N1CCN(CCCn2c(=O)c(-c3c(F)c(OC)cc(OC)c3F)cc3cnc(NC)nc32)CC1]

Step 1

To a solution of methyl 3,5-dimethoxybenzoate (8 g, 40.77 mmol) in ACN (120 mL) at 0° C. was added Selectfluor (36 g, 101.92 mmol). The resulting solution was stirred overnight at room temperature and then water was added. The resulting solution was extracted with DCM and the organic layer was concentrated. The residue was purified by chromatography (DCM/pet. ether (1:3)) to afford 2.96 g (31%) of methyl 2,6-difluoro-3,5-dimethoxybenzoate as a light yellow liquid.

Step 2

To a solution of $LiAlH_4$ (727 mg, 19.12 mmol) in THF (30 mL) at 0° C. was added a solution of methyl 2,6-difluoro-3,5-dimethoxybenzoate (2.96 g, 12.75 mmol) in THF (30 mL) dropwise. The resulting solution was stirred for 4 h at room temperature. The reaction was then quenched by the addition of water and aq. NaOH (15%). The resulting solution was extracted with DCM and the organic layer was concentrated. The residue was purified by chromatography (hexane/ether (3:2)) to afford 1.58 g (61%) of (2,6-difluoro-3,5-dimethoxyphenyl)methanol as a colorless semi-solid.

Step 3

To a solution of (2,6-difluoro-3,5-dimethoxyphenyl)methanol (1.58 g, 7.74 mmol) in DCM (50 mL) at 0° C. was added MsCl (1.76 g, 15.36 mmol,) and TEA (2 equiv). The resulting solution was stirred overnight at room temperature and then quenched with water (100 mL). The resulting solution was extracted with DCM and the organic layer was concentrated to afford 1.74 g (80%) of (2,6-difluoro-3,5-dimethoxyphenyl)methyl methanesulfonate as a light yellow solid.

Step 4

To a solution of (2,6-difluoro-3,5-dimethoxyphenyl)methyl methanesulfonate (1.74 g, 6.16 mmol) in DMSO (30 mL) was added NaCN (300 mg, 6.12 mmol). The resulting solution was stirred at 40° C. and then quenched with aq. NaHCO₃. The resulting solution was extracted with EtOAc and the organic layer was concentrated. The residue was purified by chromatography (DCM/pet. ether (1:1)) to afford 550 mg (42%) of 2-(2,6-difluoro-3,5-dimethoxyphenyl)acetonitrile as a light yellow solid.

The title compound was then prepared as described in Example 68, Steps 5 and 6. MS (ESI, pos. ion) m/z: 529.2 (M+1).

Example 85

Synthesis of (S)-8-(3-(4-acryloylpiperazin-1-yl)propyl)-6-(2,6-dichloro-3,5-dimethoxyphenyl)-2-((1-ethoxypropan-2-yl)amino)pyrido[2,3-d]pyrimidin-7(8H)-one

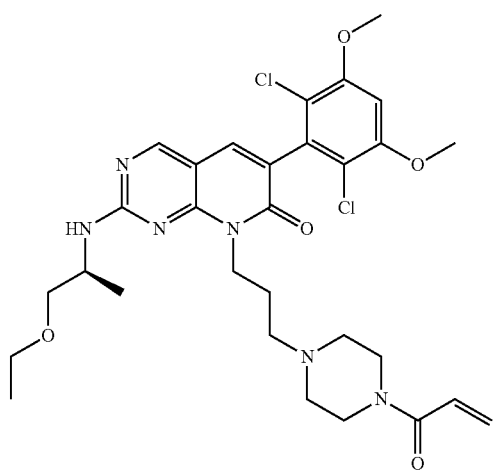 [SMILES: C=CC(=O)N1CCN(CCCn2c(=O)c(-c3c(Cl)c(OC)cc(OC)c3Cl)cc3cnc(N[C@@H](C)COCC)nc32)CC1]

The title compound was prepared as described in Example 6 except (S)-1-ethoxypropan-2-amine was used in Step 5. MS (ESI, pos. ion) m/z: 633.0 (M+1).

Example 86

Synthesis of (E)-8-(3-(4-(but-2-enoyl)piperazin-1-yl)propyl)-6-(2,6-dichloro-3,5-dimethoxyphenyl)-2-(methylamino)pyrido[2,3-d]pyrimidin-7(8H)-one

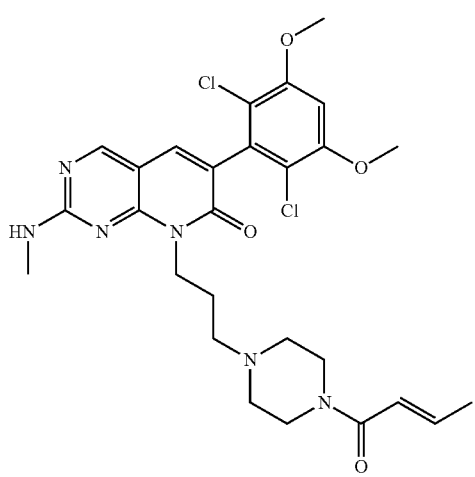 [SMILES: C/C=C/C(=O)N1CCN(CCCn2c(=O)c(-c3c(Cl)c(OC)cc(OC)c3Cl)cc3cnc(NC)nc32)CC1]

The title compound was prepared as described in Example 6 except (E)-but-2-enoyl chloride was used in Step 8. MS (ESI, pos. ion) m/z: 575.3 (M+1).

Example 87

Synthesis of (E)-2-amino-8-(3-(4-(but-2-enoyl)piperazin-1-yl)propyl)-6-(2,6-dichloro-3,5-dimethoxyphenyl)pyrido[2,3-d]pyrimidin-7(8H)-one

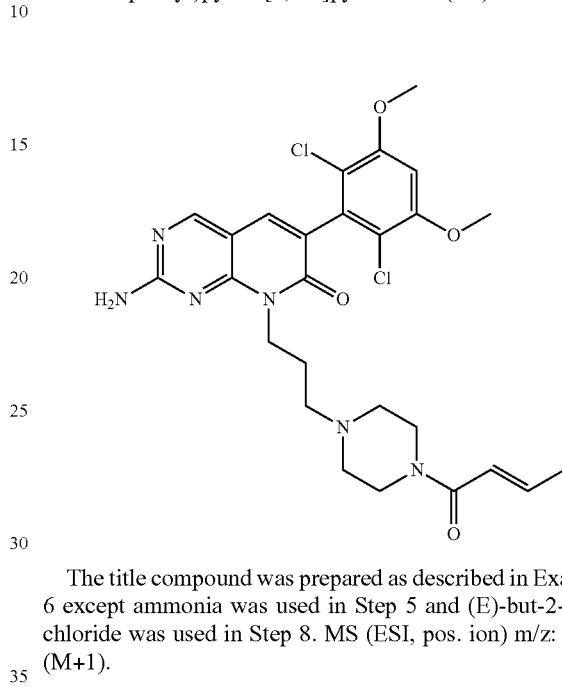

The title compound was prepared as described in Example 6 except ammonia was used in Step 5 and (E)-but-2-enoyl chloride was used in Step 8. MS (ESI, pos. ion) m/z: 561.0 (M+1).

Example 88

Synthesis of methyl (8-(2-((1-acryloylazetidin-3-yl)oxy)ethyl)-6-(2,6-dichloro-3,5-dimethoxy-phenyl)-7-oxo-7,8-dihydropyrido[2,3-d]pyrimidin-2-yl)carbamate

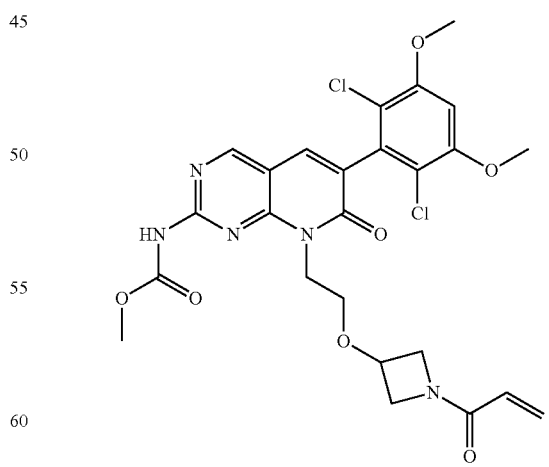

Step 1

To a solution of tert-butyl 3-[2-[2-amino-6-(2,6-dichloro-3,5-dimethoxyphenyl)-7-oxo-7H,8H-pyrido[2,3-d]pyrimidin-8-yl]ethoxy]azetidine-1-carboxylate (180 mg, 0.32 mmol) in THF (20 mL) was added dimethyl carbonate (287 mg, 3.19 mmol) and tBuOK (357 mg, 3.19 mmol). The resulting solution was stirred for 2 hr at room temperature and then it was diluted with DCM and washed with sat. NaCl. The organic layer was dried over $Na_2SO_4$ and concentrated to afford 170 mg (86%) of tert-butyl 3-[2-[6-(2,6-dichloro-3,5-dimethoxyphenyl)-2-[(methoxy-carbonyl)amino]-7-oxo-7H,8H-pyrido[2,3-d]pyrimidin-8-yl]ethoxy]azetidine-1-carboxylate as a yellow solid.

The title compound was prepared as described in Example 14, Steps 7 and 8. MS (ESI, pos. ion) m/z: 578.0 (M+1).

Example 89

Synthesis of 8-(2-((1-acryloyl-3-methylazetidin-3-yl)oxy)ethyl)-6-(2,6-dichloro-3,5-dimethoxyphenyl)-2-(methylamino)pyrido[2,3-d]pyrimidin-7(8H)-one

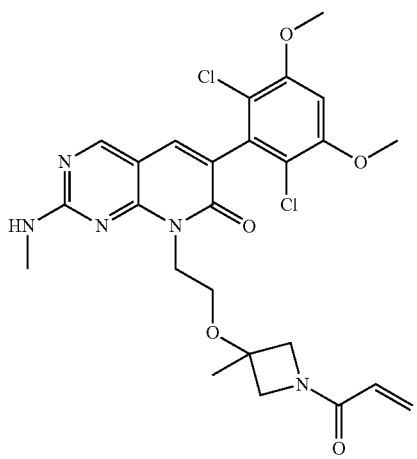 [SMILES: C=CC(=O)N1CC(C)(OCCn2c(=O)c(-c3c(Cl)c(OC)cc(OC)c3Cl)cc3cnc(NC)nc32)C1]

The title compound was prepared as described in Example 14 except tert-butyl 3-hydroxy-3-methylazetidine-1-carboxylate was used in Step 1. MS (ESI, pos. ion) m/z: 548.0 (M+1).

Example 90

Synthesis of (E)-8-(2-((1-(but-2-enoyl)azetidin-3-yl)oxy)ethyl)-6-(2,6-dichloro-3,5-dimethoxyphenyl)-2-(methylamino)pyrido[2,3-d]pyrimidin-7(8H)-one

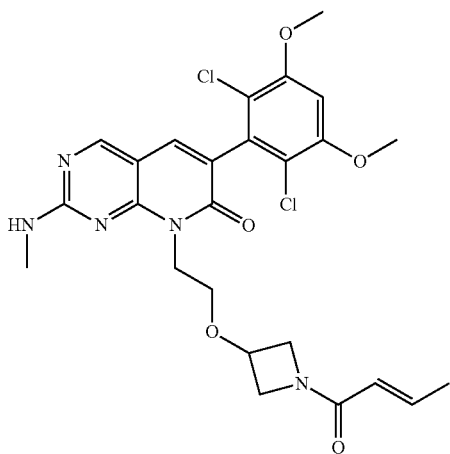 [SMILES: C/C=C/C(=O)N1CC(OCCn2c(=O)c(-c3c(Cl)c(OC)cc(OC)c3Cl)cc3cnc(NC)nc32)C1]

The title compound was prepared as described in Example 14 except (E)-but-2-enoyl chloride was used in Step 8. MS (ESI, pos. ion) m/z: 548.0 (M+1).

Example 91

Synthesis of 8-(2-((1-acryloylazetidin-3-yl)oxy)ethyl)-6-(2,6-dichloro-3,5-dimethoxyphenyl)-2-((3-(4-ethylpiperazin-1-yl)propyl)amino)pyrido[2,3-d]pyrimidin-7(8H)-one

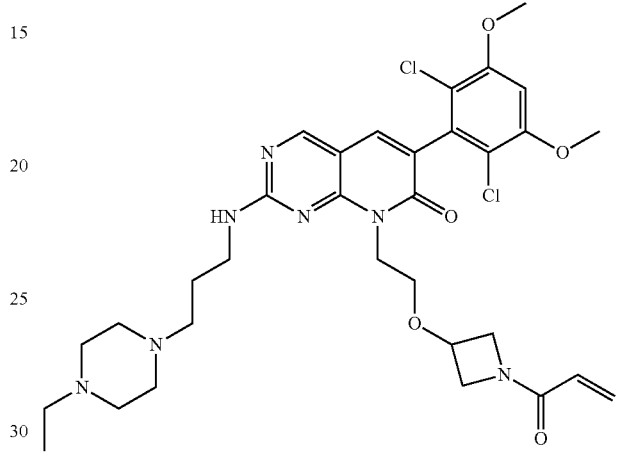

The title compound was prepared as described in Example 14 except 3-(4-ethylpiperazin-1-yl)propan-1-amine was used in Step 6. MS (ESI, pos. ion) m/z: 674.4 (M+1).

Example 92

Synthesis of 8-(2-((1-acryloylazetidin-3-yl)oxy)ethyl)-6-(2,6-dichloro-3,5-dimethoxyphenyl)-2-((2-(dimethylamino)ethyl)amino)pyrido[2,3-d]pyrimidin-7(8H)-one

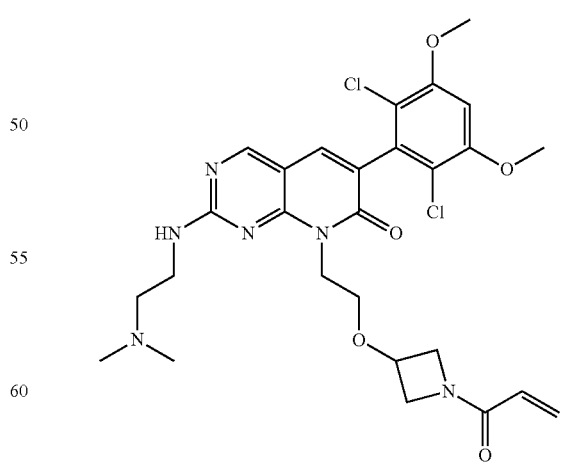

The title compound was prepared as described in Example 14 except $N^1,N^1$-dimethyl-ethane-1,2-diamine was used in Step 6. MS (ESI, pos. ion) m/z: 591.0 (M+1).

Example 93

Synthesis of 8-(2-((1-acryloylazetidin-3-yl)oxy)ethyl)-6-(2,6-dichloro-3,5-dimethoxyphenyl)-2-((2-(pyrrolidin-1-yl)ethyl)amino)pyrido[2,3-d]pyrimidin-7(8H)-one

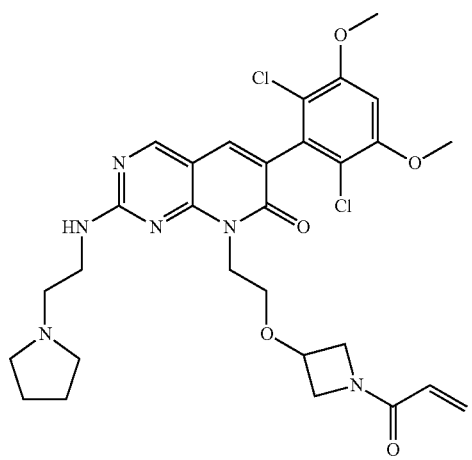 [SMILES: C=CC(=O)N1CC(OCCn2c(=O)c(-c3c(Cl)c(OC)cc(OC)c3Cl)cc3cnc(NCCN4CCCC4)nc32)C1]

The title compound was prepared as described in Example 14 except 2-(pyrrolidin-1-yl)-ethanamine was used in Step 6. MS (ESI, pos. ion) m/z: 591.0 (M+1).

Example 94

Synthesis of 8-(2-((1-acryloylazetidin-3-yl)oxy)ethyl)-6-(2,6-dichloro-3,5-dimethoxyphenyl)-2-((2-(4-ethylpiperazin-1-yl)ethyl)amino)pyrido[2,3-d]pyrimidin-7(8H)-one

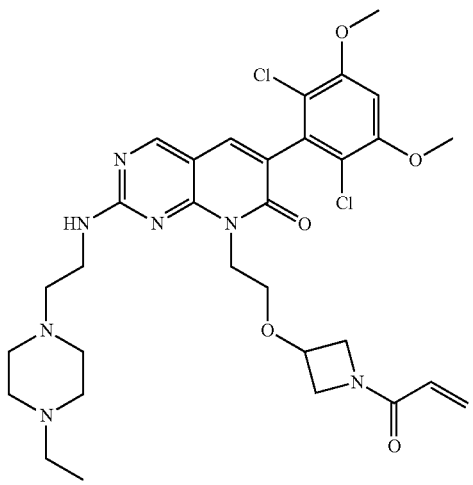 [SMILES: C=CC(=O)N1CC(OCCn2c(=O)c(-c3c(Cl)c(OC)cc(OC)c3Cl)cc3cnc(NCCN4CCN(CC)CC4)nc32)C1]

The title compound was prepared as described in Example 14 except 2-(4-ethylpiperazin-1-yl)ethanamine was used in Step 6. MS (ESI, pos. ion) m/z: 660.3 (M+1).

Example 95

Synthesis of 8-(2-((1-acryloylazetidin-3-yl)oxy)ethyl)-6-(2,6-dichloro-3,5-dimethoxyphenyl)-2-(((1-ethylpiperidin-4-yl)methyl)amino)pyrido[2,3-d]pyrimidin-7(8H)-one

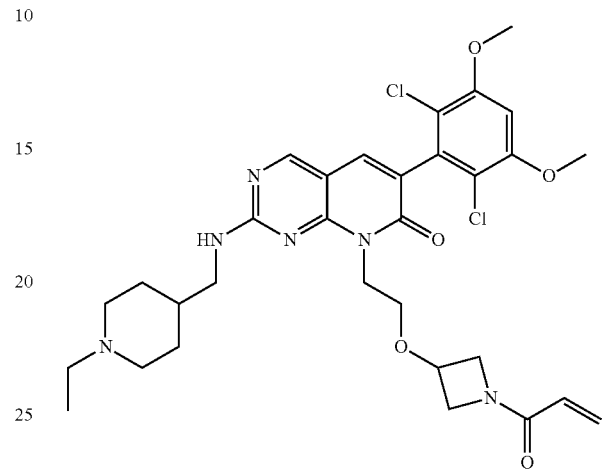

The title compound was prepared as described in Example 14 except (1-ethylpiperidin-4-yl)methanamine was used in Step 6. MS (ESI, pos. ion) m/z: 645.2 (M+1).

Example 96

Synthesis of 8-(2-((1-acryloylazetidin-3-yl)oxy)ethyl)-6-(2,6-dichloro-3,5-dimethoxyphenyl)-2-((3-morpholinopropyl)amino)pyrido[2,3-d]pyrimidin-7(8H)-one

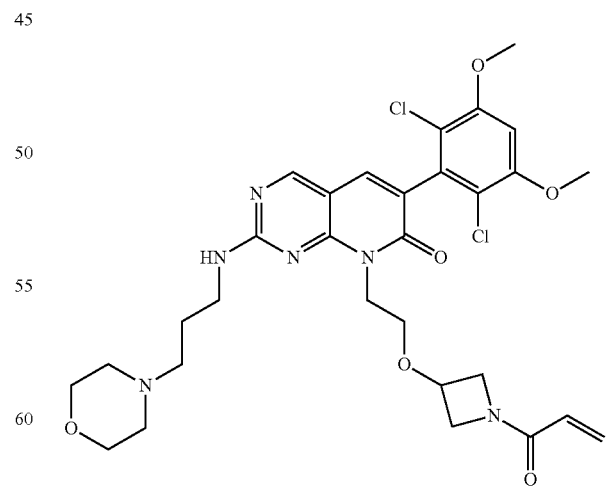

The title compound was prepared as described in Example 14 except 3-morpholinopropan-1-amine was used in Step 6. MS (ESI, pos. ion) m/z: 647.3 (M+1).

Example 97

Synthesis of 8-(2-((1-acryloylazetidin-3-yl)oxy)ethyl)-6-(2,6-dichloro-3,5-dimethoxyphenyl)-2-((3-(4-methylpiperazin-1-yl)propyl)amino)pyrido[2,3-d]pyrimidin-7(8H)-one

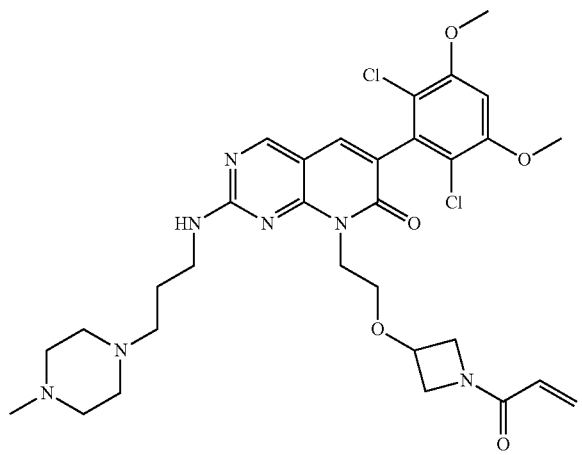 [SMILES: C=CC(=O)N1CC(OCCn2c(=O)c(-c3c(Cl)c(OC)cc(OC)c3Cl)cc3cnc(NCCCN4CCN(C)CC4)nc32)C1]

The title compound was prepared as described in Example 14 except 3-(4-methyl-piperazin-1-yl)propan-1-amine was used in Step 6. MS (ESI, pos. ion) m/z: 674.4 (M+1).

Example 98

Synthesis of 8-(2-((1-acryloylazetidin-3-yl)oxy)ethyl)-6-(2,6-dichloro-3,5-dimethoxyphenyl)-2-((1-methylpiperidin-4-yl)amino)pyrido[2,3-d]pyrimidin-7(8H)-one

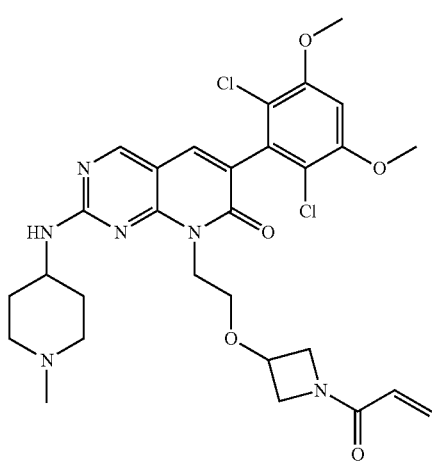 [SMILES: C=CC(=O)N1CC(OCCn2c(=O)c(-c3c(Cl)c(OC)cc(OC)c3Cl)cc3cnc(NC4CCN(C)CC4)nc32)C1]

The title compound was prepared as described in Example 14 except 1-methylpiperidin-4-amine was used in Step 6. MS (ESI, pos. ion) m/z: 617.1 (M+1).

Example 99

Synthesis of 8-(2-((1-acryloylazetidin-3-yl)oxy)ethyl)-6-(2,6-dichloro-3,5-dimethoxyphenyl)-2-((3-(pyrrolidin-1-yl)propyl)amino)pyrido[2,3-d]pyrimidin-7(8H)-one

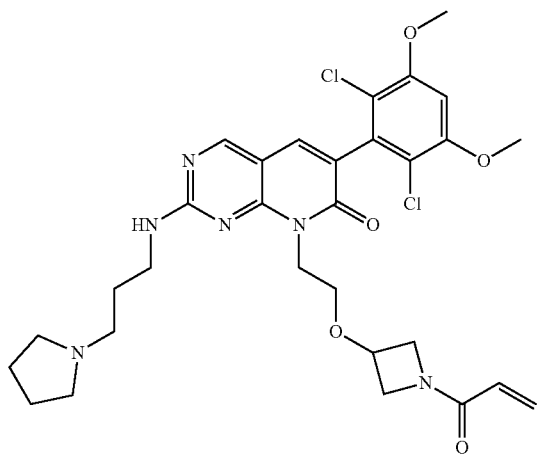 [SMILES: C=CC(=O)N1CC(OCCn2c(=O)c(-c3c(Cl)c(OC)cc(OC)c3Cl)cc3cnc(NCCCN4CCCC4)nc32)C1]

The title compound was prepared as described in Example 14 except 3-(pyrrolidin-1-yl)-propan-1-amine was used in Step 6. MS (ESI, pos. ion) m/z: 631.1 (M+1).

Example 100

Synthesis of 8-(2-((1-acryloylazetidin-3-yl)oxy)ethyl)-6-(2,6-dichloro-3,5-dimethoxyphenyl)-2-((2-(diethylamino)ethyl)amino)pyrido[2,3-d]pyrimidin-7(8H)-one

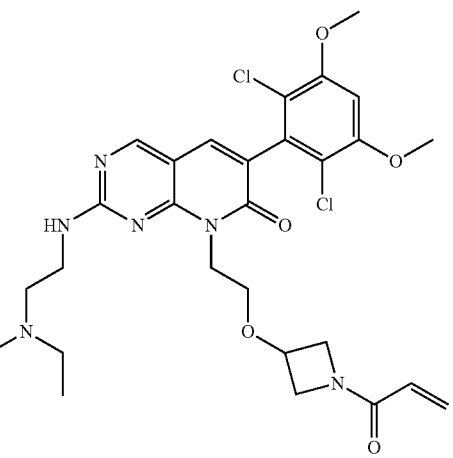

The title compound was prepared as described in Example 14 except $N^1,N^1$-diethylethane-1,2-diamine was used in Step 6. MS (ESI, pos. ion) m/z: 619.0 (M+1).

Example 101

Synthesis of 8-(2-((1-acryloylazetidin-3-yl)oxy)ethyl)-6-(2,6-dichloro-3,5-dimethoxyphenyl)-2-((3-(diethylamino)propyl)amino)pyrido[2,3-d]pyrimidin-7(8H)-one

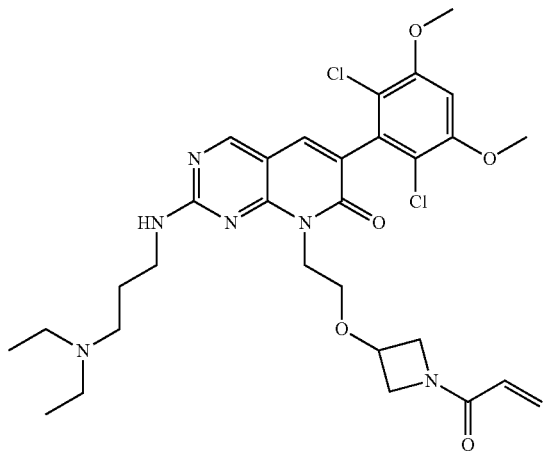 [SMILES: C=CC(=O)N1CC(OCCn2c(=O)c(-c3c(Cl)c(OC)cc(OC)c3Cl)cc3cnc(NCCCN(CC)CC)nc32)C1]

The title compound was prepared as described in Example 14 except $N^1,N^1$-diethyl-propane-1,3-diamine was used in Step 6. MS (ESI, pos. ion) m/z: 633.0 (M+1).

Example 102

Synthesis of 8-(2-((1-acryloylazetidin-3-yl)oxy)ethyl)-6-(2,6-dichloro-3,5-dimethoxyphenyl)-2-((2-(2-methoxyethoxy)ethyl)amino)pyrido[2,3-d]pyrimidin-7(8H)-one

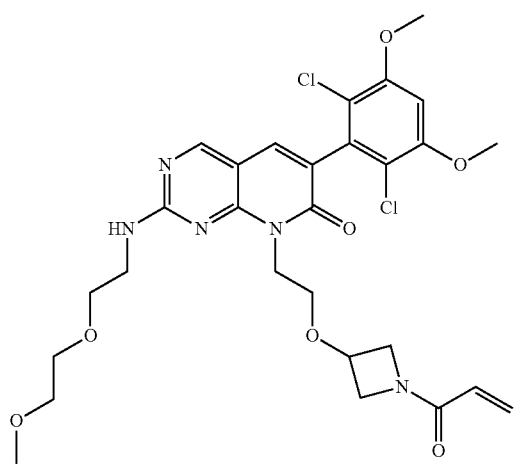 [SMILES: C=CC(=O)N1CC(OCCn2c(=O)c(-c3c(Cl)c(OC)cc(OC)c3Cl)cc3cnc(NCCOCCOC)nc32)C1]

The title compound was prepared as described in Example 14 except 2-(2-methoxyethoxy)ethanamine was used in Step 6. MS (ESI, pos. ion) m/z: 622.1 (M+1).

Example 103

Synthesis of 8-(2-((1-acryloylazetidin-3-yl)oxy)ethyl)-6-(2,6-dichloro-3,5-dimethoxyphenyl)-2-((4-(diethylamino)butyl)amino)pyrido[2,3-d]pyrimidin-7(8H)-one

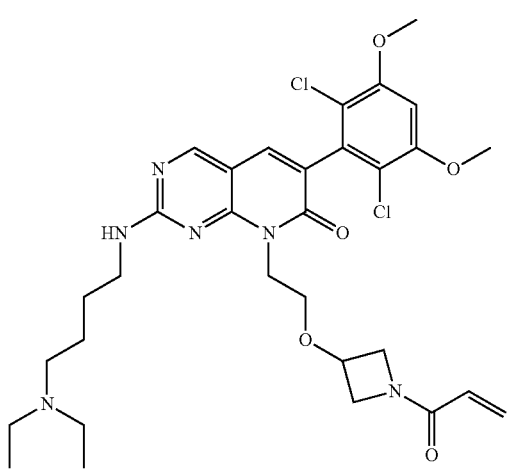 [SMILES: C=CC(=O)N1CC(OCCn2c(=O)c(-c3c(Cl)c(OC)cc(OC)c3Cl)cc3cnc(NCCCCN(CC)CC)nc32)C1]

The title compound was prepared as described in Example 14 except $N^1,N^1$-diethylbutane-1,4-diamine was used in Step 6. MS (ESI, pos. ion) m/z: 647.2 (M+1).

Example 104

Synthesis of 8-(2-((1-acryloylazetidin-3-yl)oxy)ethyl)-6-(2,6-dichloro-3,5-dimethoxyphenyl)-2-((3-(dimethylamino)propyl)amino)pyrido[2,3-d]pyrimidin-7(8H)-one

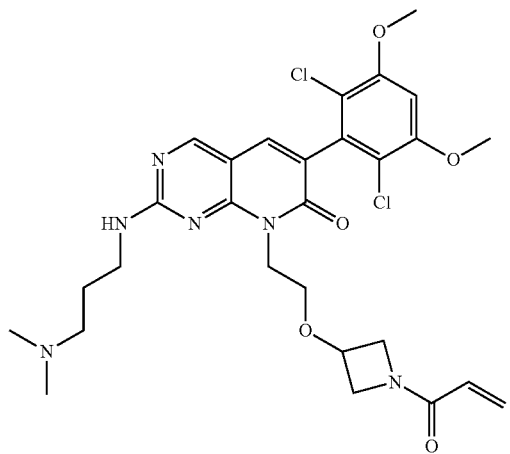 [SMILES: C=CC(=O)N1CC(OCCn2c(=O)c(-c3c(Cl)c(OC)cc(OC)c3Cl)cc3cnc(NCCCN(C)C)nc32)C1]

The title compound was prepared as described in Example 14 except N',N'-dimethyl-propane-1,3-diamine was used in Step 6. MS (ESI, pos. ion) m/z: 605.2 (M+1).

Example 105

Synthesis of 8-(2-((1-acryloylazetidin-3-yl)oxy)ethyl)-6-(2,6-dichloro-3,5-dimethoxyphenyl)-2-(((1-methylpiperidin-4-yl)methyl)amino)pyrido[2,3-d]pyrimidin-7(8H)-one

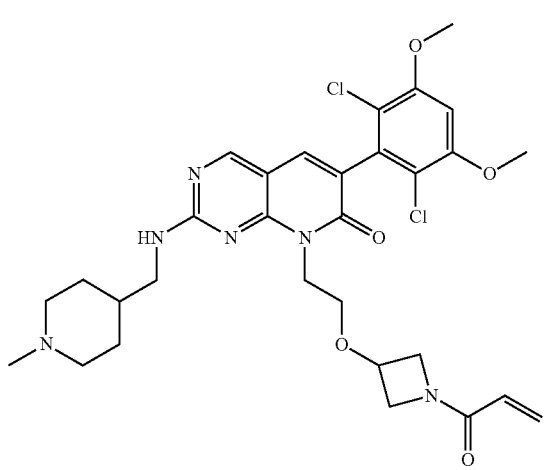 [SMILES: C=CC(=O)N1CC(OCCn2c(=O)c(-c3c(Cl)c(OC)cc(OC)c3Cl)cc3cnc(NCC4CCN(C)CC4)nc32)C1]

The title compound was prepared as described in Example 14 except (1-methylpiperidin-4-yl)methanamine was used in Step 6. MS (ESI, pos. ion) m/z: 631.2 (M+1).

Example 106

Synthesis of 8-(2-((1-acryloylazetidin-3-yl)oxy)ethyl)-2-amino-6-(2-chloro-3,5-dimethoxy-phenyl)pyrido[2,3-d]pyrimidin-7(8H)-one

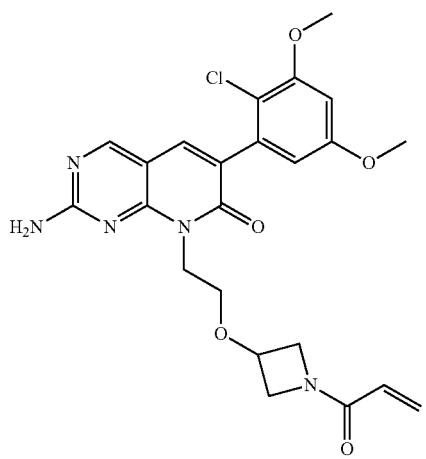 [SMILES: C=CC(=O)N1CC(OCCn2c(=O)c(-c3cc(OC)cc(OC)c3Cl)cc3cnc(N)nc32)C1]

The title compound was prepared as described in Example 14 except 6-(2-chloro-3,5-dimethoxyphenyl)-2-(methylthio)pyrido[2,3-d]pyrimidin-7(8H)-one was used in Step 4 and ammonia was used in Step 6. MS (ESI, pos. ion) m/z: 486.2 (M+1).

Example 107

Synthesis of 8-(2-((1-acryloylazetidin-3-yl)oxy)-2-methylpropyl)-6-(2-chloro-3,5-dimethoxy-phenyl)-2-(methylamino)pyrido[2,3-d]pyrimidin-7(8H)-one

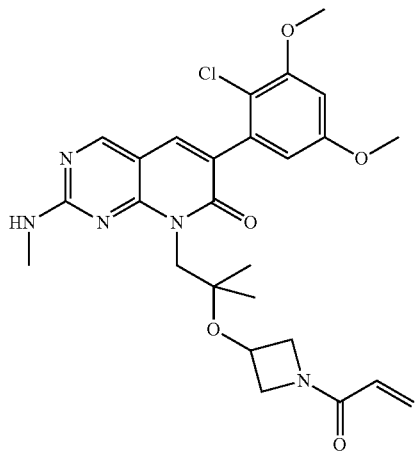 [SMILES: C=CC(=O)N1CC(OC(C)(C)Cn2c(=O)c(-c3cc(OC)cc(OC)c3Cl)cc3cnc(NC)nc32)C1]

The title compound was prepared as described in Example 14 except methyl 2-bromo-2-methylpropanoate (commercial) was used in Step 1 and 6-(2-chloro-3,5-dimethoxyphenyl)-2-(methylthio)pyrido[2,3-d]pyrimidin-7(8H)-one was used in Step 4. MS (ESI, pos. ion) m/z: 528.2 (M+1).

Example 108

Synthesis of 8-(2-((1-acryloylazetidin-3-yl)oxy)-2-methylpropyl)-6-(2,6-dichloro-3,5-dimethoxyphenyl)-2-(methylamino)pyrido[2,3-d]pyrimidin-7(8H)-one

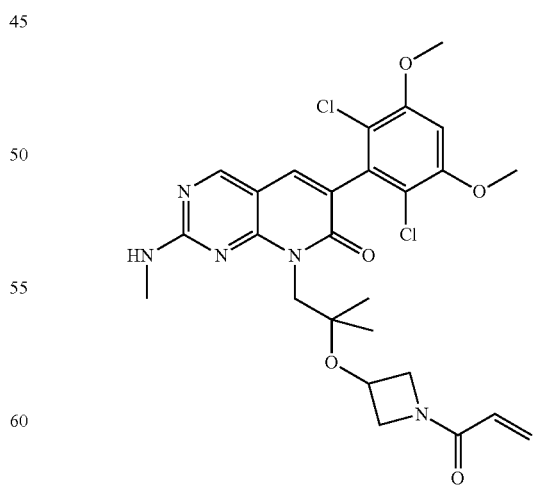

The title compound was prepared as described in Example 14 except methyl 2-bromo-2-methylpropanoate was used in Step 1. MS (ESI, pos. ion) m/z: 562.1 (M+1).

Example 109

Synthesis of 8-(2-((1-acryloylazetidin-3-yl)oxy)ethyl)-6-(2,6-dichloro-3,5-dimethoxyphenyl)-2-(((1r,4r)-4-hydroxycyclohexyl)amino)pyrido[2,3-d]pyrimidin-7(8H)-one

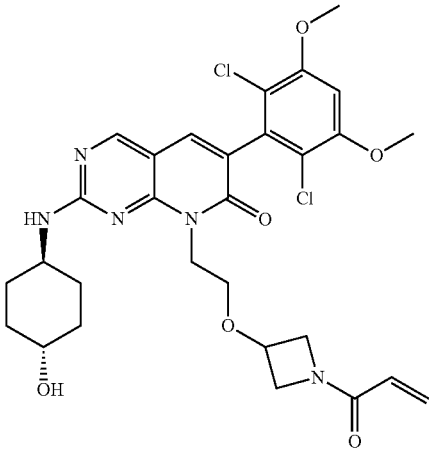 [SMILES: C=CC(=O)N1CC(OCCn2c(=O)c(-c3c(Cl)c(OC)cc(OC)c3Cl)cc3cnc(N[C@H]4CC[C@H](O)CC4)nc32)C1]

The title compound was prepared as described in Example 14 except (1r,4r)-4-aminocyclohexanol was used in Step 6. MS (ESI, pos. ion) m/z: 618.1 (M+1).

Example 110

Synthesis of 8-(2-((1-acryloylazetidin-3-yl)(methyl)amino)ethyl)-6-(2,6-dichloro-3,5-dimethoxyphenyl)-2-(ethylamino)pyrido[2,3-d]pyrimidin-7(8H)-one

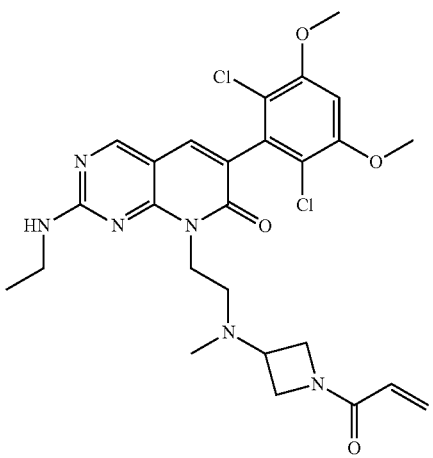

The title compound was prepared as described in Example 80 except ethanamine was used in Step 8. MS (ESI, pos. ion) m/z: 560.8 (M+1).

Example 111

Synthesis of 8-(2-((1-acryloylazetidin-3-yl)(ethyl)amino)ethyl)-6-(2,6-dichloro-3,5-dimethoxyphenyl)-2-(methylamino)pyrido[2,3-d]pyrimidin-7(8H)-one

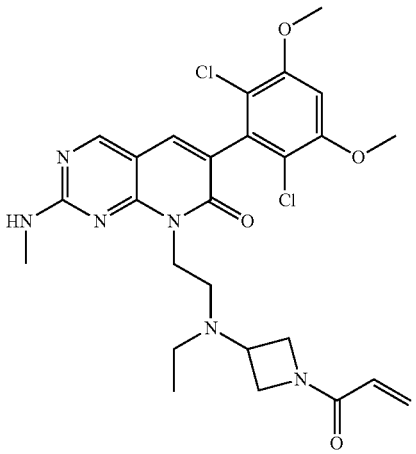

The title compound was prepared as described in Example 80 except 2-(ethylamino)-ethanol was used in Step 3. MS (ESI, pos. ion) m/z: 561.1 (M+1).

Example 112

Synthesis of (R)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one

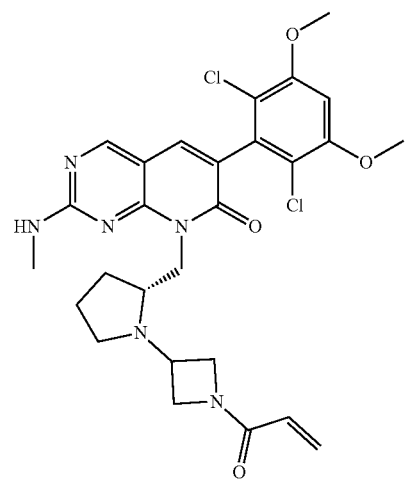 [SMILES: C=CC(=O)N1CC(N2CCC[C@@H]2Cn2c(=O)c(-c3c(Cl)c(OC)cc(OC)c3Cl)cc3cnc(NC)nc32)C1]

The title compound was prepared as described in Example 80 except (R)-pyrrolidin-2-ylmethanol used in Step 3. MS (ESI, pos. ion) m/z: 573.2 (M+1).

Example 113

Synthesis of (S)-8-((1-(1-acryloylazetidin-3-yl)pyrrolidin-2-yl)methyl)-6-(2,6-dichloro-3,5-dimethoxyphenyl)-2-(methylamino)pyrido[2,3-d]pyrimidin-7(8H)-one

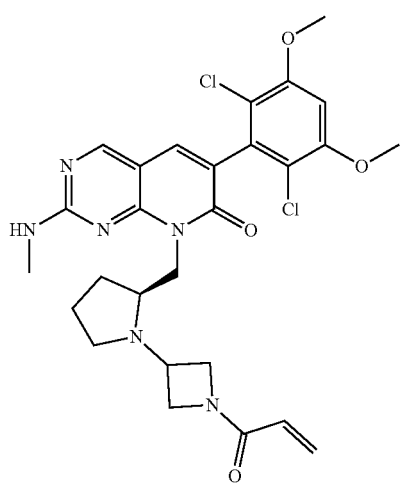 [SMILES: C=CC(=O)N1CC(N2CCC[C@H]2Cn2c(=O)c(-c3c(Cl)c(OC)cc(OC)c3Cl)cc3cnc(NC)nc32)C1]

The title compound was prepared as described in Example 80 except (S)-pyrrolidin-2-ylmethanol was used in Step 3. MS (ESI, pos. ion) m/z: 573.2 (M+1).

Example 114

Synthesis of 8-(2-((1-acryloylazetidin-3-yl)(methyl)amino)ethyl)-2-amino-6-(2,6-dichloro-3,5-dimethoxyphenyl)pyrido[2,3-d]pyrimidin-7(8H)-one

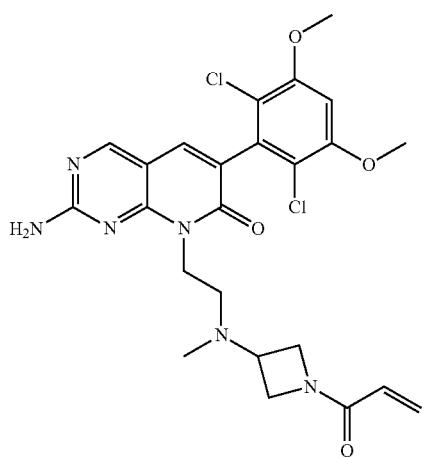 [SMILES: C=CC(=O)N1CC(N(C)CCn2c(=O)c(-c3c(Cl)c(OC)cc(OC)c3Cl)cc3cnc(N)nc32)C1]

The title compound was prepared as described in Example 80 except ammonia was used in Step 8. MS (ESI, pos. ion) m/z: 533.4 (M+1).

Example 115

Synthesis of (E)-8-(2-((1-(but-2-enoyl)azetidin-3-yl)(methyl)amino)ethyl)-6-(2,6-dichloro-3,5-dimethoxyphenyl)-2-(methylamino)pyrido[2,3-d]pyrimidin-7(8H)-one

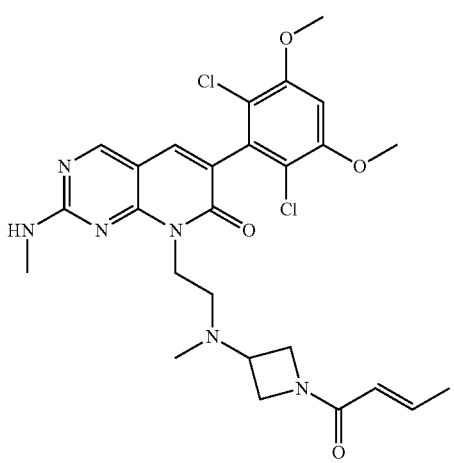 [SMILES: C/C=C/C(=O)N1CC(N(C)CCn2c(=O)c(-c3c(Cl)c(OC)cc(OC)c3Cl)cc3cnc(NC)nc32)C1]

The title compound was prepared as described in Example 80 except (E)-but-2-enoyl chloride was used in Step 11. MS (ESI, pos. ion) m/z: 561.1 (M+1).

Example 116

Synthesis of (R)-8-(2-((1-acryloylazetidin-3-yl)(methyl)amino)ethyl)-6-(2,6-dichloro-3,5-dimethoxyphenyl)-2-((1-methoxypropan-2-yl)amino)pyrido[2,3-d]pyrimidin-7(8H)-one

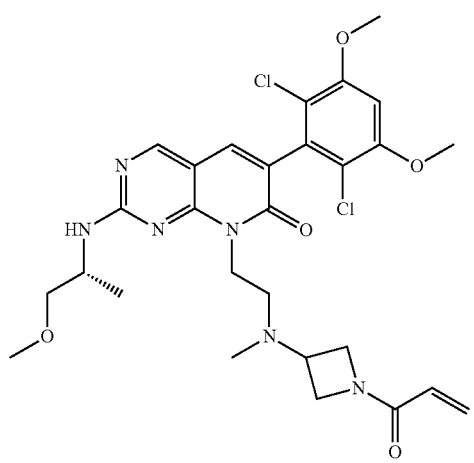 [SMILES: C=CC(=O)N1CC(N(C)CCn2c(=O)c(-c3c(Cl)c(OC)cc(OC)c3Cl)cc3cnc(N[C@H](C)COC)nc32)C1]

The title compound was prepared as described in Example 80 except (R)-1-methoxy-propan-2-amine was used in Step 8. MS (ESI, pos. ion) m/z: 605.5 (M+1).

Example 117

Synthesis of 8-(2-((1-acryloylazetidin-3-yl)amino) ethyl)-6-(2,6-dichloro-3,5-dimethoxyphenyl)-2-(methylamino)pyrido[2,3-d]pyrimidin-7(8H)-one

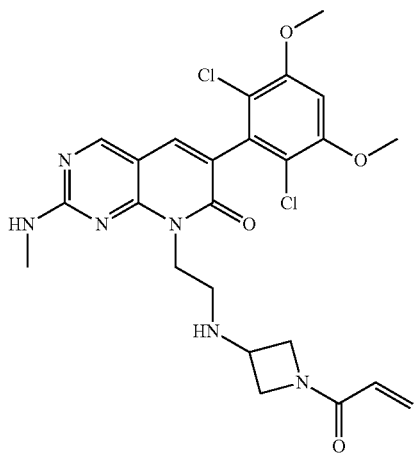

Step 1

To a solution of tert-butyl N-(2-hydroxyethyl)carbamate (2 g, 12.41 mmol) in DCM (100 mL) was added TEA (3.7 g, 36.56 mmol) and MsCl (2.1 g, 18.42 mmol). The resulting solution was stirred for 3 h at room temperature and water was added. The resulting solution was extracted with DCM and the organic layer was washed with sat. NaCl. The mixture was dried over $Na_2SO_4$ and concentrated to afford 2.5 g (84%) of tert-butyl N-[2-(methanesulfonyloxy)ethyl]carbamate as a colorless oil.

Step 2

To a solution of 6-(2,6-dichloro-3,5-dimethoxyphenyl)-2-(methylsulfanyl)-7H,8H-pyrido[2,3-d]pyrimidin-7-one (800 mg, 2.01 mmol) in DMF (80 mL) was added tert-butyl N-[2-(methanesulfonyloxy)ethyl]carbamate (720 mg, 3.01 mmol) and $K_2CO_3$ (832 mg, 6.02 mmol). The resulting mixture was stirred overnight at 70° C. and then quenched with water. The resulting solution was extracted with EtOAc and the organic layer was washed with sat. NaCl. The mixture was dried over $Na_2SO_4$ and concentrated to afford 1 g (92%) of tert-butyl N-[2-[6-(2,6-dichloro-3,5-dimethoxyphenyl)-2-(methylsulfanyl)-7-oxo-7H,8H-pyrido[2,3-d]pyrimidin-8-yl]ethyl]-carbamate as a yellow solid.

Step 3

To a solution of tert-butyl N-[2-[6-(2,6-dichloro-3,5-dimethoxyphenyl)-2-(methyl-sulfanyl)-7-oxo-7H,8H-pyrido[2,3-d]pyrimidin-8-yl]ethyl]carbamate (1 g, 1.85 mmol) in DCM (10 mL) was added TFA (5 mL). The resulting solution was stirred for 2 h at room temperature and then concentrated. The residue was diluted with water and the pH was adjusted to 7 with aq. $NaHCO_3$. The resulting solution was extracted with DCM and the organic layer was dried over $Na_2SO_4$ and concentrated. The residue was purified by chromatography (DCM/MeOH (100:1)) to afford 0.8 g (98%) of 8-(2-aminoethyl)-6-(2,6-dichloro-3,5-dimethoxyphenyl)-2-(methylsulfanyl)-7H,8H-pyrido[2,3-d]pyrimidin-7-one as a yellow solid.

Step 4

To a solution of 8-(2-aminoethyl)-6-(2,6-dichloro-3,5-dimethoxyphenyl)-2-(methyl-sulfanyl)-7H,8H-pyrido[2,3-d]pyrimidin-7-one (800 mg, 1.81 mmol) in DCM (50 mL) was added tert-butyl 3-oxoazetidine-1-carboxylate (500 mg, 2.92 mmol). The reaction mixture was stirred for overnight at 0° C. and then $NaBH_3CN$ (200 mg, 3.18 mmol) was added. The resulting solution was stirred for 5 h at room temperature and then the reaction was quenched with water. The resulting solution was extracted with DCM and the organic layer was dried over $Na_2SO_4$ and concentrated. The residue was purified by chromatography (EtOAc/pet. ether (1:1)) to afford 400 mg (37%) of tert-butyl 3-([2-[6-(2,6-dichloro-3,5-dimethoxyphenyl)-2-(methyl-sulfanyl)-7-oxo-7H,8H-pyrido[2,3-d]pyrimidin-8-yl]ethyl]amino)azetidine-1-carboxylate as a yellow solid.

Step 5

To a solution of tert-butyl 3-([2-[6-(2,6-dichloro-3,5-dimethoxyphenyl)-2-(methyl-sulfanyl)-7-oxo-7H,8H-pyrido[2,3-d]pyrimidin-8-yl]ethyl]amino)azetidine-1-carboxylate (300 mg, 0.50 mmol) in DCM (50 mL) at 0° C. was added TEA (152 mg, 1.50 mmol), 4-DMAP (10 mg, cat) and then TFAA (149 mg, 0.75 mmol) dropwise. The resulting solution was stirred for 2 h at room temperature and then water was added. The resulting solution was extracted with DCM and the organic layer was washed with sat. NaCl. The mixture was dried over $Na_2SO_4$ and concentrated to provide 280 mg (80%) of tert-butyl 3-(N-[2-[6-(2,6-dichloro-3,5-dimethoxy-phenyl)-2-(methylsulfanyl)-7-oxo-7H,8H-pyrido[2,3-d]pyrimidin-8-yl]ethyl]-2,2,2-trifluoro-acetamido)azetidine-1-carboxylate as a yellow solid.

Step 6

To a solution of tert-butyl 3-(N-[2-[6-(2,6-dichloro-3,5-dimethoxyphenyl)-2-(methyl-sulfanyl)-7-oxo-7H,8H-pyrido[2,3-d]pyrimidin-8-yl]ethyl]-2,2,2-trifluoro-acetamido)azetidine-1-carboxylate (280 mg, 0.40 mmol) in DCM (50 mL) was added m-CPBA (208 mg, 1.21 mmol). The resulting solution was stirred for 2 h at room temperature and then water was added. The resulting solution was extracted with DCM and the organic layer was washed with sat. $NaHCO_3$. The mixture was dried over $Na_2SO_4$ and concentrated to afford 300 mg (crude) of tert-butyl 3-(N-[2-[6-(2,6-dichloro-3,5-dimethoxyphenyl)-2-methanesulfonyl-7-oxo-7H,8H-pyrido[2,3-d]pyrimidin-8-yl]ethyl]-2,2,2-trifluoroacetamido)azetidine-1-carboxylate as a yellow solid.

Step 7

A solution of tert-butyl 3-(N-[2-[6-(2,6-dichloro-3,5-dimethoxyphenyl)-2-methane-sulfonyl-7-oxo-7H,8H-pyrido[2,3-d]pyrimidin-8-yl]ethyl]-2,2,2-trifluoroacetamido)azetidine-1-carboxylate (300 mg, 0.41 mmol) and $MeNH_2$ (0.4 mL, 2M in THF) was stirred for 2 h at 50° C. The reaction solution was then concentrated and the residue was purified by chromatography (DCM/MeOH (80:1)) to afford 200 mg (72%) of tert-butyl 3-(N-[2-[6-(2,6-dichloro-3,5-dimethoxyphenyl)-2-(methylamino)-7-oxo-7H,8H-pyrido[2,3-d]pyrimidin-8-yl]ethyl]-2,2,2-trifluoroacetamido)azetidine-1-carboxylate as a yellow solid.

Step 8

To a solution of tert-butyl 3-(N-[2-[6-(2,6-dichloro-3,5-dimethoxyphenyl)-2-(methyl-amino)-7-oxo-7H,8H-pyrido[2,3-d]pyrimidin-8-yl]ethyl]-2,2,2-trifluoroacetamido)-azetidine-1-carboxylate (200 mg, 0.30 mmol) in DCM (4 mL) was added TFA (2 mL). The resulting solution was stirred for 2 h at room temperature and then concentrated. The residue was diluted with water and the pH was adjusted to 7 with aq. $NaHCO_3$. The resulting solution was extracted with DCM and the organic layer was concentrated to afford 180 mg (crude) of N-(azetidin-3-yl)-N-[2-[6-(2,6-dichloro- 3,5-dimethoxyphenyl)-2-(methylamino)-7-oxo-7H,8H-pyrido[2,3-d]pyrimidin-8-yl]-ethyl]-2,2,2-trifluoroacetamide as a brown solid.

Step 9

To a solution of N-(azetidin-3-yl)-N-[2-[6-(2,6-dichloro-3,5-dimethoxyphenyl)-2-(methylamino)-7-oxo-7H,8H-pyrido[2,3-d]pyrimidin-8-yl]ethyl]-2,2,2-trifluoroacetamide (180 mg, 0.31 mmol) in DCM/MeOH (20/20 mL) was added TEA (47 mg, 0.46 mmol) and prop-2-enoyl chloride (34 mg, 0.38 mmol). The resulting solution was stirred for 3 h at room temperature and then concentrated. The residue was purified by chromatography (DCM/MeOH (50:1)) to afford 150 mg (74%) of N-[2-[7-chloro-6-(2,6-dichloro-3,5-dimethoxyphenyl)-2-(methylamino)-7H,8H-pyrido[2,3-d]pyrimidin-8-yl]ethyl]-2,2,2-trifluoro-N-[1-(prop-2-enoyl)azetidin-3-yl]acetamide as a yellow solid.

Step 10

To a solution of N-[2-[6-(2,6-dichloro-3,5-dimethoxyphenyl)-2-(methylamino)-7-oxo-7H,8H-pyrido[2,3-d]pyrimidin-8-yl]ethyl]-2,2,2-trifluoro-N-[1-(prop-2-enoyl)azetidin-3-yl]acetamide (150 mg, 0.24 mmol) in MeOH/$H_2$O (20/20 mL) was added 5% aq. $K_2CO_3$ (10 mL). The resulting solution was stirred for 3 h at room temperature and then extracted with DCM. The organic layer was dried over $Na_2SO_4$ and concentrated. The crude product (150 mg) was purified by Prep-HPLC to afford 36.5 mg (29%) of 6-(2,6-dichloro-3,5-dimethoxyphenyl)-2-(methyl-amino)-8-(2-[[1-(prop-2-enoyl)azetidin-3-yl]amino]ethyl)-7H,8H-pyrido[2,3-d]pyrimidin-7-one as a white solid. MS (ESI, pos. ion) m/z: 533.1 (M+1).

Example 118

Synthesis of (S)-8-(2-((1-acryloylazetidin-3-yl)(methyl)amino)ethyl)-6-(2,6-dichloro-3,5-dimethoxyphenyl)-2-((1-methoxypropan-2-yl)amino)pyrido[2,3-d]pyrimidin-7(8H)-one

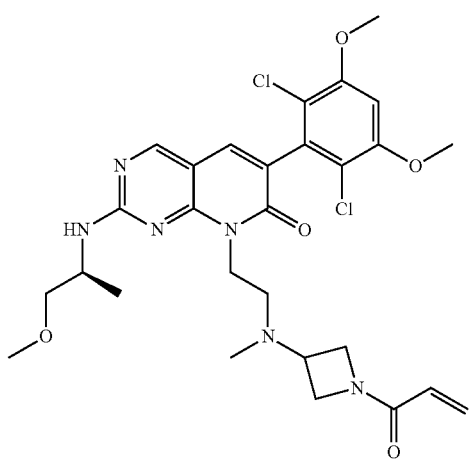 [SMILES: C=CC(=O)N1CC(N(C)CCn2c(=O)c(-c3c(Cl)c(OC)cc(OC)c3Cl)cc3cnc(N[C@@H](C)COC)nc32)C1]

The title compound was prepared as described in Example 80 except (S)-1-methoxy-propan-2-amine was used in Step 8. MS (ESI, pos. ion) m/z: 605.1 (M+1).

Example 119

Synthesis of 8-(2-((1-acryloylazetidin-3-yl)(methyl)amino)ethyl)-6-(2,6-dichloro-3,5-dimethoxy-phenyl)-2-((2-morpholinoethyl)amino)pyrido[2,3-d]pyrimidin-7(8H)-one

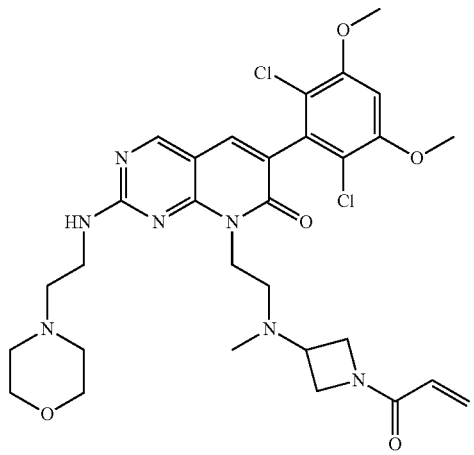 [SMILES: C=CC(=O)N1CC(N(C)CCn2c(=O)c(-c3c(Cl)c(OC)cc(OC)c3Cl)cc3cnc(NCCN4CCOCC4)nc32)C1]

The title compound was prepared as described in Example 80 except 2-morpholinoethanamine was used in Step 8. MS (ESI, pos. ion) m/z: 605.1 (M+1).

Example 120

Synthesis of 8-(2-((1-acryloylazetidin-3-yl)(2-methoxyethyl)amino)ethyl)-6-(2,6-dichloro-3,5-dimethoxyphenyl)-2-(methylamino)pyrido[2,3-d]pyrimidin-7(8H)-one

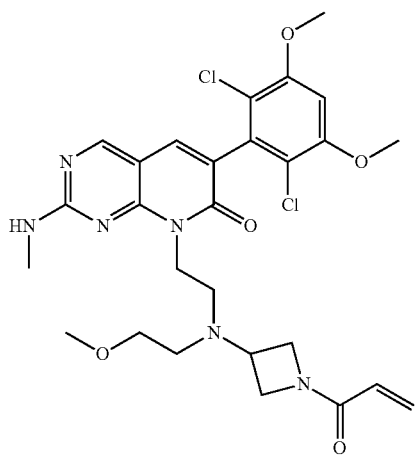 [SMILES: C=CC(=O)N1CC(N(CCOC)CCn2c(=O)c(-c3c(Cl)c(OC)cc(OC)c3Cl)cc3cnc(NC)nc32)C1]

Step 1

A mixture of 2-methoxyethan-1-amine (880 mg, 11.72 mmol), tert-butyl 3-oxoazetidine-1-carboxylate (2 g, 11.68 mmol), AcOH (0.2 mL), Palladium on carbon (2 g) and MeOH (50 mL) was placed under an atmosphere of $H_2$. The resulting solution was stirred overnight at room temperature and then solids were filtered. The filtrate was concentrated and the residue was purified by chromatography (EtOAc/pet. ether (1:1)) to afford 1.29 g (48%) of tert-butyl 3-[(2-methoxyethyl)amino]azetidine-1-carboxylate as a yellow oil.

Step 2

A mixture of tert-butyl 3-[(2-methoxyethyl)amino]azetidine-1-carboxylate (1.19 g, 5.17 mmol), 2-bromoethan-1-ol (770 mg, 6.16 mmol), Na₂CO₃ (660 mg, 6.23 mmol) and MeCN (50 mL) was stirred overnight at 65° C. The reaction mixture was cooled and the solids were filtered. The resulting filtrate was concentrated and the residue was purified by chromatography (DCM/MeOH (5:1)) to afford 1.1 g (78%) of tert-butyl 3-[(2-hydroxyethyl)(2-methoxyethyl)-amino]azetidine-1-carboxylate as yellow oil.

The title compound was prepared as described in Example 80 starting from Step 5. MS (ESI, pos. ion) m/z: 591.2 (M+1).

Example 121

Synthesis of 8-(2-((1-acryloylazetidin-3-yl)(2-methoxyethyl)amino)ethyl)-6-(2,6-dichloro-3,5-dimethoxyphenyl)-2-(ethylamino)pyrido[2,3-d]pyrimidin-7(8H)-one

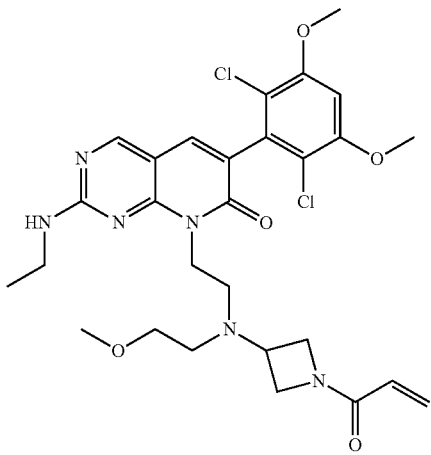 [SMILES: C=CC(=O)N1CC(N(CCOC)CCn2c(=O)c(-c3c(Cl)c(OC)cc(OC)c3Cl)cc3cnc(NCC)nc32)C1]

The title compound was prepared as described in Example 120 except ethanamine was used in Step 8. MS (ESI, pos. ion) m/z: 605.2 (M+1).

Example 122

Synthesis of 8-(2-((1-acryloylazetidin-3-yl)(isopropyl)amino)ethyl)-6-(2,6-dichloro-3,5-dimethoxyphenyl)-2-(methylamino)pyrido[2,3-d]pyrimidin-7(8H)-one

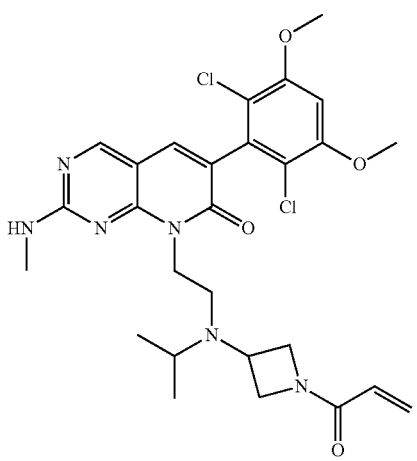 [SMILES: C=CC(=O)N1CC(N(CCn2c(=O)c(-c3c(Cl)c(OC)cc(OC)c3Cl)cc3cnc(NC)nc32)C(C)C)C1]

The title compound was prepared as described in Example 80 except 2-(isopropyl-amino)ethanol was used in Step 3. MS (ESI, pos. ion) m/z: 575.1 (M+1).

Example 123

Synthesis of (S)-8-(2-((1-acryloylazetidin-3-yl)(methyl)amino)propyl)-6-(2,6-dichloro-3,5-dimethoxyphenyl)-2-(methylamino)pyrido[2,3-d]pyrimidin-7(8H)-one

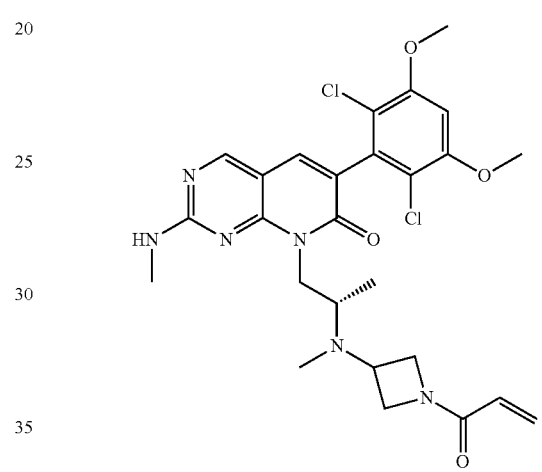

Step 1

A mixture of (2S)-2-(methylamino)propanoic acid (3.6 g, 34.91 mmol), NaBH₃CN (3 g, 47.62 mmol), tert-butyl 3-oxoazetidine-1-carboxylate (5 g, 29.21 mmol), MeOH (30 mL) and 4A M.S. (2 g) was stirred overnight at room temperature. The solids were filtered and the resulting filtrate was concentrated and the residue was purified by chromatography (DCM/EtOAc (10:1)) to afford 3.5 g (39%) of (2S)-2-([1-[(tert-butoxy)carbonyl]azetidin-3-yl](methyl)amino)propanoic acid as a colorless oil.

Step 2

A solution of (2S)-2-([1-[(tert-butoxy)carbonyl]azetidin-3-yl](methyl)amino)propanoic acid (1 g, 3.87 mmol), BH₃/THF (7 mL, 1.50 equiv) and THF (10 mL) was stirred for 8 h at room temperature. The reaction mixture was then quenched with water and the resulting solution was diluted with EtOAc. The organic layer was separated and then concentrated. The residue was purified by chromatography (DCM/EtOAc (5:1)) to afford 0.3 g (32%) of tert-butyl 3-[[(2S)-1-hydroxypropan-2-yl](methyl)amino]azetidine-1-carboxylate as a colorless oil.

The title compound was prepared as described in Example 80 starting from Step 5. MS (ESI, pos. ion) m/z: 561.1 (M+1).

Example 124

Synthesis of 8-(2-((1-acryloylazetidin-3-yl)(2-methoxyethyl)amino)ethyl)-2-amino-6-(2,6-dichloro-3,5-dimethoxyphenyl)pyrido[2,3-d]pyrimidin-7(8H)-one

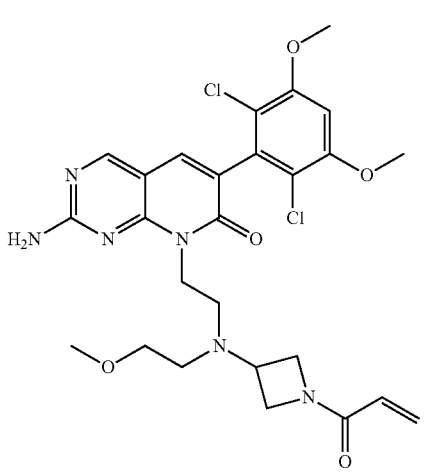 [SMILES: C=CC(=O)N1CC(N(CCOC)CCn2c(=O)c(-c3c(Cl)c(OC)cc(OC)c3Cl)cc3cnc(N)nc32)C1]

The title compound was prepared as described in Example 120 except ammonia was used in Step 8. MS (ESI, pos. ion) m/z: 577.1 (M+1).

Example 125

Synthesis of (R)-8-(2-((1-acryloylazetidin-3-yl)(methyl)amino)propyl)-6-(2,6-dichloro-3,5-dimethoxyphenyl)-2-(methylamino)pyrido[2,3-d]pyrimidin-7(8H)-one

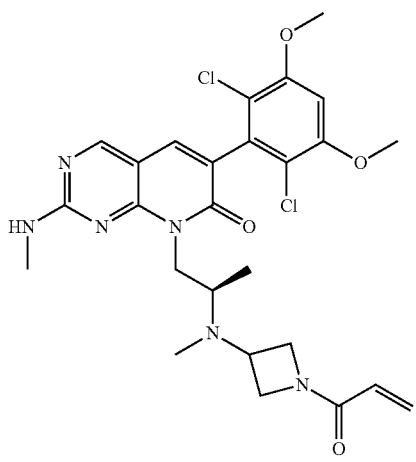 [SMILES: C=CC(=O)N1CC(N(C)[C@H](C)Cn2c(=O)c(-c3c(Cl)c(OC)cc(OC)c3Cl)cc3cnc(NC)nc32)C1]

The title compound was prepared as described in Example 123 except (R)-2-(methyl-amino)-propanoic acid was used in Step 1. MS (ESI, pos. ion) m/z: 563.1 (M+1).

Example 126

Synthesis of (S)-8-(2-((1-acryloylazetidin-3-yl)(methyl)amino)-3-methylbutyl)-6-(2,6-dichloro-3,5-dimethoxyphenyl)-2-(methylamino)pyrido[2,3-d]pyrimidin-7(8H)-one

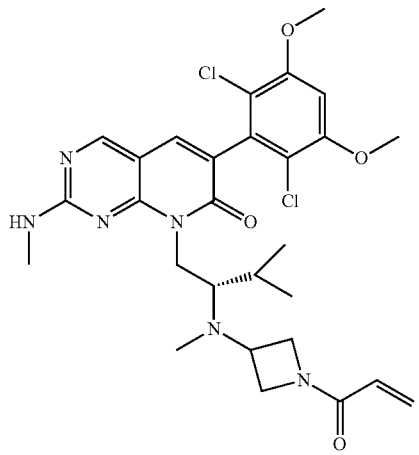 [SMILES: C=CC(=O)N1CC(N(C)[C@H](Cn2c(=O)c(-c3c(Cl)c(OC)cc(OC)c3Cl)cc3cnc(NC)nc32)C(C)C)C1]

The title compound was prepared as described in Example 125 except (S)-3-methyl-2-(methylamino)butanoic acid was used in Step 1. MS (ESI, pos. ion) m/z: 589.3 (M+1).

Example 127

Synthesis of 8-(2-((1-acryloylpiperidin-4-yl)(methyl)amino)ethyl)-6-(2,6-dichloro-3,5-dimethoxyphenyl)-2-(methylamino)pyrido[2,3-d]pyrimidin-7(8H)-one

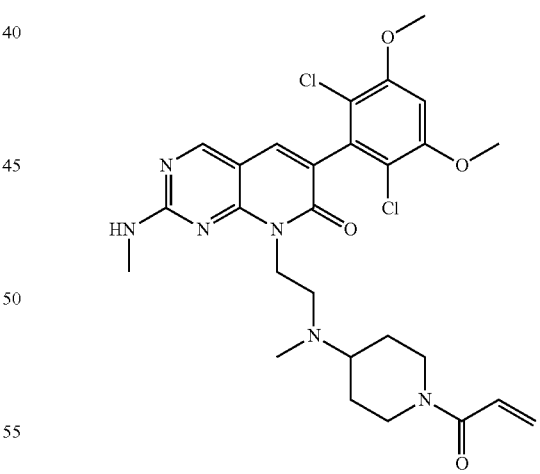

Step 1

A mixture of tert-butyl 4-(methylamino)piperidine-1-carboxylate (6 g, 28.00 mmol), $K_2CO_3$ (11.61 g, 84.00 mmol) and methyl 2-bromoacetate (4.69 g, 30.66 mmol) in acetone (100 mL) was stirred at 0° C. in a water/ice bath and then the resulting solution was stirred overnight at room temperature. The solids were filtered and the filtrate was concentrated. The residue was purified by chromatography (DCM/EtOAc (10:1)) to afford 7.4 g (92%) of tert-butyl 4-[(2-methoxy-2-oxoethyl)(methyl)amino]piperidine-1-carboxylate as a yellow oil.

Step 2

To a solution of tert-butyl 4-[(2-methoxy-2-oxoethyl)(methyl)amino]piperidine-1-carboxylate (5.94 g, 20.74 mmol) in THF (100 mL) at 0° C. was added LiAlH$_4$ (630 mg, 16.60 mmol). The resulting solution was stirred for 1 h at room temperature and then H$_2$O/NaOH (15%)/H$_2$O (0.6 ml/0.6 ml/1.8 ml) was added. The solids were filtered and the filtrate was concentrated to afford 4.64 g (87%) of tert-butyl 4-[(2-hydroxyethyl)(methyl)amino]-piperidine-1-carboxylate as a yellow oil.

The title compound was prepared as described in Example 80 starting from Step 5. MS (ESI, pos. ion) m/z: 575.2 (M+1).

Example 128

Synthesis of 8-(2-((1-acryloylpiperidin-4-yl)(methyl)amino)ethyl)-2-amino-6-(2,6-dichloro-3,5-dimethoxyphenyl)pyrido[2,3-d]pyrimidin-7(8H)-one

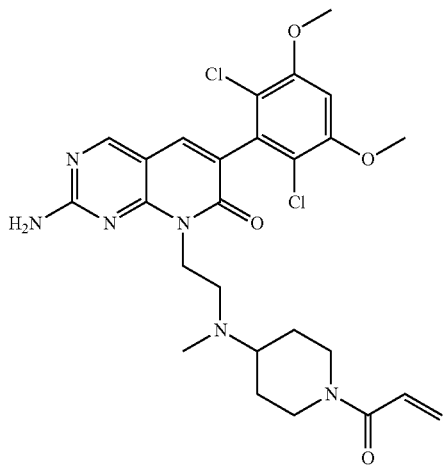 [SMILES: C=CC(=O)N1CCC(N(C)CCn2c(=O)c(-c3c(Cl)c(OC)cc(OC)c3Cl)cc3cnc(N)nc32)CC1]

The title compound was prepared as described in Example 127 except ammonia was used in Step 8. MS (ESI, pos. ion) m/z: 561.2 (M+1).

Example 129

Synthesis of 8-(2-((1-acryloylpiperidin-4-yl)(methyl)amino)ethyl)-6-(2,6-dichloro-3,5-dimethoxy-phenyl)-2-(ethylamino)pyrido[2,3-d]pyrimidin-7(8H)-one

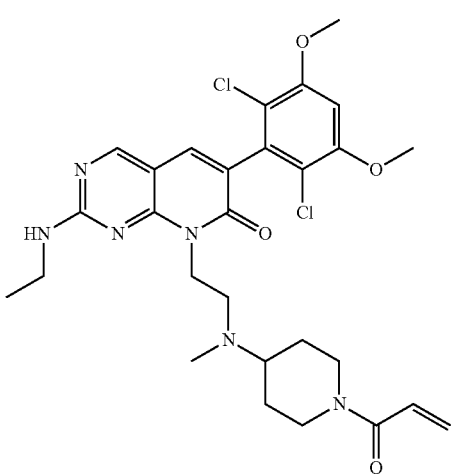 [SMILES: C=CC(=O)N1CCC(N(C)CCn2c(=O)c(-c3c(Cl)c(OC)cc(OC)c3Cl)cc3cnc(NCC)nc32)CC1]

The title compound was prepared as described in Example 127 except ethanamine was used in Step 8. MS (ESI, pos. ion) m/z: 589.1 (M+1).

Example 130

Synthesis of 8-(2-((1-acryloylpiperidin-4-yl)(methyl)amino)ethyl)-6-(2,6-dichloro-3,5-dimethoxy-phenyl)-2-(isopropylamino)pyrido[2,3-d]pyrimidin-7(8H)-one

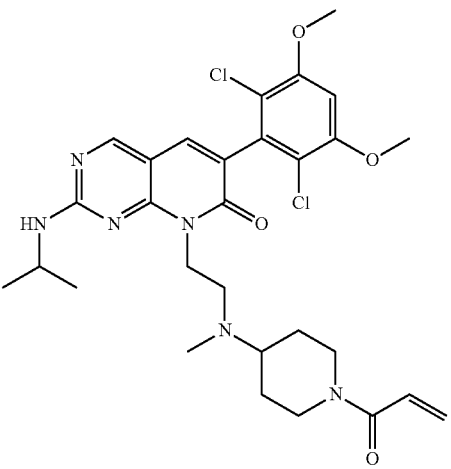 [SMILES: C=CC(=O)N1CCC(N(C)CCn2c(=O)c(-c3c(Cl)c(OC)cc(OC)c3Cl)cc3cnc(NC(C)C)nc32)CC1]

The title compound was prepared as described in Example 129 except propan-2-amine was used in Step 8. MS (ESI, pos. ion) m/z: 603.2 (M+1).

Example 131

Synthesis of 8-(2-((1-acryloylpiperidin-4-yl)(ethyl)amino)ethyl)-6-(2,6-dichloro-3,5-dimethoxy-phenyl)-2-(methylamino)pyrido[2,3-d]pyrimidin-7(8H)-one

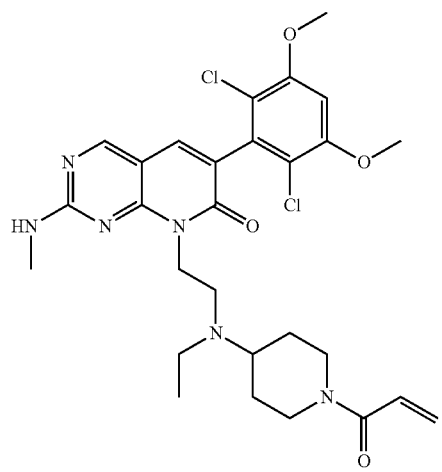 [SMILES: C=CC(=O)N1CCC(N(CC)CCn2c(=O)c(-c3c(Cl)c(OC)cc(OC)c3Cl)cc3cnc(NC)nc32)CC1]

Step 1

A mixture of tert-butyl 4-oxopiperidine-1-carboxylate (5 g, 25.09 mmol), Palladium/carbon (1 g), ethanol (50 mL)

and ethanamine (2.1 mL) was stirred under an atmosphere of H₂ overnight at room temperature. The solids were filtered and the filtrate was concentrated to afford 4.8 g (84%) of tert-butyl 4-(ethylamino)piperidine-1-carboxylate as a colorless oil.

Step 2

A mixture of 2-bromoethan-1-ol (2.4 g, 19.21 mmol), tert-butyl 4-(ethylamino)piperidine-1-carboxylate (3 g, 13.14 mmol) and Na₂CO₃ (2.1 g, 19.81 mmol) in ACN (100 mL) was stirred overnight at 65° C. The solids were filtered and the filtrate was concentrated to afford 3 g (84%) of tert-butyl 4-[ethyl(2-hydroxyethyl)amino]piperidine-1-carboxylate as a colorless oil.

Step 3

A solution of tert-butyl 4-[ethyl(2-hydroxyethyl)amino]piperidine-1-carboxylate (3 g, 11.01 mmol), CBr₄ (7.8 g) and TPP (7.8 g, 29.74 mmol) in DCM (200 ml) was stirred for 2 h at room temperature. The solids were filtered and the filtrate was concentrated. The residue was purified by chromatography (DCM/EtOAc (30:1)) to afford 1 g (27%) of tert-butyl 4-[(2-bromoethyl)(ethyl)amino]piperidine-1-carboxylate as a light yellow oil.

Step 4

A mixture of tert-butyl 4-[(2-bromoethyl)(ethyl)amino]piperidine-1-carboxylate (300 mg, 0.89 mmol), K₂CO₃ (340 mg, 2.46 mmol, 3.00 equiv) and 6-(2,6-dichloro-3,5-dimethoxyphenyl)-2-(methylsulfanyl)-7H,8H-pyrido[2,3-d]pyrimidin-7-one (414 mg, 1.14 mmol) in acetone (20 mL) was stirred overnight at 60° C. The solids were filtered and the filtrate was concentrated. The residue was purified by chromatography (DCM/MeOH (25:1)) to afford 230 mg (42%) of tert-butyl 4-([2-[6-(2,6-dichloro-3,5-dimethoxyphenyl)-2-(methylsulfanyl)-7-oxo-7H,8H-pyrido[2,3-d]pyrimidin-8-yl]ethyl](ethyl)amino)piperidine-1-carboxylate as a yellow solid.

Step 5

A solution of tert-butyl 4-([2-[6-(2,6-dichloro-3,5-dimethoxyphenyl)-2-(methylsulfanyl)-7-oxo-7H,8H-pyrido[2,3-d]pyrimidin-8-yl]ethyl](ethyl)amino)piperidine-1-carboxylate (170 mg, 0.27 mmol), NCS (147 mg), TEA (0.025 mL), AcOH (10 mL) and water (0.02 mL) was stirred for 4 hr at room temperature and then sat. NaHCO₃ (300 mL) was added. The resulting solution was washed with DCM and the layers separated. The organic layer was washed brine, dried over Na₂SO₄ and concentrated to afford 180 mg (96%) of tert-butyl 4-([2-[6-(2,6-dichloro-3,5-dimethoxyphenyl)-2-methanesulfonyl-7-oxo-7H,8H-pyrido[2,3-d]pyrimidin-8-yl]ethyl](ethyl)-amino)piperidine-1-carboxylate as a yellow solid.

Step 6

A solution of tert-butyl 4-([2-[6-(2,6-dichloro-3,5-dimethoxyphenyl)-2-methanesulfonyl-7-oxo-7H,8H-pyrido[2,3-d]pyrimidin-8-yl]ethyl](ethyl)amino)piperidine-1-carboxylate (300 mg, 0.44 mmol), methanamine (0.45 mL), t-BuOH (20 mL) and TEA (0.134 mL, 3.00 equiv) was stirred for 4 h at 60° C. The resulting mixture was concentrated to afford 200 mg (72%) of tert-butyl 4-([2-[6-(2,6-dichloro-3,5-dimethoxyphenyl)-2-(methylamino)-7-oxo-7H,8H-pyrido[2,3-d]-pyrimidin-8-yl]ethyl](ethyl)amino)piperidine-1-carboxylate as a yellow solid.

Step 7

A solution of tert-butyl 4-([2-[6-(2,6-dichloro-3,5-dimethoxyphenyl)-2-(methylamino)-7-oxo-7H,8H-pyrido[2,3-d]pyrimidin-8-yl]ethyl](ethyl)amino)piperidine-1-carboxylate (200 mg, 0.31 mmol) and TFA (2 mL) in DCM (10 mL) was stirred for 4 h at room temperature and then sat. NaHCO₃ (30 mL) was added. The resulting solution was washed with DCM and the layers were separated. The organic layer was washed brine, dried over Na₂SO₄ and concentrated to afford 130 mg (77%) of 6-(2,6-dichloro-3,5-dimethoxyphenyl)-8-[2-[ethyl(piperidin-4-yl)amino]-ethyl]-2-(methylamino)-7H,8H-pyrido[2,3-d]pyrimidin-7-one as a yellow solid.

Step 8

A solution of 6-(2,6-dichloro-3,5-dimethoxyphenyl)-8-[2-[ethyl(piperidin-4-yl)amino]-ethyl]-2-(methylamino)-7H,8H-pyrido[2,3-d]pyrimidin-7-one (100 mg, 0.19 mmol), prop-2-enoyl chloride (18 mg, 0.20 mmol) and TEA (60 mg) in DCM/MeOH (1:1) (20 mL) was stirred for 4 h at room temperature. The resulting mixture was concentrated and the residue was purified by Prep-HPLC to afford 13.3 mg (12%) of 8-(2-((1-acryloylpiperidin-4-yl)(ethyl)amino)ethyl)-6-(2,6-dichloro-3,5-dimethoxyphenyl)-2-(methylamino)pyrido[2,3-d]pyrimidin-7(8H)-one as an off-white solid. MS (ESI, pos. ion) m/z: 589.3 (M+1).

Example 132

Synthesis of 8-(2-((1-acryloylpiperidin-4-yl)(ethyl)amino)ethyl)-6-(2,6-dichloro-3,5-dimethoxyphenyl)-2-(ethylamino)pyrido[2,3-d]pyrimidin-7(8H)-one

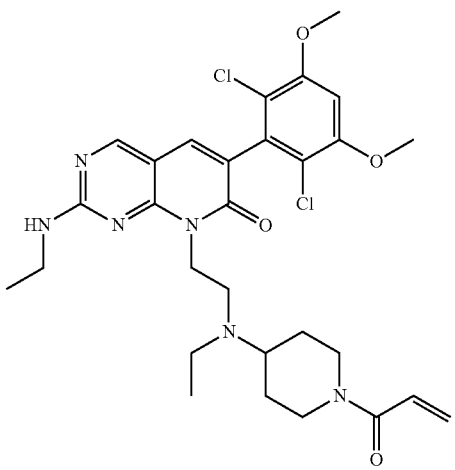 [SMILES: C=CC(=O)N1CCC(N(CC)CCn2c(=O)c(-c3c(Cl)c(OC)cc(OC)c3Cl)cc3cnc(NCC)nc32)CC1]

The title compound was prepared as in Example 131 except ethanamine was used in Step 6. MS (ESI, pos. ion) m/z: 603.2 (M+1).

Example 133

Synthesis of 8-(2-((1-acryloylpiperidin-4-yl)(ethyl)amino)ethyl)-6-(2,6-dichloro-3,5-dimethoxyphenyl)-2-(isopropylamino)pyrido[2,3-d]pyrimidin-7(8H)-one

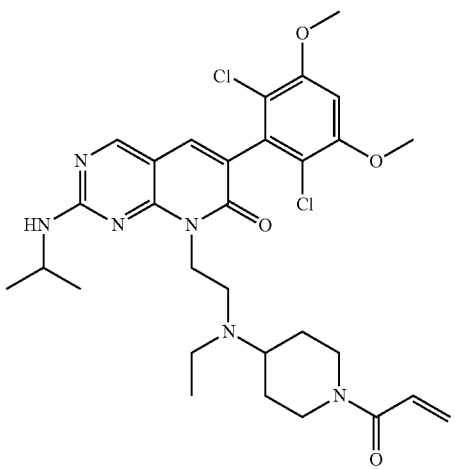 [SMILES: C=CC(=O)N1CCC(N(CC)CCn2c(=O)c(-c3c(Cl)c(OC)cc(OC)c3Cl)cc3cnc(NC(C)C)nc32)CC1]

The title compound was prepared as in Example 131 except propan-2-amine was used in Step 6. MS (ESI, pos. ion) m/z: 617.2 (M+1).

Example 134

Synthesis of (R)—N-(1-(2-(6-(2,6-dichloro-3,5-dimethoxyphenyl)-2-(methylamino)-7-oxopyrido[2,3-d]pyrimidin-8(7H)-yl)ethyl)piperidin-3-yl)acrylamide

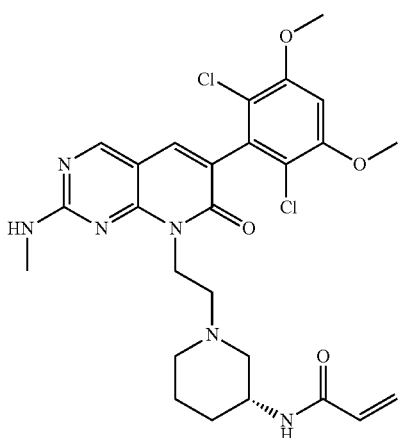 [SMILES: C=CC(=O)N[C@@H]1CCCN(CCn2c(=O)c(-c3c(Cl)c(OC)cc(OC)c3Cl)cc3cnc(NC)nc32)C1]

Step 1

A mixture of (R)-tert-butyl piperidin-3-ylcarbamate (2 g, 9.99 mmol), Na$_2$CO$_3$ (1.59 g, 15.00 mmol), 2-bromoethan-1-ol (1.625 g, 13.00 mmol) in ACN (20 mL), was stirred for 8 h at 60° C. The solids were filtered and the resulting filtrate was concentrated. The residue was purified by chromatography (DCM/MeOH (30:1)) to afford 2.24 g (92%) of (R)-tert-butyl (1-(2-hydroxyethyl)piperidin-3-yl)carbamate as a yellow oil.

Step 2

A solution of (R)-tert-butyl (1-(2-hydroxyethyl)piperidin-3-yl)carbamate (4 g, 16.37 mmol), TPP (8.6 g, 32.79 mmol), imidazole (2.23 g) and I$_2$ (8.3 g) in DCM (50 mL) was stirred for 1 h at room temperature. The resulting mixture was washed with water and then brine. The organic layer was dried over Na$_2$SO$_4$ and concentrated. The residue was purified by chromatography (EtOAc/pet. ether (1:10)) to afford 4.6 g (79%) of (R)-tert-butyl (1-(2-iodoethyl)-piperidin-3-yl)carbamate as a yellow solid.

Step 3

A mixture of (R)-tert-butyl (1-(2-iodoethyl)piperidin-3-yl)carbamate (350 mg, 0.99 mmol), 6-(2,6-dichloro-3,5-dimethoxyphenyl)-2-(methylsulfanyl)-7H,8H-pyrido[2,3-d]pyrimidin-7-one (393 mg, 0.99 mmol) and K$_2$CO$_3$ (138 mg, 1.00 mmol) in acetone (10 mL) was stirred for 8 h at 60° C. The resulting mixture was then concentrated and the residue was purified by chromatography (DCM/EtOAc (10:1)) to afford 425 mg (69%) of (R)-tert-butyl (1-(2-(6-(2,6-dichloro-3,5-dimethoxyphenyl)-2-(methylthio)-7-oxopyrido[2,3-d]pyrimidin-8(7H)-yl)ethyl)-piperidin-3-yl)carbamate as a solid.

Step 4

To a solution of (R)-tert-butyl (1-(2-(6-(2,6-dichloro-3,5-dimethoxyphenyl)-2-(methylthio)-7-oxopyrido[2,3-d]pyrimidin-8(7H)-yl)ethyl)piperidin-3-yl)carbamate (300 mg, 0.48 mmol) HOAC (2.22 mL), water (0.0432 mL) and TEA (0.0336 mL) was added NCS (96 mg, 0.72 mmol). The resulting solution was stirred for 1 h at room temperature and then the pH was adjusted to 7 with K$_2$CO$_3$ and then NaHCO$_3$ was added to adjust the pH to 9. The resulting mixture was washed with sat. NaCl followed with the addition of DCM (2 mL) and CH$_3$NH$_2$ (1.2 mL). The resulting solution was stirred for 30 min at 38° C. and then concentrated. The residue was purified by chromatography (DCM/meOH (25:1)) to afford 214 mg (74%) of (R)-tert-butyl (1-(2-(6-(2,6-dichloro-3,5-dimethoxyphenyl)-2-(methylamino)-7-oxopyrido[2,3-d]pyrimidin-8(7H)-yl)ethyl)piperidin-3-yl)carbamate as a solid.

Step 5

To a solution of (R)-tert-butyl (1-(2-(6-(2,6-dichloro-3,5-dimethoxyphenyl)-2-(methyl-amino)-7-oxopyrido[2,3-d]pyrimidin-8(7H)-yl)ethyl)piperidin-3-yl)carbamate (350 mg, 0.58 mmol) in DCM (10 mL) was added TFA (1 mL). The resulting solution was stirred for 2 h at room temperature and then the pH was adjusted to 9 with NaHCO$_3$. The resulting mixture was washed sat. NaCl and dried over Na$_2$SO$_4$ and concentrated to afford 289 mg (99%) of (R)-8-(2-(3-aminopiperidin-1-yl)ethyl)-6-(2,6-dichloro-3,5-dimethoxyphenyl)-2-(methylamino)pyrido[2,3-d]pyrimidin-7(8H)-one as a solid.

Step 6

To a solution of (R)-8-(2-(3-aminopiperidin-1-yl)ethyl)-6-(2,6-dichloro-3,5-dimethoxy-phenyl)-2-(methylamino)pyrido[2,3-d]pyrimidin-7(8H)-one (30 mg, 0.06 mmol), DCM (10 mL), MeOH (1 mL) and TEA (11.92 mg) was added prop-2-enoyl chloride (8 mg, 0.09 mmol). The resulting solution was stirred for 3 h at room temperature and then washed with water and brine. The organic layer was dried over Na$_2$SO$_4$ and concentrated. The residue was purified by Prep-HPLC to afford 50.7 mg of (R)—N-(1-(2-(6-(2,6-dichloro-3,5-dimethoxyphenyl)-2-(methyl-amino)-7-oxopyrido[2,3-d]pyrimidin-8(7H)-yl)ethyl)piperidin-3-yl)acrylamide as a white solid.

MS (ESI, pos. ion) m/z: 561.1 (M+1).

Example 135

Synthesis of (R)—N-(1-(2-(6-(2,6-dichloro-3,5-dimethoxyphenyl)-2-(ethylamino)-7-oxopyrido[2,3-d]-pyrimidin-8(7H)-yl)ethyl)piperidin-3-yl)acrylamide

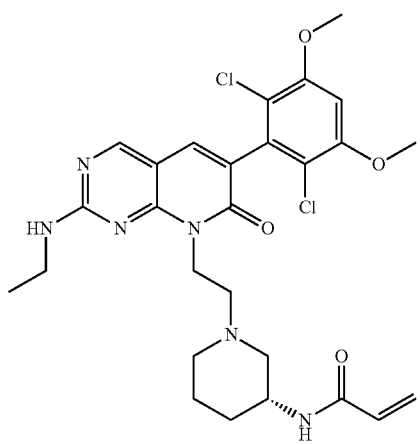 [SMILES: C=CC(=O)N[C@@H]1CCCN(CCn2c(=O)c(-c3c(Cl)c(OC)cc(OC)c3Cl)cc3cnc(NCC)nc32)C1]

The title compound was prepared as Example 134 except ethanamine was used in Step 4.

MS (ESI, pos. ion) m/z: 575.2 (M+1).

Example 136

Synthesis of (S)—N-(1-(2-(6-(2,6-dichloro-3,5-dimethoxyphenyl)-2-(methylamino)-7-oxopyrido-[2,3-d]pyrimidin-8(7H)-yl)ethyl)piperidin-3-yl)acrylamide

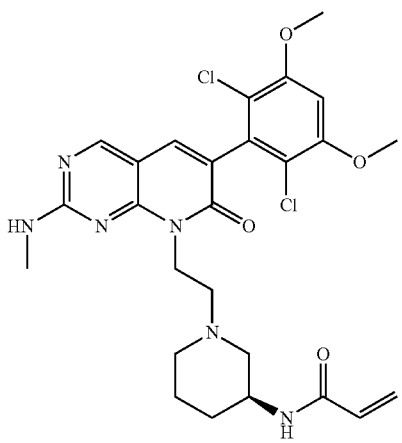 [SMILES: C=CC(=O)N[C@H]1CCCN(CCn2c(=O)c(-c3c(Cl)c(OC)cc(OC)c3Cl)cc3cnc(NC)nc32)C1]

The title compound was prepared as Example 134 except (S)-tert-butyl piperidin-3-ylcarbamate was used in Step 1. MS (ESI, pos. ion) m/z: 561.1 (M+1).

Example 137

Synthesis of (S)—N-(1-(2-(6-(2,6-dichloro-3,5-dimethoxyphenyl)-2-(ethylamino)-7-oxopyrido[2,3-d]-pyrimidin-8(7H)-yl)ethyl)piperidin-3-yl)acrylamide

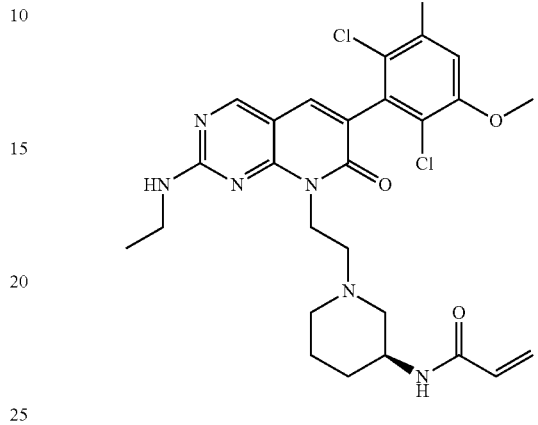

The title compound was prepared as Example 134 except (S)-tert-butyl piperidin-3-ylcarbamate was used in Step 1 and ethanamine was used in Step 4. MS (ESI, pos. ion) m/z: 575.2 (M+1).

Example 138

Synthesis of (S)—N-(1-(2-(6-(2,6-dichloro-3,5-dimethoxyphenyl)-2-(methylamino)-7-oxopyrido[2,3-d]pyrimidin-8(7H)-yl)ethyl)pyrrolidin-3-yl)acrylamide

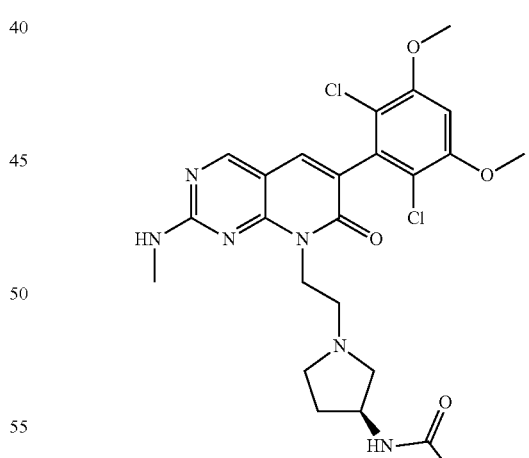

Step 1

A mixture of tert-butyl N-[(3S)-pyrrolidin-3-yl]carbamate (5 g, 26.85 mmol), 2-bromo-ethan-1-ol (4.33 g, 34.65 mmol) and $Na_2CO_3$ (4.27 g, 40.29 mmol) in ACN (50 mL) was stirred for 6 h at 65° C. The solids were filtered and the filtrate was concentrated. The residue was purified by chromatography (EtOAc/pet. ether (1:1)) to afford 4.5 g (73%) of tert-butyl N-[(3S)-1-(2-hydroxyethyl)pyrrolidin-3-yl]carbamate as a yellow oil.

Step 2

To a solution of tert-butyl N-[(3S)-1-(2-hydroxyethyl)pyrrolidin-3-yl]carbamate (1.5 g, 6.51 mmol) and pyridine (1.03 g, 13.02 mmol) in DCM (25 mL) at 0° C. was added SOCl$_2$ (1.15 g, 9.75 mmol) and the resulting solution was stirred for 2 h at 0° C. Water was then added and the pH was adjusted to 8 with sat. NaHCO$_3$. The resulting solution was extracted with DCM and the organic layer was washed with sat. NaCl and dried over Na$_2$SO$_4$ and concentrated to afford 1.15 g (71%) of tert-butyl N-[(3S)-1-(2-chloroethyl)pyrrolidin-3-yl]carbamate as a brown oil.

The title compound was prepared as Example 135, Steps 3 to 6. MS (ESI, pos. ion) m/z: 547.1 (M+1).

Example 139

Synthesis of (S)—N-(1-(2-(6-(2,6-dichloro-3,5-dimethoxyphenyl)-2-(ethylamino)-7-oxopyrido[2,3-d]-pyrimidin-8(7H)-yl)ethyl)pyrrolidin-3-yl)acrylamide

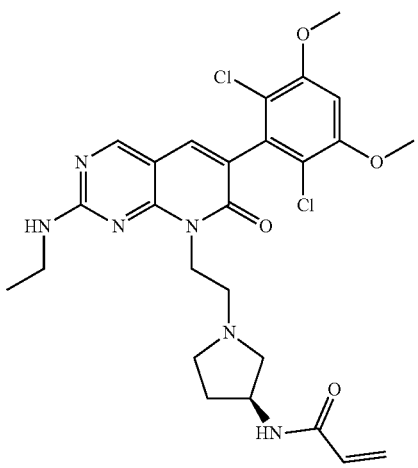 [SMILES: C=CC(=O)N[C@H]1CCN(CCn2c(=O)c(-c3c(Cl)c(OC)cc(OC)c3Cl)cc3cnc(NCC)nc32)C1]

The title compound was prepared as Example 138 except ethanamine was used. MS (ESI, pos. ion) m/z: 561.1 (M+1).

Example 140

Synthesis of (R)—N-(1-(2-(6-(2,6-dichloro-3,5-dimethoxyphenyl)-2-(methylamino)-7-oxopyrido[2,3-d]pyrimidin-8(7H)-yl)ethyl)pyrrolidin-3-yl)acrylamide

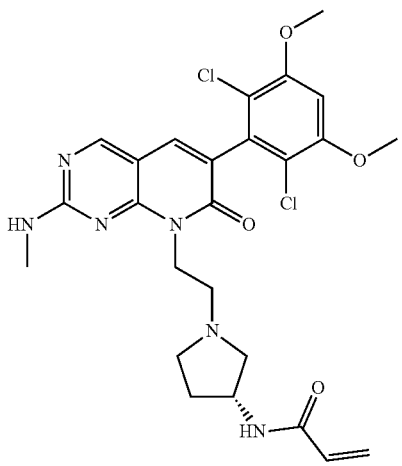 [SMILES: C=CC(=O)N[C@@H]1CCN(CCn2c(=O)c(-c3c(Cl)c(OC)cc(OC)c3Cl)cc3cnc(NC)nc32)C1]

The title compound was prepared as Example 138 except (R)-tert-butyl pyrrolidin-3-ylcarbamate was used in Step 1. MS (ESI, pos. ion) m/z: 547.2 (M+1).

Example 141

Synthesis of (R)—N-(1-(2-(6-(2,6-dichloro-3,5-dimethoxyphenyl)-2-(ethylamino)-7-oxopyrido[2,3-d]pyrimidin-8(7H)-yl)ethyl)pyrrolidin-3-yl)acrylamide

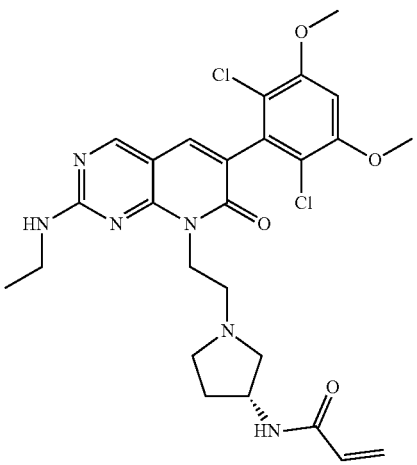 [SMILES: C=CC(=O)N[C@@H]1CCN(CCn2c(=O)c(-c3c(Cl)c(OC)cc(OC)c3Cl)cc3cnc(NCC)nc32)C1]

The title compound was prepared as Example 140 except (R)-tert-butyl pyrrolidin-3-ylcarbamate was used in Step 1 and ethanamine was used. MS (ESI, pos. ion) m/z: 561.2 (M+1).

Example 142

Synthesis of 1-(3-(4-acryloylpiperazin-1-yl)propyl)-3-(2,6-dichloro-3,5-dimethoxyphenyl)-7-(methylamino)-1,6-naphthyridin-2(1H)-one

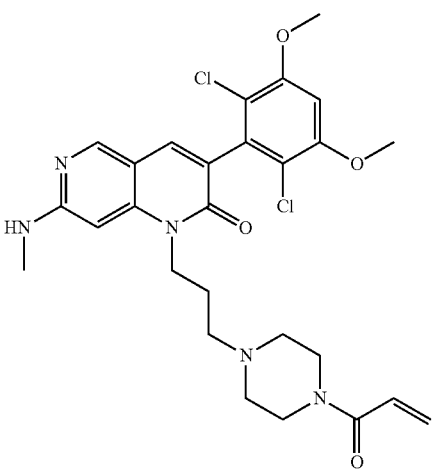

Step 1

To a solution of ethyl 4,6-dichloronicotinate (15 g, 68 mmol), TEA (8.25 g, 81.5 mmol) in MeCN (200 mL) at 0°

C. was added (2,4-dimethoxyphenyl)methanamine (12 g, 71 mmol) over 0.5 h. The mixture was stirred at rt for 16 h and then concentrated. The residue was diluted with EtOAc, washed with water, brine, dried over $Na_2SO_4$ and then concentrated to afford ethyl 6-chloro-4-((2,4-dimethoxybenzyl)amino)nicotinate (22 g, 92%) as a yellow solid.

Step 2

A mixture of ethyl 6-chloro-4-((2,4-dimethoxybenzyl)amino)nicotinate (15 g, 42.8 mmol) and TFA (80 mL) was heated to 50° C. for 3 h. After cooling to room temperature, the solvent was removed and the residue was adjusted to pH=8 with aq. $NaHCO_3$ and extracted with EtOAc. The organic layer was washed with brine, dried over $Na_2SO_4$, filtered and concentrated. The residue was purified by chromatography (silica gel, PE:EtOAc=4:1) to afford ethyl 4-amino-6-chloronicotinate (5.1 g, 61%) as a white solid.

Step 3

$LiAlH_4$ (1.9 g) was suspended in THF (50 mL) and cooled to −78° C. and then a solution of ethyl 4-amino-6-chloronicotinate (5.1 g, 25.4 mmol) in THF (70 mL), was added dropwise. The resulting mixture was stirred at −78° C. for 3 h and then warmed to rt, A MeOH/EtOAc (1/1) mixture was added slowly and the solids were filtered out. The filtrate was concentrated and the residue was purified by chromatography (silica gel, PE:EtOAc=10:1 to 5:1) to afford (4-amino-6-chloropyridin-3-yl)methanol (2.6 g, 65%) as a pale yellow solid.

Step 4

(4-Amino-6-chloropyridin-3-yl)methanol (2.6 g, 16.4 mmol) was dissolved in DCM (80 mL) along with $MnO_2$ (14.3 g). The mixture was stirred at rt for 24 h. $MnO_2$ was filtered off and the filtrate was concentrated to afford 4-amino-6-chloronicotinaldehyde (1.67 g, 65%) as a white solid.

Step 5

A mixture of 4-amino-6-chloronicotinaldehyde (2.6 g, 16.7 mmol), methyl 2-(3,5-dimethoxyphenyl)acetate (4.48 g, 20 mmol) and $K_2CO_3$ (4.6 g, 33.4 mmol) in DMF (50 mL) at 100° C. was stirred for 7 h and then water (50 mL) was added. The solids were filtered and the filtered cake was washed with EtOAc. The filtered solids was dried to afford 7-chloro-3-(3,5-dimethoxyphenyl)-1,6-naphthyridin-2(1H)-one (2.2 g, 41%) as a white solid.

Step 6

To a solution of 7-chloro-3-(3,5-dimethoxyphenyl)-1,6-naphthyridin-2(1H)-one (2.2 g, 7.0 mmol) in AcOH (40 mL) was added TEA (1.4 g, 14.0 mL) and NCS (2.8 g, 21.0 mL). The mixture was stirred at rt for 4 h and then filtered and the filtered solid was dried to afford 7-chloro-3-(2,6-dichloro-3,5-dimethoxyphenyl)-1,6-naphthyridin-2(1H)-one (2.68 g, 86%) as a white solid.

Step 7

To a mixture of 7-chloro-3-(2,6-dichloro-3,5-dimethoxyphenyl)-1,6-naphthyridin-2(1H)-one (2.52 g, 5.65 mmol), $K_2CO_3$ (1.8 g, 13.0 mmol) and $Cs_2CO_3$ (0.42 g, 1.3 mmol) in DMF (60 mL) was added tert-butyl 4-(3-(methylsulfonyloxy)propyl)piperazine-1-carboxylate (3.1 g, 9.72 mmol). The mixture was stirred at 60° C. for 4 hr and then water was added. The solids were collected by filtration and dried to afford tert-butyl 4-(3-(7-chloro-3-(2,6-dichloro-3,5-dimethoxyphenyl)-2-oxo-1,6-naphthyridin-1(2H)-yl)propyl)piperazine-1-carboxylate (2.3 g, 68%) as a white solid.

Step 8

A solution of tert-butyl 4-(3-(7-chloro-3-(2,6-dichloro-3,5-dimethoxyphenyl)-2-oxo-1,6-naphthyridin-1(2H)-yl)propyl)piperazine-1-carboxylate (400 mg, 0.65 mmol) and methanamine (6 mL, 2 mol/L in THF, 12 mmol) in DMSO (2 mL) was stirred at 120° C. for 24 h in a sealed tube. The mixture was then cooled, concentrated and purified by chromatography (silica gel, PE:EtOAc=1:2) to afford tert-butyl 4-(3-(3-(2,6-dichloro-3,5-dimethoxyphenyl)-7-(methylamino)-2-oxo-1,6-naphthyridin-1(2H)-yl)propyl)piperazine-1-carboxylate (295 mg, 74%) as a yellow solid.

Step 9

To a solution of tert-butyl 4-(3-(3-(2,6-dichloro-3,5-dimethoxyphenyl)-7-(methylamino)-2-oxo-1,6-naphthyridin-1(2H)-yl)propyl)piperazine-1-carboxylate (295 mg, 0.49 mmol) in dioxane (6 mL) was added conc. HCl (4 mL). The mixture was stirred at rt for 2 h and then concentrated. The residue was adjusted to pH=8 with aq. $NaHCO_3$ and extracted with EtOAc. The organic layer was dried over $Na_2SO_4$ and concentrated to afford 3-(2,6-dichloro-3,5-dimethoxyphenyl)-7-(methylamino)-1-(3-(piperazin-1-yl)propyl)-1,6-naphthyridin-2(1H)-one (180 mg, crude) as a yellow solid.

Step 10

To a solution of 3-(2,6-dichloro-3,5-dimethoxyphenyl)-7-(methylamino)-1-(3-(piperazin-1-yl)propyl)-1,6-naphthyridin-2(1H)-one (180 mg, crude) in sat. $NaHCO_3$ (2 mL) and THF (4 mL) at 0° C. was added acryloyl chloride (97 mg, 1.06 mmol). After 1 h, water (20 mL) was added and the mixture was extracted with EtOAc. The organic layer was dried over $Na_2SO_4$ and concentrated. The residue was purified by Prep-TLC (DCM/MeOH=10:1) to afford 1-(3-(4-acryloylpiperazin-1-yl)propyl)-3-(2,6-dichloro-3,5-dimethoxyphenyl)-7-(methylamino)-1,6-naphthyridin-2(1H)-one (43.5 mg, 22%) as a white solid. MS (ESI, pos. ion) m/z: 560.1 (M+1).

Example 143

Synthesis of (S)-1-(3-(4-acryloylpiperazin-1-yl)propyl)-3-(2,6-dichloro-3,5-dimethoxyphenyl)-7-((1-methoxypropan-2-yl)amino)-1,6-naphthyridin-2(1H)-one

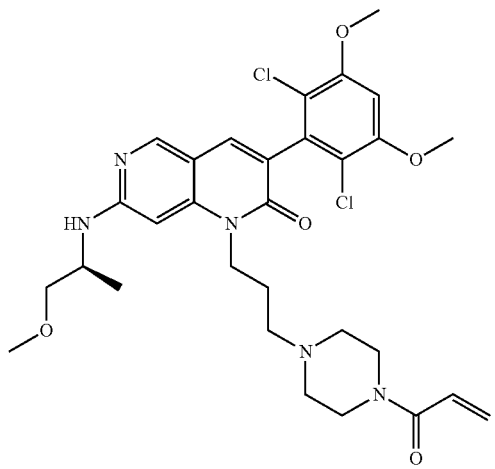 [SMILES: C=CC(=O)N1CCN(CCCn2c(=O)c(-c3c(Cl)c(OC)cc(OC)c3Cl)cc3cnc(N[C@@H](C)COC)cc32)CC1]

The title compound was prepared as in Example 142 except (S)-1-methoxypropan-2-amine was used in Step 8. MS (ESI, pos. ion) m/z: 617.9 (M+1).

Example 144

Synthesis of 1-(2-((1-acryloylazetidin-3-yl)oxy) ethyl)-3-(2,6-dichloro-3,5-dimethoxyphenyl)-7-(methylamino)-1,6-naphthyridin-2(1H)-one

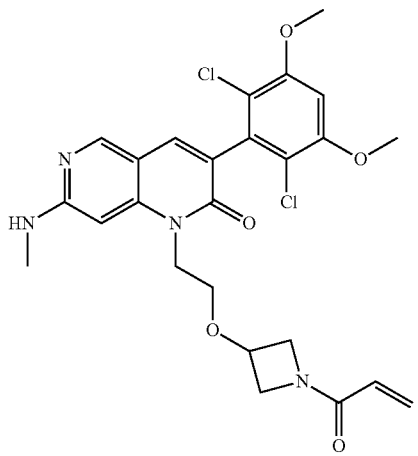

The title compound was prepared as in Example 142 except tert-butyl 3-(2-((methyl-sulfonyl)oxy)ethoxy)azetidine-1-carboxylate was used in Step 7. MS (ESI, pos. ion) m/z: 532.9 (M+1).

Example 145

Synthesis of 1-(2-((1-acryloylazetidin-3-yl)oxy) ethyl)-3-(2,6-dichloro-3,5-dimethoxyphenyl)-7-((2-morpholinoethyl)amino)-1,6-naphthyridin-2(1H)-one

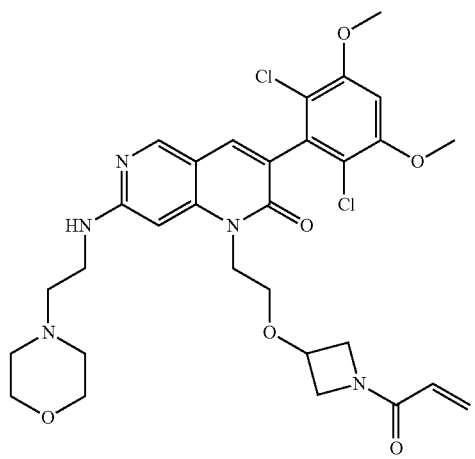 [SMILES: C=CC(=O)N1CC(OCCn2c(=O)c(-c3c(Cl)c(OC)cc(OC)c3Cl)cc3cnc(NCCN4CCOCC4)cc32)C1]

The title compound was prepared as in Example 142 except tert-butyl 3-(2-((methyl-sulfonyl)oxy)ethoxy)azetidine-1-carboxylate was used in Step 7 and 2-morpholinoethanamine was used in Step 8. MS (ESI, pos. ion) m/z: 632.0 (M+1).

Example 146

Synthesis of (S)-1-(2-((1-acryloylazetidin-3-yl)oxy) ethyl)-3-(2,6-dichloro-3,5-dimethoxyphenyl)-7-((1-methoxypropan-2-yl)amino)-1,6-naphthyridin-2(1H)-one

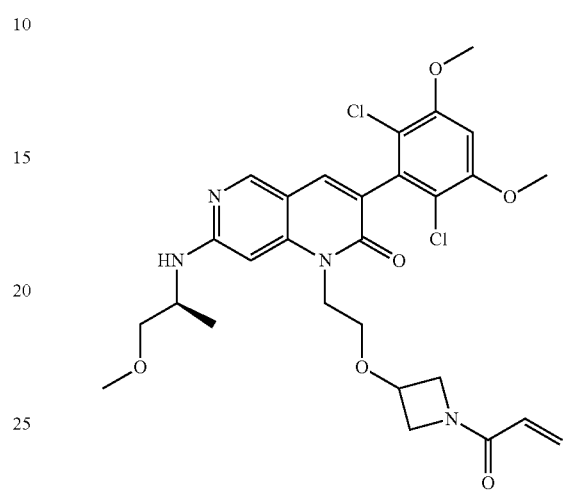

The title compound was prepared as in Example 142 except tert-butyl 3-(2-((methyl-sulfonyl)oxy)ethoxy)azetidine-1-carboxylate was used in Step 7 and (S)-1-methoxypropan-2-amine was used in Step 8. MS (ESI, pos. ion) m/z: 590.9 (M+1).

Example 147

Synthesis of 1-(3-(4-acryloylpiperazin-1-yl)propyl)-3-(2,6-dichloro-3,5-dimethoxyphenyl)-7-(ethylamino)-1,6-naphthyridin-2(1H)-one

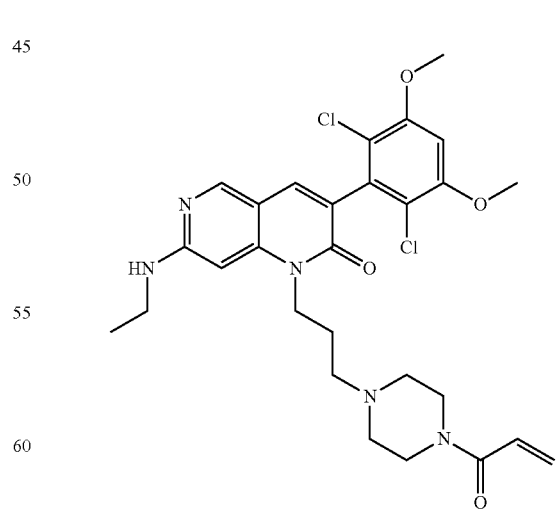

The title compound was prepared as in Example 142 except ethanamine was used in Step 8. MS (ESI, pos. ion) m/z: 574.0 (M+1).

Example 148

Synthesis of 1-(3-(4-acryloylpiperazin-1-yl)propyl)-7-amino-3-(2,6-dichloro-3,5-dimethoxy-phenyl)-1,6-naphthyridin-2(1H)-one

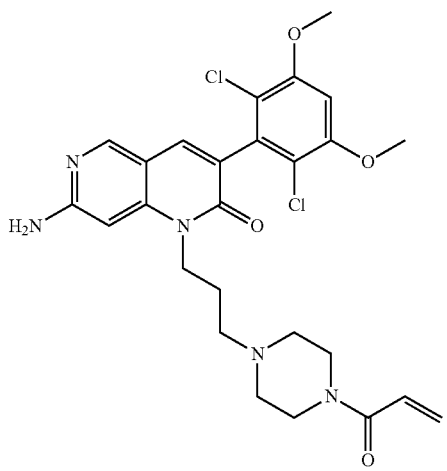 [SMILES: C=CC(=O)N1CCN(CCCn2c(=O)c(-c3c(Cl)c(OC)cc(OC)c3Cl)cc3cnc(N)cc32)CC1]

Step 1

A mixture of tert-butyl 4-(3-(7-chloro-3-(2,6-dichloro-3,5-dimethoxyphenyl)-2-oxo-1,6-naphthyridin-1(2H)-yl)propyl)piperazine-1-carboxylate (122 mg, 0.2 mmol), diphenylmethanimine (54 mg, 0.3 mmol), Pd$_2$(dba)$_3$ (18 mg, 0.02 mmol), BINAP (12 mg, 0.02 mmol) and t-BuONa (38 mg, 0.4 mmol) in toluene (4 mL) was stirred at 110° C. for 4 h under a N$_2$ atmosphere. The mixture was then cooled, concentrated and purified by chromatography (silica gel, PE:EtOAc=10:1) to afford tert-butyl 4-(3-(3-(2,6-dichloro-3,5-dimethoxyphenyl)-7-((diphenylmethylene)amino)-2-oxo-1,6-naphthyridin-1(2H)-yl)propyl)piperazine-1-carboxylate (90 mg, 59%) as a white solid.

The title compound was then prepared as in Example 142, Step 9 and 10. MS (ESI, pos. ion) m/z: 546.0 (M+1).

Example 149

Synthesis of 1-(3-(4-acryloylpiperazin-1-yl)propyl)-3-(2,6-dichloro-3,5-dimethoxyphenyl)-7-((2-methoxyethyl)amino)-1,6-naphthyridin-2(1H)-one

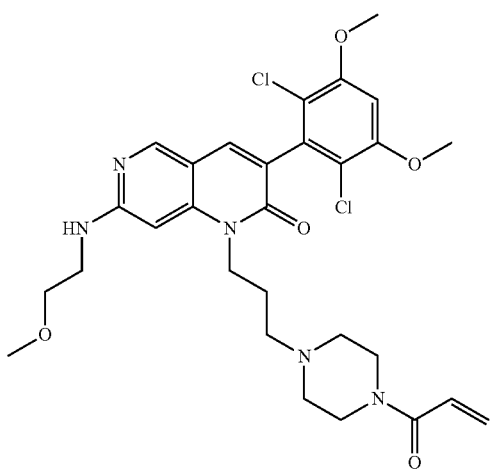 [SMILES: C=CC(=O)N1CCN(CCCn2c(=O)c(-c3c(Cl)c(OC)cc(OC)c3Cl)cc3cnc(NCCOC)cc32)CC1]

The title compound was prepared as in Example 142 except 2-methoxyethanamine was used in Step 8. MS (ESI, pos. ion) m/z: 604.0 (M+1).

Example 150

Synthesis of 1-(3-(4-acryloylpiperazin-1-yl)propyl)-3-(2,6-dichloro-3,5-dimethoxyphenyl)-7-((2-(2-methoxyethoxy)ethyl)amino)-1,6-naphthyridin-2(1H)-one

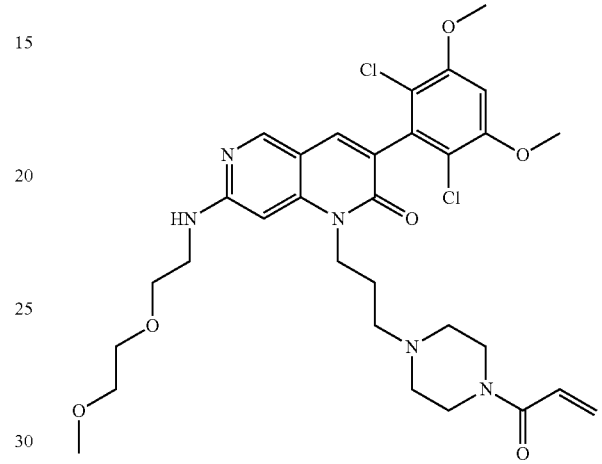

The title compound was prepared as in Example 142 except 2-(2-methoxyethoxy)-ethanamine was used in Step 8. MS (ESI, pos. ion) m/z: 648.0 (M+1).

Example 151

Synthesis of 1-(2-((1-acryloylazetidin-3-yl)(methyl)amino)ethyl)-3-(2,6-dichloro-3,5-dimethoxyphenyl)-7-(ethylamino)-1,6-naphthyridin-2(1H)-one

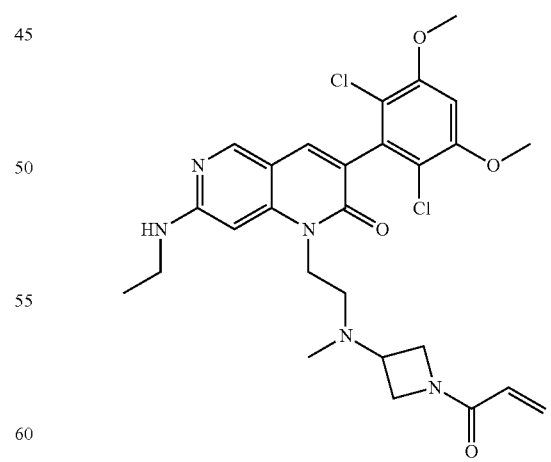

Step 1

To a solution of tert-butyl 3-oxoazetidine-1-carboxylate (3.0 g, 17.4 mmol) and 2-aminoethanol (1.57 g, 26.2 mmol) in MeOH (50 mL) was added AcOH (0.5 mL) and Pd/C (1.0 g, 10% on carbon). After the addition, the reaction mixture was stirred under an atmosphere of $H_2$ at room temperature for 18 hrs. The reaction mixture was filtered and the filtered cake was washed with MeOH. The filtrate was concentrated and the resulting residue was purified by chromatography (DCM:MeOH=30:1) to afford tert-butyl 3-((2-hydroxyethyl)amino)azetidine-1-carboxylate (3.0 g, 79%).

Step 2

To a solution of tert-butyl 3-((2-hydroxyethyl)amino)azetidine-1-carboxylate (2.3 g, 10.6 mmol) and paraformaldehyde (1.59 g, 53 mmol) in MeOH (50 mL) was added AcOH (0.5 mL), and Pd/C (1.0 g, 10% on carbon). The reaction mixture was stirred under an atmosphere of $H_2$ at room temperature for 18 hrs. The reaction mixture was filtered and the filtered cake was washed with MeOH. The filtrate was concentrated and the resulting residue was purified by chromatography (DCM:MeOH=30:1) to afford tert-butyl 3-((2-hydroxyethyl)-(methyl)amino)azetidine-1-carboxylate (1.7 g, 69.4%).

Step 3

To a solution of tert-butyl 3-((2-hydroxyethyl)(methyl)amino)azetidine-1-carboxylate (750 mg, 3.26 mmol) in DCM (15 mL) was added TEA (658 mg, 6.52 mmol) and MsCl (558 mg, 4.89 mmol). The reaction mixture was stirred at room temperature for 2 hrs and then quenched with water and extracted with DCM. The organic layer was dried over $Na_2SO_4$ and concentrated to afford tert-butyl 3-(methyl (2-((methylsulfonyl)oxy)ethyl)amino)azetidine-1-carboxylate (680 mg, crude).

The title compound was prepared as in Example 142 starting from Step 7 and ethanamine was used in Step 8. MS (ESI, pos. ion) m/z: 559.7 (M+1).

Example 152

Synthesis of 1-(2-((1-acryloylazetidin-3-yl)(ethyl)amino)ethyl)-3-(2,6-dichloro-3,5-dimethoxy-phenyl)-7-(ethylamino)-1,6-naphthyridin-2(1H)-one

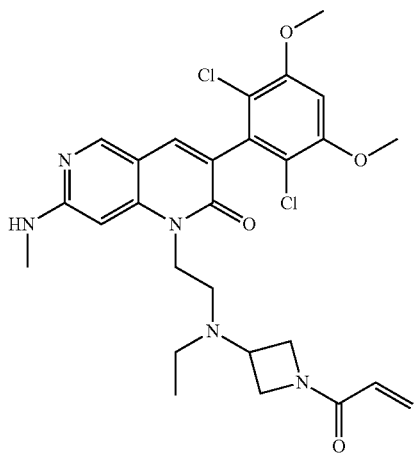 [SMILES: C=CC(=O)N1CC(N(CC)CCn2c(=O)c(-c3c(Cl)c(OC)cc(OC)c3Cl)cc3cnc(NC)cc32)C1]

The title compound was prepared as in Example 151 except acetaldehyde was used in Step 2 and methanamine was used in Step 8. MS (ESI, pos. ion) m/z: 559.7 (M+1).

BIOLOGICAL EXAMPLES

Example 1

FGFR Family Enzymatic Activity Assay

A Caliper-based kinase assay (Caliper Life Sciences, Hopkinton, MA) was used to measure inhibition of FGFR family (FGFR1, FGFR2, FGFR3, FGFR4) kinase activity of a compound of Formula (III). Serial dilutions of test compounds were incubated with either human recombinant FGFR1 (0.5 nM), FGFR2 (0.1 nM, FGFR3 (0.9 nM), or FGFR4 (2 nM), ATP (FGFR1: 100 µM; FGFR2: 75 µM; FGFR3: 120 µM; FGFR4: 250 µM) and a phosphoacceptor peptide substrate FAM-KKKKEEIYFFF-CONH$_2$ (1 µM) at room temperature for 3 h. The reaction was then terminated with EDTA, final concentration 20 mM and the phosphorylated reaction product was quantified on a Caliper LabChip 3000. Percent inhibition was calculated for each compound dilution and the concentration that produced 50% inhibition was calculated. This value is presented as the $IC_{50}$. The $IC_{50}$ values $IC_{50}$ values (uM) for a representative no. of compounds of the disclosure are provided below.

| Cpd No. (see Cpd table 1 above) | FGFR1 in (uM) |
|---|---|
| 1 | 0.0099 |
| 2 | 0.0023 |
| 3 | 0.0165 |
| 4 | 0.002 |
| 5 | 0.0878 |
| 6 | 0.0006 |
| 7 | 0.0001 |
| 8 | 0.0017 |
| 9 | 0.0009 |
| 10 | 0.0019 |
| 11 | 0.0009 |
| 12 | 0.0014 |
| 13 | 0.0006 |
| 14 | 0.0004 |
| 15 | 0.0007 |
| 16 | 0.0004 |
| 17 | 0.0018 |
| 18 | 0.0039 |
| 19 | 0.0003 |
| 20 | 0.0057 |
| 21 | 0.0022 |
| 22 | 0.0019 |
| 23 | 0.0037 |
| 23 | 0.0037 |
| 24 | 0.004 |
| 24 | 0.004 |
| 25 | 0.0018 |
| 26 | 0.0011 |
| 27 | 0.0009 |
| 28 | 0.0022 |
| 29 | 0.0011 |
| 30 | 0.0028 |
| 30 | 0.0028 |
| 31 | 0.0022 |
| 32 | 0.0008 |
| 33 | 0.001 |
| 34 | 0.002 |
| 35 | 0.0038 |
| 36 | 0.0018 |
| 37 | 0.001 |
| 38 | 0.0011 |
| 39 | 0.0079 |
| 40 | 0.0034 |
| 41 | 0.0022 |
| 42 | 0.0039 |
| 43 | 0.0048 |
| 44 | 0.0013 |
| 45 | 0.0016 |
| 46 | 0.0009 |
| 47 | 0.0052 |
| 48 | 0.0053 |
| 49 | 0.0053 |
| 50 | 0.0123 |
| 51 | 0.0016 |
| 52 | 0.0033 |
| 53 | 0.0018 |

| Cpd No. (see Cpd table 1 above) | FGFR1 in (uM) |
| --- | --- |
| 54 | 0.0007 |
| 55 | 0.001 |
| 56 | 0.0007 |
| 57 | 0.0014 |
| 58 | 0.0018 |
| 60 | 0.0022 |
| 61 | 0.0013 |
| 62 | 0.002 |
| 63 | 0.0012 |
| 64 | 0.0009 |
| 65 | 0.0028 |
| 66 | 3.5101 |
| 67 | 0.0008 |
| 68 | 0.001 |
| 69 | 0.002 |
| 70 | 0.0013 |
| 71 | 0.0017 |
| 72 | 0.0123 |
| 73 | 0.0021 |
| 74 | 0.0018 |
| 75 | 0.0011 |
| 76 | 0.0017 |
| 77 | 0.0016 |
| 78 | 0.003 |
| 79 | 0.0039 |
| 80 | 0.001 |
| 82 | 0.003 |
| 83 | 0.0011 |
| 85 | 0.003 |
| 86 | 0.0027 |
| 87 | 0.0053 |
| 88 | 0.0046 |
| 89 | 0.0036 |
| 90 | 0.0146 |
| 91 | 0.0012 |
| 92 | 0.0076 |
| 93 | 0.0119 |
| 94 | 0.0012 |
| 95 | 0.0012 |
| 96 | 0.0042 |
| 97 | 0.0034 |
| 98 | 0.0072 |
| 99 | 0.0069 |
| 100 | 0.0396 |
| 101 | 0.0097 |
| 102 | 0.0057 |
| 103 | 0.0015 |
| 104 | 0.0017 |
| 105 | 0.0025 |
| 106 | 0.0015 |
| 107 | 0.0025 |
| 108 | 0.0044 |
| 109 | 0.0013 |
| 110 | 0.0008 |
| 111 | 0.0016 |
| 112 | 0.0028 |
| 113 | 0.0014 |
| 114 | 0.0011 |
| 115 | 0.0051 |
| 116 | 0.0017 |
| 117 | 0.0009 |
| 118 | 0.0021 |
| 119 | 0.0013 |
| 120 | 0.0011 |
| 121 | 0.0017 |
| 122 | 0.0021 |
| 123 | 0.0022 |
| 124 | 0.0018 |
| 125 | 0.0011 |
| 126 | 0.0042 |
| 127 | 0.0015 |
| 128 | 0.0027 |
| 129 | 0.0014 |
| 130 | 0.0013 |
| 131 | 0.0031 |
| 132 | 0.0019 |
| 133 | 0.0029 |
| 134 | 0.0033 |
| 135 | 0.0014 |
| 136 | 0.0035 |
| 137 | 0.0021 |
| 138 | 0.0054 |
| 139 | 0.0038 |
| 140 | 0.0023 |
| 141 | 0.0017 |
| 142 | 0.0012 |
| 143 | 0.0027 |
| 144 | 0.002 |
| 145 | 0.0033 |
| 146 | 0.0078 |
| 147 | 0.0013 |
| 148 | 0.0014 |
| 149 | 0.0016 |
| 150 | 0.001 |
| 153 | 0.0007 |
| 154 | 0.022 |
| 155 | 0.002 |
| 156 | 0.0026 |
| 157 | 0.0017 |
| 158 | 0.0015 |
| 159 | 0.0019 |
| 160 | 0.0019 |
| 163 | 0.0008 |

Example 2

Inhibition of FGFR2-Dependent Cell Growth

The cell-based effects of FGFR inhibitors were determined by measuring inhibition of FGFR-dependent cell line growth. The cell lines SNU-16 was used for these assays. SNU-16 cells were seeded in a 96-well plate at 5,000 cells per well in RPMI 1640 high glucose medium with 1000 fetal bovine serum (FBS. Cells were incubated at 37° C. for 24 hrs. in 500 $CO_2$. Compound dilutions were added to cells starting at a concentration of 30 uM and decreasing in tripling dilutions. The final DMSO concentration was 0.1%. The concentration range was adjusted as needed for compounds of different potencies. The cells treated with compounds were incubated for 72 hrs. at 37° C. in 500 $CO_2$. At the end of the 72 hour incubation period, cell viability was determined using the Cell-titer Glo Luminescence assay from Promega. Percent inhibition of cell growth was calculated as a percentage of untreated cell viability. The percent inhibition was plotted as a function of log compound concentration. The $IC_{50}$ was then calculated for each compound using Prism software from GraphPad. The $IC_{50}$ values (uM) for a representative no. of compounds of the disclosure are provided below.

| Cpd No. (see Cpd table 1 above) | SNU16 $IC_{50}$ values (uM) |
| --- | --- |
| 1 | 0.0162 |
| 2 | 0.0012 |
| 3 | 0.0250 |
| 4 | 0.0012 |

| Cpd No. (see Cpd table 1 above) | SNU16 IC$_{50}$ values (uM) |
|---|---|
| 5 | 0.1686 |
| 6 | 0.0026 |
| 7 | 0.0033 |
| 8 | 0.0088 |
| 9 | 0.0037 |
| 10 | 0.0163 |
| 11 | 0.0018 |
| 12 | 0.0024 |
| 13 | 0.0012 |
| 14 | 0.0005 |
| 15 | 0.0035 |
| 16 | 0.0027 |
| 17 | 0.0022 |
| 18 | 0.0053 |
| 19 | 0.0015 |
| 23 | 0.004 |
| 24 | 0.0106 |
| 25 | 0.0047 |
| 27 | 0.0018 |
| 28 | 0.0025 |
| 29 | 0.0187 |
| 31 | 0.0338 |
| 32 | 0.0019 |
| 33 | 0.0037 |
| 34 | 0.0078 |
| 35 | 0.004 |
| 36 | 0.0022 |
| 37 | 0.0018 |
| 38 | 0.0019 |
| 40 | 0.008 |
| 41 | 0.008 |
| 42 | 0.0142 |
| 43 | 0.003 |
| 44 | 0.0037 |
| 45 | 0.0044 |
| 46 | 0.0039 |
| 51 | 0.003 |
| 52 | 0.0069 |
| 53 | 0.0047 |
| 54 | 0.0037 |
| 55 | 0.0161 |
| 56 | 0.0064 |
| 57 | 0.0128 |
| 58 | 0.0086 |
| 60 | 0.0083 |
| 61 | 0.003 |
| 62 | 0.0067 |
| 63 | 0.0074 |
| 66 | >5 |
| 67 | 0.0049 |
| 70 | 0.0036 |
| 71 | 0.0044 |
| 73 | 0.0095 |
| 74 | 0.0127 |
| 75 | 0.0072 |
| 80 | 0.0034 |
| 82 | 0.018 |
| 83 | 0.0026 |
| 85 | 0.0107 |
| 86 | 0.0274 |
| 88 | 0.008 |
| 89 | 0.0048 |
| 91 | 0.0036 |
| 94 | 0.0042 |
| 95 | 0.0072 |
| 96 | 0.0032 |
| 103 | 0.0056 |
| 104 | 0.0074 |
| 107 | 0.0083 |
| 108 | 0.019 |
| 109 | 0.0061 |
| 110 | 0.0013 |
| 111 | 0.0020 |
| 112 | 0.0045 |
| 113 | 0.0050 |
| 114 | 0.0007 |
| 115 | 0.0227 |
| 116 | 0.001 |
| 119 | 0.0022 |
| 120 | 0.0013 |
| 121 | 0.0017 |
| 127 | 0.0034 |
| 134 | 0.0045 |
| 143 | 0.007 |
| 144 | 0.0021 |
| 145 | 0.0032 |
| 146 | 0.0066 |

Example 3

FGFR1 Cell-Based Activity Assay Utilizing IL3-Dependent BA/F3 Cells

An engineered, cell-based assay was utilized to test the potency of FGFR1 inhibitors in a cellular context. In this system, IL3-dependent Ba/F3 cells were modified to express an activated form of FGFR1 kinase domain. Following removal of IL3 from the culture media, the modified cells were dependent on the activity of the recombinant kinase for proliferation and survival. In these studies, Ba/F3 cells were transformed by inducting TEL fusions using viral vectors. If the compound of interest specifically blocked the activity of FGFR1, the modified cells underwent programmed cell death. The amount of cell survival was quantified using CellTiter-Glo, a well-established luminescent cell viability method. Compounds were evaluated at multiple doses using a maximum compound concentration of 5 uM and a 3-fold dilution series from this concentration.

Example 4

Tumor Xenograft Models for Assessing Efficacy of FGFR Inhibitors

Figure 2:
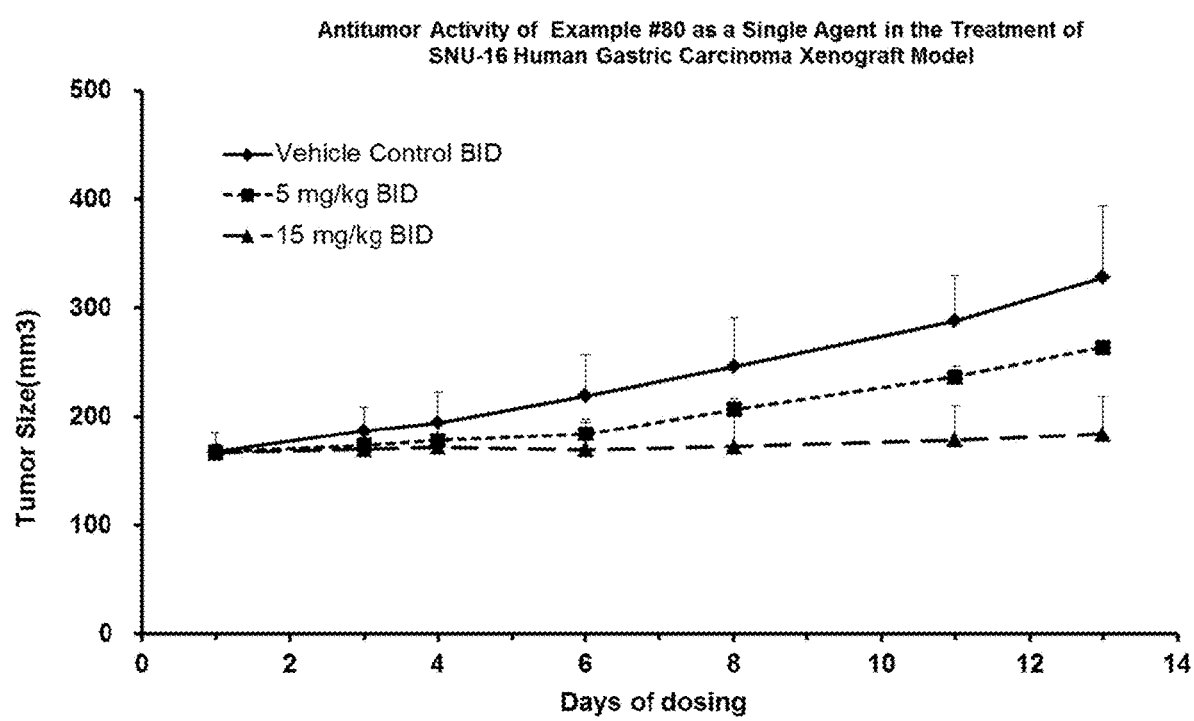

Human Gastric Tumor Model:

SNU-16 human gastric cancer cell line was used to generate a xenograft model to determine the effects of a FGFR inhibitor of the present disclosure (test compound) as a single agent treatment to target FGFR-dependent tumor growth. SNU-16 cells were grown in tissue culture as described in Example 2 above. For tumor inoculation, approximately $1 \times 10^7$ cells were mixed with Matrigel (1:1) and were implanted into the rear flank of immunocompromised Balb/c nu/nu mice. Tumor-bearing mice were monitored twice weekly in two dimensions using a caliper and the volume expressed in mm$^3$ using the formula: $V=0.5 \, a \times b^2$ where a and b are the long and short diameters of the tumor respectively. Once tumor volume reached a mean average of 175 mm$^3$ mice were randomized into 3 groups (n=8-10 per group) receiving either vehicle control (0.5% methyl cellulose w/w) or the test compound at 5, 10, or 20 mg/kg BID by oral gavage. Dosing continued for 5-21 days with tumor volumes measured daily or every other day. Mean tumor growth volumes are shown for compounds of Example 61 and Example 80 in FIGS. 1 and 2 below respectively, show strong tumor growth inhibition (see FIGS. 1 and 2).

Figure 3:
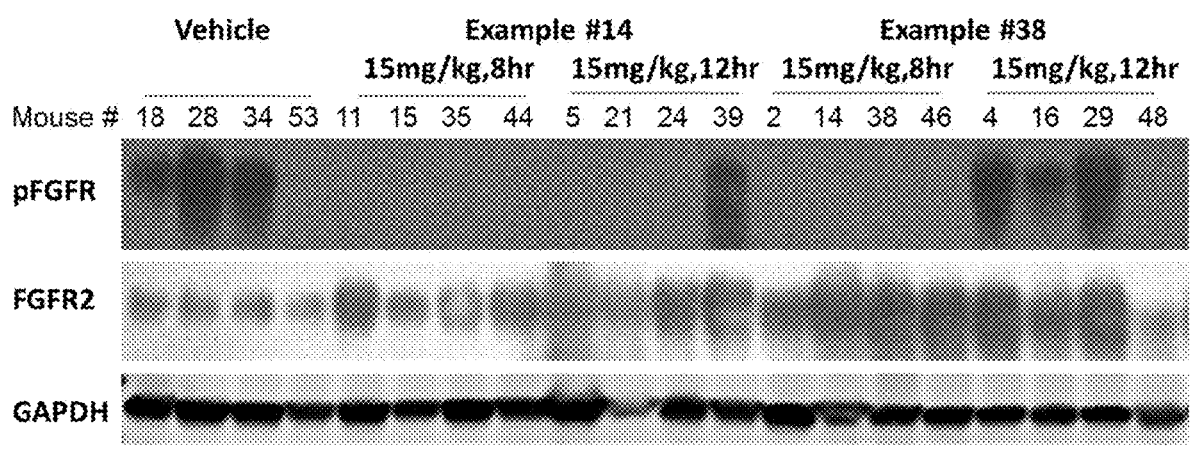

In addition to anti-tumor response study, SNU-16 xenograft model was used to access in vivo pharmacodynamics activity of a disclosure compound. Inhibition of FGFR pathway was assessed by detection of FGFR auto phosphorylation activity. Once the tumors reached approximately 300 mm$^3$, tumor bearing mice (n=4 per group) were dosed at 15 mg/kg. Tumor samples were collected at 8 h or 12 h post the last dosing. FGFR auto phosphorylation activity results on tumor samples indicated that compounds of Example #14 and Example #38 significantly inhibited FGFR phosphorylation at 8 h and the p-FGFR inhibitory effect could last for at least 12 h for the compound of Example #14 15 mg/kg treated tumors (see FIG. 3).

Human Bladder Tumor Model:

An RT4 human bladder tumor model was used to determine the effect of a FGFR inhibitor of the present disclosure (test compound) as a single agent on human bladder cancer. Each mouse was inoculated subcutaneously at the upper right back with RT4 tumor cells (1×10$^7$) mixed with Matrigel at a 1:1 ratio. The treatments were started at day 7 after tumor inoculation. Animals were randomized into 5 treatment groups (n=7 per group). Group 1 received the vehicle control (0.5% methyl cellulose). Group 2 received 5 mg/kg; Group 3 received 10 mg/kg BID, Group 4 received 12.5 mg/kg BID and Group 5 received 15 mg/kg BID of the test compound. Animals received compound by oral gavage. It was observed that the mean tumor size of the vehicle treated group (Group-1) reached 535 mm$^3$ on day 29 after tumor inoculation. Compound treatment at 15 mg/kg produced significant antitumor activity and induced tumor regression (TR=−5.1%); the mean tumor size was 116 mm$^3$ (TGI value=78%). Compound treatment at 12.5 mg/kg, 10 mg/kg and 15 mg/kg all produced significant antitumor activities; the mean tumor sizes were 126 mm$^3$, 189 mm$^3$, and 217 mm$^3$ (TGI value=77%, 65% and 60%, respectively).

Example 5

Recovery of Kinase Activity Upon Dialysis

Standard experimental methods to establish irreversible inhibition are known in the art. Protein dialysis is one such method. A solution containing a protein kinase that is inhibited by a compound of the present disclosure is subjected to extensive dialysis to establish if the kinase inhibitor is irreversible. Partial or complete recovery of protein kinase activity over time during dialysis is indicative of reversibility.

Method:

A compound of the present disclosure and/or a pharmaceutically acceptable salt thereof described herein (50 nM) was added to a solution of FGFR1 protein kinase (2 nM) in a buffer containing 50 mM Hepes pH 7.5, 0.1% bovine serum albumin, 5 mM magnesium chloride, 1 mM dithiothreitol, and 0.01% Triton X-100. Dialysis occurred at 22° C. for 1 day, 2 days, and 3 days with a change of dialysis buffer twice daily. Aliquots were removed from the dialysis cassettes and analyzed for FGFR1 kinase activity using the Caliper LabChip 3000 System. For compound of synthetic Example 6, the kinase enzymatic activity did not return upon dialysis.

Example 6

Irreversibility of Binding

The following approach was developed to differentiate compounds that form irreversible covalent bonds with their targets from compounds that bind reversibly. Reactions were prepared with the FGFR1 protein target at a higher concentration (2 µM) than the compounds of interest (0.6 µM). Irreversible and reversible compounds bound the target and became depleted from solution. The reactions were then treated with trypsin (to a final concentration of 0.6 mg/ml), disrupting proper folding of the target. It was found that the trypsin digestion returns reversible compounds to solution due to dissociation from the target while irreversible covalent compounds remained bound to the target. The concentration of compound in solution was assessed both preceding and following trypsin digestion using high performance liquid chromatography (HPLC) coupled to tandem mass spectrometry. Compounds that were irreversible covalent inhibitors of FGFR were depleted from solution in the perturbed state indicating that they were irreversible.

Example 7

Mass Spectral Analysis

A protein kinase that is inhibited by an irreversible kinase inhibitor described herein (e.g. a compound of Formula I) may be subjected to mass spectral analysis to assess the formation of irreversible covalent adducts. Suitable analytical methods to examine intact full protein or peptide fragments generated upon tryptic cleavage of the protein kinase are generally known in the art (see Lipton, Mary S., Ljiljana, Pasa-Tolic, Eds. Mass Spectrometry of Proteins and Peptides, Methods and Protocols, Second Edition. Humana Press. 2009). Such methods identify irreversible covalent protein adducts by observing a mass peak that corresponds to the mass of a control sample plus the mass of an irreversible adduct. Two such methods are described below.

Method A:

Mass Spectral Analysis of Intact Full Kinase

Method: A protein kinase (5 uM) is incubated with the irreversible kinase inhibitor (25-100 uM, 5-20 equiv) for 1 h at room temperature in buffer (20 mM Hepes [pH 8.0], 100 mM NaCl, 10 mM MgCl$_2$). A control sample is also prepared which does not have the addition of the irreversible kinase inhibitor. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software. (see patent application WO2014 011900, and PCT/US2010/048916)

Results: High-resolution intact mass spectrometry analysis of a kinase that is inhibited by an irreversible kinase inhibitor will reveal a spectrum that contains a new peak (e.g. a peak not present in the control sample without inhibitor) in the mass spectrum corresponding to the molecular mass of the kinase plus the molecular mass of the irreversible kinase inhibitor. On the basis of this experiment, an irreversible protein adduct will be apparent to one skilled in the art.

Method B:

Mass Spectral Analysis of Kinase Tryptic Digest

Method: A protein (10-100 pmols) is incubated with the reversible kinase inhibitor (100-1000 pmols, 10 equiv) for 3 hrs prior to tryptic digestion. Iodoacetamide may be used as the alkylating agent after compound incubation. A control sample is also prepared which does not have the addition of the irreversible kinase inhibitor. For tryptic digests a 1 ul aliquot (3.3 pmols) is diluted with 10 ul of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50). (see PCT/US2010/048916)

Results: High-resolution mass spectrometry analysis of the tryptic fragments of a kinase that is inhibited by an irreversible kinase inhibitor will reveal a spectrum that contains modified peptides that are not present in the control sample. On the basis of this experiment, irreversible protein adducts will be apparent to one skilled in the art. Furthermore, on the basis of the exact mass and MS-MS fragmentation pattern, the sequence of the modified peptide may be ascertained, there by defining the cysteine residue that is the site of covalent modification.

Example 8

Potency of Compounds in Cells
FGFR Cell-Based Activity Assay Utilizing HUVECs Cells The data herein demonstrate the use of human umbilical vein endothelial cells (HUVECs) to determine compound potency to FGFR pathway activity. Extracellular-signal-regulated kinases (ERKs) activity, effectors of FGFR pathway, was utilized to develop a FGFR-targeted assay to determine compound potency. Human umbilical vein endothelial cells (HUVECs) cell-based effects of FGFR inhibitors were determined by measuring inhibition of compounds on FGF-induced MAP kinases activation, (phosphorylation of p44 and p42 MAP Kinase or phospho-Erk1/2) using PerkinElmer pERK SureFire Kit. Approximately 30,000 HUVECs were seeded per well in a 96-well cell culture plate at 37° C. overnight. Cells were incubated in recommended HUVECs media with 10% fetal bovine serum (Cells were incubated at 37° C. for 24 hrs. in 50 $CO_2$). After 24 h, media were removed and replaced by serum free media for 1 hr prior to compound treatment. Compound dilutions were added to cells starting at a concentration of 1 uM and decreasing in tripling dilutions to a final concentration of 0.05 nM. The cells treated with compounds of the present disclosure were incubated for 1 hr at 37° C. in 5 $CO_2$. At the end of the 1 h incubation period, cells were stimulated with 50 ng/ml of FGF2 for 10 mins. The reaction was stopped with 100 ul of ice cold PBS and washed once with cold PBS. After washing, cells were lysed with 50 uL of 1× lysis buffer from pERK SureFire kit (Perkin Elmer). Lysates were incubated in a pERK SureFire reaction mixture for a total of 4 hrs. At the end of the incubation period, pERK activity was measured using an Envision multilabel reader (Perkin Elmer). The raw signals for pERK activity were used to calculate $IC_{50}$ inhibition value as a function of log compound concentration for each compound using Prism software from GraphPad. The $IC_{50}$ values for a representative no. of compounds of the disclosure are provided below.

| Cpd No. (see Cpd table 1 above) | HUVEC |
| --- | --- |
| 2 | 0.0115 |
| 4 | 0.0114 |
| 6 | 0.0011 |
| 7 | 0.0030 |
| 8 | 0.0347 |

-continued

| Cpd No. (see Cpd table 1 above) | HUVEC |
| --- | --- |
| 9 | 0.0063 |
| 10 | 0.0134 |
| 11 | 0.0017 |
| 12 | 0.0032 |
| 14 | 0.0008 |
| 15 | 0.0056 |
| 16 | 0.0015 |
| 17 | 0.0078 |
| 18 | 0.0165 |
| 19 | 0.0024 |
| 23 | 0.0046 |
| 24 | 0.0029 |
| 25 | 0.0076 |
| 27 | 0.0024 |
| 28 | 0.0019 |
| 30 | 0.0043 |
| 32 | 0.0015 |
| 33 | 0.0041 |
| 34 | 0.0056 |
| 35 | 0.004 |
| 36 | 0.001 |
| 37 | 0.001 |
| 38 | 0.0023 |
| 40 | 0.0124 |
| 41 | 0.005 |
| 43 | 0.0277 |
| 44 | 0.0037 |
| 45 | 0.0063 |
| 46 | 0.0034 |
| 51 | 0.0033 |
| 53 | 0.005 |
| 54 | 0.0025 |
| 55 | 0.0026 |
| 61 | 0.0022 |
| 62 | 0.0055 |
| 63 | 0.0027 |
| 68 | 0.001 |
| 70 | 0.0044 |
| 71 | 0.0048 |
| 73 | 0.0054 |
| 74 | |
| 75 | 0.0027 |
| 80 | 0.001 |
| 82 | 0.0022 |
| 83 | 0.0024 |
| 88 | 0.0063 |
| 89 | 0.004 |
| 90 | 0.0155 |
| 91 | 0.0033 |
| 92 | 0.0337 |
| 93 | 0.1066 |
| 94 | 0.0034 |
| 95 | 0.0232 |
| 107 | 0.0097 |
| 108 | 0.0064 |
| 110 | 0.0033 |
| 111 | 0.0014 |
| 112 | 0.0018 |
| 113 | 0.0035 |
| 114 | 0.0013 |
| 115 | 0.0182 |
| 127 | 0.0041 |

Example 9

Determination of Drug-Kinase Residence Time for FGFR1

The following is a protocol to distinguish whether a compound and/or a pharmaceutically acceptable salt thereof disclosed herein displays a slow or non-existent dissociation rate from FGFR1, such as typically would occur if an irreversible covalent bond is formed between the compound and the target. The read-out for slow or non-existent dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM MgCl$_2$, 0.01% Triton X-100, and 1 mM EGTA.

The first step of the procedure was incubation of 500 nM FGFR1 (Invitrogen Cat. #PV3146) with 1.5 uM of a compound of the present disclosure for 60 minutes in a volume of 10 ul. The mixture was then diluted 40-fold by mixture of 2 ul FGFR1/compound with 78 ul buffer. A 10 ul volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For FGFR1, the competition solution contained 8 uM Tracer 236 (Invitrogen Cat. #PV5592), which is a proprietary high affinity ligand for FGFR1 coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in FGFR1.

After addition of 10 ul of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to FGFR1 was detected using TR-FRET between the Europium moiety of the Anti-histidine antibody and the AlexaFluor 647 group of Tracer 236. Binding was evaluated using a Perkin Elmer Envision instrument (Model 2101) equipped with filters and mirrors compatible with LANCE-type TR-FRET experiments. Data were plotted as percentage of signal obtained in the absence of a compound. The background signal was obtained by omission of FGFR1 from the reaction. Results: Tracer was typically prevented from binding by a compound of the present disclosure and/or a pharmaceutically acceptable salt thereof.

Example 10

Durability of Binding in Cells

In addition to durability of binding of irreversible inhibitors to FGFR to recombinant protein, the durability can be assessed in FGFR containing cells. A system to test the durability of binding in cells involved treating SNU16 gastric carcinoma cells that had been incubated with the protein synthesis inhibitor cycloheximide at 5 ug/ml with compound for a time period adequate for complete binding to occur (e.g., one hour), followed by removal of the compound from the cell culture medium by extensive washing. Then at 4 h after washing away the compound, the FGFR2-containing SNU16 cells were examined for FGFR2 occupancy of the test compound using an FGFR specific fluorescence occupancy probe or by monitoring a downstream readout of FGFR signaling such as phosphoFGFR or phosphoERK. Cellular durability 4 h post-washout was a property of covalent irreversible binding of inhibitors to FGFR2 in SNU16 cells.

FORMULATION EXAMPLES

The following are representative pharmaceutical formulations containing a compound of the present disclosure.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:

1. A method of treating a disease in a patient, the method comprising administering a compound of Formula (III):

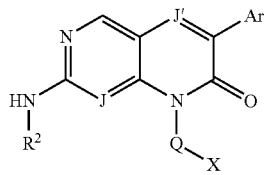

wherein:
J is N;
J' is CH;
Ar is phenyl substituted with one, two, three, or four substituents independently selected from alkoxy and halo;
$R^2$ is hydrogen or alkyl; and
Q is alkylene; and
X is a group of formula (a):

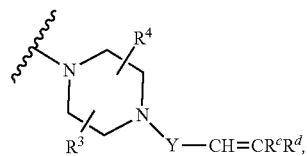

wherein:
each $R^3$ is hydrogen or alkyl; and
each $R^4$ is hydrogen or alkyl;
Y is —CO—;
$R^c$ is hydrogen or alkyl; and
$R^d$ is hydrogen or alkyl;
or a pharmaceutically acceptable salt thereof;
wherein the disease is chosen from skeletal dysplasia, craniosynostosis, and dwarf syndromes.

2. The method of claim 1, wherein Q is n-propylene.
3. The method of claim 1, wherein $R^2$ is alkyl.
4. The method of claim 1, wherein $R^2$ is hydrogen.
5. The method of claim 1, wherein Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl.
6. The method of claim 1, wherein Ar is 2-chloro-3,5-dimethoxy-phenyl, 3,5-dimethoxyphenyl, 2-chlorophenyl, or 2,6-dichloro-3,5-dimethoxyphenyl.
7. The method of claim 1, wherein $R^c$ and $R^d$ are hydrogen.
8. The method of any of the claims 1, 2, 3, 4, 5, 6 and 7 or a pharmaceutically acceptable salt thereof wherein $R^c$ is alkyl and $R^d$ is hydrogen.
9. The method of claim 1, wherein the compound of Formula (III) is selected from:
8-(3-(4-acryloylpiperazin-1-yl) propyl)-2-amino-6-(2,6-dichloro-3,5-dimethoxyphenyl)pyrido[2,3-d]pyrimidin-7 (8H)-one; or
8-(3-(4-acryloylpiperazin-1-yl) propyl)-6-(2,6-dichloro-3,5-dimethoxyphenyl)-2-(methylamino)pyrido[2,3-d]pyrimidin-7 (8H)-one;
and a pharmaceutically acceptable salt thereof.
10. The method of claim 1, wherein the compound of Formula (III) is selected from:
8-(3-(4-acryloylpiperazin-1-yl) propyl)-6-(2,6-dichloro-3,5-dimethoxyphenyl)-2-(methylamino)pyrido[2,3-d]pyrimidin-7 (8H)-one;
and a pharmaceutically acceptable salt thereof.
11. The method of claim 1, wherein the skeletal dysplasia is chosen from achondroplasia, hypochondroplasia, thanatophoric dysplasia, and platyspondylic lethal skeletal dysplasia.

* * * * *